United States Patent
Murphy Kessabi et al.

(10) Patent No.: US 8,415,272 B2
(45) Date of Patent: Apr. 9, 2013

(54) QUINOLINE DERIVATIVES AND THEIR USE AS FUNGICIDES

(75) Inventors: Fiona Murphy Kessabi, Stein (CH); Laura Quaranta, Stein (CH); Renaud Beaudegnies, Stein (CH); Hans-Georg Brunner, Lausen (CH); Fredrik Cederbaum, Stein (CH)

(73) Assignee: Syngenta Crop Protection LLC, Greensboro, NC (US)

( * ) Notice: Subject to any disclaimer, the term of this patent is extended or adjusted under 35 U.S.C. 154(b) by 0 days.

(21) Appl. No.: 12/811,725

(22) PCT Filed: Jan. 8, 2009

(86) PCT No.: PCT/EP2009/000069
§ 371 (c)(1),
(2), (4) Date: Jul. 6, 2010

(87) PCT Pub. No.: WO2009/087098
PCT Pub. Date: Jul. 16, 2009

(65) Prior Publication Data
US 2010/0280068 A1     Nov. 4, 2010

(30) Foreign Application Priority Data
Jan. 10, 2008  (GB) .................................. 0800407.9

(51) Int. Cl.
*C07D 215/38*     (2006.01)

(52) U.S. Cl.
USPC ............ 504/247; 546/159; 546/161; 546/163

(58) Field of Classification Search ................ 504/247; 546/159, 161, 163
See application file for complete search history.

(56) References Cited

U.S. PATENT DOCUMENTS
2010/0298356 A1 *  11/2010  Murphy et al. ............ 514/266.1

FOREIGN PATENT DOCUMENTS
| JP | 2001089453 | 4/2001 |
| WO | 99/33810 | 7/1999 |
| WO | 2004047538 | 6/2004 |
| WO | 2008110355 | 9/2008 |

* cited by examiner

*Primary Examiner* — D M Seaman
(74) *Attorney, Agent, or Firm* — R. Kody Jones

(57) ABSTRACT

Compounds of the general Formula (1) wherein the substituents are as defined in claim 1, are useful as fungicides.

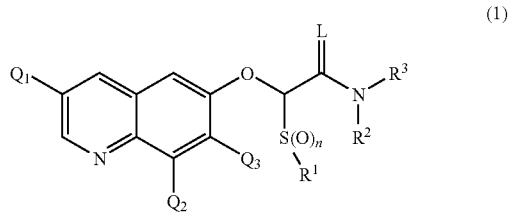

(1)

14 Claims, No Drawings

QUINOLINE DERIVATIVES AND THEIR USE AS FUNGICIDES

This application is a 371 of International Application No. PCT/EP2009/000069 filed Jan. 8, 2009, which claims priority to GB 0800407.9 filed Jan. 10, 2008, the contents of which are incorporated herein by reference.

This invention relates to novel quinolinyloxyalkanoic acid amides, processes for preparing them, to compositions containing them and to methods of using them to combat fungi, especially fungal infections of plants.

Certain quinolinyloxyalkanoic acid amide derivatives and their use as agricultural and horticultural bactericides are disclosed, for example, in WO 04/047538.

The present invention is concerned with the provision of particular substituted quinoline-6-yloxyalkanoic acid amides for use mainly as plant fungicides.

Thus according to the present invention there is provided a compound of the general formula I

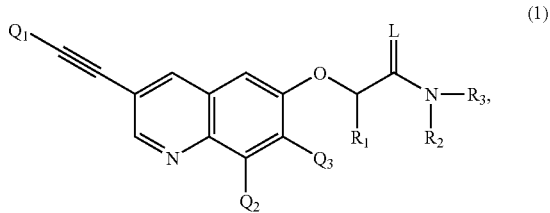

(1)

wherein $Q^1$ is hydrogen, $C_{1-4}$ alkyl, tri-$C_{1-4}$ alkylsilanyl, hydroxy-$C_{1-6}$ alkyl, alkoxy-$C_{1-6}$ alkyl, halo-$C_{1-6}$ alkyl or halogen, $Q^2$ and $Q^3$, independently of each other, are hydrogen, $C_{1-3}$ alkyl, halo-$C_{1-3}$ alkyl or halogen, $R^1$ is $C_{1-4}$ alkyl, halo($C_{1-4}$)alkyl, $C_{3-4}$cycloalkyl, $C_{1-4}$alkoxy, halo($C_{1-4}$)alkoxy, $C_{3-4}$-cycloalkoxy, $C_{1-4}$alkylthio, $C_{1-4}$alkylsulphinyl, $C_{1-4}$alkylsulphonyl, halo($C_{1-4}$)alkylthio, halo($C_{1-4}$) alkylsulphinyl, halo($C_{1-4}$) alkylsulphonyl, $C_{3-4}$cycloalkylthio, $C_{3-4}$cyclo-alkylsulphinyl or $C_{3-4}$cycloalkylsulphonyl, $R^2$ is hydrogen, $C_{1-6}$ alkyl, $C_{3-4}$ cycloalkyl, $C_{2-8}$ alkenyl, cyano, hydroxy, $C_{1-4}$ alkoxy, halo($C_{1-4}$)alkyl, cyano($C_{1-4}$)alkyl, $C_{1-4}$ alkoxy($C_{1-4}$)alkyl, $C_{1-4}$ alkoxy($C_{1-4}$)alkoxy($C_{1-4}$)alkyl or benzyloxy($C_{1-4}$)alkyl, wherein the phenyl ring is optionally substituted with $C_{1-4}$ alkoxy, $R^3$ is —$(CR^aR^b)_p(CR^cR^d)_q(X)_r(CR^eR^f)_sR^4$, wherein
$R^a$, $R^b$, $R^c$, $R^d$, $R^e$ and $R^f$, independently of each other, are hydrogen, $C_{1-6}$ alkyl, halogen, halo($C_{1-6}$)alkyl, hydroxy ($C_{1-6}$)alkyl, $C_{1-4}$ alkoxy($C_{1-4}$alkyl, $C_{3-5}$ alkenyloxy($C_{1-4}$) alkyl, $C_{3-5}$ alkynyloxy-$C_{1-4}$-alkyl, $C_{2-5}$ alkenyl or $C_{2-5}$ alkynyl, cyano, hydroxy, $C_{1-4}$ alkoxy, $C_{3-5}$ alkenyloxy, $C_{3-5}$ alkynyloxy or $C_{1-4}$ alkoxycarbonyl, or $R^aR^b$, $R^cR^d$ or $R^eR^f$ may join to form a 3 to 8 membered carbocyclic or heterocyclic ring containing a heteroatom selected from sulfur, oxygen and $NR^o$, wherein $R^o$ is hydrogen or optionally substituted $C_{1-6}$alkyl, where the carbocyclic or heterocyclic ring is optionally substituted with halo or $C_{1-4}$ alkyl, X is (CO), (CO)O, O(CO), O or $S(O)_t$, wherein t is 0, 1 or 2, or X is NH or $N(C_{1-6})$alkyl, p, r and s, independently of each other, are 0 or 1, q is 0, 1 or 2, $R^4$ is hydrogen, optionally substituted $C_{1-6}$ alkyl, formyl, cyano, optionally substituted $C_{2-6}$ alkenyl, or —C≡C—$R^5$, wherein $R^5$ is hydrogen, $C_{1-8}$ alkyl optionally substituted with halogen, hydroxy, $C_{1-6}$ alkoxy, $C_{1-3}$ alkoxy($C_{1-3}$)alkoxy, cyano, $C_{1-4}$ alkylcarbonyloxy, aminocarbonyloxy, mono- or di($C_{1-4}$)-alkylaminocarbonyloxy, tri($C_{1-4}$)alkylsilyloxy or —$S(O)_g(C_{1-6})$alkyl, wherein g is 0, 1 or 2, or $R^5$ is $C_{3-6}$ cycloalkyl optionally substituted with halogen, hydroxy, $C_{1-6}$ alkoxy, $C_{1-3}$ alkoxy-($C_{1-3}$)alkoxy, cyano, $C_{1-4}$ alkylcarbonyloxy, aminocarbonyloxy, mono- or di($C_{1-4}$) alkyl-aminocarbonyloxy, tri($C_{1-4}$alkylsilyloxy or —$S(O)_g$ $(C_{1-6})$alkyl, wherein g is 0, 1 or 2, or $R^5$ is $C_{3-6}$ cycloalkyl($C_{1-4}$alkyl, wherein the alkyl and/or cycloalkyl moiety is optionally substituted with halogen, hydroxy, $C_{1-6}$ alkoxy, $C_{1-3}$ alkoxy($C_{1-3}$)alkoxy, cyano, $C_{1-4}$ alkyl-carbonyloxy, aminocarbonyloxy, mono- or di($C_{1-4}$alkylaminocarbonyloxy, tri($C_{1-4}$)alkyl-silyloxy or —$S(O)_g(C_{1-6})$alkyl, wherein g is 0, 1 or 2, or $R^5$ is optionally substituted aryl, optionally substituted aryl ($C_{1-4}$)alkyl, optionally substituted aryloxy($C_{1-4}$alkyl, optionally substituted heteroaryl or optionally substituted heteroaryl($C_{1-4}$alkyl or optionally substituted heteroaryloxy($C_{1-4}$)alkyl, where these heteroaryls contain a heteroatom selected from sulphur, oxygen or $NR^{ooo}$, wherein $R^{ooo}$ is hydrogen or optionally substituted $C_{1-6}$alkyl, or $R^4$ is optionally substituted $C_{3-6}$ cycloalkyl, optionally substituted $C_{5-6}$ cycloalkenyl, optionally substituted aryl, optionally substituted heteroaryl or an optionally substituted 5- to 8-membered ring optionally containing a heteroatom selected from sulfur, oxygen or $NR^o$, wherein $R^o$ is hydrogen or optionally substituted $C_{1-6}$alkyl, or $R^2$ and $R^3$ may join to form a 5- or 6-membered ring optionally substituted with halogen, $C_{1-4}$ alkyl, mono- or di-($C_{1-4}$alkylaminocarbonyl, and optionally containing a heteroatom selected from sulphur, oxygen and $NR^{oo}$, wherein $R^{oo}$ is $C_{1-4}$ alkyl optionally substituted with halogen, $C_{1-6}$ alkoxy or cyano, or $R^{oo}$ is phenyl optionally substituted with nitro, $C_{1-4}$ alkyl, halo($C_{1-4}$)alkyl, $C_{1-4}$ alkylcarbonyl or heteroaryl, or $R^2$ and $R^3$ may join to form an optionally substituted 6,6-membered bicycle, L is sulfur or oxygen, and salts and N-oxides of the compounds of the formula I.

The compounds of the invention contain at least one asymmetric carbon atom and may exist as enantiomers (or as pairs of diastereoisomers) or as mixtures of such. Compounds of general formula (I) can therefore exist as racemates, diastereoisomers, or single enantiomers, and the invention includes all possible isomers or isomer mixtures in all proportions. It is to be expected that for any given compound, one isomer may be more fungicidally active than another.

N-oxides of the compounds of the formula I preferably denote the N-oxides formed by the quinoline moiety.

The salts which the compounds of the formula I can form are preferably those formed by interaction of these compounds with acids. The term "acid" comprises mineral acids such as hydrogen halides, sulphuric acid, phosphoric acid etc. as well as organic acids, preferably the commonly used alkanoic acids, for example formic acid, acetic acid and propionic acid.

Except where otherwise stated, alkyl groups and alkyl moieties of alkoxy, alkylthio, etc., suitably contain from 1 to 8, typically from 1 to 3, carbon atoms in the form of straight or branched chains. Examples are methyl, ethyl, n- and isopropyl and n-, sec-, iso- and tert-butyl. Where alkyl moieties contain 5 or 6 carbon atoms, examples are n-pentyl and n-hexyl. Examples of suitable optional substituents of alkyl groups and moieties include halo, hydroxy, $C_{1-4}$ alkoxy, $C_{1-4}$ alkoxy($C_{1-4}$)alkoxy, $C_{3-5}$ alkenyl and $C_{3-5}$ alkynyl, cyano, optionally substituted aryl and optionally substituted heteroaryl. Where the optional substituent is halo, the haloalkyl group or moiety is typically monochloromethyl, monofluoromethyl, dichloromethyl, difluoromethyl, trichloromethyl or trifluoromethyl.

Preferably, except where otherwise stated, alkyl groups and alkyl moieties of alkoxy, alkylthio, etc., suitably contain from 1 to 8, typically from 1 to 3, carbon atoms in the form of straight or branched chains. Examples are methyl, ethyl, n- and iso-propyl and n-, sec, iso- and tent-butyl. Where alkyl moieties contain 5 or 6 carbon atoms, examples are n-pentyl and n-hexyl. Examples of suitable optional substituents of alkyl groups and moieties include halo, hydroxy, $C_1$ alkoxy and $C_{1-4}$ alkoxy($C_{1-4}$)alkoxy, $C_{3-5}$ alkenyl and $C_{3-5}$ alkynyl and cyano.

Except where otherwise stated, alkenyl and alkynyl moieties also suitably contain from 2 to 6, typically from 2 to 4, carbon atoms in the form of straight or branched chains. Examples are allyl, ethynyl and propargyl. Optional substituents include halo, alkoxy, optionally substituted aryl and optionally substituted heteroaryl.

Halo includes fluoro, chloro, bromo and iodo.

Preferably, except where otherwise stated, alkenyl and alkynyl moieties also suitably contain from 2 to 6, typically from 2 to 4, carbon atoms in the form of straight or branched chains. Examples are allyl, ethynyl and propargyl. Optional substituents include halo and alkoxy.

Aryl is usually phenyl but also includes naphthyl, anthryl and phenanthryl. Heteroaryl is typically a 5- to 8-membered aromatic ring containing one or more sulphur, oxygen or NR moieties as heteroatoms, which may be fused to one or more other aromatic or heteroaromatic rings, such as a benzene ring. Examples are thienyl, furyl, pyrrolyl, isoxazolyl, oxazolyl, thiazolyl, oxadiazolyl, pyrazolyl, imidazolyl, triazolyl, isothiazolyl, tetrazolyl, thiadiazolyl, pyridyl, pyrimidinyl, pyrazinyl, pyridazinyl, triazinyl, benzofuranyl, benzothienyl, dibenzofuranyl, dibenzothienyl, benzothiazolyl, benzoxazolyl, benzimidazolyl, indolyl, quinolyl, isoquinolyl, quinazolinyl and quinoxalinyl groups and, where appropriate, N-oxides and salts thereof. Carbocyclic rings typically contain 3 to 8 carbon atoms and comprise cycloalkyl, preferably containing 3 to 6, or, more preferably, 3 or 4 carbon atoms, and cycloalkylene having 5 or 6 carbon atoms. These cycloalkylene rings may contain 1 or 2 double bonds. The carbocyclic rings may also contain heteroatoms such as oxygen, nitrogen or sulphur. Examples are pyrrolidinyl, piperidinly, tetrahydrofuranyl, dioxanyl, furanyl, pyranyl, thiophenyl and thiopyranyl. Any of the aryl, heteroaryl, carbocycle and heterocycle values are optionally substituted. Except where otherwise stated, substituents which may be present include one or more of the following: halo, hydroxy, mercapto, $C_{1-6}$ alkyl (especially methyl and ethyl), $C_{2-6}$ alkenyl (especially allyl), $C_{2-6}$ alkynyl (especially propargyl), $C_{1-6}$ alkoxy (especially methoxy), $C_{2-6}$ alkenyloxy (especially allyloxy), $C_{2-6}$ alkynyloxy (especially propargyloxy), halo($C_{1-6}$)alkyl (especially trifluoromethyl), halo($C_{1-6}$)alkoxy (especially trifluoromethoxy), —S(O)$_m$($C_{1-6}$)alkyl wherein m is 0, 1 or 2 and the alkyl is optionally substituted with halo, hydroxy($C_{1-6}$)alkyl, $C_{1-4}$ alkoxy($C_{1-4}$)alkyl, $C_{1-4}$alkoxy($C_{1-4}$alkoxy, $C_{3-6}$ cycloalkyl, $C_{3-6}$ cycloalkyl($C_{1-4}$)alkyl, optionally substituted aryl (especially optionally substituted phenyl), optionally substituted heteroaryl (especially optionally substituted pyridyl or pyrimidinyl), optionally substituted aryloxy (especially optionally substituted phenoxy), optionally substituted heteroaryloxy (especially optionally substituted pyridyloxy or pyrimidinyloxy), optionally substituted —S(O)$_m$aryl wherein m is 0, 1 or 2 (especially optionally substituted phenylthio), optionally substituted —S(O)$_m$heteroaryl wherein m is 0, 1 or 2 (especially optionally substituted pyridylthio or pyrimidinylthio), optionally substituted aryl($C_{1-4}$)alkyl (especially optionally substituted benzyl, optionally substituted phenethyl and optionally substituted phenyl n-propyl) in which the alkyl moiety is optionally substituted with hydroxy, optionally substituted heteroaryl($C_{1-4}$alkyl (especially optionally substituted pyridyl- or pyrimidinyl($C_{1-4}$)alkyl), optionally substituted aryl($C_{2-4}$)alkenyl (especially optionally substituted phenylethenyl), optionally substituted heteroaryl($C_{2-4}$)alkenyl (especially optionally substituted pyridylethenyl or pyrimidinylethenyl), optionally substituted aryl($C_{1-4}$)alkoxy (especially optionally substituted benzyloxy and phenethyloxy), optionally substituted heteroaryl($C_{1-4}$alkoxy (especially optionally substituted pyridyl($C_{1-4}$)alkoxy or pyrimidinyl ($C_{1-4}$)alkoxy), optionally substituted aryloxy-($C_{1-4}$alkyl (especially phenoxymethyl), optionally substituted heteroaryloxy-($C_{1-4}$)alkyl (especially optionally substituted pyridyloxy or pyrimidinyloxy($C_{1-4}$)alkyl), optionally substituted —S(O)$_m$($C_{1-4}$)alkylaryl wherein m is 0, 1 or 2 (especially optionally substituted benzylthio and phenethylthio), optionally substituted —S(O)$_m$($C_{1-4}$)alkylheteroaryl wherein m is 0, 1 or 2 (especially optionally substituted pyridyl($C_{1-4}$) alkylthio or pyrimidinyl($C_{1-4}$)-alkylthio), optionally substituted —($C_{1-4}$)alkylS(O)$_m$aryl wherein m is 0, 1 or 2 (especially phenylthiomethyl), optionally substituted —($C_{1-4}$) alkyl S(O)$_m$heteroaryl wherein m is 0, 1 or 2 (especially optionally substituted pyridylthio($C_{1-4}$alkyl or pyrimidinylthio($C_{1-4}$)alkyl), acyloxy, including $C_{1-4}$ alkanoyloxy (especially acetyloxy) and benzoyloxy, cyano, isocyano, thiocyanato, isothiocyanato, nitro, NR$^g$R$^h$, —NHCOR$^g$, —NHCONR$^g$R$^h$, —CONR$^g$R$^h$, —CO$_2$R$^g$, —SO$_2$R$^i$, —OSO$_2$R$^i$, —COR$^g$, —CR$^g$=NR$^h$ or —N=CR$^g$R$^h$ in which R$^i$ is $C_{1-4}$ alkyl, halo($C_{1-4}$)alkyl, $C_{1-4}$ alkoxy, halo ($C_{1-4}$)alkoxy, $C_{1-4}$ alkylthio, $C_{3-6}$ cycloalkyl, $C_{3-6}$ cycloalkyl($C_{1-4}$)alkyl, phenyl or benzyl, the phenyl and benzyl groups being optionally substituted with halogen, $C_{1-4}$ alkyl or $C_{1-4}$ alkoxy and R$^g$ and R$^h$ are independently hydrogen, $C_{1-4}$ alkyl, halo($C_{1-4}$)alkyl, $C_{1-4}$ alkoxy, halo($C_{1-4}$)alkoxy, $C_{1-4}$ alkylthio, $C_{3-6}$ cycloalkyl, $C_{3-6}$ cycloalkyl($C_{1-4}$)alkyl, phenyl or benzyl, the phenyl and benzyl groups being optionally substituted with halogen, $C_{1-4}$ alkyl or $C_{1-4}$ alkoxy.

Preferably, in the compounds of the formula (1), $Q^1$ is hydrogen, $C_{1-4}$ alkyl, halo($C_{1-4}$)alkyl, hydroxy($C_{1-4}$)alkyl or tri-$C_{1-3}$ alkylsilanyl, $Q^2$ and $Q^3$, independently of each other, are hydrogen, ($C_{1-3}$ alkyl or halogen, R$^i$ is $C_{1-4}$ alkyl, ($C_{1-4}$) alkoxy or ($C_{1-4}$)alkylthio, R$^2$ is hydrogen, R$^3$ is —(CR$^a$R$^b$)$_p$(CR$^c$R$^d$)$_q$(X)$_r$(CR$^e$R$^f$)$_s$R$^4$, wherein R$^a$, R$^b$, R$^c$, R$^d$, R$^e$ and R$^f$, independently of each other, are hydrogen, $C_{1-6}$ alkyl, halo ($C_{1-6}$)alkyl, hydroxy($C_{1-6}$)alkyl, $C_{2-4}$ alkenyl or $C_{2-4}$ alkynyl, halogen, cyano, hydroxyl or ($C_{1-4}$)alkoxy, $C_{3-5}$ alkenyloxy or $C_{3-5}$ alkynyloxy, or R$^a$ und R$^b$ may join to form a 3 to 8 membered carbocyclic ring, X is (CO) or O, p, r and s, independently of each other, are 0 or 1, q is 0, 1 or 2, R$^4$ is hydrogen, $C_{1-6}$ alkyl, $C_{1-6}$ alkyl substituted with halo, hydroxy, $C_{1-4}$ alkoxy, $C_{3-5}$ alkenyloxy or $C_{3-5}$ alkynyloxy, $C_{1-4}$ alkoxy($C_{1-4}$)alkoxy, $C_{3-5}$ alkenyl, $C_{3-5}$ alkynyl or cyano, or R$^4$ is formyl, cyano or —C≡C—R$^5$, wherein R$^5$ is hydrogen or $C_{1-4}$ alkyl or $C_{1-4}$ alkyl substituted with halo, hydroxy, $C_{1-4}$ alkoxy, $C_{3-5}$ alkenyloxy or $C_{3-5}$ alkynyloxy, $C_{1-4}$ alkoxy ($C_{1-4}$)alkoxy or cyano, and L is oxygen.

More preferably, $Q^1$ is hydrogen, methyl, ethyl, fluoromethyl, hydroxymethyl, or trimethylsilanyl, $Q^2$ and $Q^3$, independently of each other, are hydrogen, methyl, fluoro, chloro or bromo, R$^1$ is ethyl, methoxy or methylthio, R$^2$ is hydrogen, R$^3$ is —(CR$^a$R$^b$)$_p$(CR$^c$R$^d$)$_q$(X)$_r$(CR$^e$R$^f$)$_s$R$^4$, wherein R$^a$, R$^b$, R$^c$, R$^d$, R$^e$ and R$^f$, independently of each other, are hydrogen, $C_{1-4}$ alkyl, halo($C_{1-4}$)alkyl, hydroxy($C_{1-4}$)alkyl, $C_{2-3}$ alkynyl, $C_{3-5}$ alkenyloxy or $C_{3-5}$ alkynyloxy, cyano or ($C_{1-3}$)alkoxy, or $R^a$ und $R^b$ may join to form a 3 or 4 membered carbocyclic ring, X is (CO) or O, p, r and s, independently of each other, are 0 or 1, q is 0, 1 or 2, $R^4$ is hydrogen, $C_{1-6}$ alkyl, halo($C_{1-4}$)alkyl, hydroxy($C_{1-4}$)alkyl, $C_{1-4}$ alkoxy-$C_{1-6}$alkyl, $C_{3-5}$ alkenyloxy or $C_{3-5}$ alkynyloxy, formyl, cyano or —C≡CR$^5$, wherein $R^5$ is hydrogen, methyl, ethyl, methoxymethyl, allyloxymethyl or propargyloxymethyl and L is oxygen.

Even more preferably, $Q^1$ is hydrogen, methyl, fluoromethyl, hydroxymethyl or trimethylsilanyl, $Q^2$ and $Q^3$, independently of each other, are hydrogen, methyl, fluoro, chloro or bromo, $R^1$ is ethyl, methoxy or methylthio, $R^2$ is hydrogen, $R^3$ is $(CR^aR^b)_p(CR^cR^d)_q(X)_r(CR^eR^f)_sR^4$, wherein $R^a$, $R^b$, $R^c$, $R^d$, $R^e$ and $R^f$, independently of each other, are hydrogen, $C_{1-3}$ alkyl, halo($C_{1-3}$)alkyl, hydroxy($C_{1-3}$)alkyl, $C_{2-3}$ alkynyl, methoxy, allyloxy, propargyloxy or cyano, or $R^a$ und $R^b$ may join to form a 3 or 4 membered carbocyclic ring, X is O, p, q, r and s, independently of each other, are 0 or 1, $R^4$ is hydrogen, $C_{1-4}$ alkyl, especially, methyl, fluoro($C_{1-3}$)alkyl, especially fluoromethyl, hydroxy($C_{1-3}$)alkyl, $C_{1-3}$ alkoxy-$C_{1-3}$ alkyl, especially methoxymethyl and ethoxymethyl, $C_{3-5}$ alkenyloxy, especially allyloxy, or $C_{3-5}$ alkynyloxyl, specially propargyloxy, formyl, cyano or —C≡CR$^5$, wherein $R^5$ is hydrogen, methyl, methoxymethyl, allyloxymethyl or propargyloxymethyl and L is oxygen.

In a preferred group of the compounds of the formula (1) $R^aR^b$, $R^cR^d$ or $R^eR^f$ may join to form a 3 to 8 membered carbocyclic or heterocyclic ring containing a heteroatom selected from sulphur or oxygen.

In a preferred group of the compounds of the formula (1) $R^4$ is $C_{3-6}$cycloalkyl or $C_{3-6}$ cycloalkyl substituted with $C_{1-3}$alkyl, hydroxymethyl, formyl, cyano, $C_{2-4}$alkenyl or $C_{2-4}$alkynyl.

More preferably, $R^4$ is cyclobutyl or cyclobutyl substituted with $C_{1-3}$alkyl, especially methyl, hydroxymethyl, formyl, cyano, $C_{2-4}$alkenyl, especially vinyl, or $C_{2-4}$alkynyl, especially ethynyl.

In a preferred group of the compounds of the formula (1) $Q^1$ is hydrogen, methyl, hydroxymethyl, fluoromethyl or trimethylsilyl.

In another preferred group of the compounds of the formula (1) $Q^1$ is hydrogen.

In another preferred group of the compounds of the formula (1) $Q^1$, $Q^2$ and $Q^3$ are hydrogen.

In another preferred group of the compounds of the formula (1) $Q^1$ is hydrogen and $Q^2$ is fluoro, chloro or bromo.

In another preferred group of the compounds of the formula (1) $Q^1$ is hydrogen, $Q^2$ is fluoro, chloro or bromo and $Q^3$ is hydrogen.

In another preferred group of the compounds of the formula (1) Q1 is hydrogen, Q2 is fluoro and $Q^3$ is fluoro.

In another preferred group of the compounds of the formula (1) $Q^1$ is hydrogen, $Q^2$ is fluoro or chloro and $Q^3$ is hydrogen.

In another preferred group of the compounds of the formula (1) $Q^1$ is hydrogen, $Q^2$ is fluoro and $Q^3$ is methyl.

In another preferred group of the compounds of the formula (1) $Q^1$ is hydrogen, $Q^2$ is chloro and $Q^3$ is hydrogen.

In another preferred group of the compounds of the formula (1) $Q^1$ is hydrogen, $Q^2$ is fluoro and $Q^3$ is hydrogen.

In another preferred group of the compounds of the formula (1) $Q^1$ is hydrogen and $Q^3$ is fluoro.

In another preferred group of the compounds of the formula (1) $Q^1$ is hydrogen, $Q^3$ is fluoro and $Q^2$ is hydrogen.

In another preferred group of the compounds of the formula (1) $Q^1$ is hydrogen and $Q^2$ is methyl.

In another preferred group of the compounds of the formula (1) $Q^1$ is hydrogen, $Q^2$ is methyl and $Q^3$ is hydrogen.

In another preferred group of the compounds of the formula (1) $Q^1$ is hydrogen, $Q^2$ is methyl and $Q^3$ is fluorine.

In another preferred group of the compounds of the formula (1) $Q^1$ is hydrogen and $R^3$ is $—(CR^aR^b)_p(CR^cR^d)_q(X)_r(CR^eR^f)_sR^4$, wherein p, q and r are 0, s is 1, $R^e$ and $R^f$ are methyl or ethyl, and $R^4$ is ethynyl, propynyl, methoxymethylethynyl, ethoxymethylethynyl, methoxyethylethynyl, allyloxymethyletynyl or propargyloxymethylethynyl.

In another preferred group of the compounds of the formula (1) $Q^1$ is hydrogen and $R^3$ is $—(CR^aR^b)_p(CR^cR^d)_q(X)_r(CR^eR^f)_sR^4$, wherein $R^a$, $R^b$, $R^c$, $R^d$, $R^e$ and $R^f$, independently of each other, are hydrogen, methyl or cyano, X is O, p, r and s are 0 or 1, q is 0, 1 or 2 and $R^4$ is hydrogen, methyl, methoxymethyl, formyl, cyano, ethenyl or ethynyl, or $R^a$ and $R^b$ may join to form a propylene chain to complete, together with the carbon atom to which they are attached, a cyclobutyl ring.

More preferably, $Q^1$ is hydrogen and $R^3$ is $—(CR^aR^b)_p(CR^cR^d)_q(X)_r(CR^eR^f)_sR^4$, wherein $R^a$ and $R^b$ are methyl, p is 1, q is 0, r is 0, s is 1, $R^e$ and $R^f$ are hydrogen and $R^4$ is hydrogen.

More preferably, $Q^1$ is hydrogen and $R^3$ is $—(CR^aR^b)_p(CR^cR^d)_q(X)_r(CR^eR^f)_sR^4$, wherein $R^a$ and $R^b$ join to form a propylene chain to complete, together with the carbon atom to which they are attached, a cyclobutyl ring, p is 1, q is 0, r is 0, s is 1, $R^e$ and $R^f$ are hydrogen and $R^4$ is hydrogen.

More preferably, $Q^1$ is hydrogen and $R^3$ is $—(CR^aR^b)_p(CR^cR^d)_q(X)_r(CR^eR^f)_sR^4$, wherein $R^a$ and $R^b$ join to form a propylene chain to complete, together with the carbon atom to which they are attached, a cyclobutyl ring, p is 1, q is 0, r is 0, s is 0, and $R^4$ is hydrogen, $C_{1-4}$ alkyl, fluoro($C_{1-3}$)alkyl, hydroxy($C_{1-3}$)alkyl, $C_{1-3}$ alkoxy-$C_{1-3}$ alkyl, $C_{3-5}$ alkenyloxy or $C_{3-5}$ alkynyloxy, formyl, cyano or —C≡CR$^5$, wherein $R^5$ is hydrogen.

Even more preferably, $Q^1$ is hydrogen and $R^3$ is $—(CR^aR^b)_p(CR^cR^d)_q(X)_r(CR^eR^f)_sR^4$, wherein $R^a$ and $R^b$ join to form a propylene chain to complete, together with the carbon atom to which they are attached, a cyclobutyl ring, p is 1, q is 0, r is 0, s is 0, and $R^4$ is hydrogen, methyl, hydroxymethyl, methoxymethyl, allyloxymethyl or propargyloxymethyl, formyl, cyano or —C≡CR$^5$, wherein $R^5$ is hydrogen.

More preferably, $Q^1$ is hydrogen and $R^3$ is $—(CR^aR^b)_p(CR^cR^d)_q(X)_r(CR^eR^f)_sR^4$, wherein $R^a$ is methyl, $R^b$ is cyano, p is 1, $R^c$ and $R^d$ are hydrogen, q is 1, X is O, r is 1, $R^e$ and $R^f$ are hydrogen, s is 1, and $R^4$ is hydrogen, methyl, ethenyl or ethynyl.

More preferably, $Q^1$ is hydrogen and $R^3$ is $—(CR^aR^b)_p(CR^cR^d)_q(X)_r(CR^eR^f)_sR^4$, wherein $R^a$ is methyl, $R^b$ is cyano, p is 1, $R^c$ and $R^d$ are hydrogen, q is 1, X is O, r is 1, s is 0, and $R^4$ is hydrogen, methyl.

More preferably, $Q^1$ is hydrogen and $R^3$ is $—(CR^aR^b)_p(CR^cR^d)_q(X)_r(CR^eR^f)_sR^4$, wherein $R^a$ is methyl, $R^b$ is ethynyl, p is 1, $R^c$ and $R^d$ are hydrogen, q is 1, X is O, r is 1, $R^e$ and $R^f$ are hydrogen, s is 1, and $R^4$ is hydrogen, methyl, ethenyl or ethynyl.

More preferably, $Q^1$ is hydrogen and $R^3$ is $—(CR^aR^b)_p(CR^cR^d)_q(X)_r(CR^eR^f)_sR^4$, wherein $R^a$ is methyl, $R^b$ is ethynyl, p is 1, $R^c$ and $R^d$ are hydrogen, q is 1, X is O, r is 1, s is 0, and $R^4$ is hydrogen, methyl.

More preferably, $Q^1$ is hydrogen and $R^3$ is $—(CR^aR^b)_p(CR^cR^d)_q(X)_r(CR^eR^f)_sR^4$, wherein $R^a$ is methyl, $R^b$ is ethynyl, p is 1, $R^c$ and $R^d$ are hydrogen, q is 0, r is 0, s is 0, and $R^4$ is formyl or ethynyl.

More preferably, $Q^1$ is hydrogen and $R^3$ is $—(CR^aR^b)_p(CR^cR^d)_q(X)_r(CR^eR^f)_sR^4$, wherein $R^a$ and $R^b$ join to form a propylene chain to complete, together with the carbon atom to which they are attached, a cyclobutyl ring, p is 1, $R^c$ and $R^d$ are hydrogen, q is 1, X is O, r is 1, $R^e$ and $R^f$ are hydrogen, s is 1, and $R^4$ is hydrogen, methyl, ethenyl or ethynyl.

More preferably, $Q^1$ is hydrogen and $R^3$ is —$(CR^aR^b)_p$ $(CR^cR^d)_q(X)_r(CR^eR^f)_sR^4$, wherein $R^a$ and $R^b$ are ethynyl, p is 1, q is 0, r is 0, s is 1, $R^e$ and $R^f$ are hydrogen and $R^4$ is hydrogen.

In another preferred group of the compounds of the formula (1), p is 1, r is 0 and s is 1, q is 1.

In another preferred group of the compounds of the formula (1), p is 1, r is 0 and s is 0, q is 0.

In another preferred group of the compounds of the formula (1), p is 1, r is 0 and s is 0, q is 1.

More preferably, $Q^1$ is hydrogen and $R^3$ is —$(CR^aR^b)_p$ $(CR^cR^d)_q(X)_r(CR^eR^f)_sR^4$, wherein $R^a$ is methyl, $R^b$ is hydroxy($C_{1-3}$)alkyl, $C_{1-3}$ alkoxy($C_{1-3}$)alkyl, $C_{3-4}$ alkenyloxy ($C_{1-3}$)alkyl, $C_{3-4}$ alkynyloxy-$C_{1-3}$-alkyl, p is 1, $R^c$ and $R^d$ are hydrogen, q is 1, X is O, r is 1, s is 0, and $R^4$ is hydroxy ($C_{1-3}$)alkyl, $C_{1-3}$ alkoxy($C_{1-3}$)alkyl, $C_{3-4}$ alkenyloxy($C_{1-3}$) alkyl, $C_{3-4}$ alkynyloxy-$C_{1-3}$-alkyl.

More preferably, $Q^1$ is hydrogen and $R^3$ is —$(CR^aR^b)_p$ $(CR^cR^d)_q(X)_r(CR^eR^f)_sR^4$, wherein $R^a$ is methyl, $R^b$ is hydroxymethyl, $C_{1-3}$ alkoxymethyl, especially methoxymethyl, $C_{3-4}$ alkenyloxymethyl, especially allyloxymethyl, $C_{3-4}$ alkynyloxymethyl, especially propargyloxymethyl, p is 1, $R^c$ and $R^d$ are hydrogen, q is 1, r is 0, s is 0, and $R^4$ is hydroxymethyl, $C_{1-3}$ alkoxymethyl, especially methoxymethyl, $C_{3-4}$ alkenyloxymethyl, especially allyloxymethyl, $C_{3-4}$ alkynyloxymethyl, especially propargyloxymethyl.

More preferably, $Q^1$ is hydrogen and $R^3$ is —$(CR^aR^b)_p$ $(CR^cR^d)_q(X)_r(CR^eR^f)_sR^4$, wherein $R^a$ is methyl, $R^b$ is formyl, p is 1, $R^c$ and $R^d$ are hydrogen, q is 1, X is O, r is 1, s is 0, and $R^4$ is hydrogen, $C_{1-4}$ alkyl, $C_{3-5}$ alkenyl or $C_{3-5}$ alkynyl.

More preferably, $Q^1$ is hydrogen and $R^3$ is —$(CR^aR^b)_p$ $(CR^cR^d)_q(X)_r(CR^eR^f)_sR^4$, wherein $R^a$ is methyl, $R^b$ is formyl, p is 1, $R^c$ and $R^d$ are hydrogen, q is 1, X is O, r is 1, s is 0, and $R^4$ is hydrogen, methyl, ethyl, $C_{3-4}$ alkenyl, especially allyl, or $C_{3-4}$ alkynyl, especially propargyl.

More preferably, $Q^1$ is hydrogen and $R^3$ is —$(CR^aR^b)_p$ $(CR^cR^d)_q(X)_r(CR^eR^f)_sR^4$, wherein $R^a$ is methyl, $R^b$ is formyl, p is 1, q is 0, r is 0, s is 0, and $R^4$ is hydrogen, methyl, ethyl, ethynyl, cyano.

In a preferred group of the compounds of the formula (1) $R^aR^b$, $R^cR^d$ or $R^eR^f$ may join to form a 3 to 8 membered carbocyclic or heterocyclic ring containing a heteroatom selected from sulphur or oxygen, and p is 1, q is 1, r is 0 and s is 1.

In a preferred group of the compounds of the formula (1) $Q^1$ is hydrogen, methyl, hydroxymethyl, fluoromethyl or trimethylsilyl, and p is 1, q is 1, r is 0 and s is 1.

In another preferred group of the compounds of the formula (1) $Q^1$ is hydrogen and p is 1, q is 1, r is 0 and s is 1.

In another preferred group of the compounds of the formula (1) $Q^1$, $Q^2$ and $Q^3$ are hydrogen and p is 1, q is 1, r is 0 and s is 1.

In another preferred group of the compounds of the formula (1) $Q^1$ is hydrogen and $Q^2$ is fluoro, chloro or bromo and p is 1, q is 1, r is 0 and s is 1.

In another preferred group of the compounds of the formula (1) $Q^1$ is hydrogen, $Q^2$ is fluoro, chloro or bromo and $Q^3$ is hydrogen, p is 1, q is 1, r is 0 and s is 1.

In another preferred group of the compounds of the formula (1) Q1 is hydrogen, Q2 is fluoro, $Q^3$ is fluoro and p is 1, q is 1, r is 0 and s is 1.

In another preferred group of the compounds of the formula (1) $Q^1$ is hydrogen, $Q^2$ is fluoro or chloro, $Q^3$ is hydrogen and p is 1, q is 1, r is 0 and s is 1.

In another preferred group of the compounds of the formula (1) $Q^1$ is hydrogen, $Q^2$ is methyl, $Q^3$ is fluoro and p is 1, q is 1, r is 0 and s is 1.

In another preferred group of the compounds of the formula (1) $Q^1$ is hydrogen, $Q^2$ is chloro, $Q^3$ is hydrogen and p is 1, q is 1, r is 0 and s is 1.

In another preferred group of the compounds of the formula (1) $Q^1$ is hydrogen, $Q^2$ is fluoro, $Q^3$ is hydrogen and p is 1, q is 1, r is 0 and s is 1.

In another preferred group of the compounds of the formula (1) $Q^1$ is hydrogen, $Q^3$ is fluoro and p is 1, q is 1, r is 0 and s is 1.

In another preferred group of the compounds of the formula (1) $Q^1$ is hydrogen, $Q^3$ is fluoro, $Q^2$ is hydrogen and p is 1, q is 1, r is 0 and s is 1.

In another preferred group of the compounds of the formula (1) $Q^1$ is hydrogen, $Q^2$ is methyl and p is 1, q is 1, r is 0 and s is 1.

In another preferred group of the compounds of the formula (1) $Q^1$ is hydrogen, $Q^2$ is methyl, $Q^3$ is hydrogen and p is 1, q is 1, r is 0 and s is 1.

In another preferred group of the compounds of the formula (1) $Q^1$ is hydrogen, $Q^2$ is methyl, $Q^3$ is fluorine and p is 1, q is 1, r is 0 and s is 1.

In a preferred group of the compounds of the formula (1) $R^aR^b$, $R^cR^d$ or $R^eR^f$ may join to form a 3 to 8 membered carbocyclic or heterocyclic ring containing a heteroatom selected from sulphur or oxygen, and p is 1, q is 1, r is 0 and s is 0.

In a preferred group of the compounds of the formula (1) $Q^1$ is hydrogen, methyl, hydroxymethyl, fluoromethyl or trimethylsilyl, and p is 1, q is 1, r is 0 and s is 0.

In another preferred group of the compounds of the formula (1) $Q^1$ is hydrogen and p is 1, q is 1, r is 0 and s is 0.

In another preferred group of the compounds of the formula (1) $Q^1$, $Q^2$ and $Q^3$ are hydrogen and p is 1, q is 1, r is 0 and s is 0.

In another preferred group of the compounds of the formula (1) $Q^1$ is hydrogen and $Q^2$ is fluoro, chloro or bromo and p is 1, q is 1, r is 0 and s is 0.

In another preferred group of the compounds of the formula (1) $Q^1$ is hydrogen, $Q^2$ is fluoro, chloro or bromo and $Q^3$ is hydrogen, p is 1, q is 1, r is 0 and s is 0.

In another preferred group of the compounds of the formula (1) Q1 is hydrogen, Q2 is fluoro, $Q^3$ is fluoro and p is 1, q is 1, r is 0 and s is 0.

In another preferred group of the compounds of the formula (1) $Q^1$ is hydrogen, $Q^2$ is fluoro or chloro, $Q^3$ is hydrogen and p is 1, q is 1, r is 0 and s is 0.

In another preferred group of the compounds of the formula (1) $Q^1$ is hydrogen, $Q^2$ is methyl, $Q^3$ is fluoro and p is 1, q is 1, r is 0 and s is 0.

In another preferred group of the compounds of the formula (1) $Q^1$ is hydrogen, $Q^2$ is fluoro, $Q^3$ is hydrogen and p is 1, q is 1, r is 0 and s is 0.

In another preferred group of the compounds of the formula (1) $Q^1$ is hydrogen, $Q^3$ is fluoro and p is 1, q is 1, r is 0 and s is 0.

In another preferred group of the compounds of the formula (1) $Q^1$ is hydrogen, $Q^3$ is fluoro, $Q^2$ is hydrogen and p is 1, q is 1, r is 0 and s is 0.

In another preferred group of the compounds of the formula (1) $Q^1$ is hydrogen, $Q^2$ is methyl and p is 1, q is 1, r is 0 and s is 0.

In another preferred group of the compounds of the formula (1) $Q^1$ is hydrogen, $Q^2$ is methyl, $Q^3$ is hydrogen and p is 1, q is 1, r is 0 and s is 0.

In another preferred group of the compounds of the formula (1) $Q^1$ is hydrogen, $Q^2$ is methyl, $Q^3$ is fluorine and p is 1, q is 1, r is 0 and s is 0.

In a preferred group of the compounds of the formula (1) $R^aR^b$ may join to form a 3 to 8 membered carbocyclic or heterocyclic ring containing a heteroatom selected from sulphur or oxygen, and p is 1, q, r and s are 0.

In a preferred group of the compounds of the formula (1) $Q^1$ is hydrogen, methyl, hydroxymethyl, fluoromethyl or trimethylsilyl, and p is 1, q, r and s are 0.

In another preferred group of the compounds of the formula (1) $Q^1$ is hydrogen and p is 1, q, r and s are 0.

In another preferred group of the compounds of the formula (1) $Q^1$, $Q^2$ and $Q^3$ are hydrogen and p is 1, q, r and s are 0.

In another preferred group of the compounds of the formula (1) $Q^1$ is hydrogen and $Q^2$ is fluoro, chloro or bromo and p is 1, q, r and s are 0.

In another preferred group of the compounds of the formula (1) $Q^1$ is hydrogen, $Q^2$ is fluoro, chloro or bromo and $Q^3$ is hydrogen, p is 1, q, r and s are 0.

In another preferred group of the compounds of the formula (1) Q1 is hydrogen, Q2 is fluoro, $Q^3$ is fluoro and p is 1, q, r and s are 0.

In another preferred group of the compounds of the formula (1) $Q^1$ is hydrogen, $Q^2$ is fluoro or chloro, $Q^3$ is hydrogen and p is 1, q, r and s are 0.

In another preferred group of the compounds of the formula (1) $Q^1$ is hydrogen, $Q^2$ is methyl, $Q^3$ is fluoro and p is 1, q, r and s are 0.

In another preferred group of the compounds of the formula (1) $Q^1$ is hydrogen, $Q^2$ is chloro, $Q^3$ is hydrogen and p is 1, q, r and s are 0.

in another preferred group of the compounds of the formula (1) $Q^1$ is hydrogen, $Q^2$ is fluoro, $Q^3$ is hydrogen and p is 1, q, r and s are 0.

In another preferred group of the compounds of the formula (1) $Q^1$ is hydrogen, $Q^3$ is fluoro and p is 1, q, r and s are 0.

In another preferred group of the compounds of the formula (1) $Q^1$ is hydrogen, $Q^3$ is fluoro, $Q^2$ is hydrogen and p is 1, q, r and s are 0.

In another preferred group of the compounds of the formula (1) $Q^1$ is hydrogen, $Q^2$ is methyl and p is 1, q, r and s are 0.

In another preferred group of the compounds of the formula (1) $Q^1$ is hydrogen, $Q^2$ is methyl, $Q^3$ is hydrogen and p is 1, q, r and s are 0.

In another preferred group of the compounds of the formula (1) $Q^1$ is hydrogen, $Q^2$ is methyl, $Q^3$ is fluorine and p is 1, q, r and s are 0.

In another preferred group of the compounds of the formula (1) $R^1$ is methylthio.

In another preferred group of the compounds of the formula (1) $R^1$ is methoxymethyl.

In another preferred group of the compounds of the formula (1) $R^1$ is ethyl.

In another preferred group of the compounds of the formula (1) $R^2$ is hydrogen.

In another preferred group of the compounds of the formula (1) L is oxygen.

In another preferred group of the compounds of the formula (1) L is sulphur. Compounds that form part of the invention are illustrated in Tables 1 to 1981 below. Melting points (mp) and/or diagnostic molecular ion (eg $M^+$, $[M+1]^+$) values and/or spectroscopic ($^1H$ NMR) data are provided in Examples 1-13 while biological activities are provided in Example 6.

TABLE 1

The compounds in Table 1 are of the general formula (I) where Q1 is methyl, Q2 is hydrogen, Q3 is hydrogen, L is O, $R^1$ is methyl, and $R^2$ and $R^3$ have the values given in the table below.

| Compound No. | $R^2$ | $R^3$ |
|---|---|---|
| 1 | H | $CH_3$ |
| 2 | $CH_3$ | $CH_3$ |
| 3 | H | $C_2H_5$ |
| 4 | $C_2H_5$ | $C_2H_5$ |
| 5 | H | prop-2-yl |
| 6 | $CH_3$ | prop-2-yl |
| 7 | prop-2-yl | prop-2-yl |
| 8 | $CH_3$ | n-butyl |
| 9 | H | but-2-yl |
| 10 | H | 2-methyl-prop-1-yl |
| 11 | 2-methyl-prop-1-yl | 2-methyl-prop-1-yl |
| 12 | H | tert-$C_4H_9$ |
| 13 | $CH_3$ | tert-$C_4H_9$ |
| 14 | H | pent-2-yl |
| 15 | H | pent-3-yl |
| 16 | H | 2-methyl-but-2-yl |
| 17 | H | 3-methyl-but-1-yl |
| 18 | H | 3-methyl-pent-2-yl |
| 19 | H | 4-methyl-pent-2-yl |
| 20 | H | 3,3-dimethyl-but-2-yl |
| 21 | H | 2-methyl-hex-2-yl |
| 22 | H | 2,4-dimethyl-pent-2-yl |
| 23 | H | 2,4,4-trimethyl-but-2-yl |
| 24 | H | 2,4,4-trimethyl-pent-2-yl |
| 25 | H | Cl—n-$C_3H_6$— |
| 26 | H | Cl—$CH_2(CH_3)_2$C— |
| 27 | H | $F_3C(CH_3)_2$C— |
| 28 | H | NC—$CH_2$— |
| 29 | $CH_3$ | NC—$CH_2$— |
| 30 | NC—$CH_2$— | NC—$CH_2$— |

TABLE 1-continued

The compounds in Table 1 are of the general formula (I) where Q1 is methyl, Q2 is hydrogen, Q3 is hydrogen, L is O, $R^1$ is methyl, and $R^2$ and $R^3$ have the values given in the table below.

| Compound No. | $R^2$ | $R^3$ |
|---|---|---|
| 31 | H | $(NC)_2CH-$ |
| 32 | H | $NC-C_2H_4-$ |
| 33 | $CH_3$ | $NC-C_2H_4-$ |
| 34 | $NC-C_2H_4-$ | $NC-C_2H_4-$ |
| 35 | H | $(CH_3)_2C(CN)-$ |
| 36 | H | $C_2H_5(CH_3)C(CN)-$ |
| 37 | H | $(C_2H_5)_2C(CN)-$ |
| 38 | H | $(CH_3)_2CH(CH_3)C(CN)-$ |
| 39 | H | $HO-CH_2(CH_3)_2C-$ |
| 40 | H | $HO-C_2H_4(CH_3)_2C-$ |
| 41 | H | 1-hydroxy-2-(hydroxymethyl)-prop-2-yl |
| 42 | H | 1-hydroxy-2-(methoxymethyl)prop-2-yl |
| 43 | H | 1-methoxy-2-(methoxymethyl)prop-2-yl |
| 44 | H | 1-hydroxy-2-(hydroxymethyl)-but-2-yl |
| 45 | $C_2H_5OC_2H_4-$ | $C_2H_5OC_2H_4-$ |
| 46 | $CH_3$ | $(CH_3O)_2CHCH_2-$ |
| 47 | H | $CH_3O-CH_2(CH_3)_2C-$ |
| 48 | H | $CH_3O-C_2H_4(CH_3)_2C-$ |
| 49 | H | $C_2H_5O-C_2H_4(CH_3)_2C-$ |
| 50 | H | $CH_3S-CH_2(CH_3)_2C-$ |
| 51 | H | $FCH_2(CH_3)C(CN)-$ |
| 52 | H | $CH_3OCH_2(CH_3)C(CN)-$ |
| 53 | H | $CH_3SCH_2(CH_3)C(CN)-$ |
| 54 | H | $CH_3(CO)(CH_3)_2C-$ |
| 55 | H | $CH_3CHBr(CO)(CH_3)_2C-$ |
| 56 | H | $CH_3(CO)(OH)CH(CH_3)_2C-$ |
| 57 | H | $CH_3OC_2H_4(CO)(CH_3)_2C-$ |
| 58 | H | $CH_3(CO)CH_2(CH_3)_2C-$ |
| 59 | H | $CH_3O(CO)(CH_3)CH-$ |
| 60 | H | $CH_3O(CO)(CH_3)_2C-$ |
| 61 | H | $C_2H_5O(CO)C_2H_4-$ |
| 62 | H | $CH_3NH(CO)(CH_3)_2C-$ |
| 63 | H | $(CH_3)_2N(CO)(CH_3)_2C-$ |
| 64 | H | $CH_3O(CH_2)_2OCH_2OCH_2(CH_3)_2C-$ |
| 65 | H | $tert-C_4H_9(CH_3)_2SiO-CH_2(CH_3)_2C-$ |
| 66 | H | $tert-C_4H_9(CH_3)_2SiO-C_2H_4(CH_3)_2C-$ |
| 67 | H | $4-FPhCH_2OCH_2(CH_3)_2C-$ |
| 68 | H | $C_2H_5OCH_2(CH_3)_2C-$ |
| 69 | H | $CH_3OCH_2CH_2OCH_2(CH_3)_2C-$ |
| 70 | H | $CH_2=CHCH_2-$ |
| 71 | $CH_2=CHCH_2-$ | $CH_2=CHCH_2-$ |
| 72 | H | $CH_2=C(CH_3)CH_2-$ |
| 73 | H | $CH_2=CH(CH_3)CH-$ |
| 74 | H | $CH_2=CH(CH_3)_2C-$ |
| 75 | H | $CH_3(CO)CH=CH-$ |
| 76 | $CH_3$ | $CH_3(CO)CH=CH-$ |
| 77 | H | pent-3-en-2-yl |
| 78 | H | 2-methyl-hex-3-en-2-yl (E) |
| 79 | H | 2-methyl-hex-3-en-2-yl (Z) |
| 80 | H | 2-methyl-pent-4-en-3-on-2-yl |
| 81 | H | $CH_3O(CO)CH=(Cl)C(CH_3)_2C-$ |
| 82 | H | $C_6H_5-C(CH_3)=CH(CH_3)_2C-$ |
| 83 | $CH_2=CHCH_2-$ | $CH_2=CHCH_2OC_2H_4-$ |
| 84 | H | $CH\equiv CCH_2-$ |
| 85 | $CH_3$ | $CH\equiv CCH_2-$ |
| 86 | H | cycloprop-1-yl |
| 87 | $NC-C_2H_4-$ | cycloprop-1-yl |
| 88 | cycloprop-1-yl | cycloprop-1-yl |
| 89 | H | 1-cyano-cycloprop-1-yl |
| 90 | H | 2-cyano-cycloprop-1-yl |
| 91 | H | 1-methoxycarbonyl-cycloprop-1-yl |
| 92 | H | 1-[N,N-dimethylaminocarbonyl]-cycloprop-1-yl |
| 93 | H | 1-[N-methyl-N-methoxy-aminocarbonyl]-cycloprop-1-yl |
| 94 | H | 1-cyano-1-cyclopropyl-eth-1-yl |
| 95 | H | cyclopent-1-yl |
| 96 | H | 1-cyano-cyclopent-1-yl |
| 97 | H | cyclohex-1-yl |
| 98 | $CH_2=CHCH_2-$ | cyclohex-1-yl |
| 99 | H | 4-cyano-cyclohex-1-yl |
| 100 | H | 1-cyano-4-methyl-cyclohex-1-yl |

TABLE 1-continued

The compounds in Table 1 are of the general formula (I) where Q1 is methyl, Q2 is hydrogen, Q3 is hydrogen, L is O, $R^1$ is methyl, and $R^2$ and $R^3$ have the values given in the table below.

| Compound No. | $R^2$ | $R^3$ |
| --- | --- | --- |
| 101 | H | 4-tert-butyl-1-cyano-cyclohex-1-yl |
| 102 | H | 2-methyl-3-cyanotetrahydro-furan-3-yl |
| 103 | H | 5-methyl-1,3-dioxolan-5-yl |
| 104 | H | 5-ethyl-1,3-dioxolan-5-yl |
| 105 | H | 3,5-dimethyl-1,3-dioxolan-5-yl |
| 106 | H | N-ethoxycarbonyl-piperid-4-yl |
| 107 | H | morpholino |
| 108 | H | cyclohex-1-yl-methyl |
| 109 | H | 4-cyano-cyclopenten-3-yl |
| 110 | H | 5-tert-butyl-2H-1,3,4-thiadiazin-2-yl |
| 111 | H | 2-(cyclohexen-1-yl)-eth-1-yl |
| 112 | H | fur-2-yl |
| 113 | H | 5-methoxycarbonyl-fur-2-yl |
| 114 | H | thien-2-yl |
| 115 | H | 2-methoxycarbonyl-thien-3-yl |
| 116 | H | 4-methoxycarbonyl-thien-3-yl |
| 117 | H | oxazol-2-yl |
| 118 | H | 5-methyl-isoxazol-3-yl |
| 119 | H | 4-cyano-3-methyl-isoxazol-5-yl |
| 120 | H | thiazol-2-yl |
| 121 | H | 5-ethylthio-1,3,4-thiadiazol-2-yl |
| 122 | H | fur-2-ylmethyl |
| 123 | H | cyanofur-1-ylmethyl |
| 124 | H | thien-2-ylmethyl |
| 125 | H | $C_6H_5$— |
| 126 | H | 2-Cl—$C_6H_4$— |
| 127 | H | 2-I—$C_6H_4$— |
| 128 | H | 2-NC—$C_6H_4$— |
| 129 | H | 3-$CF_3$—$C_6H_4$— |
| 130 | H | 3-$CH_3$S—$C_6H_4$— |
| 131 | H | 3-$CH_3$O(CO)—$C_6H_4$— |
| 132 | H | 4-Cl—$C_6H_4$— |
| 133 | H | 4-F—$C_6H_4$— |
| 134 | H | 4-$CF_3$O—$C_6H_4$— |
| 135 | H | 4-$(C_2H_5)_2$N—$C_6H_4$— |
| 136 | H | 4-(N-methyl-N-acetyl-amino)-phenyl |
| 137 | H | 2,4-dichlorophenyl |
| 138 | H | 4-methoxy-2-methylphenyl |
| 139 | H | 3,4-dichlorophenyl |
| 140 | H | 3-chloro-4-fluorophenyl |
| 141 | H | 2,5-difluorophenyl |
| 142 | H | 5-fluoro-2-methylphenyl |
| 143 | H | 5,6,7,8-tetrahydronaphth-2-yl |
| 144 | H | 2,3-dihydrobenzofuran-5-yl-methyl |
| 145 | H | 5-cyano-4,6-dimethoxy-pyrid-2-yl |
| 146 | H | 2,6-dimethoxy-pyrid-3-yl |
| 147 | H | 6-chloro-pyridazin-3-yl |
| 148 | H | 4,6-dimethoxy-pyrimid-2-yl |
| 149 | H | 2-chloro-5-fluoro-pyrimid-6-yl |
| 150 | H | $C_6H_5CH_2$— |
| 151 | $CH_3$ | $C_6H_5CH_2$— |
| 152 | H | 2-F—$C_6H_4CH_2$— |
| 153 | H | 2-Cl—$C_6H_4CH_2$— |
| 154 | $CH_3$ | 2-Cl—$C_6H_4CH_2$— |
| 155 | H | 2-$NO_2$—$C_6H_4CH_2$— |
| 156 | H | 2-$CH_3$—$C_6H_4CH_2$— |
| 157 | H | 2-$CH_3$O—$C_6H_4CH_2$— |
| 158 | H | 2-$CHF_2$O—$C_6H_4CH_2$— |
| 159 | H | 2-$CH_3$S—$C_6H_4CH_2$— |
| 160 | H | 2-$CF_3$S—$C_6H_4CH_2$— |
| 161 | H | 3-Cl—$C_6H_4CH_2$— |
| 162 | H | 3-I—$C_6H_4CH_2$— |
| 163 | H | 3-$CH_3$—$C_6H_4CH_2$— |
| 164 | H | 3-$CH_3$O—$C_6H_4CH_2$— |
| 165 | H | 4-F—$C_6H_4CH_2$— |
| 166 | H | 4-Cl—$C_6H_4CH_2$— |
| 167 | H | 4-$CH_3$—$C_6H_4CH_2$— |
| 168 | H | 4-$CF_3$—$C_6H_4CH_2$— |
| 169 | H | 4-$CH_3$O—$C_6H_4CH_2$— |
| 170 | H | 4-$CF_3$O—$C_6H_4CH_2$— |
| 171 | H | 2,6-di-F—$C_6H_3CH_2$— |
| 172 | 3-methyl-but-2-en-1-yl | 2,5-di-F—$C_6H_3CH_2$— |
| 173 | H | 2-F-4-Cl—$C_6H_3CH_2$— |
| 174 | H | 2-F-6-Cl—$C_6H_3CH_2$— |

TABLE 1-continued

The compounds in Table 1 are of the general formula (I) where Q1 is methyl, Q2 is hydrogen, Q3 is hydrogen, L is O, $R^1$ is methyl, and $R^2$ and $R^3$ have the values given in the table below.

| Compound No. | $R^2$ | $R^3$ |
|---|---|---|
| 175 | H | 2,6-di-Cl—$C_6H_3CH_2$— |
| 176 | 4-methyl-pent-2-en-1-yl | 3,4-di-Cl—$C_6H_3CH_2$— |
| 177 | H | 2-F-6-$CH_3O$—$C_6H_3CH_2$— |
| 178 | H | 2,4,5-tri-F—$C_6H_2CH_2$— |
| 179 | H | 2,4-di-Cl-6-$CH_3$—$C_6H_2CH_2$— |
| 180 | H | 3,4,5-tri-$CH_3O$—$C_6H_2CH_2$— |
| 181 | H | $C_6H_5$—$CH(CH_3)$— |
| 182 | H | 4-F—$C_6H_4$—$CH(CH_3)$— |
| 183 | H | 4-$NO_2$—$C_6H_4$—$CH(CH_3)$— |
| 184 | H | 4-n-pentyl-$C_6H_4$—$CH(CH_3)$— |
| 185 | H | 4-$CH_3SO_2$—$C_6H_4$—$CH(CH_3)$— |
| 186 | H | $C_6H_5(CO)CH_2$— |
| 187 | H | $C_6H_5$—$CH(CN)$— |
| 188 | H | $C_6H_5$—$(CH_3O)CH$— |
| 189 | H | $C_6H_5$—$(CH_3)_2C$— |
| 190 | H | m-Cl—$C_6H_5$—$(CH_3)_2C$— |
| 191 | H | 3,5-di-Cl—$C_6H_3$—$(CH_3)_2C$— |
| 192 | H | $C_6H_5$—$(C_2H_5O(CO))CH$— |
| 193 | H | phenethyl |
| 194 | H | 3-methoxy-4-propargyloxy-phenethyl |
| 195 | H | 3-methoxy-4-(pent-2-yn-1-yloxy)-phenethyl |
| 196 | H | 2-methyl-3-phenyl-prop-2-yl |
| 197 | H | $C_6H_5O$—$C_2H_4$— |
| 198 | H | 4-F—$C_6H_4$—$CH_2OCH_2(CH_3)_2C$— |
| 199 | H | $C_6H_5$—$CH_2O(CO)C_2H_4$— |
| 200 | H | naphth-2-yl-$(CH_3)CH$— |
| 201 | NC—$C_2H_4$— | pyrid-3-ylmethyl |
| 202 | $CH_3$ | 2-pyrid-2-yleth-1-yl |
| 203 | H | 2-(3-chloro-5-trifluoromethyl-pyrid-2-yl)oxyeth-1-yl |
| 204 | H | 2-methyl-4-pyrazin-2-yl-but-3-on-2-yl |
| 205 |  | —$(CH_2)_4$— |
| 206 |  | —$(CH_2)_5$— |
| 207 |  | —$(CH_2)_4CH(C_2H_5)$— |
| 208 |  | —$C_3H_6CH[(CO)N(C_2H_5)_2]CH_2$— |
| 209 |  | —$CH(CH_3)CH=CHCH(CH_3)$— |
| 210 |  | —$CH_2$— and —$C_2H_4$— attached to adjacent positions of a cyclohexane ring |
| 211 |  | —$C_2H_4OC_2H_4$— |
| 212 |  | —$CH_2CH(CH_3)OCH(CH_3)CH_2$— |
| 213 |  | —$C_2H_4SCH_2$— |
| 214 |  | —$C_2H_4SC_2H_4$— |
| 215 |  | —$(CH_2)_2NH(CH_2)_2$— |
| 216 |  | —$(CH_2)_2N(p$-$NO_2$—$C_6H_4)(CH_2)_2$— |
| 217 |  | —$(CH_2)_2N(m$-$CF_3$—$C_6H_4)(CH_2)_2$— |
| 218 |  | —$(CH_2)_2N(p$-$CH_3CO$—$C_6H_4)(CH_2)_2$— |
| 219 |  | —$(CH_2)_2N(pyrid$-$2$-$yl)(CH_2)_2$— |
| 220 | H | $(H_2C=CHCH_2OCH_2)(CH_3)_2C$— |
| 221 | H | $(HC\equiv CCH_2OCH_2)(CH_3)_2C$— |
| 222 | H | $(CH_3CH_2OCH_2)(CH_3)_2C$— |
| 223 | H | $((CH_3)_2CHOCH_2)(CH_3)_2C$— |
| 224 | H | $C_6H_5CH_2OCH_2(CH_3)_2C$— |
| 225 | H | $(HC\equiv CCH_2OCH_2CH_2)(CH_3)C(CN)$— |
| 226 | H | 4-F—$C_6H_4$—$CH_2(CH_3)C(CN)$— |
| 227 | H | 4-Cl—$C_6H_4$—$CH_2(CH_3)C(CN)$— |
| 228 | H | 4-$CH_3O$—$C_6H_4$—$CH_2CH_2(CH_3)C(CN)$— |
| 229 | H | 2-Cl—$C_6H_4$—$CH_2(CH_3)C(CN)$— |
| 230 | H | $(CH_3)_2CH$—$CH_2(CH_3)C(CN)$— |
| 231 | H | 1-methoxymethyl-cycloprop-1-yl |
| 232 | H | 1-benzyloxymethyl-cycloprop-1-yl |
| 233 | H | 1-methoxymethoxy-2-methyl-prop-2-yl |
| 235 | H | 1-cyclopropyl-eth-1-yl |
| 236 | H | 2-fluoro-eth-1-yl |
| 237 | H | 2,2,2-trifluoro-1-methyl-eth-1-yl |
| 238 | H | $HC\equiv CC(CH_3)_2$— |
| 239 | $CH_3$ | $HC\equiv CC(CH_3)_2$— |
| 240 | H | $HC\equiv CC(CH_2CH_3)(CH_3)$— |
| 241 | $CH_3$ | $HC\equiv CC(CH_2CH_3)(CH_3)$— |

TABLE 1-continued

The compounds in Table 1 are of the general formula (I) where Q1 is methyl, Q2 is hydrogen, Q3 is hydrogen, L is O, $R^1$ is methyl, and $R^2$ and $R^3$ have the values given in the table below.

| Compound No. | $R^2$ | $R^3$ |
|---|---|---|
| 242 | H | HC≡CC(CH$_2$CH$_2$)— |
| 243 | CH$_3$ | HC≡CC(CH$_2$CH$_2$)— |
| 244 | H | (H$_3$C)C≡CC(CH$_3$)$_2$— |
| 245 | CH$_3$ | (H$_3$C)C≡CC(CH$_3$)$_2$— |
| 246 | H | (H$_3$C)C≡CC(CH$_2$CH$_3$)(CH$_3$)— |
| 247 | CH$_3$ | (H$_3$C)C≡CC(CH$_2$CH$_3$)(CH$_3$)— |
| 248 | H | (H$_3$C)C≡CC(CH$_2$CH$_2$)— |
| 249 | CH$_3$ | (H$_3$C)C≡CC(CH$_2$CH$_2$)— |
| 250 | H | (HOCH$_2$)C≡CC(CH$_3$)$_2$— |
| 251 | H | (CH$_3$OCH$_2$)C≡CC(CH$_3$)$_2$— |
| 252 | H | (HOCH$_2$)C≡CC(CH$_3$)(CH$_2$CH$_3$)— |
| 253 | H | (CH$_3$CH$_2$OCH$_2$)C≡CC(CH$_3$)$_2$— |
| 254 | H | (CH$_3$OCH$_2$)C≡CC(CH$_3$)(CH$_2$CH$_3$)— |
| 255 | H | (CH$_3$OC$_2$H$_4$OC$_2$H$_4$)C≡CC(CH$_3$)$_2$— |
| 256 | H | (Cl—n-C$_3$H$_6$)C≡CC(CH$_3$)$_2$— |
| 257 | H | (NC—n-C$_3$H$_6$)C≡CC(CH$_3$)$_2$— |
| 258 | H | (CH$_3$SCH$_2$)C≡CC(CH$_3$)$_2$— |
| 259 | H | (C$_6$H$_5$)C≡CC(CH$_3$)$_2$— |
| 260 | H | (CH$_3$)$_2$(CH$_3$O)CC≡CC(CH$_3$)$_2$— |
| 261 | H | H$_2$C≡CHCH$_2$OCH$_2$(CH$_3$)CH— |
| 262 | H | HC≡CCH$_2$OCH$_2$(CH$_3$)CH— |
| 263 | H | (CH$_3$CH$_2$OCH$_2$)(CH$_3$)CH— |
| 264 | H | (CH$_3$OCH$_2$)(CH$_3$)CH— |
| 265 | H | ((CH$_3$)$_2$CHOCH$_2$)(CH$_3$)CH— |
| 266 | H | C$_6$H$_5$CH$_2$OCH$_2$(CH$_3$)CH— |
| 267 | H | (CH$_3$CH$_2$OCH$_2$)(CH$_3$)CH— |
| 268 | H | 3-Methyl-oxetan-3-yl- |
| 269 | H | (cC$_4$H$_7$)CH$_3$C— |
| 270 | H | FCH$_2$(CH$_3$)CH— |
| 271 | H | ClCH$_2$(CH$_3$)CH— |
| 272 | H | FCH$_2$CH$_2$(CH$_3$)CH— |
| 273 | H | ClCH$_2$CH$_2$(CH$_3$)CH— |
| 274 | H | FCH$_2$(CH$_3$)$_2$C— |
| 275 | H | FCH$_2$CH$_2$(CH$_3$)$_2$C— |
| 276 | H | ClCH$_2$CH$_2$(CH$_3$)$_2$C— |
| 277 | H | CH$_3$OCH$_2$OCH$_2$C(CH$_3$)$_2$— |
| 278 | H | tetrahydro-furan-2-ylmethyl |
| 279 | H | 1-(tetrahydro-furan-2-yl)ethyl |
| 280 | H | 1-methyl-1-(tetrahydro-furan-2-yl)ethyl |
| 281 | H | 2-[1,3]dioxolan-2-yl-ethyl |
| 282 | H | 2-[1,3]dioxolan-2-yl-1-methyl-ethyl |
| 283 | H | 2-[1,3]dioxolan-2-yl-1,1-dimethyl-ethyl |
| 284 | H | prop-1-yl |
| 285 | CH$_3$ | prop-1-yl |
| 286 | H | thiophen-3-ylmethyl |
| 287 | H | 1-(thiophen-3-yl)-eth-1-yl |
| 289 | H | 1-methyl-1-(thiophen-3-yl)-eth-1-yl |
| 290 | H | cyclopent-1-yl |
| 291 | H | 3-F—C$_6$H$_4$—CH$_2$— |
| 292 | H | 3-F—C$_6$H$_4$—CH(CH$_3$)— |
| 293 | H | 3-F—C$_6$H$_4$—C(CH$_3$)$_2$— |
| 294 | H | C$_2$H$_5$C≡CC(CH$_3$)$_2$— |
| 295 | H | nC$_3$H$_7$C≡CC(CH$_3$)$_2$— |
| 296 | H | i-C$_3$H$_7$C≡CC(CH$_3$)$_2$— |
| 297 | H | n-C$_4$H$_9$C≡CC(CH$_3$)$_2$— |
| 298 | H | sec-C$_4$H$_9$C≡CC(CH$_3$)$_2$— |
| 299 | H | iso-C$_4$H$_9$C≡CC(CH$_3$)$_2$— |
| 300 | H | tert-C$_4$H$_9$C≡CC(CH$_3$)$_2$— |
| 301 | H | HOC$_2$H$_4$C≡CC(CH$_3$)$_2$— |
| 302 | H | CH$_3$(CH$_3$O)(CH)C≡CC(CH$_3$)$_2$— |
| 303 | H | (nC$_3$H$_7$OCH$_2$)C≡CC(CH$_3$)$_2$— |
| 304 | H | (nC$_3$H$_7$OCH$_2$CH$_2$)C≡CC(CH$_3$)$_2$— |
| 305 | H | (tert-C$_4$H$_9$OCH$_2$)C≡CC(CH$_3$)$_2$— |
| 306 | H | (tert-C$_4$H$_9$OCH$_2$CH$_2$)C≡CC(CH$_3$)$_2$— |
| 307 | H | (NCCH$_2$)C≡CC(CH$_3$)$_2$— |
| 308 | H | (NCCH$_2$CH$_2$)C≡CC(CH$_3$)$_2$— |
| 309 | H | (C$_6$H$_5$OCH$_2$)C≡CC(CH$_3$)$_2$— |
| 310 | H | (C$_6$H$_5$OCH$_2$CH$_2$)C≡CC(CH$_3$)$_2$— |
| 311 | H | (4-FC$_6$H$_5$)C≡CC(CH$_3$)$_2$— |
| 312 | H | (4-ClC$_6$H$_5$)C≡CC(CH$_3$)$_2$— |
| 313 | H | (4-BrC$_6$H$_5$)C≡CC(CH$_3$)$_2$— |
| 314 | H | (4-CH$_3$—C$_6$H$_5$)C≡CC(CH$_3$)$_2$— |
| 315 | H | (3-FC$_6$H$_5$)C≡CC(CH$_3$)$_2$— |
| 316 | H | (3-ClC$_6$H$_5$)C≡CC(CH$_3$)$_2$— |
| 317 | H | (3-CH$_3$—C$_6$H$_5$)C≡CC(CH$_3$)$_2$— |

TABLE 1-continued

The compounds in Table 1 are of the general formula (I) where Q1 is methyl, Q2 is hydrogen, Q3 is hydrogen, L is O, $R^1$ is methyl, and $R^2$ and $R^3$ have the values given in the table below.

| Compound No. | $R^2$ | $R^3$ |
|---|---|---|
| 318 | H | $(2\text{-}FC_6H_5)C{=}CC(CH_3)_2{-}$ |
| 319 | H | $(2\text{-}ClC_6H_5)C{=}CC(CH_3)_2{-}$ |
| 320 | H | $H(O)C(CH_3OCH_2)(CH_3)C{-}$ |
| 321 | H | $(2\text{-}CH_3{-}C_6H_5)C{=}CC(CH_3)_2{-}$ |
| 322 | H | $(\text{thien-2-yl})C{=}CC(CH_3)_2{-}$ |
| 323 | H | $(\text{thien-3-yl})C{=}CC(CH_3)_2{-}$ |
| 324 | H | Cyclobutyl- |
| 325 | H | 1-cyano-cyclobut-1-yl- |
| 326 | H | $(O)HC(CH_3)_2C{-}$ |
| 327 | H | $(CH_3O)_2C(CH_3)_2C{-}$ |
| 328 | H | $(CH_3CH_2O)_2C(CH_3)_2C{-}$ |
| 329 | H | $(O(CH_2)_2O)C(CH_3)_2C{-}$ |
| 330 | H | $(O(CH_2)_2O)C(CH_3)_2C{-}$ |
| 331 | H | $HC{\equiv}CC(CH3)(CH_2OCH_3){-}$ |
| 332 | H | 1-methyl-cyclobut-1-yl |
| 333 | H | $HC{\equiv}CCH_2OCH_2C(CH_3)(CH_2OCH_3){-}$ |
| 334 | H | 1-Prop-2-ynyloxymethyl-cyclobut-1-yl |
| 335 | H | 1-methoxymethyl-cyclobut-1-yl |
| 336 | H | 1-Ethynyl-cyclobut-1-yl |
| 337 | H | 1-fluoromethyl-cyclobut-1-yl |
| 338 | H | $HC{\equiv}CCH_2CH_2{-}$ |
| 339 | H | $HC{\equiv}CCH_2CH(CH_3){-}$ |
| 340 | H | $HC{\equiv}CCH_2C(CH_3)_2{-}$ |
| 341 | H | $(\text{cyclobutyl})C{=}CC(CH_3)_2{-}$ |
| 342 | H | $(\text{cyclopentyl})C{=}CC(CH_3)_2{-}$ |
| 343 | H | $(FCH_2)C{=}CC(CH_3)_2{-}$ |
| 344 | H | $(F_2CH)C{=}CC(CH_3)_2{-}$ |
| 345 | H | $(FCH_2CH_2)C{=}CC(CH_3)_2{-}$ |
| 346 | H | $(F_2CHCH_2)C{=}CC(CH_3)_2{-}$ |
| 347 | H | $(Fn\text{-}C_3H_6)C{=}CC(CH_3)_2{-}$ |
| 348 | H | $(CH_3OCH_2CH_2)C{=}CC(CH_3)_2{-}$ |
| 349 | H | $(CH_3CH_2OCH_2CH_2)C{=}CC(CH_3)_2{-}$ |
| 350 | H | $NC{-}n\text{-}C_4H_8C{=}CC(CH_3)_2{-}$ |
| 351 | H | $(CH_3)_2C(CN)CH_2C{=}CC(CH_3)_2{-}$ |
| 252 | H | $Cl_2CHCH_2C{=}CC(CH_3)_2{-}$ |
| 353 | H | $Cl_2CHC{=}CC(CH_3)_2{-}$ |
| 354 | H | $\text{allyl}OCH_2C{=}CC(CH_3)_2{-}$ |
| 355 | H | $\text{allyl}OCH_2CH_2C{=}CC(CH_3)_2{-}$ |
| 356 | H | $\text{allyl}OCH_2CH_2CH_2C{=}CC(CH_3)_2{-}$ |
| 357 | H | $\text{propargyl}OCH_2C{=}CC(CH_3)_2{-}$ |
| 358 | H | $\text{propargyl}OCH_2CH_2C{=}CC(CH_3)_2{-}$ |
| 359 | H | $\text{propargyl}OCH_2CH_2CH_2C{=}CC(CH_3)_2{-}$ |
| 360 | H | $CH_3OCH_2CH_2OCH_2C{=}CC(CH_3)_2{-}$ |
| 361 | H | $C_2H_5OCH_2CH_2OCH_2C{=}CC(CH_3)_2{-}$ |
| 362 | H | $C_2H_5OCH_2CH_2OCH_2CH_2C{=}CC(CH_3)_2{-}$ |
| 363 | H | $CH_3OCH_2OCH_2C{=}CC(CH_3)_2{-}$ |
| 364 | H | $C_2H_5OCH_2OCH_2C{=}CC(CH_3)_2{-}$ |
| 365 | H | $\text{tert-}C_4H_9(CH_3)_2SiOCH_2C{=}CC(CH_3)_2{-}$ |
| 366 | H | $\text{tert-}C_4H_9(CH_3)_2SiOC_2H_4C{=}CC(CH_3)_2{-}$ |
| 367 | H | $ClCH_2C{=}CC(CH_3)_2{-}$ |
| 368 | H | $ClCH_2CH_2C{=}CC(CH_3)_2{-}$ |
| 369 | H | $BrCH_2C{=}CC(CH_3)_2{-}$ |
| 370 | H | $BrCH_2CH_2C{=}CC(CH_3)_2{-}$ |
| 371 | H | $Br{-}n\text{-}C_3H_6C{=}CC(CH_3)_2{-}$ |
| 372 | H | $CH_3OCH_2CH_2OCH_2OCH_2C{=}CC(CH_3)_2{-}$ |
| 373 | H | tetrahydropyran-2-yl-$OCH_2C{=}CC(CH_3)_2{-}$ |
| 374 | H | tetrahydrofuran-2-yl-$OCH_2C{=}CC(CH_3)_2{-}$ |
| 375 | H | Tetrahydrofuran-2-yl$CH_2C{=}CC(CH_3)_2{-}$ |
| 376 | H | Oxiran-2-yl$C{=}CC(CH_3)_2{-}$ |
| 377 | H | Oxetan-2-yl$C{=}CC(CH_3)_2{-}$ |
| 378 | H | $HOCH_2C(CH_3)(CH_2OCH_3){-}$ |
| 379 | H | $CH_3OCH_2C(CH_3)(CH_2OCH_3){-}$ |

Table 2

The compounds in Table 2 are of the general formula (I) where Q1 is methyl, Q2 is hydrogen, Q3 is hydrogen, L is O, $R^1$ is ethyl, and $R^2$ and $R^3$ have the values given in the Table 1. Thus, compound 1 of Table 2 is the same as compound 1 of Table 1 except that in compound 1 of Table 2 $R^1$ is ethyl. Similarly, compounds 2 to 379 of Table 2 are the same as compounds 2 to 379 of Table 1, respectively, except that in the compounds of Table 2 $R^1$ is ethyl.

Table 3

The compounds in Table 3 are of the general formula (I) where Q1 is methyl, Q2 is hydrogen, Q3 is hydrogen, L is O, $R^1$ is methoxy, and $R^2$ and $R^3$ have the values given in the Table 1. Thus, compound 1 of Table 3 is the same as compound 1 of Table 1 except that in compound 1 of Table 3 $R^1$ is methoxy. Similarly, compounds 2 to 379 of Table 3 are the same as compounds 2 to 379 of Table 1, respectively, except that in the compounds of Table 3 $R^1$ is methoxy.

Table 4

The compounds in Table 4 are of the general formula (I) where Q1 is methyl, Q2 is hydrogen, Q3 is hydrogen, L is O, $R^1$ is ethoxy, and $R^2$ and $R^3$ have the values given in the Table 1. Thus, compound 1 of Table 4 is the same as compound 1 of Table 1 except that in compound 1 of Table 4 $R^1$ is ethoxy. Similarly, compounds 2 to 379 of Table 4 are the same as compounds 4 to 379 of Table 1, respectively, except that in the compounds of Table 2 $R^1$ is ethoxy.

Table 5

The compounds in Table 5 are of the general formula (I) where Q1 is methyl, Q2 is hydrogen, Q3 is hydrogen, L is O, $R^1$ is thiomethyl, and $R^2$ and $R^3$ have the values given in the Table 1. Thus, compound 1 of Table 5 is the same as compound 1 of Table 1 except that in compound 1 of Table 5 $R^1$ is thiomethyl. Similarly, compounds 2 to 379 of Table 5 are the same as compounds 2 to 379 of Table 1, respectively, except that in the compounds of Table 5 $R^1$ is thiomethyl.

Table 6

The compounds in Table 6 are of the general formula (I) where Q1 is methyl, Q2 is hydrogen, Q3 is hydrogen, L is O, $R^1$ is thioethyl, and $R^2$ and $R^3$ have the values given in the Table 1. Thus, compound 1 of Table 6 is the same as compound 1 of Table 1 except that in compound 1 of Table 6 $R^1$ is thioethyl. Similarly, compounds 2 to 379 of Table 6 are the same as compounds 2 to 379 of Table 1, respectively, except that in the compounds of Table 6 $R^1$ is thioethyl.

Table 7

The compounds in Table 7 are of the general formula (I) where Q1 is methyl, Q2 is methyl, Q3 is hydrogen, L is O, $R^1$ is methyl, and $R^2$ and $R^3$ have the values given in the Table 1. Thus, compound 1 of Table 7 is the same as compound 1 of Table 1 except that in compound 1 of Table 7 Q2 is methyl. Similarly, compounds 2 to 379 of Table 7 are the same as compounds 2 to 379 of Table 1, respectively, except that in the compounds of Table 7 Q2 is methyl.

Table 8

The compounds in Table 8 are of the general formula (I) where Q1 is methyl, Q2 is methyl, Q3 is hydrogen, L is O, $R^1$ is ethyl, and $R^2$ and $R^3$ have the values given in the Table 1. Thus, compound 1 of Table 8 is the same as compound 1 of Table 1 except that in compound 1 of Table 8 $R^1$ is ethyl and Q2 is methyl. Similarly, compounds 2 to 379 of Table 8 are the same as compounds 2 to 379 of Table 1, respectively, except that in the compounds of Table 8 $R^1$ is ethyl and Q2 is methyl.

Table 9

The compounds in Table 9 are of the general formula (I) where Q1 is methyl, Q2 is methyl, Q3 is hydrogen, L is O, $R^1$ is methoxy, and $R^2$ and $R^3$ have the values given in the Table 1. Thus, compound 1 of Table 9 is the same as compound 1 of Table 1 except that in compound 1 of Table 9 $R^1$ is methoxy and Q2 is methyl. Similarly, compounds 2 to 379 of Table 9 are the same as compounds 2 to 379 of Table 1, respectively, except that in the compounds of Table 9 $R^1$ is methoxy and Q2 is methyl.

Table 10

The compounds in Table 10 are of the general formula (I) where Q1 is methyl, Q2 is methyl, Q3 is hydrogen, L is O, $R^1$ is ethoxy, and $R^2$ and $R^3$ have the values given in the Table 1. Thus, compound 1 of Table 10 is the same as compound 1 of Table 1 except that in compound 1 of Table 10 $R^1$ is ethoxy and Q2 is methyl. Similarly, compounds 2 to 379 of Table 10 are the same as compounds 2 to 379 of Table 1, respectively, except that in the compounds of Table 10 $R^1$ is ethoxy and Q2 is methyl.

Table 11

The compounds in Table 11 are of the general formula (I) where Q1 is methyl, Q2 is methyl, Q3 is hydrogen, L is O, $R^1$ is thiomethyl, and $R^2$ and $R^3$ have the values given in the Table 1. Thus, compound 1 of Table 11 is the same as compound 1 of Table 1 except that in compound 1 of Table 11 $R^1$ is thiomethyl and Q2 is methyl. Similarly, compounds 2 to 379 of Table 11 are the same as compounds 2 to 379 of Table 1, respectively, except that in the compounds of Table 11 $R^1$ is thiomethyl and Q2 is methyl.

Table 12

The compounds in Table 12 are of the general formula (I) where Q1 is methyl, Q2 is methyl, Q3 is hydrogen, L is O, $R^1$ is thioethyl, and $R^2$ and $R^3$ have the values given in the Table 1. Thus, compound 1 of Table 12 is the same as compound 1 of Table 1 except that in compound 1 of Table 12 $R^1$ is thioethyl and Q2 is methyl. Similarly, compounds 2 to 379 of Table 12 are the same as compounds 2 to 379 of Table 1, respectively, except that in the compounds of Table 12 $R^1$ is thioethyl and Q2 is methyl.

Table 13

The compounds in Table 13 are of the general formula (I) where Q1 is methyl, Q2 is fluoro, Q3 is hydrogen, L is O, $R^1$ is methyl, and $R^2$ and $R^3$ have the values given in the Table 1. Thus, compound 1 of Table 13 is the same as compound 1 of Table 1 except that in compound 1 of Table 13 Q2 is fluoro. Similarly, compounds 2 to 379 of Table 13 are the same as compounds 2 to 379 of Table 1, respectively, except that in the compounds of Table 13 Q2 is fluoro.

Table 14

The compounds in Table 14 are of the general formula (I) where Q1 is methyl, Q2 is fluoro, Q3 is hydrogen, L is O, $R^1$ is ethyl, and $R^2$ and $R^3$ have the values given in the Table 1. Thus, compound 1 of Table 14 is the same as compound 1 of Table 1 except that in compound 1 of Table 14 Q2 is fluoro and $R^1$ is ethyl. Similarly, compounds 2 to 379 of Table 14 are the same as compounds 2 to 379 of Table 1, respectively, except that in the compounds of Table 14 Q2 is fluoro and $R^1$ is ethyl.

Table 15

The compounds in Table 15 are of the general formula (I) where Q1 is methyl, Q2 is fluoro, Q3 is hydrogen, L is O, $R^1$ is methoxy, and $R^2$ and $R^3$ have the values given in the Table 1. Thus, compound 1 of Table 15 is the same as compound 1 of Table 1 except that in compound 1 of Table 15 Q2 is fluoro and $R^1$ is methoxy. Similarly, compounds 2 to 379 of Table 15 are the same as compounds 2 to 379 of Table 1, respectively, except that in the compounds of Table 15 Q2 is fluoro and $R^1$ is methoxy.

Table 16

The compounds in Table 16 are of the general formula (I) where Q1 is methyl, Q2 is fluoro, Q3 is hydrogen, L is O, $R^1$ is ethoxy, and $R^2$ and $R^3$ have the values given in the Table 1. Thus, compound 1 of Table 16 is the same as compound 1 of Table 1 except that in compound 1 of Table 16 Q2 is fluoro and $R^1$ is ethoxy. Similarly, compounds 2 to 379 of Table 16 are the same as compounds 2 to 379 of Table 1, respectively, except that in the compounds of Table 16 Q2 is fluoro and $R^1$ is ethoxy.

Table 17

The compounds in Table 17 are of the general formula (I) where Q1 is methyl, Q2 is fluoro, Q3 is hydrogen, L is O, $R^1$ is thiomethyl, and $R^2$ and $R^3$ have the values given in the Table 1. Thus, compound 1 of Table 17 is the same as compound 1 of Table 1 except that in compound 1 of Table 17 Q2 is fluoro and $R_1$ is thiomethyl. Similarly, compounds 2 to 379 of Table 17 are the same as compounds 2 to 379 of Table 1, respectively, except that in the compounds of Table 17 Q2 is fluoro and R1 is thiomethyl.

Table 18

The compounds in Table 18 are of the general formula (I) where Q1 is methyl, Q2 is fluoro, Q3 is hydrogen, L is O, $R^1$ is thioethyl, and $R^2$ and $R^3$ have the values given in the Table 1. Thus, compound 1 of Table 18 is the same as compound 1 of Table 1 except that in compound 1 of Table 18 Q2 is fluoro and $R^1$ is thioethyl. Similarly, compounds 2 to 379 of Table 18 are the same as compounds 2 to 379 of Table 1, respectively, except that in the compounds of Table 18 Q2 is fluoro and $R^1$ is thioethyl.

Table 19

The compounds in Table 19 are of the general formula (I) where Q1 is methyl, Q2 is chloro, Q3 is hydrogen, L is O, $R^1$ is methyl, and $R^2$ and $R^3$ have the values given in the Table 1. Thus, compound 1 of Table 19 is the same as compound 1 of Table 1 except that in compound 1 of Table 19 Q2 is chloro. Similarly, compounds 2 to 379 of Table 19 are the same as compounds 2 to 379 of Table 1, respectively, except that in the compounds of Table 19 Q2 is chloro.

Table 20

The compounds in Table 20 are of the general formula (I) where Q1 is methyl, Q2 is chloro, Q3 is hydrogen, L is O, $R^1$ is ethyl, and $R^2$ and $R^3$ have the values given in the Table 1. Thus, compound 1 of Table 20 is the same as compound 1 of Table 1 except that in compound 1 of Table 20 Q2 is chloro and $R^1$ is ethyl. Similarly, compounds 2 to 379 of Table 20 are the same as compounds 2 to 379 of Table 1, respectively, except that in the compounds of Table 20 Q2 is chloro and $R^1$ is ethyl.

Table 21

The compounds in Table 21 are of the general formula (I) where Q1 is methyl, Q2 is chloro, Q3 is hydrogen, L is O, $R^1$ is methoxy, and $R^2$ and $R^3$ have the values given in the Table 1. Thus, compound 1 of Table 21 is the same as compound 1 of Table 1 except that in compound 1 of Table 21 Q2 is chloro and $R^1$ is methoxy. Similarly, compounds 2 to 379 of Table 21 are the same as compounds 2 to 379 of Table 1, respectively, except that in the compounds of Table 21 Q2 is chloro and $R^1$ is methoxy.

Table 22

The compounds in Table 22 are of the general formula (I) where Q1 is methyl, Q2 is chloro, Q3 is hydrogen, L is O, $R^1$ is ethoxy, and $R^2$ and $R^3$ have the values given in the Table 1. Thus, compound 1 of Table 22 is the same as compound 1 of Table 1 except that in compound 1 of Table 22 Q2 is chloro and $R^1$ is ethoxy. Similarly, compounds 2 to 379 of Table 22 are the same as compounds 2 to 379 of Table 1, respectively, except that in the compounds of Table 22 Q2 is chloro and $R^1$ is ethoxy.

Table 23

The compounds in Table 23 are of the general formula (I) where Q1 is methyl, Q2 is chloro, Q3 is hydrogen, L is O, $R^1$ is thiomethyl, and $R^2$ and $R^3$ have the values given in the Table 1. Thus, compound 1 of Table 23 is the same as compound 1 of Table 1 except that in compound 1 of Table 23 Q2 is chloro and $R^1$ is thiomethyl. Similarly, compounds 2 to 379 of Table 23 are the same as compounds 2 to 379 of Table 1, respectively, except that in the compounds of Table 23 Q2 is chloro and $R^1$ is thiomethyl.

Table 24

The compounds in Table 24 are of the general formula (I) where Q1 is methyl, Q2 is chloro, Q3 is hydrogen, L is O, $R^1$ is thioethyl, and $R^2$ and $R^3$ have the values given in the Table 1. Thus, compound 1 of Table 24 is the same as compound 1 of Table 1 except that in compound 1 of Table 24 Q2 is chloro and $R^1$ is thioethyl. Similarly, compounds 2 to 379 of Table 24 are the same as compounds 2 to 379 of Table 1, respectively, except that in the compounds of Table 24 Q2 is chloro and $R^1$ is thioethyl.

Table 25

The compounds in Table 95 are of the general formula (I) where Q1 is methyl, Q2 is bromo, Q3 is hydrogen, L is O, $R^1$ is methyl, and $R^2$ and $R^3$ have the values given in the Table 1. Thus, compound 1 of Table 25 is the same as compound 1 of Table 1 except that in compound 1 of Table 25 Q2 is bromo. Similarly, compounds 2 to 379 of Table 25 are the same as compounds 2 to 379 of Table 1, respectively, except that in the compounds of Table 25 Q2 is bromo.

Table 26

The compounds in Table 26 are of the general formula (I) where Q1 is methyl, Q2 is bromo, Q3 is hydrogen, L is O, $R^1$ is ethyl, and $R^2$ and $R^3$ have the values given in the Table 1. Thus, compound 1 of Table 26 is the same as compound 1 of Table 1 except that in compound 1 of Table 26 Q2 is bromo and $R^1$ is ethyl. Similarly, compounds 2 to 379 of Table 26 are the same as compounds 2 to 379 of Table 1, respectively, except that in the compounds of Table 26 R Q2 is bromo and $R^1$ is ethyl.

Table 27

The compounds in Table 27 are of the general formula (I) where Q1 is methyl, Q2 is bromo, Q3 is hydrogen, L is O, $R^1$ is methoxy, and $R^2$ and $R^3$ have the values given in the Table 1. Thus, compound 1 of Table 27 is the same as compound 1 of Table 1 except that in compound 1 of Table 27 Q2 is bromo and $R^1$ is methoxy. Similarly, compounds 2 to 379 of Table 27 are the same as compounds 2 to 379 of Table 1, respectively, except that in the compounds of Table 27 Q2 is bromo and $R^1$ is methoxy.

Table 28

The compounds in Table 28 are of the general formula (I) where Q1 is methyl, Q2 is bromo, Q3 is hydrogen, L is O, $R^1$ is ethoxy, and $R^2$ and $R^3$ have the values given in the Table 1. Thus, compound 1 of Table 28 is the same as compound 1 of Table 1 except that in compound 1 of Table 28 Q2 is bromo and $R^1$ is ethoxy. Similarly, compounds 2 to 379 of Table 28 are the same as compounds 2 to 379 of Table 1, respectively, except that in the compounds of Table 28 Q2 is bromo and $R^1$ is ethoxy.

Table 29

The compounds in Table 29 are of the general formula (I) where Q1 is methyl, Q2 is bromo, Q3 is hydrogen, L is O, $R^1$ is thiomethyl, and $R^2$ and $R^3$ have the values given in the Table 1. Thus, compound 1 of Table 29 is the same as compound 1 of Table 1 except that in compound 1 of Table 29 Q2 is bromo and $R^1$ is thiomethyl. Similarly, compounds 2 to 379 of Table 29 are the same as compounds 2 to 379 of Table 1, respectively, except that in the compounds of Table 29 Q2 is bromo and $R^1$ is thiomethyl.

Table 30

The compounds in Table 30 are of the general formula (I) where Q1 is methyl, Q2 is bromo, Q3 is hydrogen, L is O, $R^1$ is thioethyl, and $R^2$ and $R^3$ have the values given in the Table 1. Thus, compound 1 of Table 30 is the same as compound 1 of Table 1 except that in compound 1 of Table 30 Q2 is bromo and $R^1$ is thioethyl. Similarly, compounds 2 to 379 of Table 30 are the same as compounds 2 to 379 of Table 1, respectively, except that in the compounds of Table 30 Q2 is bromo and $R^1$ is thioethyl.

Table 31
The compounds in Table 31 are of the general formula (I) where Q1 is methyl, Q2 is iodo, Q3 is hydrogen, L is O, $R^1$ is methyl, and $R^2$ and $R^3$ have the values given in the Table 1. Thus, compound 1 of Table 31 is the same as compound 1 of Table 1 except that in compound 1 of Table 31 Q2 is iodo. Similarly, compounds 2 to 379 of Table 31 are the same as compounds 2 to 379 of Table 1, respectively, except that in the compounds of Table 31 Q2 is iodo.

Table 32
The compounds in Table 32 are of the general formula (I) where Q1 is methyl, Q2 is iodo, Q3 is hydrogen, L is O, $R^1$ is ethyl, and $R^2$ and $R^3$ have the values given in the Table 1. Thus, compound 1 of Table 32 is the same as compound 1 of Table 1 except that in compound 1 of Table 32 Q2 is iodo and $R^1$ is ethyl. Similarly, compounds 2 to 379 of Table 32 are the same as compounds 2 to 379 of Table 1, respectively, except that in the compounds of Table 32 Q2 is iodo and $R^1$ is ethyl.

Table 33
The compounds in Table 33 are of the general formula (I) where Q1 is methyl, Q2 is iodo, Q3 is hydrogen, L is O, $R^1$ is methyl, and $R^2$ and $R^3$ have the values given in the Table 1. Thus, compound 1 of Table 33 is the same as compound 1 of Table 1 except that in compound 1 of Table 33 Q2 is iodo and $R^1$ is methoxy. Similarly, compounds 2 to 379 of Table 33 are the same as compounds 2 to 379 of Table 1, respectively, except that in the compounds of Table 33 Q2 is iodo and $R^1$ is methoxy.

Table 34
The compounds in Table 34 are of the general formula (I) where Q1 is methyl, Q2 is iodo, Q3 is hydrogen, L is O, $R^1$ is methyl, and $R^2$ and $R^3$ have the values given in the Table 1. Thus, compound 1 of Table 34 is the same as compound 1 of Table 1 except that in compound 1 of Table 34 Q2 is iodo and $R^1$ is ethoxy. Similarly, compounds 2 to 379 of Table 34 are the same as compounds 2 to 379 of Table 1, respectively, except that in the compounds of Table 34 Q2 is iodo and $R^1$ is ethoxy.

Table 35
The compounds in Table 15 are of the general formula (I) where Q1 is methyl, Q2 is iodo, Q3 is hydrogen, L is O, $R^1$ is methyl, and $R^2$ and $R^3$ have the values given in the Table 1. Thus, compound 1 of Table 35 is the same as compound 1 of Table 1 except that in compound 1 of Table 35 Q2 is iodo and $R^1$ is thiomethyl. Similarly, compounds 2 to 379 of Table 35 are the same as compounds 2 to 379 of Table 1, respectively, except that in the compounds of Table 35 Q2 is iodo and $R^1$ is thiomethyl.

Table 36
The compounds in Table 36 are of the general formula (I) where Q1 is methyl, Q2 is iodo, Q3 is hydrogen, L is O, $R^1$ is methyl, and $R^2$ and $R^3$ have the values given in the Table 1. Thus, compound 1 of Table 36 is the same as compound 1 of Table 1 except that in compound 1 of Table 36 Q2 is iodo and $R^1$ is thioethyl. Similarly, compounds 2 to 379 of Table 36 are the same as compounds 2 to 379 of Table 1, respectively, except that in the compounds of Table 36 Q2 is iodo and $R^1$ is thioethyl.

Table 37
The compounds in Table 37 are of the general formula (I) where Q1 is methyl, Q2 is hydrogen, Q3 is methyl, L is O, $R^1$ is methyl, and $R^2$ and $R^3$ have the values given in the Table 1. Thus, compound 1 of Table 37 is the same as compound 1 of Table 1 except that in compound 1 of Table 37 Q3 is methyl. Similarly, compounds 2 to 379 of Table 37 are the same as compounds 2 to 379 of Table 1, respectively, except that in the compounds of Table 37 Q3 is methyl.

Table 38
The compounds in Table 38 are of the general formula (I) where Q1 is methyl, Q2 is hydrogen, Q3 is methyl, L is O, $R^1$ is ethyl, and $R^2$ and $R^3$ have the values given in the Table 1. Thus, compound 1 of Table 38 is the same as compound 1 of Table 1 except that in compound 1 of Table 38 Q3 is methyl and $R^1$ is ethyl. Similarly, compounds 2 to 379 of Table 38 are the same as compounds 2 to 379 of Table 1, respectively, except that in the compounds of Table 38 Q3 is methyl and $R^1$ is ethyl.

Table 39
The compounds in Table 39 are of the general formula (I) where Q1 is methyl, Q2 is hydrogen, Q3 is methyl, L is O, $R^1$ is methoxy, and $R^2$ and $R^3$ have the values given in the Table 1. Thus, compound 1 of Table 39 is the same as compound 1 of Table 1 except that in compound 1 of Table 39 Q3 is methyl and $R^1$ is methoxy. Similarly, compounds 2 to 379 of Table 39 are the same as compounds 2 to 379 of Table 1, respectively, except that in the compounds of Table 39 Q3 is methyl and $R^1$ is methoxy.

Table 40
The compounds in Table 39 are of the general formula (I) where Q1 is methyl, Q2 is hydrogen, Q3 is methyl, L is O, $R^1$ is ethoxy, and $R^2$ and $R^3$ have the values given in the Table 1. Thus, compound 1 of Table 40 is the same as compound 1 of Table 1 except that in compound 1 of Table 40 Q3 is methyl and $R^1$ is ethoxy. Similarly, compounds 2 to 379 of Table 40 are the same as compounds 2 to 379 of Table 1, respectively, except that in the compounds of Table 40 Q3 is methyl and $R^1$ is ethoxy.

Table 41
The compounds in Table 41 are of the general formula (I) where Q1 is methyl, Q2 is hydrogen, Q3 is methyl, L is O, $R^1$ is thiomethyl, and $R^2$ and $R^3$ have the values given in the Table 1. Thus, compound 1 of Table 41 is the same as compound 1 of Table 1 except that in compound 1 of Table 41 Q3 is methyl and $R^1$ is thiomethyl. Similarly, compounds 2 to 379 of Table 41 are the same as compounds 2 to 379 of Table 1, respectively, except that in the compounds of Table 41 Q3 is methyl and $R^1$ is thiomethyl.

Table 42
The compounds in Table 42 are of the general formula (I) where Q1 is methyl, Q2 is hydrogen, Q3 is methyl, L is O, $R^1$ is thioethyl, and $R^2$ and $R^3$ have the values given in the Table 1. Thus, compound 1 of Table 42 is the same as compound 1 of Table 1 except that in compound 1 of Table 42 Q3 is methyl and $R^1$ is thioethyl. Similarly, compounds 2 to 379 of Table 42 are the same as compounds 2 to 379 of Table 1, respectively, except that in the compounds of Table 42 Q3 is methyl and $R^1$ is thioethyl.

Table 43
The compounds in Table 43 are of the general formula (I) where Q1 is methyl, Q2 is hydrogen, Q3 is fluoro, L is O, $R^1$ is methyl, and $R^2$ and $R^3$ have the values given in the Table 1. Thus, compound 1 of Table 43 is the same as compound 1 of Table 1 except that in compound 1 of Table 43 Q3 is fluoro. Similarly, compounds 2 to 379 of Table 43 are the same as compounds 2 to 379 of Table 1, respectively, except that in the compounds of Table 43 Q3 is fluoro.

Table 44
The compounds in Table 44 are of the general formula (I) where Q1 is methyl, Q2 is hydrogen, Q3 is fluoro, L is O, $R^1$ is ethyl, and $R^2$ and $R^3$ have the values given in the Table 1. Thus, compound 1 of Table 44 is the same as compound 1 of Table 1 except that in compound 1 of Table 44 Q3 is fluoro and $R^1$ is ethyl. Similarly, compounds 2 to 379 of Table 44 are the same as compounds 2 to 379 of Table 1, respectively, except that in the compounds of Table 44 Q3 is fluoro and $R^1$ is ethyl.

Table 45

The compounds in Table 45 are of the general formula (I) where Q1 is methyl, Q2 is hydrogen, Q3 is fluoro, L is O, $R^1$ is methoxy, and $R^2$ and $R^3$ have the values given in the Table 1. Thus, compound 1 of Table 45 is the same as compound 1 of Table 1 except that in compound 1 of Table 45 Q3 is fluoro and $R^1$ is methoxy. Similarly, compounds 2 to 379 of Table 45 are the same as compounds 2 to 379 of Table 1, respectively, except that in the compounds of Table 45 Q3 is fluoro and $R^1$ is methoxy.

Table 46

The compounds in Table 46 are of the general formula (I) where Q1 is methyl, Q2 is hydrogen, Q3 is fluoro, L is O, $R^1$ is ethoxy, and $R^2$ and $R^3$ have the values given in the Table 1. Thus, compound 1 of Table 46 is the same as compound 1 of Table 1 except that in compound 1 of Table 46 Q3 is fluoro and $R^1$ is ethoxy. Similarly, compounds 2 to 379 of Table 46 are the same as compounds 2 to 379 of Table 1, respectively, except that in the compounds of Table 46 Q3 is fluoro and $R^1$ is ethoxy.

Table 47

The compounds in Table 47 are of the general formula (I) where Q1 is methyl, Q2 is hydrogen, Q3 is fluoro, L is O, $R^1$ is thiomethyl, and $R^2$ and $R^3$ have the values given in the Table 1. Thus, compound 1 of Table 47 is the same as compound 1 of Table 1 except that in compound 1 of Table 47 Q3 is fluoro and $R^1$ is thiomethyl. Similarly, compounds 2 to 379 of Table 47 are the same as compounds 2 to 379 of Table 1, respectively, except that in the compounds of Table 47 Q3 is fluoro and $R^1$ is thiomethyl.

Table 48

The compounds in Table 48 are of the general formula (I) where Q1 is methyl, Q2 is hydrogen, Q3 is fluoro, L is O, $R^1$ is thioethyl, and $R^2$ and $R^3$ have the values given in the Table 1. Thus, compound 1 of Table 48 is the same as compound 1 of Table 1 except that in compound 1 of Table 48 Q3 is fluoro and $R^1$ is thioethyl. Similarly, compounds 2 to 379 of Table 48 are the same as compounds 2 to 379 of Table 1, respectively, except that in the compounds of Table 48 Q3 is fluoro and $R^1$ is thioethyl.

Table 49

The compounds in Table 49 are of the general formula (I) where Q1 is methyl, Q2 is hydrogen, Q3 is chloro, L is O, $R^1$ is methyl, and $R^2$ and $R^3$ have the values given in the Table 1. Thus, compound 1 of Table 49 is the same as compound 1 of Table 1 except that in compound 1 of Table 49 Q3 is chloro. Similarly, compounds 2 to 379 of Table 49 are the same as compounds 2 to 379 of Table 1, respectively, except that in the compounds of Table 49 Q3 is chloro.

Table 50

The compounds in Table 50 are of the general formula (I) where Q1 is methyl, Q2 is hydrogen, Q3 is chloro, L is O, $R^1$ is ethyl, and $R^2$ and $R^3$ have the values given in the Table 1. Thus, compound 1 of Table 50 is the same as compound 1 of Table 1 except that in compound 1 of Table 50 Q3 is chloro and $R^1$ is ethyl. Similarly, compounds 2 to 379 of Table 50 are the same as compounds 2 to 379 of Table 1, respectively, except that in the compounds of Table 50 Q3 is chloro and $R^1$ is ethyl.

Table 51

The compounds in Table 51 are of the general formula (I) where Q1 is methyl, Q2 is hydrogen, Q3 is chloro, L is O, $R^1$ is methoxy, and $R^2$ and $R^3$ have the values given in the Table 1. Thus, compound 1 of Table 51 is the same as compound 1 of Table 1 except that in compound 1 of Table 51 Q3 is chloro and $R^1$ is methoxy. Similarly, compounds 2 to 379 of Table 51 are the same as compounds 2 to 379 of Table 1, respectively, except that in the compounds of Table 51 Q3 is chloro and $R^1$ is methoxy.

Table 52

The compounds in Table 52 are of the general formula (I) where Q1 is methyl, Q2 is hydrogen, Q3 is chloro, L is O, $R^1$ is ethoxy, and $R^2$ and $R^3$ have the values given in the Table 1. Thus, compound 1 of Table 52 is the same as compound 1 of Table 1 except that in compound 1 of Table 52 Q3 is chloro and $R^1$ is ethoxy. Similarly, compounds 2 to 379 of Table 52 are the same as compounds 2 to 379 of Table 1, respectively, except that in the compounds of Table 52 Q3 is chloro and $R^1$ is ethoxy.

Table 53

The compounds in Table 53 are of the general formula (I) where Q1 is methyl, Q2 is hydrogen, Q3 is chloro, L is O, $R^1$ is thiomethyl, and $R^2$ and $R^3$ have the values given in the Table 1. Thus, compound 1 of Table 53 is the same as compound 1 of Table 1 except that in compound 1 of Table 53 Q3 is chloro and $R^1$ is thiomethyl. Similarly, compounds 2 to 379 of Table 53 are the same as compounds 2 to 379 of Table 1, respectively, except that in the compounds of Table 53 Q3 is chloro and $R^1$ is thiomethyl.

Table 54

The compounds in Table 54 are of the general formula (I) where Q1 is methyl, Q2 is hydrogen, Q3 is chloro, L is O, $R^1$ is thioethyl, and $R^2$ and $R^3$ have the values given in the Table 1. Thus, compound 1 of Table 54 is the same as compound 1 of Table 1 except that in compound 1 of Table 54 Q3 is chloro and $R^1$ is thioethyl. Similarly, compounds 2 to 379 of Table 54 are the same as compounds 2 to 379 of Table 1, respectively, except that in the compounds of Table 54 Q3 is chloro and $R^1$ is thioethyl.

Table 55

The compounds in Table 55 are of the general formula (I) where Q1 is methyl, Q2 is methyl, Q3 is fluoro, L is O, $R^1$ is methyl, and $R^2$ and $R^3$ have the values given in the Table 1. Thus, compound 1 of Table 55 is the same as compound 1 of Table 1 except that in compound 1 of Table 55 Q2 is methyl and Q3 is fluoro. Similarly, compounds 2 to 379 of Table 55 are the same as compounds 2 to 379 of Table 1, respectively, except that in the compounds of Table 55 Q2 is methyl and Q3 is fluoro.

Table 56

The compounds in Table 56 are of the general formula (I) where Q1 is methyl, Q2 is methyl, Q3 is fluoro, L is O, $R^1$ is ethyl, and $R^2$ and $R^3$ have the values given in the Table 1. Thus, compound 1 of Table 56 is the same as compound 1 of Table 1 except that in compound 1 of Table 56 Q2 is methyl, Q3 is fluoro and $R^1$ is ethyl. Similarly, compounds 2 to 379 of Table 56 are the same as compounds 2 to 379 of Table 1, respectively, except that in the compounds of Table 56 Q2 is methyl, Q3 is fluoro and $R^1$ is ethyl.

Table 57

The compounds in Table 57 are of the general formula (I) where Q1 is methyl, Q2 is methyl, Q3 is fluoro, L is O, $R^1$ is methoxy, and $R^2$ and $R^3$ have the values given in the Table 1. Thus, compound 1 of Table 57 is the same as compound 1 of Table 1 except that in compound 1 of Table 57 Q2 is methyl, Q3 is fluoro and $R^1$ is methoxy. Similarly, compounds 2 to 379 of Table 57 are the same as compounds 2 to 379 of Table 1, respectively, except that in the compounds of Table 57 Q2 is methyl, Q3 is fluoro and $R^1$ is methoxy.

Table 58

The compounds in Table 58 are of the general formula (I) where Q1 is methyl, Q2 is methyl, Q3 is fluoro, L is O, $R^1$ is ethoxy, and $R^2$ and $R^3$ have the values given in the Table 1.

Thus, compound 1 of Table 58 is the same as compound 1 of Table 1 except that in compound 1 of Table 58 Q2 is methyl, Q3 is fluoro and $R^1$ is ethoxy. Similarly, compounds 2 to 379 of Table 58 are the same as compounds 2 to 379 of Table 1, respectively, except that in the compounds of Table 58 Q2 is methyl, Q3 is fluoro and $R^1$ is ethoxy.

Table 59

The compounds in Table 59 are of the general formula (I) where Q1 is methyl, Q2 is methyl, Q3 is fluoro, L is O, $R^1$ is thiomethyl, and $R^2$ and $R^3$ have the values given in the Table 1. Thus, compound 1 of Table 59 is the same as compound 1 of Table 1 except that in compound 1 of Table 59 Q2 is methyl, Q3 is fluoro and $R^1$ is thiomethyl. Similarly, compounds 2 to 379 of Table 59 are the same as compounds 2 to 379 of Table 1, respectively, except that in the compounds of Table 59 Q2 is methyl, Q3 is fluoro and $R^1$ is thiomethyl.

Table 60

The compounds in Table 60 are of the general formula (I) where Q1 is methyl, Q2 is methyl, Q3 is fluoro, L is O, $R^1$ is thioethyl, and $R^2$ and $R^3$ have the values given in the Table 1. Thus, compound 1 of Table 60 is the same as compound 1 of Table 1 except that in compound 1 of Table 60 Q2 is methyl, Q3 is fluoro and $R^1$ is thioethyl. Similarly, compounds 2 to 379 of Table 60 are the same as compounds 2 to 379 of Table 1, respectively, except that in the compounds of Table 60 Q2 is methyl, Q3 is fluoro and $R^1$ is thioethyl.

Table 61

The compounds in Table 61 are of the general formula (I) where Q1 is methyl, Q2 is fluoro, Q3 is fluoro, L is O, $R^1$ is methyl, and $R^2$ and $R^3$ have the values given in the Table 1. Thus, compound 1 of Table 61 is the same as compound 1 of Table 1 except that in compound 1 of Table 61 Q2 is fluoro and Q3 is fluoro. Similarly, compounds 2 to 379 of Table 61 are the same as compounds 2 to 379 of Table 1, respectively, except that in the compounds of Table 61 Q2 is fluoro and Q3 is fluoro.

Table 62

The compounds in Table 62 are of the general formula (I) where Q1 is methyl, Q2 is fluoro, Q3 is fluoro, L is O, $R^1$ is ethyl, and $R^2$ and $R^3$ have the values given in the Table 1. Thus, compound 1 of Table 62 is the same as compound 1 of Table 1 except that in compound 1 of Table 62 Q2 is fluoro, Q3 is fluoro and $R^1$ is ethyl. Similarly, compounds 2 to 379 of Table 62 are the same as compounds 2 to 379 of Table 1, respectively, except that in the compounds of Table 62 Q2 is fluoro, Q3 is fluoro and $R^1$ is ethyl.

Table 63

The compounds in Table 63 are of the general formula (I) where Q1 is methyl, Q2 is fluoro, Q3 is fluoro, L is O, $R^1$ is methoxy, and $R^2$ and $R^3$ have the values given in the Table 1. Thus, compound 1 of Table 63 is the same as compound 1 of Table 1 except that in compound 1 of Table 63 Q2 is fluoro, Q3 is fluoro and $R^1$ is methoxy. Similarly, compounds 2 to 379 of Table 63 are the same as compounds 2 to 379 of Table 1, respectively, except that in the compounds of Table 63 Q2 is fluoro, Q3 is fluoro and $R^1$ is methoxy.

Table 64

The compounds in Table 64 are of the general formula (I) where Q1 is methyl, Q2 is fluoro, Q3 is fluoro, L is O, $R^1$ is ethoxy, and $R^2$ and $R^3$ have the values given in the Table 1. Thus, compound 1 of Table 64 is the same as compound 1 of Table 1 except that in compound 1 of Table 64 Q2 is fluoro, Q3 is fluoro and $R^1$ is ethoxy. Similarly, compounds 2 to 379 of Table 64 are the same as compounds 2 to 379 of Table 1, respectively, except that in the compounds of Table 64 Q2 is fluoro, Q3 is fluoro and $R^1$ is ethoxy.

Table 65

The compounds in Table 65 are of the general formula (I) where Q1 is methyl, Q2 is fluoro, Q3 is fluoro, L is O, $R^1$ is thiomethyl, and $R^2$ and $R^3$ have the values given in the Table 1. Thus, compound 1 of Table 65 is the same as compound 1 of Table 1 except that in compound 1 of Table 65 Q2 is fluoro, Q3 is fluoro and $R^1$ is thiomethyl. Similarly, compounds 2 to 379 of Table 65 are the same as compounds 2 to 379 of Table 1, respectively, except that in the compounds of Table 65 Q2 is fluoro, Q3 is fluoro and $R^1$ is thiomethyl.

Table 66

The compounds in Table 66 are of the general formula (I) where Q1 is methyl, Q2 is fluoro, Q3 is fluoro, L is O, $R^1$ is thioethyl, and $R^2$ and $R^3$ have the values given in the Table 1. Thus, compound 1 of Table 66 is the same as compound 1 of Table 1 except that in compound 1 of Table 66 Q2 is fluoro, Q3 is fluoro and $R^1$ is thioethyl. Similarly, compounds 2 to 379 of Table 66 are the same as compounds 2 to 379 of Table 1, respectively, except that in the compounds of Table 66 Q2 is fluoro, Q3 is fluoro and $R^1$ is thioethyl.

Table 67

The compounds in Table 67 are of the general formula (I) where Q1 is methyl, Q2 is chloro, Q3 is fluoro, L is O, $R^1$ is methyl, and $R^2$ and $R^3$ have the values given in the Table 1. Thus, compound 1 of Table 67 is the same as compound 1 of Table 1 except that in compound 1 of Table 67 Q2 is chloro and Q3 is fluoro. Similarly, compounds 2 to 379 of Table 67 are the same as compounds 2 to 379 of Table 1, respectively, except that in the compounds of Table 67 Q2 is chloro and Q3 is fluoro.

Table 68

The compounds in Table 68 are of the general formula (I) where Q1 is methyl, Q2 is chloro, Q3 is fluoro, L is O, $R^1$ is ethyl, and $R^2$ and $R^3$ have the values given in the Table 1. Thus, compound 1 of Table 68 is the same as compound 1 of Table 1 except that in compound 1 of Table 68 Q2 is chloro, Q3 is fluoro and $R^1$ is ethyl. Similarly, compounds 2 to 379 of Table 68 are the same as compounds 2 to 379 of Table 1, respectively, except that in the compounds of Table 68 Q2 is chloro, Q3 is fluoro and $R^1$ is ethyl.

Table 69

The compounds in Table 69 are of the general formula (I) where Q1 is methyl, Q2 is chloro, Q3 is fluoro, L is O, $R^1$ is methoxy, and $R^2$ and $R^3$ have the values given in the Table 1. Thus, compound 1 of Table 69 is the same as compound 1 of Table 1 except that in compound 1 of Table 69 Q2 is chloro, Q3 is fluoro and $R^1$ is methoxy. Similarly, compounds 2 to 379 of Table 69 are the same as compounds 2 to 379 of Table 1, respectively, except that in the compounds of Table 69 Q2 is chloro, Q3 is fluoro and $R^1$ is methoxy.

Table 70

The compounds in Table 70 are of the general formula (I) where Q1 is methyl, Q2 is chloro, Q3 is fluoro, L is O, $R^1$ is ethoxy, and $R^2$ and $R^3$ have the values given in the Table 1. Thus, compound 1 of Table 70 is the same as compound 1 of Table 1 except that in compound 1 of Table 70 Q2 is chloro, Q3 is fluoro and $R^1$ is ethoxy. Similarly, compounds 2 to 379 of Table 70 are the same as compounds 2 to 379 of Table 1, respectively, except that in the compounds of Table 70 Q2 is chloro, Q3 is fluoro and $R^1$ is ethoxy.

Table 71

The compounds in Table 71 are of the general formula (I) where Q1 is methyl, Q2 is chloro, Q3 is fluoro, L is O, $R^1$ is thiomethyl, and $R^2$ and $R^3$ have the values given in the Table 1. Thus, compound 1 of Table 71 is the same as compound 1 of Table 1 except that in compound 1 of Table 71 Q2 is chloro, Q3 is fluoro and $R^1$ is thiomethyl. Similarly, compounds 2 to 379 of Table 71 are the same as compounds 2 to 379 of Table 1, respectively, except that in the compounds of Table 71 Q2 is chloro, Q3 is fluoro and R¹ is thiomethyl.

Table 72

The compounds in Table 72 are of the general formula (I) where Q1 is methyl, Q2 is chloro, Q3 is fluoro, L is O, R¹ is thioethyl, and R² and R³ have the values given in the Table 1. Thus, compound 1 of Table 72 is the same as compound 1 of Table 1 except that in compound 1 of Table 72 Q2 is chloro, Q3 is fluoro and R¹ is thioethyl. Similarly, compounds 2 to 379 of Table 72 are the same as compounds 2 to 379 of Table 1, respectively, except that in the compounds of Table 72 Q2 is chloro, Q3 is fluoro and R¹ is thioethyl.

Table 73

The compounds in Table 73 are of the general formula (I) where Q1 is methyl, Q2 is bromo, Q3 is fluoro, L is O, R¹ is methyl, and R² and R³ have the values given in the Table 1. Thus, compound 1 of Table 73 is the same as compound 1 of Table 1 except that in compound 1 of Table 73 Q2 is bromo and Q3 is fluoro. Similarly, compounds 2 to 379 of Table 73 are the same as compounds 2 to 379 of Table 1, respectively, except that in the compounds of Table 73 Q2 is bromo and Q3 is fluoro.

Table 74

The compounds in Table 74 are of the general formula (I) where Q1 is methyl, Q2 is bromo, Q3 is fluoro, L is O, R¹ is ethyl, and R² and R³ have the values given in the Table 1. Thus, compound 1 of Table 74 is the same as compound 1 of Table 1 except that in compound 1 of Table 74 Q2 is bromo, Q3 is fluoro and R¹ is ethyl. Similarly, compounds 2 to 379 of Table 74 are the same as compounds 2 to 379 of Table 1, respectively, except that in the compounds of Table 74 Q2 is bromo, Q3 is fluoro and R¹ is ethyl.

Table 75

The compounds in Table 75 are of the general formula (I) where Q1 is methyl, Q2 is bromo, Q3 is fluoro, L is O, R¹ is methoxy, and R² and R³ have the values given in the Table 1. Thus, compound 1 of Table 75 is the same as compound 1 of Table 1 except that in compound 1 of Table 75 Q2 is bromo, Q3 is fluoro and R¹ is methoxy. Similarly, compounds 2 to 379 of Table 75 are the same as compounds 2 to 379 of Table 1, respectively, except that in the compounds of Table 75 Q2 is bromo, Q3 is fluoro and R¹ is methoxy.

Table 76

The compounds in Table 76 are of the general formula (I) where Q1 is methyl, Q2 is bromo, Q3 is fluoro, L is O, R¹ is ethoxy, and R² and R³ have the values given in the Table 1. Thus, compound 1 of Table 76 is the same as compound 1 of Table 1 except that in compound 1 of Table 76 Q2 is bromo, Q3 is fluoro and R¹ is ethoxy. Similarly, compounds 2 to 379 of Table 76 are the same as compounds 2 to 379 of Table 1, respectively, except that in the compounds of Table 76 Q2 is bromo, Q3 is fluoro and R¹ is ethoxy.

Table 77

The compounds in Table 77 are of the general formula (I) where Q1 is methyl, Q2 is bromo, Q3 is fluoro, L is O, R¹ is thiomethyl, and R² and R³ have the values given in the Table 1. Thus, compound 1 of Table 77 is the same as compound 1 of Table 1 except that in compound 1 of Table 77 Q2 is bromo, Q3 is fluoro and R¹ is thiomethyl. Similarly, compounds 2 to 379 of Table 77 are the same as compounds 2 to 379 of Table 1, respectively, except that in the compounds of Table 77 Q2 is bromo, Q3 is fluoro and R¹ is thiomethyl.

Table 78

The compounds in Table 78 are of the general formula (I) where Q1 is methyl, Q2 is bromo, Q3 is fluoro, L is O, R¹ is thioethyl, and R² and R³ have the values given in the Table 1. Thus, compound 1 of Table 78 is the same as compound 1 of Table 1 except that in compound 1 of Table 78 Q2 is bromo, Q3 is fluoro and R¹ is thioethyl. Similarly, compounds 2 to 379 of Table 78 are the same as compounds 2 to 379 of Table 1, respectively, except that in the compounds of Table 78 Q2 is bromo, Q3 is fluoro and R¹ is thioethyl.

Table 79

The compounds in Table 79 are of the general formula (I) where Q1 is methyl, Q2 is iodo, Q3 is fluoro, L is O, R¹ is methyl, and R² and R³ have the values given in the Table 1. Thus, compound 1 of Table 79 is the same as compound 1 of Table 1 except that in compound 1 of Table 79 Q2 is iodo and Q3 is fluoro. Similarly, compounds 2 to 379 of Table 79 are the same as compounds 2 to 379 of Table 1, respectively, except that in the compounds of Table 79 Q2 is iodo and Q3 is fluoro.

Table 80

The compounds in Table 80 are of the general formula (I) where Q1 is methyl, Q2 is iodo, Q3 is fluoro, L is O, R¹ is ethyl, and R² and R³ have the values given in the Table 1. Thus, compound 1 of Table 80 is the same as compound 1 of Table 1 except that in compound 1 of Table 80 Q2 is iodo, Q3 is fluoro and R¹ is ethyl. Similarly, compounds 2 to 379 of Table 80 are the same as compounds 2 to 379 of Table 1, respectively, except that in the compounds of Table 80 Q2 is iodo, Q3 is fluoro and R¹ is ethyl.

Table 81

The compounds in Table 81 are of the general formula (I) where Q1 is methyl, Q2 is iodo, Q3 is fluoro, L is O, R¹ is methoxy, and R² and R³ have the values given in the Table 1. Thus, compound 1 of Table 81 is the same as compound 1 of Table 1 except that in compound 1 of Table 81 Q2 is iodo, Q3 is fluoro and R¹ is methoxy. Similarly, compounds 2 to 379 of Table 81 are the same as compounds 2 to 379 of Table 1, respectively, except that in the compounds of Table 81 Q2 is iodo, Q3 is fluoro and R¹ is methoxy.

Table 82

The compounds in Table 82 are of the general formula (I) where Q1 is methyl, Q2 is iodo, Q3 is fluoro, L is O, R¹ is ethoxy, and R² and R³ have the values given in the Table 1. Thus, compound 1 of Table 82 is the same as compound 1 of Table 1 except that in compound 1 of Table 82 Q2 is iodo, Q3 is fluoro and R¹ is ethoxy. Similarly, compounds 2 to 379 of Table 82 are the same as compounds 2 to 379 of Table 1, respectively, except that in the compounds of Table 82 Q2 is iodo, Q3 is fluoro and R¹ is ethoxy.

Table 83

The compounds in Table 83 are of the general formula (I) where Q1 is methyl, Q2 is iodo, Q3 is fluoro, L is O, R¹ is thiomethyl, and R² and R³ have the values given in the Table 1. Thus, compound 1 of Table 83 is the same as compound 1 of Table 1 except that in compound 1 of Table 83 Q2 is iodo, Q3 is fluoro and R¹ is thiomethyl. Similarly, compounds 2 to 379 of Table 83 are the same as compounds 2 to 379 of Table 1, respectively, except that in the compounds of Table 83 Q2 is iodo, Q3 is fluoro and R¹ is thiomethyl.

Table 84

The compounds in Table 84 are of the general formula (I) where Q1 is methyl, Q2 is iodo, Q3 is fluoro, L is O, R¹ is thioethyl, and R² and R³ have the values given in the Table 1. Thus, compound 1 of Table 84 is the same as compound 1 of Table 1 except that in compound 1 of Table 84 Q2 is iodo, Q3 is fluoro and R¹ is thioethyl. Similarly, compounds 2 to 379 of Table 84 are the same as compounds 2 to 379 of Table 1, respectively, except that in the compounds of Table 84 Q2 is iodo, Q3 is fluoro and R¹ is thioethyl.

Table 85

The compounds in Table 85 are of the general formula (I) where Q1 is methyl, Q2 is methyl, Q3 is methyl, L is O, $R^1$ is methyl, and $R^2$ and $R^3$ have the values given in the Table 1. Thus, compound 1 of Table 85 is the same as compound 1 of Table 1 except that in compound 1 of Table 85 Q2 is methyl and Q3 is methyl. Similarly, compounds 2 to 379 of Table 85 are the same as compounds 2 to 379 of Table 1, respectively, except that in the compounds of Table 85 Q2 is methyl and Q3 is methyl.

Table 86

The compounds in Table 86 are of the general formula (I) where Q1 is methyl, Q2 is methyl, Q3 is methyl, L is O, $R^1$ is ethyl, and $R^2$ and $R^3$ have the values given in the Table 1. Thus, compound 1 of Table 86 is the same as compound 1 of Table 1 except that in compound 1 of Table 86 Q2 is methyl, Q3 is methyl and $R^1$ is ethyl. Similarly, compounds 2 to 379 of Table 86 are the same as compounds 2 to 379 of Table 1, respectively, except that in the compounds of Table 86 Q2 is methyl, Q3 is methyl and $R^1$ is ethyl.

Table 87

The compounds in Table 87 are of the general formula (I) where Q1 is methyl, Q2 is methyl, Q3 is methyl, L is O, $R^1$ is methoxy, and $R^2$ and $R^3$ have the values given in the Table 1. Thus, compound 1 of Table 87 is the same as compound 1 of Table 1 except that in compound 1 of Table 87 Q2 is methyl, Q3 is methyl and $R^1$ is methoxy. Similarly, compounds 2 to 379 of Table 87 are the same as compounds 2 to 379 of Table 1, respectively, except that in the compounds of Table 87 Q2 is methyl, Q3 is methyl and $R^1$ is methoxy.

Table 88

The compounds in Table 88 are of the general formula (I) where Q1 is methyl, Q2 is methyl, Q3 is methyl, L is O, $R^1$ is ethoxy, and $R^2$ and $R^3$ have the values given in the Table 1. Thus, compound 1 of Table 88 is the same as compound 1 of Table 1 except that in compound 1 of Table 88 Q2 is methyl, Q3 is methyl and $R^1$ is ethoxy. Similarly, compounds 2 to 379 of Table 88 are the same as compounds 2 to 379 of Table 1, respectively, except that in the compounds of Table 88 Q2 is methyl, Q3 is methyl and $R^1$ is ethoxy.

Table 89

The compounds in Table 89 are of the general formula (I) where Q1 is methyl, Q2 is methyl, Q3 is methyl, L is O, $R^1$ is thiomethyl, and $R^2$ and $R^3$ have the values given in the Table 1. Thus, compound 1 of Table 89 is the same as compound 1 of Table 1 except that in compound 1 of Table 89 Q2 is methyl, Q3 is methyl and $R^1$ is thiomethyl. Similarly, compounds 2 to 379 of Table 89 are the same as compounds 2 to 379 of Table 1, respectively, except that in the compounds of Table 89 Q2 is methyl, Q3 is methyl and $R^1$ is thiomethyl.

Table 90

The compounds in Table 90 are of the general formula (I) where Q1 is methyl, Q2 is methyl, Q3 is methyl, L is O, $R^1$ is thioethyl, and $R^2$ and $R^3$ have the values given in the Table 1. Thus, compound 1 of Table 90 is the same as compound 1 of Table 1 except that in compound 1 of Table 90 Q2 is methyl, Q3 is methyl and $R^1$ is thioethyl. Similarly, compounds 2 to 379 of Table 90 are the same as compounds 2 to 379 of Table 1, respectively, except that in the compounds of Table 90 Q2 is methyl, Q3 is methyl and $R^1$ is thioethyl.

Table 91

The compounds in Table 91 are of the general formula (I) where Q1 is methyl, Q2 is fluoro, Q3 is methyl, L is O, $R^1$ is methyl, and $R^2$ and $R^3$ have the values given in the Table 1. Thus, compound 1 of Table 91 is the same as compound 1 of Table 1 except that in compound 1 of Table 91 Q2 is fluoro and Q3 is methyl. Similarly, compounds 2 to 379 of Table 91 are the same as compounds 2 to 379 of Table 1, respectively, except that in the compounds of Table 91 Q2 is fluoro and Q3 is methyl.

Table 92

The compounds in Table 92 are of the general formula (I) where Q1 is methyl, Q2 is fluoro, Q3 is methyl, L is O, $R^1$ is ethyl, and $R^2$ and $R^3$ have the values given in the Table 1. Thus, compound 1 of Table 92 is the same as compound 1 of Table 1 except that in compound 1 of Table 92 Q2 is fluoro, Q3 is methyl and $R^1$ is ethyl. Similarly, compounds 2 to 379 of Table 92 are the same as compounds 2 to 379 of Table 1, respectively, except that in the compounds of Table 92 Q2 is fluoro, Q3 is methyl and $R^1$ is ethyl.

Table 93

The compounds in Table 93 are of the general formula (I) where Q1 is methyl, Q2 is fluoro, Q3 is methyl, L is O, $R^1$ is methoxy, and $R^2$ and $R^3$ have the values given in the Table 1. Thus, compound 1 of Table 93 is the same as compound 1 of Table 1 except that in compound 1 of Table 93 Q2 is fluoro, Q3 is methyl and $R^1$ is methoxy. Similarly, compounds 2 to 379 of Table 93 are the same as compounds 2 to 379 of Table 1, respectively, except that in the compounds of Table 93 Q2 is fluoro, Q3 is methyl and $R^1$ is methoxy.

Table 94

The compounds in Table 94 are of the general formula (I) where Q1 is methyl, Q2 is fluoro, Q3 is methyl, L is O, $R^1$ is ethoxy, and $R^2$ and $R^3$ have the values given in the Table 1. Thus, compound 1 of Table 94 is the same as compound 1 of Table 1 except that in compound 1 of Table 94 Q2 is fluoro, Q3 is methyl and $R^1$ is ethoxy. Similarly, compounds 2 to 379 of Table 94 are the same as compounds 2 to 379 of Table 1, respectively, except that in the compounds of Table 94 Q2 is fluoro, Q3 is methyl and $R^1$ is ethoxy.

Table 95

The compounds in Table 95 are of the general formula (I) where Q1 is methyl, Q2 is fluoro, Q3 is methyl, L is O, $R^1$ is thiomethyl, and $R^2$ and $R^3$ have the values given in the Table 1. Thus, compound 1 of Table 95 is the same as compound 1 of Table 1 except that in compound 1 of Table 95 Q2 is fluoro, Q3 is methyl and $R^1$ is thiomethyl. Similarly, compounds 2 to 379 of Table 95 are the same as compounds 2 to 379 of Table 1, respectively, except that in the compounds of Table 95 Q2 is fluoro, Q3 is methyl and $R^1$ is thiomethyl.

Table 96

The compounds in Table 96 are of the general formula (I) where Q1 is methyl, Q2 is fluoro, Q3 is methyl, L is O, $R^1$ is thioethyl, and $R^2$ and $R^3$ have the values given in the Table 1. Thus, compound 1 of Table 96 is the same as compound 1 of Table 1 except that in compound 1 of Table 96 Q2 is fluoro, Q3 is methyl and $R^1$ is thioethyl. Similarly, compounds 2 to 379 of Table 96 are the same as compounds 2 to 379 of Table 1, respectively, except that in the compounds of Table 96 Q2 is fluoro, Q3 is methyl and $R^1$ is thioethyl.

Table 97

The compounds in Table 97 are of the general formula (I) where Q1 is methyl, Q2 is chloro, Q3 is methyl, L is O, $R^1$ is methyl, and $R^2$ and $R^3$ have the values given in the Table 1. Thus, compound 1 of Table 97 is the same as compound 1 of Table 1 except that in compound 1 of Table 97 Q2 is chloro and Q3 is methyl. Similarly, compounds 2 to 379 of Table 97 are the same as compounds 2 to 379 of Table 1, respectively, except that in the compounds of Table 97 Q2 is chloro and Q3 is methyl.

Table 98

The compounds in Table 98 are of the general formula (I) where Q1 is methyl, Q2 is chloro, Q3 is methyl, L is O, $R^1$ is ethyl, and $R^2$ and $R^3$ have the values given in the Table 1.

Thus, compound 1 of Table 98 is the same as compound 1 of Table 1 except that in compound 1 of Table 98 Q2 is chloro, Q3 is methyl and $R^1$ is ethyl. Similarly, compounds 2 to 379 of Table 98 are the same as compounds 2 to 379 of Table 1, respectively, except that in the compounds of Table 98 Q2 is chloro, Q3 is methyl and $R^1$ is ethyl.

Table 99

The compounds in Table 99 are of the general formula (I) where Q1 is methyl, Q2 is chloro, Q3 is methyl, L is O, $R^1$ is methoxy, and $R^2$ and $R^3$ have the values given in the Table 1. Thus, compound 1 of Table 99 is the same as compound 1 of Table 1 except that in compound 1 of Table 99 Q2 is chloro, Q3 is methyl and $R^1$ is methoxy. Similarly, compounds 2 to 379 of Table 99 are the same as compounds 2 to 379 of Table 1, respectively, except that in the compounds of Table 99 Q2 is chloro, Q3 is methyl and $R^1$ is methoxy.

Table 100

The compounds in Table 100 are of the general formula (I) where Q1 is methyl, Q2 is chloro, Q3 is methyl, L is O, $R^1$ is ethoxy, and $R^2$ and $R^3$ have the values given in the Table 1. Thus, compound 1 of Table 100 is the same as compound 1 of Table 1 except that in compound 1 of Table 100 Q2 is chloro, Q3 is methyl and $R^1$ is ethoxy. Similarly, compounds 2 to 379 of Table 100 are the same as compounds 2 to 379 of Table 1, respectively, except that in the compounds of Table 100 Q2 is chloro, Q3 is methyl and $R^1$ is ethoxy.

Table 101

The compounds in Table 101 are of the general formula (I) where Q1 is methyl, Q2 is chloro, Q3 is methyl, L is O, $R^1$ is thiomethyl, and $R^2$ and $R^3$ have the values given in the Table 1. Thus, compound 1 of Table 101 is the same as compound 1 of Table 1 except that in compound 1 of Table 101 Q2 is chloro, Q3 is methyl and $R^1$ is thiomethyl. Similarly, compounds 2 to 379 of Table 101 are the same as compounds 2 to 379 of Table 1, respectively, except that in the compounds of Table 101 Q2 is chloro, Q3 is methyl and $R^1$ is thiomethyl.

Table 102

The compounds in Table 102 are of the general formula (I) where Q1 is methyl, Q2 is chloro, Q3 is methyl, L is O, $R^1$ is thioethyl, and $R^2$ and $R^3$ have the values given in the Table 1. Thus, compound 1 of Table 102 is the same as compound 1 of Table 1 except that in compound 1 of Table 102 Q2 is chloro, Q3 is methyl and $R^1$ is thioethyl. Similarly, compounds 2 to 379 of Table 102 are the same as compounds 2 to 379 of Table 1, respectively, except that in the compounds of Table 102 Q2 is chloro, Q3 is methyl and $R^1$ is thioethyl.

Table 103

The compounds in Table 103 are of the general formula (I) where Q1 is methyl, Q2 is bromo, Q3 is methyl, L is O, $R^1$ is methyl, and $R^2$ and $R^3$ have the values given in the Table 1. Thus, compound 1 of Table 103 is the same as compound 1 of Table 1 except that in compound 1 of Table 103 Q2 is bromo and Q3 is methyl. Similarly, compounds 2 to 379 of Table 103 are the same as compounds 2 to 379 of Table 1, respectively, except that in the compounds of Table 103 Q2 is bromo and Q3 is methyl.

Table 104

The compounds in Table 104 are of the general formula (I) where Q1 is methyl, Q2 is bromo, Q3 is methyl, L is O, $R^1$ is ethyl, and $R^2$ and $R^3$ have the values given in the Table 1. Thus, compound 1 of Table 104 is the same as compound 1 of Table 1 except that in compound 1 of Table 104 Q2 is bromo, Q3 is methyl and $R^1$ is ethyl. Similarly, compounds 2 to 379 of Table 104 are the same as compounds 2 to 379 of Table 1, respectively, except that in the compounds of Table 104 Q2 is bromo, Q3 is methyl and $R^1$ is ethyl.

Table 105

The compounds in Table 105 are of the general formula (I) where Q1 is methyl, Q2 is bromo, Q3 is methyl, L is O, $R^1$ is methoxy, and $R^2$ and $R^3$ have the values given in the Table 1. Thus, compound 1 of Table 105 is the same as compound 1 of Table 1 except that in compound 1 of Table 105 Q2 is bromo, Q3 is methyl and $R^1$ is methoxy. Similarly, compounds 2 to 379 of Table 105 are the same as compounds 2 to 379 of Table 1, respectively, except that in the compounds of Table 105 Q2 is bromo, Q3 is methyl and $R^1$ is methoxy.

Table 106

The compounds in Table 106 are of the general formula (I) where Q1 is methyl, Q2 is bromo, Q3 is methyl, L is O, $R^1$ is ethoxy, and $R^2$ and $R^3$ have the values given in the Table 1. Thus, compound 1 of Table 106 is the same as compound 1 of Table 1 except that in compound 1 of Table 106 Q2 is bromo, Q3 is methyl and $R^1$ is ethoxy. Similarly, compounds 2 to 379 of Table 106 are the same as compounds 2 to 379 of Table 1, respectively, except that in the compounds of Table 106 Q2 is bromo, Q3 is methyl and $R^1$ is ethoxy.

Table 107

The compounds in Table 107 are of the general formula (I) where Q1 is methyl, Q2 is bromo, Q3 is methyl, L is O, $R^1$ is thiomethyl, and $R^2$ and $R^3$ have the values given in the Table 1. Thus, compound 1 of Table 107 is the same as compound 1 of Table 1 except that in compound 1 of Table 107 Q2 is bromo, Q3 is methyl and $R^1$ is thiomethyl. Similarly, compounds 2 to 379 of Table 107 are the same as compounds 2 to 379 of Table 1, respectively, except that in the compounds of Table 107 Q2 is bromo, Q3 is methyl and $R^1$ is thiomethyl.

Table 108

The compounds in Table 108 are of the general formula (I) where Q1 is methyl, Q2 is bromo, Q3 is methyl, L is O, $R^1$ is thioethyl, and $R^2$ and $R^3$ have the values given in the Table 1. Thus, compound 1 of Table 108 is the same as compound 1 of Table 1 except that in compound 1 of Table 108 Q2 is bromo, Q3 is methyl and $R^1$ is thioethyl. Similarly, compounds 2 to 379 of Table 108 are the same as compounds 2 to 379 of Table 1, respectively, except that in the compounds of Table 108 Q2 is bromo, Q3 is methyl and $R^1$ is thioethyl.

Table 109

The compounds in Table 109 are of the general formula (I) where Q1 is methyl, Q2 is iodo, Q3 is methyl, L is O, $R^1$ is methyl, and $R^2$ and $R^3$ have the values given in the Table 1. Thus, compound 1 of Table 109 is the same as compound 1 of Table 1 except that in compound 1 of Table 109 Q2 is iodo and Q3 is methyl. Similarly, compounds 2 to 379 of Table 109 are the same as compounds 2 to 379 of Table 1, respectively, except that in the compounds of Table 109 Q2 is iodo and Q3 is methyl.

Table 110

The compounds in Table 110 are of the general formula (I) where Q1 is methyl, Q2 is iodo, Q3 is methyl, L is O, $R^1$ is ethyl, and $R^2$ and $R^3$ have the values given in the Table 1. Thus, compound 1 of Table 110 is the same as compound 1 of Table 1 except that in compound 1 of Table 110 Q2 is iodo, Q3 is methyl and $R^1$ is ethyl. Similarly, compounds 2 to 379 of Table 110 are the same as compounds 2 to 379 of Table 1, respectively, except that in the compounds of Table 110 Q2 is iodo, Q3 is methyl and $R^1$ is ethyl.

Table 111

The compounds in Table 111 are of the general formula (I) where Q1 is methyl, Q2 is iodo, Q3 is methyl, L is O, $R^1$ is methoxy, and $R^2$ and $R^3$ have the values given in the Table 1. Thus, compound 1 of Table 111 is the same as compound 1 of Table 1 except that in compound 1 of Table 111 Q2 is iodo, Q3 is methyl and $R^1$ is methoxy. Similarly, compounds 2 to 379 of Table 111 are the same as compounds 2 to 379 of Table 1, respectively, except that in the compounds of Table 111 Q2 is iodo, Q3 is methyl and $R^1$ is methoxy.

Table 112

The compounds in Table 112 are of the general formula (I) where Q1 is methyl, Q2 is iodo, Q3 is methyl, L is O, $R^1$ is ethoxy, and $R^2$ and $R^3$ have the values given in the Table 1. Thus, compound 1 of Table 112 is the same as compound 1 of Table 1 except that in compound 1 of Table 112 Q2 is iodo, Q3 is methyl and $R^1$ is ethoxy. Similarly, compounds 2 to 379 of Table 112 are the same as compounds 2 to 379 of Table 1, respectively, except that in the compounds of Table 112 Q2 is iodo, Q3 is methyl and $R^1$ is ethoxy.

Table 113

The compounds in Table 113 are of the general formula (I) where Q1 is methyl, Q2 is iodo, Q3 is methyl, L is O, $R^1$ is thiomethyl, and $R^2$ and $R^3$ have the values given in the Table 1. Thus, compound 1 of Table 113 is the same as compound 1 of Table 1 except that in compound 1 of Table 113 Q2 is iodo, Q3 is methyl and $R^1$ is thiomethyl. Similarly, compounds 2 to 379 of Table 113 are the same as compounds 2 to 379 of Table 1, respectively, except that in the compounds of Table 113 Q2 is iodo, Q3 is methyl and $R^1$ is thiomethyl.

Table 114

The compounds in Table 114 are of the general formula (I) where Q1 is methyl, Q2 is iodo, Q3 is methyl, L is O, $R^1$ is thioethyl, and $R^2$ and $R^3$ have the values given in the Table 1. Thus, compound 1 of Table 114 is the same as compound 1 of Table 1 except that in compound 1 of Table 114 Q2 is iodo, Q3 is methyl and $R^1$ is thioethyl. Similarly, compounds 2 to 379 of Table 114 are the same as compounds 2 to 379 of Table 1, respectively, except that in the compounds of Table 114 Q2 is iodo, Q3 is methyl and $R^1$ is thioethyl.

Tables 115 to 120

Tables 115 to 120 correspond exactly to Tables 37 to 42 (i.e. Table 115 corresponds exactly to Table 37, Table 116 corresponds exactly to Table 38, and so on) the only difference being that in each of Tables 115 to 120, Q3 is bromo instead of methyl.

Tables 121 to 150

Tables 121 to 150 correspond exactly to Tables 55 to 84 (i.e. Table 121 corresponds exactly to Table 55, Table 122 corresponds exactly to Table 56, and so on) the only difference being that in each of Tables 121 to 150, Q3 is cloro instead of fluoro.

Tables 151 to 180

Tables 151 to 180 correspond exactly to Tables 55 to 84 (i.e. Table 151 corresponds exactly to Table 55, Table 152 corresponds exactly to Table 56, and so on) the only difference being that in each of Tables 151 to 180, Q3 is bromo instead of fluoro.

Tables 181 to 360

Tables 181 to 360 correspond exactly to Tables 1 to 180 (i.e. Table 181 corresponds exactly to Table 1, Table 182 corresponds exactly to Table 2, and so on) the only difference being that in each of Tables 181 to 360, Q1 is hydroxymethyl instead of methyl.

Tables 361 to 540

Tables 361 to 540 correspond exactly to Tables 1 to 180 (i.e. Table 361 corresponds exactly to Table 1, Table 362 corresponds exactly to Table 2, and so on) the only difference being that in each of Tables 361 to 540, Q1 is methoxymethyl instead of methyl.

Tables 541 to 720

Tables 541 to 720 correspond exactly to Tables 1 to 180 (i.e. Table 541 corresponds exactly to Table 1, Table 542 corresponds exactly to Table 2, and so on) the only difference being that in each of Tables 541 to 720, Q1 is fluoromethyl instead of methyl.

Tables 721 to 900

Tables 721 to 900 correspond exactly to Tables 1 to 180 (i.e. Table 721 corresponds exactly to Table 1, Table 722 corresponds exactly to Table 2, and so on) the only difference being that in each of Tables 721 to 900, Q1 is trimethylsilyl instead of methyl.

Tables 901 to 1080

Tables 901 to 1080 correspond exactly to Tables 1 to 180 (i.e. Table 901 corresponds exactly to Table 1, Table 902 corresponds exactly to Table 2, and so on) the only difference being that in each of Tables 901 to 1080, Q1 is hydrogen instead of methyl.

Tables 1081 to 1260

Tables 1081 to 1260 correspond exactly to Tables 1 to 180 (i.e. Table 1081 corresponds exactly to Table 1, Table 1082 corresponds exactly to Table 2, and so on) the only difference being that in each of Tables 1081 to 1260, Q1 is triisopropylsilyl instead of methyl.

Tables 1261 to 1440

Tables 1261 to 1440 correspond exactly to Tables 1 to 180 (i.e. Table 1261 corresponds exactly to Table 1, Table 1262 corresponds exactly to Table 2, and so on) the only difference being that in each of Tables 1261 to 1440, Q1 is 1-hydroxy-1-methyl-eth-1-yl instead of methyl.

Tables 1441 to 1620

Tables 1441 to 1620 correspond exactly to Tables 1 to 180 (i.e. Table 1441 corresponds exactly to Table 1, Table 1442 corresponds exactly to Table 2, and so on) the only difference being that in each of Tables 1441 to 1620, Q1 is bromine instead of methyl.

Tables 1621 to 1800

Tables 1621 to 1800 correspond exactly to Tables 1 to 180 (i.e. Table 1621 corresponds exactly to Table 1, Table 1622 corresponds exactly to Table 2, and so on) the only difference being that in each of Tables 1621 to 1800, Q1 is chloromethyl instead of methyl.

Tables 1801 to 1980

Tables 1801 to 1980 correspond exactly to Tables 1 to 180 (i.e. Table 1801 corresponds exactly to Table 1, Table 1802 corresponds exactly to Table 2, and so on) the only difference being that in each of Tables 1801 to 1980, Q1 is $CH_3OCH_2OCH_2$-instead of methyl The compounds of formula (1) may be prepared as outlined in Schemes 1 to 8, 16 and 18-24 below in which Q1, Q2, Q3, $R^1$, $R^2$, $R^3$ have the meanings given above and L is O unless otherwise indicated in the text. As shown in Scheme 1, the compounds of general formula (I) may be prepared by Sonogashira reaction which is known to those skilled in the art by reacting a compound of the general formula (2) (halo=Cl, Br, I) with a compound of the general formula (3) in the presence of a transition metal catalyst, a copper salt and a base, in a suitable solvent. Typical solvents include THF, N,N-dimethylformamide, N-methylpyrrolidin-2-one, toluene, benzene, alkylamines (ie triethylamine, isopropylamine, diethylamine), acetonitrile. Suitable bases include amines like triethylamine, diethylamine, diisopropylamine, diisopropylethylamine, piperidine, pyrrolidine or potassium carbonate. Typical catalysts are homogeneous or heterogeneous palladium(0) or palladium (II) catalysts with suitable ligands.

Typical copper salt are copper iodide and copper bromide and are usually applied in substoichiometric amounts.

It is noteworthy that the brief description on each of the arrows for each conversion is for illustration purposes only and should not be regarded as limiting with respect to the sequence or each individual step.

Where typical or preferred process conditions (reaction temperature, time, solvent, mole ratios of reactants) are given, unless otherwise stated other process conditions can also be used. While optimum reaction conditions may vary with the particular reactants or solvents used, such conditions can be determined by routine optimisation procedures by one skilled in the art.

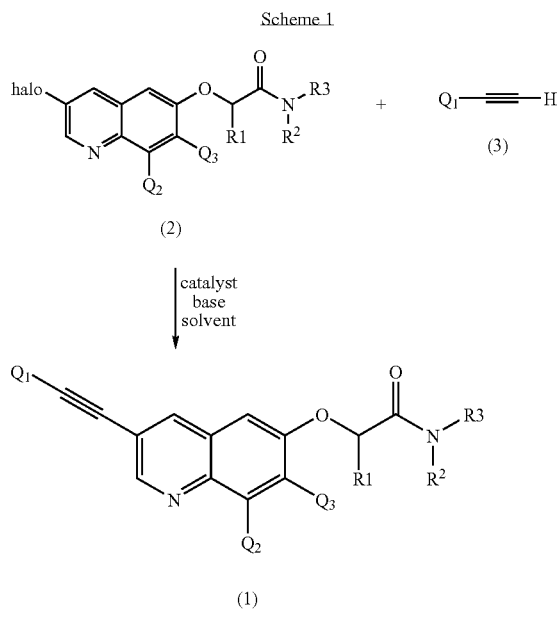

Alternatively as shown in Scheme 2, compounds of the general formula (1) may be prepared by reacting an amine of the general formula (4) with an acid derivatives such as an acid halide or the corresponding acid anhydride of the general formula (5), in the presence of a suitable inorganic or organic base, such as potassium carbonate or diisopropylethylamine, in a solvent such as dichloromethane, tetrahydrofuran or, N,N-dimethylformamide.

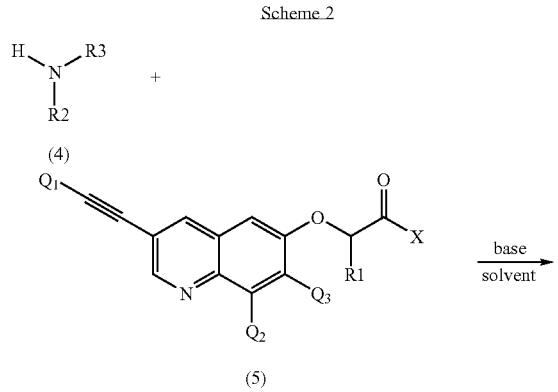

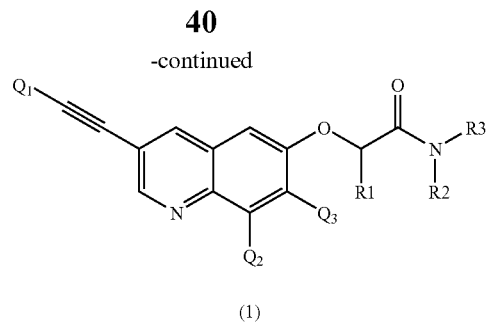

Alternatively, as shown in Scheme 3, compounds of the general formula (1) may be prepared by condensing a carboxylic acid of the general formula (6) with an amine of the general formula (4) using suitable activating reagents such as 1-hydroxybenzotriazole (HOBt), (benzotriazol-1-yloxy)-tris-(dimethylamino)-phosphonium-hexa-fluorophosphate (BOP), 1-hydroxy-7-azabenzotriazole (HOAT), N-(3-dimethylamino-propyl)-N'-ethyl-carbodiimide hydrochloride (EDC) or O-(Benzotriazol-1-yl)-N,N,N',N'-tetramethyluronium tetrafluoroborate (TBTU).

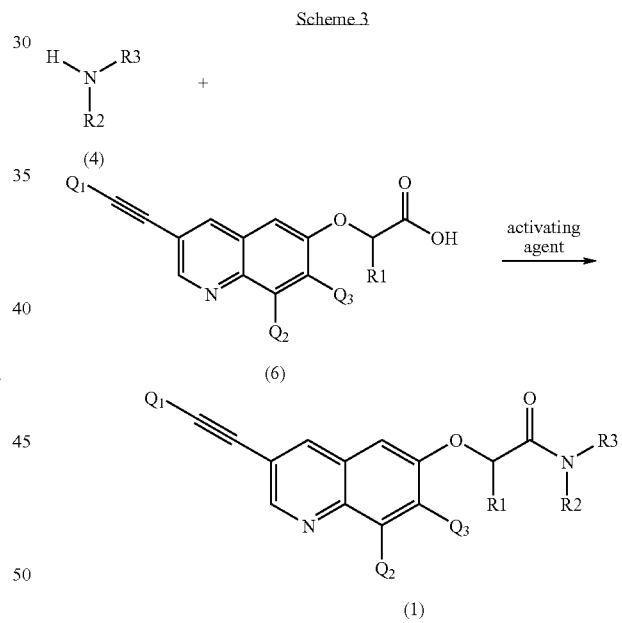

Compounds of general formula (6) or (8) can be prepared according to Scheme 4 by hydrolysis of ester (9) wherein $R^{10}$ is $C_{1-4}$ alkyl, in the presence of an alkali metal hydroxide $M^+OH^-$ (ie NaOH or LiOH) in a suitable solvent such as aqueous methanol, ethanol or THF (tetrahydrofuran) between ambient temperature and reflux, followed by acidification. Alternatively, acids of general formula (6) can be prepared by Sonogashira reaction of compounds with general formula (8) using a suitable catalyst, base and solvent (as previously described in Scheme 1).

Scheme 4

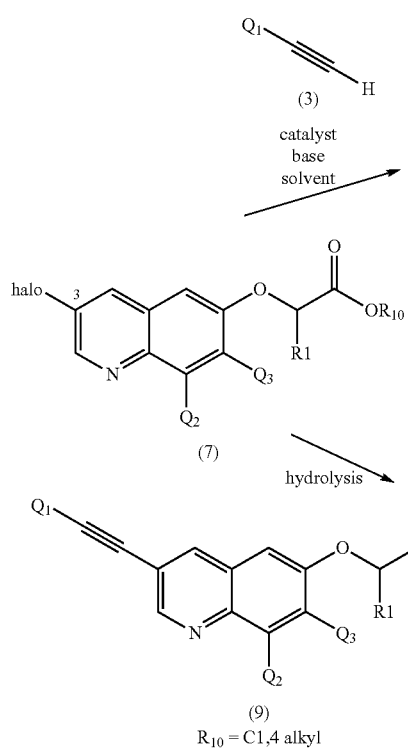

Scheme 5

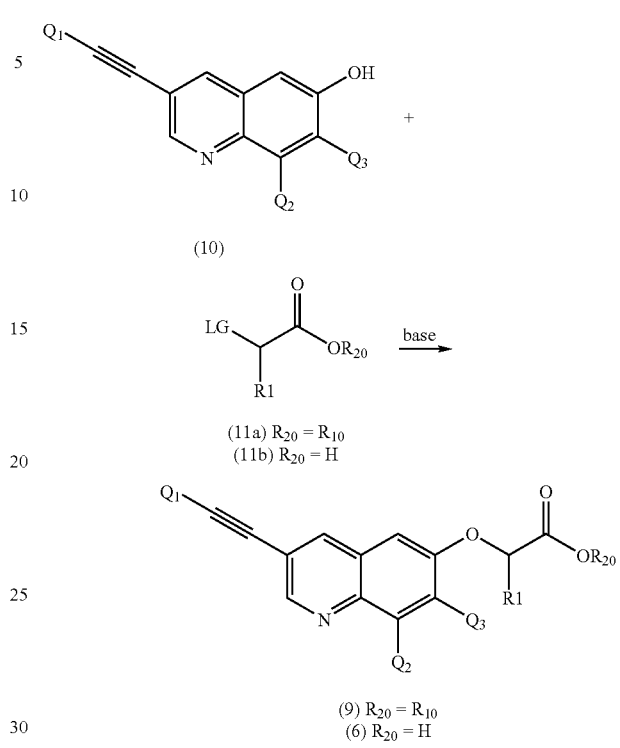

LG = leaving group

Compounds of general formula (9) can be prepared by applying suitable reaction conditions for Sonogashira coupling to ester of general formula (7), as shown in Scheme 4. Alternatively, as shown in Scheme 5, esters of general formula (9) and acids of general formula (6) may be prepared by reacting a compound of the general formula (10) with an ester or acid of general formula (11a) or (11b) respectively in the presence of a suitable base, such as potassium carbonate, calcium hydroxide, metal alkoxydes or sodium hydride, in a suitable solvent, such as N,N-dimethylformamide or THF (tetrahydrofuran).

Alternatively, as shown in Scheme 6, compound of general formula (9) may be prepared under Mitsunobu conditions by reacting a compound of the general formula (10) with a compound of the general formula (11c) wherein $R^{20}$ is (equal to $R^{10}$) $C_{1-4}$ alkyl, using a phosphine, such as triphenylphosphine and an azoester, such diethylazodicarboxylate or diisopripylazodicarboxylate.

Scheme 6

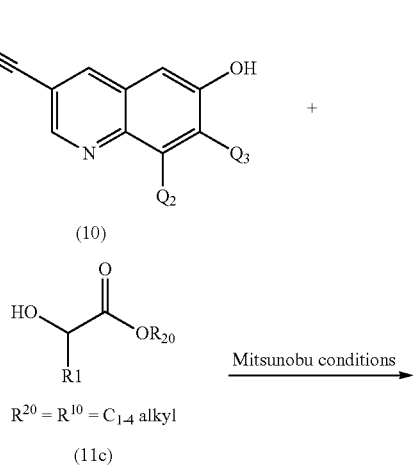

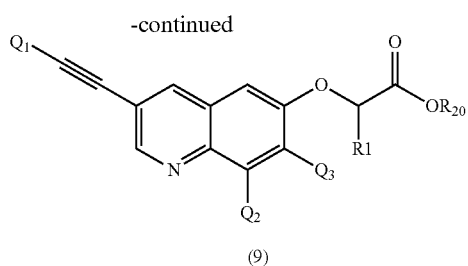

In another approach towards the preparation of compounds of the general formula (1) shown in Scheme 7, compound of general formula (11d) may be reacted with a compound of the general formula (10) under Mitsunobu conditions using a phosphine, such as triphenyl phosphine, and an azoester, such as diethyl azodicarboxylate. Compounds of general formula (11d) may be prepared from a compound of general formula (11c) where $R^{20}$ is hydrogen and an amine of general formula (4) using suitable activating reagents such as 1-hydroxybenzotriazole and N-(3-dimethylaminopropyl)-N'-ethyl-carbodiimide hydrochloride.

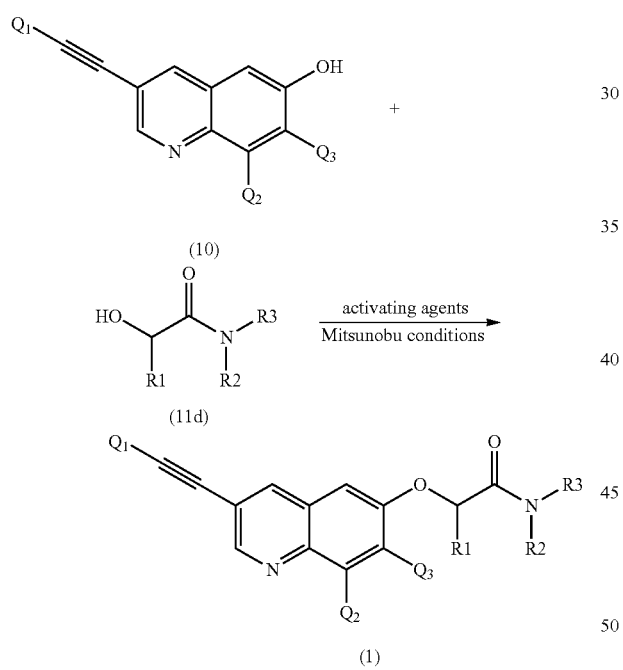

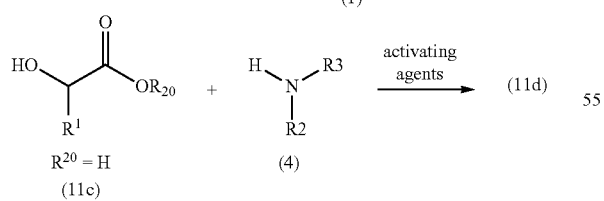

In another approach towards the preparation of compounds of the general formula (1) shown in Scheme 8, compound of general formula (11e) where LG is a leaving group (ie halogen, in particular Br and Cl) may be reacted with a compound of the general formula (10) in the presence of a base in a suitable solvent. Typical solvent include N,N-dimethylformamide, N-methylpyrrolidin-2-one, THF (tetrahydrofurane). Suitable bases include potassium carbonate, sodium hydride, metal alkoxydes, pyridine or diisopropylamine. Compound of general formula (11e) may be prepared by reacting an amine of general formula (4) with an activated carboxylic acid such as an halide or the corresponding acid anhydride of the general formula (11f), in the presence of a suitable inorganic or organic base, such as potassium carbonate or diisopropylamine, in a solvent such as dichloromethane, THF (tetrahydrofurane) or N,N-dimethylformamide.

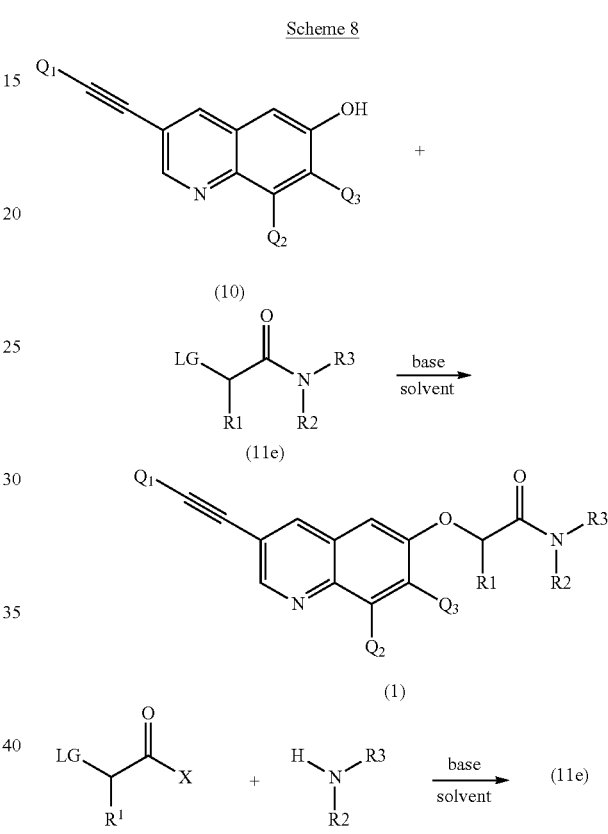

Compound of general formula (10) can be prepared using suitable reaction conditions for the Sonogashira coupling (as in Scheme 1 or Scheme 4) starting from 3-haloquinolin-6-ol derivatives of the general formula (12).

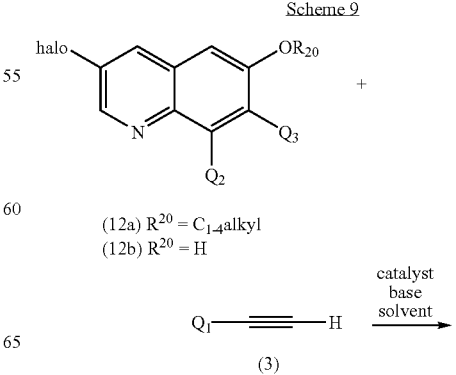

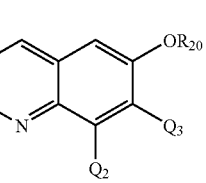

(10)

Compounds of general formula (2) and (7) may be prepared according to Scheme 5 to Scheme 8, under reaction conditions similar to those described above using starting materials of general formula (12b).

The substituted 6-hydroxy quinolines are available, or may be prepared using straightforward techniques of organic chemistry. When the compounds are not commercially available, they may be prepared from available precursors using straightforward transformations that are well known in the art that are well described in standard textbooks of heterocyclic chemistry. For example, substituted aromatic amines may be readily converted into substituted quinolin-6-ols with appropriate electrophiles, such as 2,2,3 tribromopropanal.

Compounds (11a), (11b) and (11c) are either known compounds or may be made from commercially available and/or known compounds by those skilled in the art. In addition, compounds of the general formula (9) wherein R1 is defined as in claim 1, may be prepared as shown in Scheme 10.

Thus, esters of the formula (13) may be halogenated to give haloesters of the general formula (14), by treatment with a suitable halogenating agent, such as N-bromosuccinimide, in a suitable solvent such as carbon tetrachloride, at between ambient temperature and the reflux temperature of the solvent. The haloesters of the general formula (9) can be reacted with an alkali metal compound $M^+OR_1$ or $M^+SR_1$, where M is suitably sodium or potassium in, for example, an alcohol $R_1OH$ or thiol $R_1SH$ as solvent, at between 0° C. and 60° C., preferably at ambient temperature, to give compounds of the general formula (9).

The same sequence may be applied to compounds bearing a halogen substituent at the 3 position of the quinoline ring instead of the alkynyl residue of general structure 13.

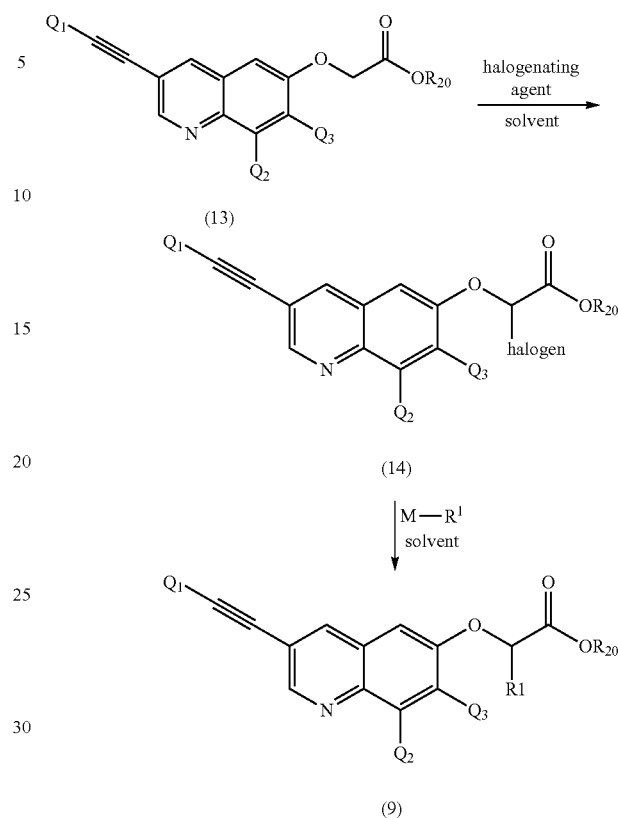

Compounds of general formula (I) where Q1 is H may be prepared according to Scheme 11 by Sonogashira reaction of a compound of general formula (2) with ethyne. Alternatively, compound (1) wherein Q1 is H may be prepared starting from compound of general formula (15b) by desilylation reaction using suitable bases like potassium carbonate, metal hydroxides or metal fluorides, in suitable solvent like methanol or tetrahydrofurane at temperature between ambient temperature and reflux. Or, compound (I) wherein Q1 is H may be prepared by treating compounds of general formula (15a) with suitable bases like metal hydroxides in suitable solvents like alcohols (ie isopropanol or ethanol) or toluene at temperature between ambient temperature and reflux.

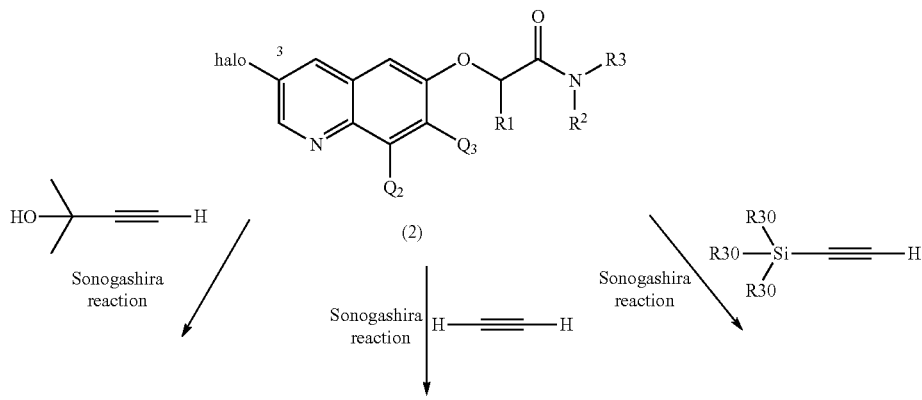

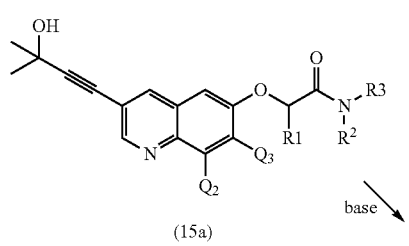

(15a)

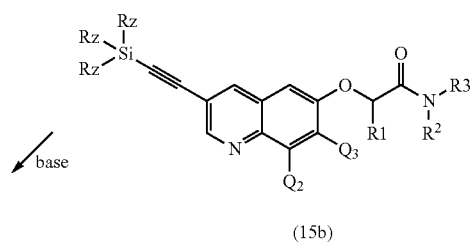

(15b)

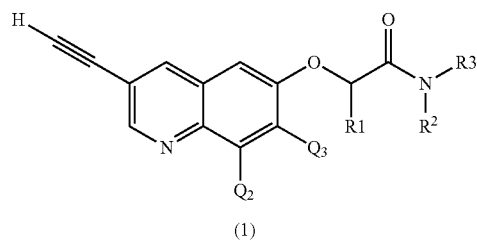

(1)

The sequences described in Scheme 11 may be applied to compounds of general formula (12a) and (12b), (8) or (7), according to Schemes 4 and 9 followed by the transformations described in the previous schemes to generate final compound of general formula (1). In a particular approach to the synthesis of compounds of general formula (1) wherein Q1 is H, as shown in Scheme 12, compound (16) is produced starting from compounds of general formula (7) using Sonogashira reaction conditions followed by treatment with a suitable base (ie NaOH) in a suitable solvent (ie EtOH and $H_2O$) to obtain compounds of general formula (6) wherein Q1 is H. Final compound of general formula (1) wherein Q1 is H may be obtained by condensing a carboxylic acid of the general formula (6) wherein Q1 is H with an amine of the general formula (4) using suitable activating reagents such as 1-hydroxybenzotriazole (HOBt), (benzotriazol-1-yloxy)-tris-(dimethylamino)-phosphonium-hexa-fluorophosphate (BOP), 1-hydroxy-7-azabenzotriazole (HOAT), N-(3-dimethylamino-propyl)-N'-ethyl-carbodiimide hydro-chloride (EDC) or O-(Benzotriazol-1-yl)-N,N,N',N'-tetramethyluronium tetrafluoro-borate (TBTU). Examples of such reactions are provided in Examples 1-12

Scheme 12

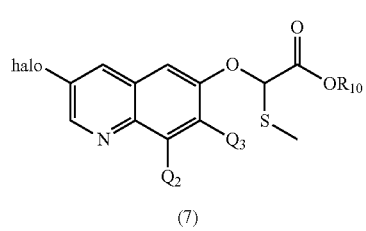

(7)

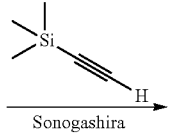

Sonogashira

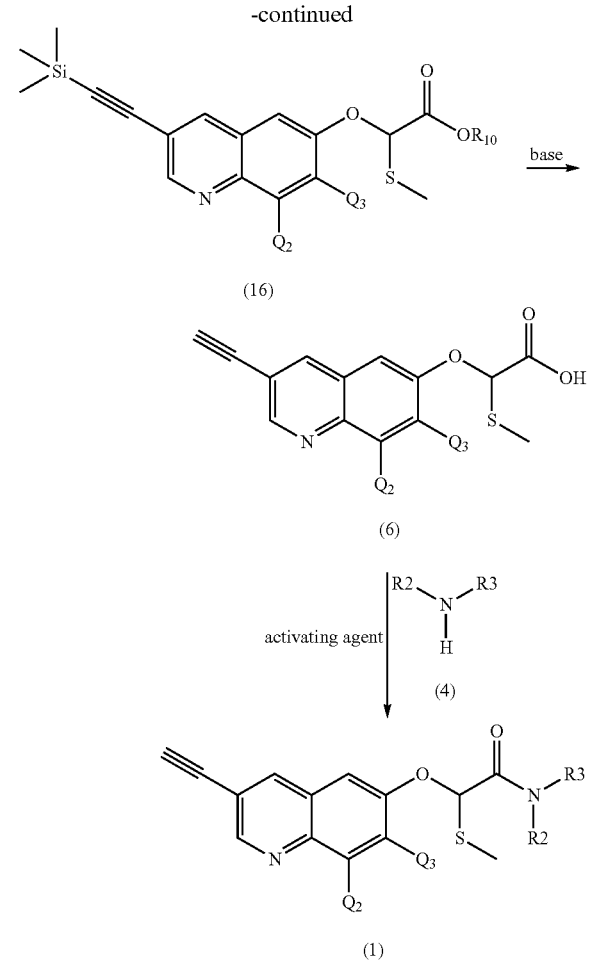

Compounds of general formula (2), (7) and (8) may be prepared by applying similar reaction conditions described in Schemes 2 to 3 and Schemes 5 to 8 to quinolinyl derivative bearing at the 3 position of the quinoline ring a halogen atom instead of an alkynyl residue, as recognised by those skilled in the art.

Compounds of general formula (2), (7) and (8), wherein the substituent at position 3 of the quinoline ring is halogen, are novel and have been specifically designed to be used by those skilled in the art as precursors to the compounds of the general formula (1) wherein the substituent at position 3 of the quinoline ring is Q1-C≡C, wherein Q1 is as defined above.

As shown in Scheme 13, amines of the general formula (18) or (20), which are examples of amines of the general formula (4) wherein $R^2$ is H, may be prepared by alkylation of an aminoalcohol of the general formula (17) or (19) using a suitable base, such as n-butyl lithium or sodium hydride, followed by reaction with a suitable alkylating reagent $R^{11}LG$, such as an alkyl iodide, for example, methyl iodide, to form an alkylated compound of the general formula (18) or (20), respectively. A carbonyl derivative $R^aCOR^b$ (21), for example formaldehyde, can be reacted with ammonia, usually in form of ammonium chloride, and cyanide, conveniently in form of an aqueous solution sodium cyanide, to provide an α-aminoalkyne (22) (Strecker synthesis).

Scheme 13

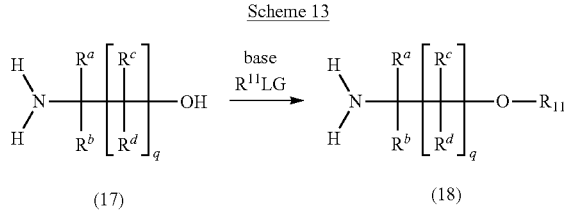

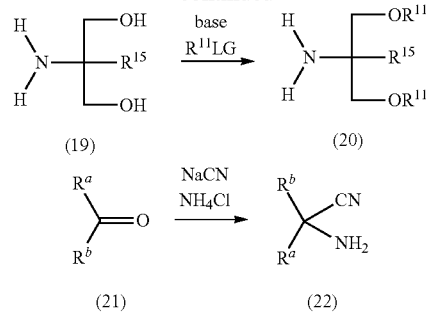

As shown in Scheme 14, silyl-protected aminoalkynes of the general formula (24) may be obtained by reacting amines of general formula (23) with 1,2-bis-(chlorodimethylsilyl)-ethane in the presence of a suitable base, such as a tertiary organic amine base, for example, triethylamine. Amines of the general formula (26), which are examples of amines of the general formula (4) wherein $R^2$ is H and $R^3$ is —$(CR^aR^b)$C≡$CR^5$, may be prepared by alkylation of a silyl-protected aminoalkyne of the general formula (24) using a suitable base, such as n-butyl lithium, followed by reaction with a suitable alkylating reagent $R^5LG$, such as an alkyl iodide, for example, methyl iodide, to form an alkylated compound of the general formula (25). The silyl protecting group may then be removed from a compound of the general formula (25) with, for example, an aqueous acid to form an aminoalkyne of the general formula (26).

Scheme 14

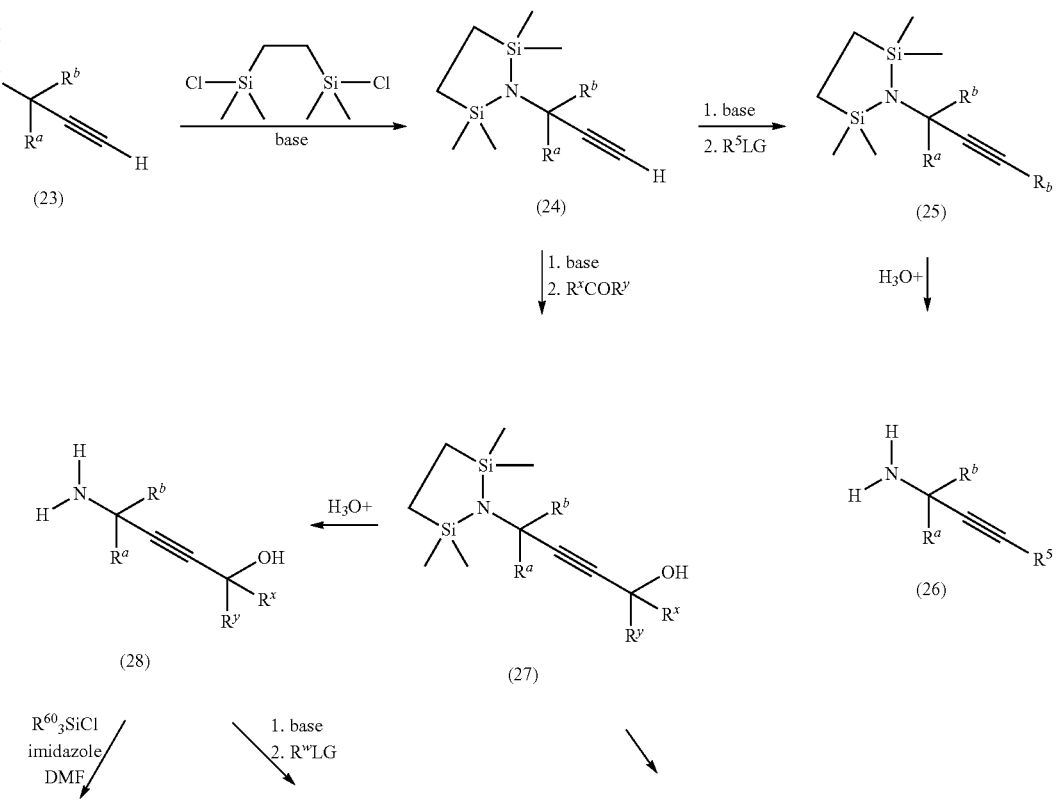

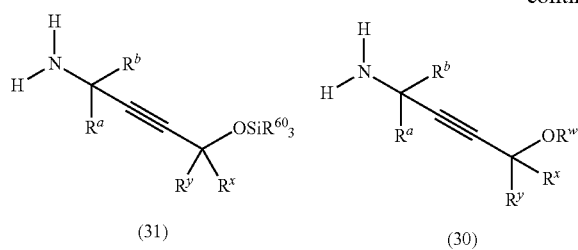 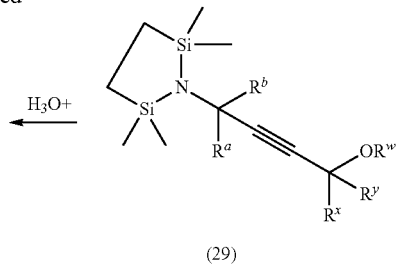

In a similar procedure, a silyl-protected aminoalkyne of the general formula (24) may be reacted with a carbonyl derivative $R^XCOR^Y$, for example formaldehyde, using a suitable base, such as n-butyl lithium, to provide an aminoalkyne (27) containing a hydroxyalkyl moiety. A compound of the general formula (27) may either first be treated with a base, such as sodium hydride or potassium bis(trimethylsilyl)amide followed by a compound $R^WLG$, where LG represents a leaving group such as a halogen, or sulphonate ester such as $OSO_2Me$, or $OSO_2$-4-tolyl, for example ethyl iodide, to give a compound of the general formula (29). After removal of the silyl protecting group, compounds of general formula (30) are obtained. Alternatively, the silyl protecting group can first be removed to yield compounds of the general formula (28). Aminoalkynes of the general formula (28) may be further derivatised by reacting with a silylating agent, for example t-butyl-dimethylsilyl chloride, to give a derivative silylated on oxygen of the general formula (31).

As shown in Scheme 15, silyl-protected aminoalkynes of the general formula (32) may be obtained by reacting silyl-protected amines of general formula (24) with chloro-alkanes bearing a suitable leaving group, for example bromide or iodide, in the presence of a suitable base, such as sodium or lithium amide base, for example, sodium bis(trimethylsilyl)amide or sodium amide. Amines of the general formula (34), which are examples of amines of the general formula (4) wherein $R^2$ is H and $R^3$ is —$(CR^aR^b)C\equiv CR^5$ may be prepared by displacement of chloride anion by cyanide, followed by removal of the silyl protecting group with, for example, an aqueous acid, to form a cyano compound of the general formula (34).

In a similar procedure, an amide of the general formula (35) can be reacted with, for example, potassium cyanide yielding a cyano amidoalkyne of the general formula (36).

Scheme 15

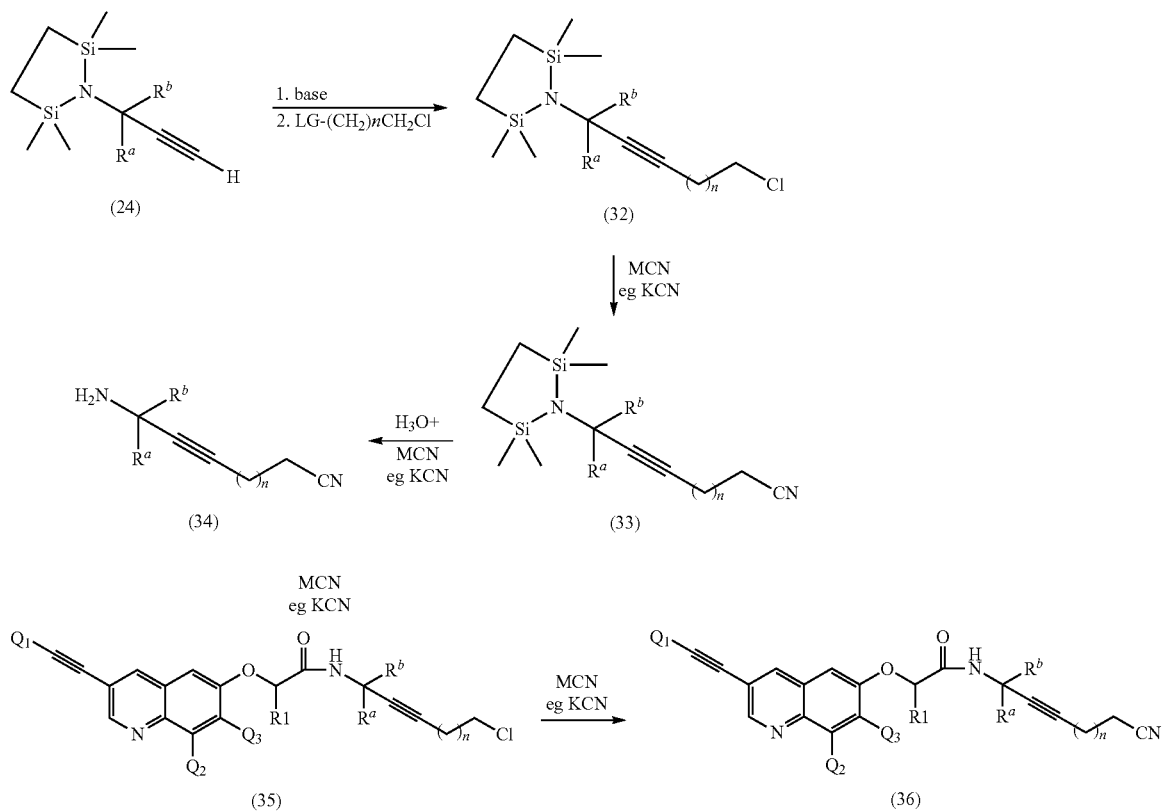

As shown in Scheme 16, compounds of the general formula (1), wherein $R^5$ is H, may be reacted under Sonogashira conditions with, for example, optionally substituted aryl or heteroaryl chlorides, bromides, iodides or triflates to form substituted aryl or heteroaryl compounds of general formula (37), which are examples of compounds of the general formula (1) wherein $R^5$ is an optionally substituted aryl or heteroaryl group. A suitable palladium catalyst is bis(triphenylphosphine)palladium (II) chloride.

Scheme 16

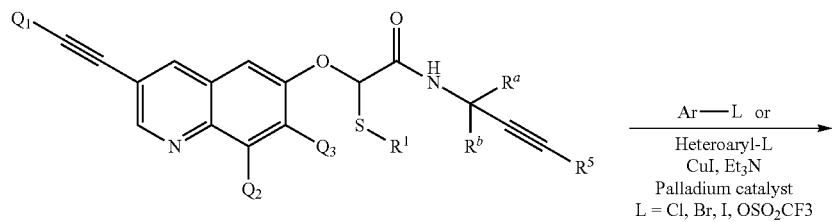

(1) where R2 = H and
R3 is ——$(CR^aR^b)CCR5$, R5 = H)

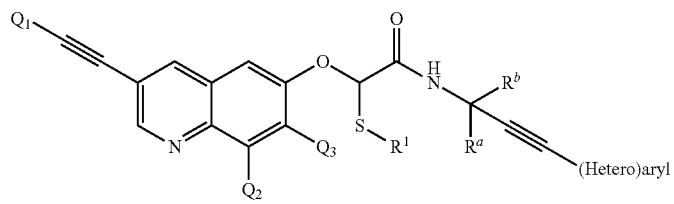

(37)

As illustrated in Scheme 17, alkyloxy-, alkenyloxy-, alkynyloxy- & hydroxyl-alkylamines of the general formula (42), wherein $R^6$ is $C_{1-4}$ alkyl, $C_{3-5}$ alkenyl, $C_{3-5}$ alkynyl, which are examples of amines of the general formula (4), may be prepared via a protection, alkylation and deprotection sequence using methods well known to those skilled in the art.

Scheme 17 eq. 1

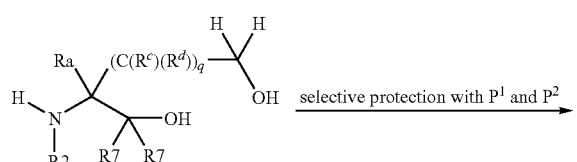

(38)

→ selective protection with $P^1$ and $P^2$

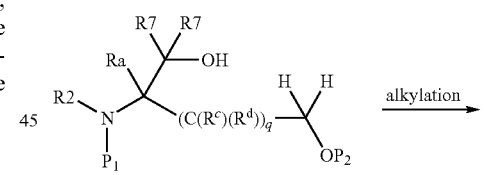

(39)

eq. 2 alkylation →

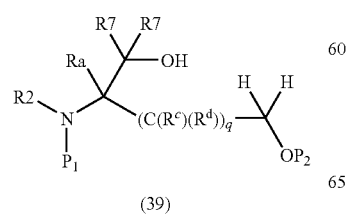

(39)

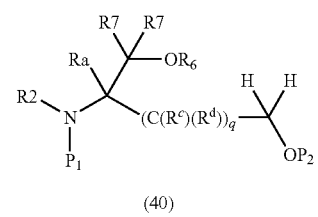

(40)

eq. 3 deprotection ($P^1$ and $P^2$) →

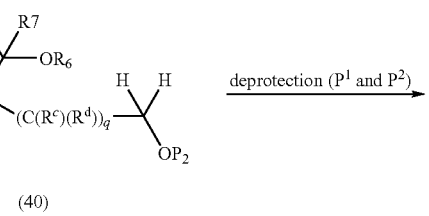

(40)

(41)

with R⁶ is independently H, $C_{1-4}$ alkyl, $C_{3-5}$ alkenyl, $C_{3-5}$ alkynyl
R⁷ is independently H, $C_{1-4}$ alkyl
P¹ and P² are independent known protecting groups which could be linked together As shown in Scheme 18, equation 1, amines of the general formula (41) are useful for the preparation of hydroxy amides of the general formula (42) via reaction with acids of the general formula (10). Alkylation of the hydroxyl function of (42) (Scheme 18, equation 2) provides compounds of the formula (43). Compounds (42) and (43) are examples of compounds of the general formula (1), wherein L is oxygen, and the definition of R³ is as given above (R³ is —$(CR^aR^b)_p$ $(CR^cR^d)_q(X)_r(CR^eR^f)_sR^4$) wherein p is 1, $R^b$ is hydroxy-$(C_{1-4}$-alkyl, $C_{1-4}$ alkoxy($C_{1-4}$)alkyl, $C_{3-5}$ alkenyloxy($C_{1-4}$) alkyl or $C_{3-5}$ alkynyloxy-$C_{1-4}$-alkyl, r is 0, s is 1, $R^e$ is hydroxy, $C_{1-4}$ alkoxy, $C_{3-5}$ alkenyloxy or $C_{3-5}$ alkynyloxy, $R^f$ is hydrogen and R⁴ is hydrogen.

Scheme 18

(43)

wherein Ar = 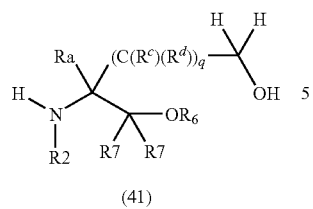

R⁶ is independently H, $C_{1-4}$ alkyl, $C_{3-5}$ alkenyl, $C_{3-5}$ alkynyl
R⁷ is independently H, $C_{1-4}$ alkyl Amides of the general formulae (42) and (43) may be also be prepared by applying approaches described in Scheme 18 and Scheme 1 starting from acids of the general formula (8) which bear a halogen at position 3 of the quinoline ring. Thus, following amidation of compounds (8) with amines of the general formula (41), a subsequent Sonogashira reaction can provide amides of the general formulae (42) while a sequence of amidation, alkylation and Sonogashira steps can provide amides of the general formulae (43)

As shown in Scheme 19, equation 1, oxidation of hydroxyl amides of the general formula (42) provides aldehydes of the general formula (44) which may be transformed into compounds of the general formula (45) bearing the terminal alkynyl function according to methods well known to those skilled in the art.

Scheme 19

-continued

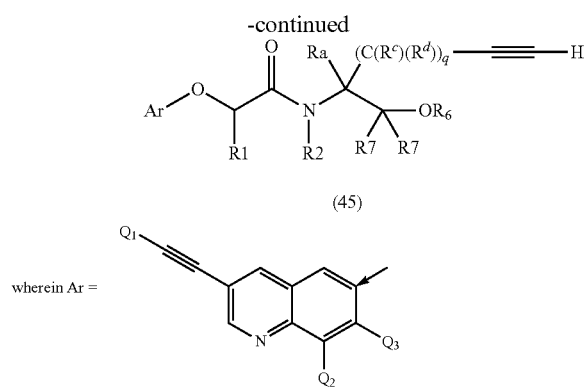

(45)

wherein Ar =

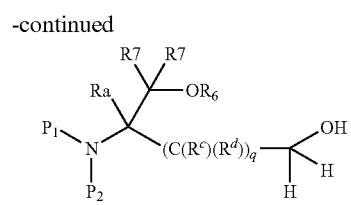

$R^6$ is independently H, $C_{1-4}$ alkyl, $C_{3-5}$ alkenyl, $C_{3-5}$ alkynyl
$R^7$ is independently H, $C_{1-4}$ alkyl Compounds (44) and (45) are examples of compounds of the general formula (1), wherein L is oxygen, and the definition of $R^3$ is as given above ($R^3$ is —$(CR^aR^b)_p(CR^cR^d)_q(X)_r(CR^eR^f)_sR^4$) wherein p is 1, $R^b$ is hydroxy-($C_{1-4}$-alkyl, $C_{1-4}$ alkoxy($C_{1-4}$)alkyl, $C_{3-5}$ alkenyloxy($C_{1-4}$)alkyl or $C_{3-5}$ alkynyloxy-$C_{1-4}$-alkyl, r is 0, s is 1, $R^e$ is hydroxy, $C_{1-4}$ alkoxy, $C_{3-5}$ alkenyloxy or $C_{3-5}$ alkynyloxy, $R^f$ is hydrogen and $R^4$ is formyl or ethynyl.

Alternatively, as illustrated in Scheme 20, equation 6, compounds (45) can also be prepared directly by coupling a carboxylic acid of the general formula (10) with an amine of the general formula (51). Amines (51), which are examples of amines of the general formula (4), where $R^2$ is hydrogen and $R^3$ is —$(CR^aR^b)_p(CR^cR^d)_q(X)_r(CR^eR^f)_sR^4$) wherein p is 1, $R^a$ is as defined above, $R^b$ is $C_{1-4}$ alkoxy($C_{1-4}$)alkyl, $C_{3-5}$ alkenyloxy($C_{1-4}$)alkyl or $C_{3-5}$ alkynyloxy-$C_{1-4}$-alkyl, r is 0, s is 0, and $R^4$ is ethynyl can be prepared as summarized in Scheme 20, equations 1-5.

Scheme 20 eq. 1

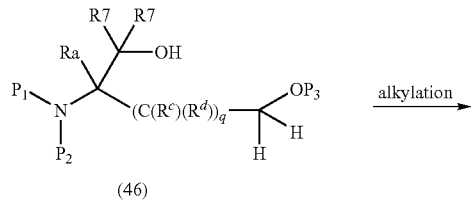

alkylation →

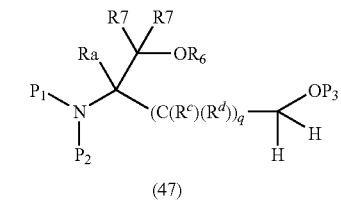

(47)

eq. 2

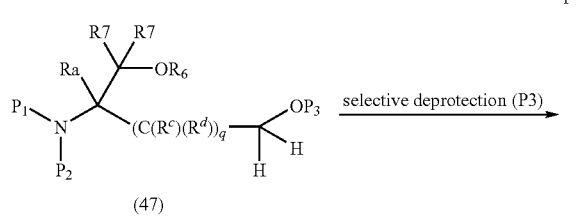

selective deprotection (P3) →

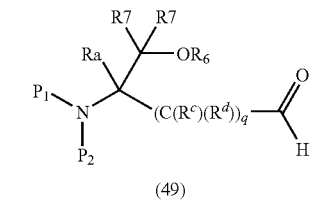

(48)

eq. 3

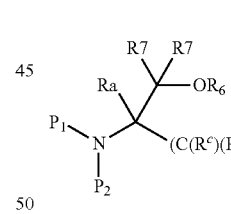

oxidation →

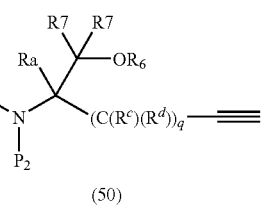

(49)

eq. 4

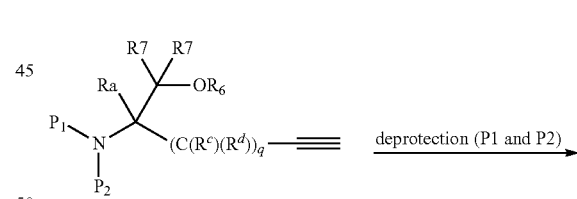

triple bond formation →

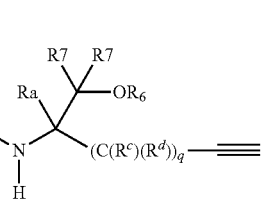

(50)

eq. 5

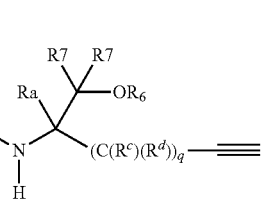

deprotection (P1 and P2) →

(51)

eq. 6

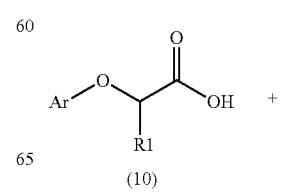 +

(10)

-continued

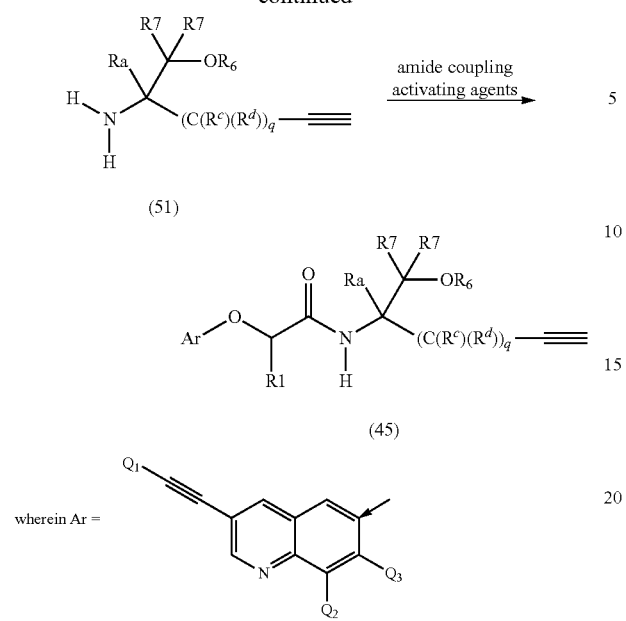

Compounds of the general formula (58), which are examples of compounds of the general formula (1), wherein L is oxygen, $R^3$ is $(CR^aR^b)_p(CR^cR^d)_q(X)_r(CR^eR^f)_sR^4)$ wherein p is 1, $R^a$, $R^c$ and $R^d$ are as defined above, $R^b$ is ethynyl, q is as defined above (0, 1 or 2), r and s are 0, $R^4$ is ethynyl may be prepared may be prepared from acids of the general formula (10) in six synthetic steps, well known to those skilled in the art as illustrated in Scheme 21.

-continued

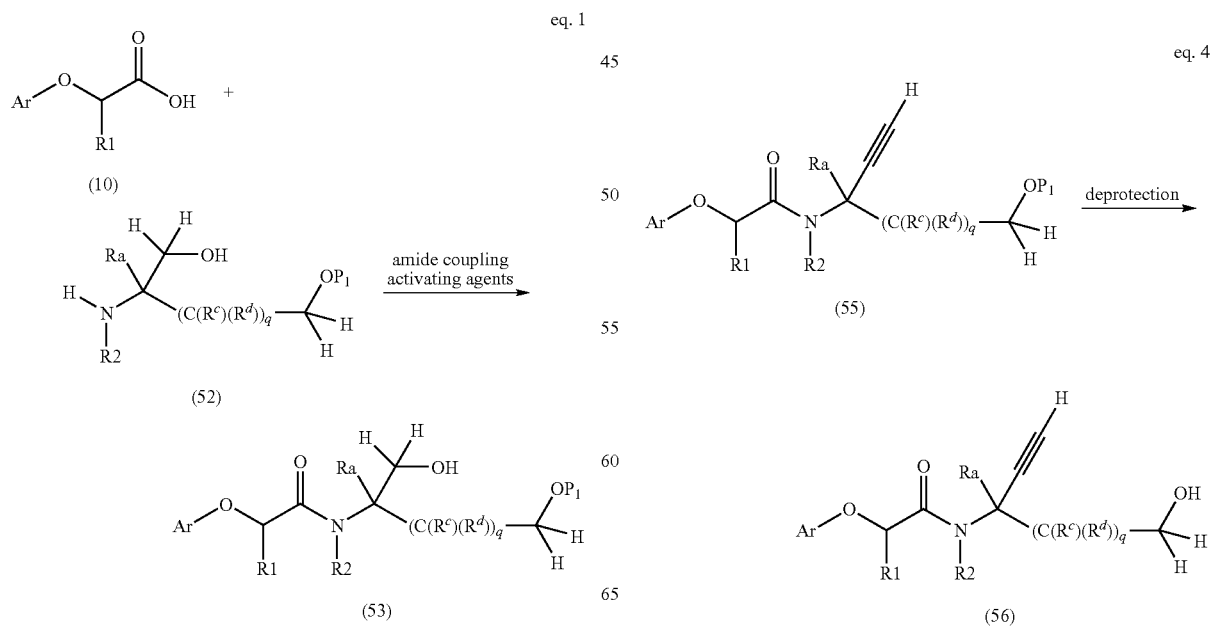

eq. 5

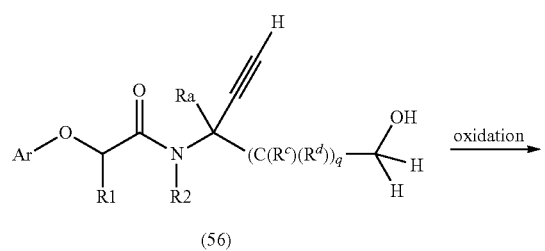

(56)

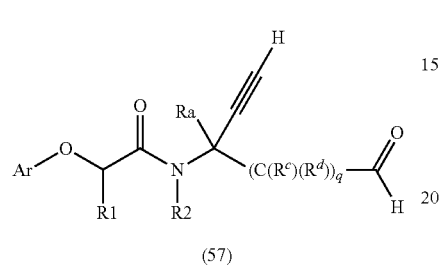

(57)

eq. 6

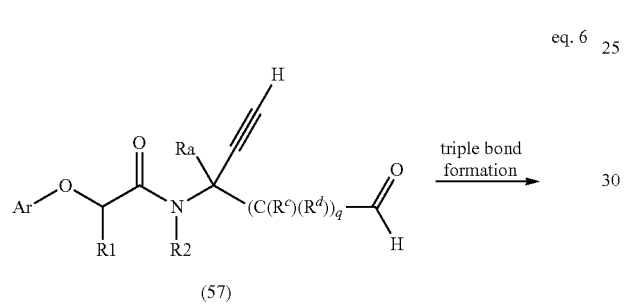

(57)

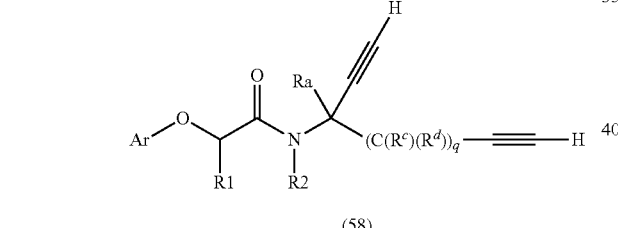

(58)

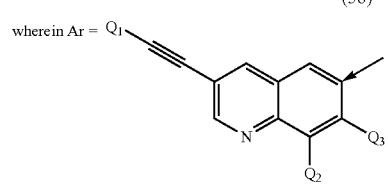

with P¹ = known protecting group

Scheme 22 eq. 1

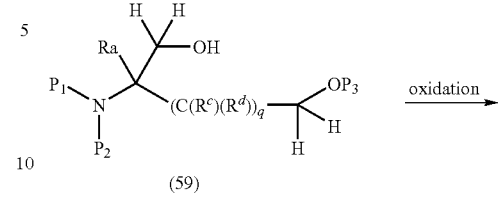

(59)

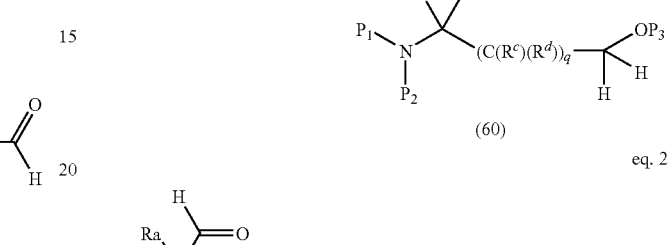

(60)

eq. 2

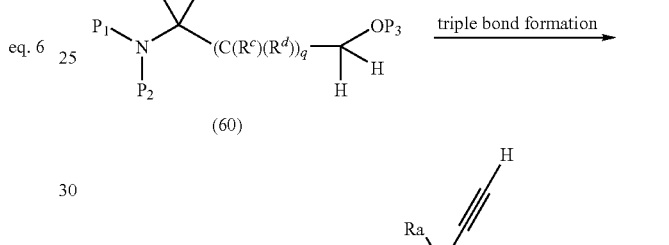

(60)

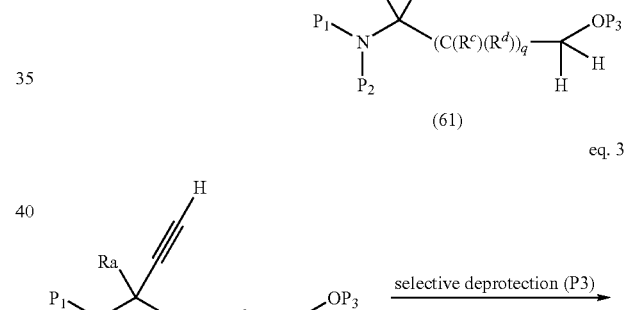

(61)

eq. 3

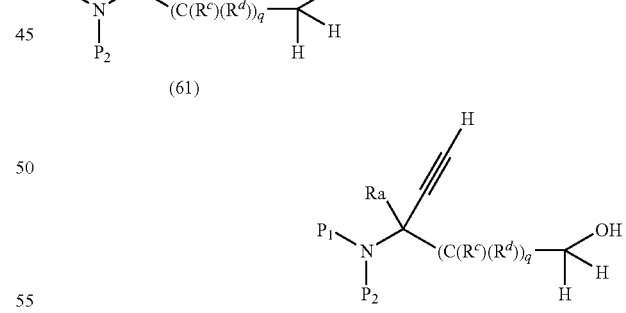

(61)

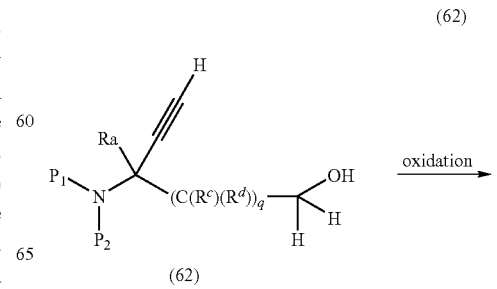

(62)

eq. 4

Alternatively, as illustrated in Scheme 22, equation 7, compounds of the general formula (58) can be prepared directly by coupling a carboxylic acid of the general formula (10) with an amine of the general formula (65). Amines (65), which are examples of amines of the general formula (4), where $R^2$ is hydrogen and $R^3$ is $-(CR^aR^b)_p(CR^cR^d)_q(X)_r(CR^eR^f)_sR^4)$ wherein p is 1, $R^a$ is as defined above, $R^b$ is ethynyl, r and s are 0, q is as defined above (0, 1 or 2), $R^c$ and $R^d$ are as defined above and $R^4$ is ethynyl, can be prepared by those skilled in the art as summarized in Scheme 22, equations 1-6.

-continued

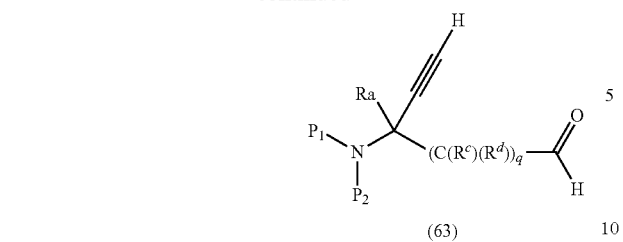

eq. 5

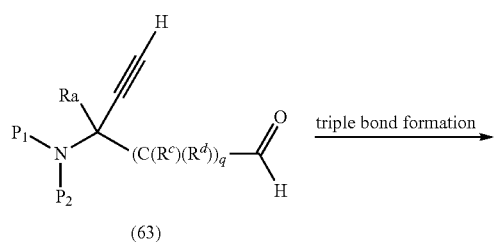

eq. 6

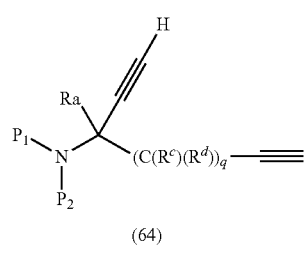

eq. 7

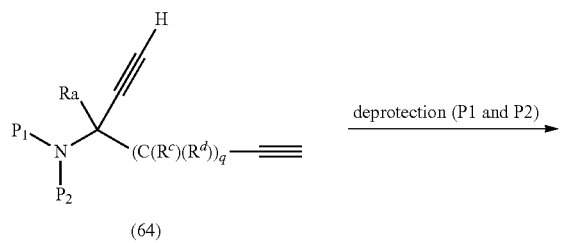

-continued (58)

wherein Ar = with $P_1$, $P_3$ are independent known protecting groups
$P_2$ is $R^2$ or known protecting group As illustrated in Scheme 23, compounds of general formulae (67) and (68) which are examples of compounds of the general formula (1) where L is oxygen, and $R^3$ is $-(CR^aR^b)_p(CR^cR^d)_q(X)_r(CR^eR^f)_sR^4$) wherein p is 1, $R^a$ and $R^b$ may join to form a 3 to 8 membered carbocyclic ring, q is 0, 1 or 2, r is 0, s is 1 and $R^e$ and $R^f$ independently of each other are hydrogen, hydroxy, $C_{1-4}$ alkoxy, $C_{3-5}$ alkenyloxy or $C_{3-5}$ alkynyloxy and $R^4$ is hydrogen may be prepared according to Scheme xx using methods known to those skilled in the art.

Scheme 23 eq. 1 eq. 2

-continued

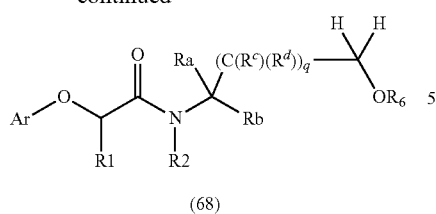

(68)

wherein Ar =

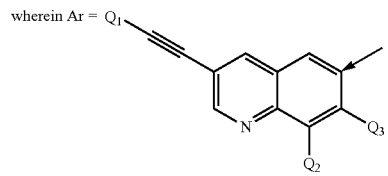

$R^6$ is independently H, $C_{1-4}$ alkyl, $C_{3-5}$ alkenyl, $C_{3-5}$ alkynyl
Ra and Rb may join to form a 3 to 8 membered carbocycle Furthermore, compounds of general formulae (69) and (70) which are examples of compounds of the general formula (1) where L is oxygen, and $R^3$ is —$(CR^aR^b)_p(CR^cR^d)_q(X)_r(CR^eR^f)_sR^4)$ wherein p is 1, $R^a$ and $R^b$ may join to form a 3 to 8 membered carbocyclic ring, q is 0, 1 or 2, r is 0 and $R^4$ is formyl or ethynyl may be prepared using methods known to those skilled in the art as illustrated in Scheme 24.

Scheme 24

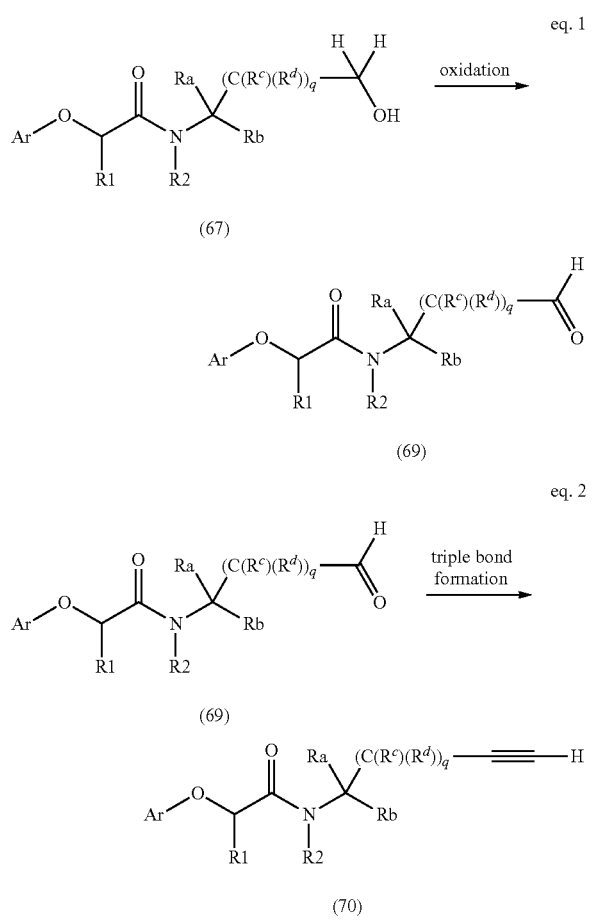

-continued

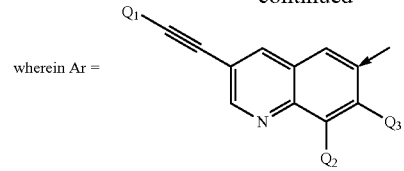

wherein Ar =

Ra and Rb may join to form a 3 to 8 membered carbocycle

Other amines of the general formula (4) are either commercially available are reported in literature publications or may be prepared by standard literature methods or standard modifications.

Thioamides (Compounds of the general formula (I) where L=S) may be prepared from the corresponding amides using thionating agents such as phosphous pentasulphide, Lawesson's or Davy's reagents or prepared from the corresponding thionoacids or thionoesters using standard literature methods or standard modifications.

Schemes 1, 2, 3, 4, 8, 11, 17eq3, 18eq2, 19eq2, 20eq6, 21eq6 and 22eq7 are preferred steps in the synthesis of the compounds of formula (1).

The compounds of formula (1) are active fungicides and may be used to control one or more of the following pathogens: *Pyricularia oryzae* (*Magnaporthe grisea*) on rice and wheat and other *Pyricularia* spp. on other hosts; *Puccinia triticina* (or *recondita*), *Puccinia striiformis* and other rusts on wheat, *Puccinia hordei, Puccinia striiformis* and other rusts on barley, and rusts on other hosts (for example turf, rye, coffee, pears, apples, peanuts, sugar beet, vegetables and ornamental plants); Phakopsora pachyrhizi on soybean, *Erysiphe cichoracearum* on cucurbits (for example melon); *Blumeria* (or *Erysiphe*) *graminis* (powdery mildew) on barley, wheat, rye and turf and other powdery mildews on various hosts, such as *Sphaerotheca macularis* on hops, *Sphaerotheca fusca* (*Sphaerotheca fuliginea*) on cucurbits (for example cucumber), *Leveillula taurica* on tomatoes, aubergine and green pepper, *Podosphaera leucotricha* on apples and *Uncinula necator* on vines; *Cochliobolus* spp., *Helminthosporium* spp., *Drechslera* spp. (*Pyrenophora* spp.), *Rhynchosporium* spp., *Mycosphaerella graminicola* (*Septoria tritici*) and *Phaeosphaeria nodorum* (*Stagonospora nodorum* or *Septoria nodorum*), *Pseudocercosporella herpotrichoides* and *Gaeumannomyces graminis* on cereals (for example wheat, barley, rye), turf and other hosts; *Cercospora arachidicola* and *Cercosporidium personatum* on peanuts and other *Cercospora* spp. on other hosts, for example sugar beet, bananas, soya beans and rice; *Botrytis cinerea* (grey mould) on tomatoes, strawberries, vegetables, vines and other hosts and other *Botrytis* spp. on other hosts; *Alternaria* spp. on vegetables (for example carrots), oil-seed rape, apples, tomatoes, potatoes, cereals (for example wheat) and other hosts; *Venturia* spp. (including *Venturia inaequalis* (scab)) on apples, pears, stone fruit, tree nuts and other hosts; *Cladosporium* spp. on a range of hosts including cereals (for example wheat) and tomatoes; *Monilinia* spp. on stone fruit, tree nuts and other hosts; *Didymella* spp. on tomatoes, turf, wheat, cucurbits and other hosts; *Phoma* spp. on oil-seed rape, turf, rice, potatoes, wheat and other hosts; *Aspergillus* spp. and *Aureobasidium* spp. on wheat, lumber and other hosts; *Ascochyta* spp. on peas, wheat, barley and other hosts; *Stemphylium* spp. (*Pleospora* spp.) on apples, pears, onions and other hosts; summer diseases (for example bitter rot (*Glomerella cingulata*), black rot or frogeye leaf spot (*Botryosphaeria obtusa*), Brooks fruit spot (*Mycosphaerella pomi*), Cedar apple rust (*Gymnosporangium juniperi-virginianae*), sooty blotch (*Gloeodes pomigena*), flyspeck (*Schizothyrium pomi*) and white rot (*Botryosphaeria dothidea*)) on apples and pears; *Plasmopara viticola* on vines; *Plasmopara halstedii* on sunflower; other downy mildews, such as *Bremia iactucae* on lettuce, *Peronospora* spp. on soybeans, tobacco, onions and other hosts, *Pseudoperonospora humuli* on hops; *Peronosclerospora maydis*, *P. philippinensis* and *P. sorghi* on maize, sorghum and other hosts and *Pseudoperonospora cubensis* on cucurbits; *Pythium* spp. (including *Pythium ultimum*) on cotton, maize, soybean, sugarbeet, vegetables, turf and other hosts; *Phytophthora infestans* on potatoes and tomatoes and other *Phytophthora* spp. on vegetables, strawberries, avocado, pepper, ornamentals, tobacco, cocoa and other hosts; *Aphanomyces* spp. on sugarbeet and other hosts; *Thanatephorus cucumeris* on rice, wheat, cotton, soybean, maize, sugarbeet and turf and other hosts *Rhizoctonia* spp. on various hosts such as wheat and barley, peanuts, vegetables, cotton and turf; *Sclerotinia* spp. on turf, peanuts, potatoes, oil-seed rape and other hosts; *Sclerotium* spp. on turf, peanuts and other hosts; *Gibberella fujikuroi* on rice; *Colletotrichum* spp. on a range of hosts including turf, coffee and vegetables; *Laetisaria fuciformis* on turf; *Mycosphaerella* spp. on bananas, peanuts, citrus, pecans, papaya and other hosts; *Diaporthe* spp. on citrus, soybean, melon, pears, lupin and other hosts; *Elsinoe* spp. on citrus, vines, olives, pecans, roses and other hosts; *Verticillium* spp. on a range of hosts including hops, potatoes and tomatoes; *Pyrenopeziza* spp. on oil-seed rape and other hosts; *Oncobasidium theobromae* on cocoa causing vascular streak dieback; *Fusarium* spp. incl. *Fusarium culmorum, F. graminearum, F. langsethiae, F. moniliforme, F. proliferatum, F. subglutinans, F. solani* and *F. oxysporum* on wheat, barely, rye, oats, maize, cotton, soybean, sugarbeet and other hosts, *Typhula* spp., *Microdochium nivale, Ustilago* spp., *Urocystis* spp., *Tilletia* spp. and *Claviceps purpurea* on a variety of hosts but particularly wheat, barley, turf and maize; *Ramularia* spp. on sugar beet, barley and other hosts; *Thielaviopsis basicola* on cotton, vegetables and other hosts; *Verticillium* spp. on cotton, vegetables and other hosts; post-harvest diseases particularly of fruit (for example *Penicillium digitatum, Penicillium italicum* and *Trichoderma viride* on oranges, *Colletotrichum musae* and *Gloeosporium musarum* on bananas and *Botrytis cinerea* on grapes); other pathogens on vines, notably *Eutypa lata, Guignardia bidwellii, Phellinus igniarus, Phomopsis viticola, Pseudopeziza tracheiphila* and *Stereum hirsutum*; other pathogens on trees (for example *Lophodermium seditiosum*) or lumber, notably *Cephaloascus fragrans, Ceratocystis* spp., *Ophiostoma piceae, Penicillium* spp., *Trichoderma pseudokoningii, Trichoderma viride, Trichoderma harzianum, Aspergillus niger, Leptographium lindbergi* and *Aureobasidium pullulans*; and fungal vectors of viral diseases (for example *Polymyxa graminis* on cereals as the vector of barley yellow mosaic virus (BYMV) and *Polymyxa betae* on sugar beet as the vector of rhizomania).

Preferably, the following pathogens are controlled. *Pyricularia oryzae* (*Magnaporthe grisea*) on rice and wheat and other *Pyricularia* spp. on other hosts; *Erysiphe cichoracearum* on cucurbits (for example melon); *Blumeria* (or *Erysiphe*) *graminis* (powdery mildew) on barley, wheat, rye and turf and other powdery mildews on various hosts, such as *Sphaerotheca macularis* on hops, *Sphaerotheca fusca* (*Sphaerotheca fuliginea*) on cucurbits (for example cucumber), *Leveillula taurica* on tomatoes, aubergine and green pepper, *Podosphaera leucotricha* on apples and *Uncinula necator* on vines; *Helminthosporium* spp., *Drechslera* spp. (*Pyrenophora* spp.), *Rhynchosporium* spp. *Mycosphaerella graminicola* (*Septoria tritici*) and *Phaeosphaeria nodorum* (*Stagonospora nodorum* or *Septoria nodorum*), *Pseudocercosporella herpotrichoides* and *Gaeumannomyces graminis* on cereals (for example wheat, barley, rye), turf and other hosts; *Cercospora arachidicola* and *Cercosporidium personatum* on peanuts and other *Cercospora* spp. on other hosts, for example sugar beet, bananas, soya beans and rice; *Botrytis cinerea* (grey mould) on tomatoes, strawberries, vegetables, vines and other hosts and other *Botrytis* spp. on other hosts; *Alternaria* spp. on vegetables (for example carrots), oil-seed rape, apples, tomatoes, potatoes, cereals (for example wheat) and other hosts; *Venturia* spp. (including *Venturia inaequalis* (scab)) on apples, pears, stone fruit, tree nuts and other hosts; *Cladosporium* spp. on a range of hosts including cereals (for example wheat) and tomatoes; *Monilinia* spp. on stone fruit, tree nuts and other hosts; *Didymella* spp. on tomatoes, turf, wheat, cucurbits and other hosts; *Phoma* spp. on oil-seed rape, turf, rice, potatoes, wheat and other hosts; *Aspergillus* spp. and *Aureobasidium* spp. on wheat, lumber and other hosts; *Ascochyta* spp. on peas, wheat, barley and other hosts; *Stemphylium* spp. (*Pleospora* spp.) on apples, pears, onions and other hosts; summer diseases (for example bitter rot (*Glomerella cingulata*), black rot or frogeye leaf spot (*Botryosphaeria obtusa*), Brooks fruit spot (*Mycosphaerella pomi*), Cedar apple rust (*Gymnosporangium juniperi-virginianae*), sooty blotch (*Gloeodes pomigena*), flyspeck (*Schizothyrium pomi*) and white rot (*Botryosphaeria dothidea*)) on apples and pears; *Plasmopara viticola* on vines; *Plasmopara halstedii* on sunflower; other downy mildews, such as *Bremia lactucae* on lettuce, *Peronospora* spp. on soybeans, tobacco, onions and other hosts, *Pseudoperonospora humuli* on hops; *Peronosclerospora maydis*, *P. philippinensis* and *P. sorghi* on maize, sorghum and other hosts and *Pseudoperonospora cubensis* on cucurbits; *Pythium* spp. (including *Pythium ultimum*) on cotton, maize, soybean, sugarbeet, vegetables, turf and other hosts; *Phytophthora infestans* on potatoes and tomatoes and other *Phytophthora* spp. on vegetables, strawberries, avocado, pepper, ornamentals, tobacco, cocoa and other hosts; *Aphanomyces* spp. on sugarbeet and other hosts; *Thanatephorus cucumeris* on rice, wheat, cotton, soybean, maize, sugarbeet and turf and other hosts *Rhizoctonia* spp. on various hosts such as wheat and barley, peanuts, vegetables, cotton and turf; *Sclerotinia* spp. on turf, peanuts, potatoes, oil-seed rape and other hosts; *Sclerotium* spp. on turf, peanuts and other hosts; *Gibberella fujikuroi* on rice; *Colletotrichum* spp. on a range of hosts including turf, coffee and vegetables; *Laetisaria fuciformis* on turf; *Mycosphaerella* spp. on bananas, peanuts, citrus, pecans, papaya and other hosts; *Fusarium* spp. in *Fusarium culmorum, F. graminearum, F. langsethiae, F. moniliforme, F. proliferatum, F. subglutinans, F. solani* and *F. oxysporum* on wheat, barely, rye, oats, maize, cotton, soybean, sugarbeet and other hosts, *Microdochium nivale, Ustilago* spp., *Urocystis* spp., *Tilletia* spp. and *Claviceps purpurea* on a variety of hosts but particularly wheat, barley, turf and maize; *Ramularia* spp. on sugar beet, barley and other hosts; *Thielaviopsis basicola* on cotton, vegetables and other hosts; *Verticillium* spp. on cotton, vegetables and other hosts; post-harvest diseases particularly of fruit (for example *Penicillium digitatum, Penicillium italicum* and *Trichoderma viride* on oranges, *Colletotrichum musae* and *Gloeosporium musarum* on bananas and *Botrytis cinerea* on grapes); other pathogens on vines, notably *Eutypa lata, Guignardia bidwellii, Phellinus igniarus, Phomopsis viticola, Pseudopeziza tracheiphila* and *Stereum hirsutum*; other pathogens on trees (for example *Lophodermium seditiosum*) or lumber, notably *Cephaloascus fragrans, Ceratocystis* spp., *Ophiostoma piceae, Penicillium* spp., *Trichoderma pseudokoningii*, *Trichoderma viride*, *Trichoderma harzianum*, *Aspergillus niger*, *Leptographium lindbergi* and *Aureobasidium pullulans*.

More preferably, the following pathogens are controlled: *Pyricularia oryzae* (*Magnaporthe grisea*) on rice and wheat and other *Pyricularia* spp. on other hosts; *Erysiphe cichoracearum* on cucurbits (for example melon); *Blumeria* (or *Erysiphe*) *graminis* (powdery mildew) on barley, wheat, rye and turf and other powdery mildews on various hosts, such as *Sphaerotheca macularis* on hops, *Sphaerotheca fusca* (*Sphaerotheca fuliginea*) on cucurbits (for example cucumber), *Leveillula taurica* on tomatoes, aubergine and green pepper, *Podosphaera leucotricha* on apples and *Uncinula necator* on vines; *Mycosphaerella graminicola* (*Septoria tritici*) and *Phaeosphaeria nodorum* (*Stagonospora nodorum* or *Septoria nodorum*), *Pseudocercosporella herpotrichoides* and *Gaeumannomyces graminis* on cereals (for example wheat, barley, rye), turf and other hosts; *Cercospora arachidicola* and *Cercosporidium personatum* on peanuts and other *Cercospora* spp. on other hosts, for example sugar beet, bananas, soya beans and rice; *Botrytis cinerea* (grey mould) on tomatoes, strawberries, vegetables, vines and other hosts and other *Botrytis* spp. on other hosts; *Alternaria* spp. on vegetables (for example carrots), oil-seed rape, apples, tomatoes, potatoes, cereals (for example wheat) and other hosts; *Venturia* spp. (including *Venturia inaequalis* (scab)) on apples, pears, stone fruit, tree nuts and other hosts; *Cladosporium* spp. on a range of hosts including cereals (for example wheat) and tomatoes; *Monilinia* spp. on stone fruit, tree nuts and other hosts; *Didymella* spp. on tomatoes, turf, wheat, cucurbits and other hosts; *Phoma* spp. on oil-seed rape, turf, rice, potatoes, wheat and other hosts; *Plasmopara viticola* on vines; *Plasmopara halstedii* on sunflower; other downy mildews, such as *Bremia lactucae* on lettuce, *Peronospora* spp. on soybeans, tobacco, onions and other hosts, *Pseudoperonospora humuli* on hops; *Peronosclerospora maydis*, *P. philippinensis* and *P. sorghi* on maize, sorghum and other hosts and *Pseudoperonospora cubensis* on cucurbits; *Pythium* spp. (including *Pythium ultimum*) on cotton, maize, soybean, sugarbeet, vegetables, turf and other hosts; *Phytophthora infestans* on potatoes and tomatoes and other *Phytophthora* spp. on vegetables, strawberries, avocado, pepper, ornamentals, tobacco, cocoa and other hosts; *Aphanomyces* spp. on sugarbeet and other hosts; *Thanatephorus cucumeris* on rice, wheat, cotton, soybean, maize, sugarbeet and turf and other hosts *Rhizoctonia* spp. on various hosts such as wheat and barley, peanuts, vegetables, cotton and turf; *Sclerotinia* spp. on turf, peanuts, potatoes, oil-seed rape and other hosts; *Sclerotium* spp. on turf, peanuts and other hosts; *Gibberella fujikuroi* on rice; *Colletotrichum* spp. on a range of hosts including turf, coffee and vegetables; *Laetisaria fuciformis* on turf; *Mycosphaerella* spp. on bananas, peanuts, citrus, pecans, papaya and other hosts; *Fusarium* spp. incl. *Fusarium culmorum*, *F. graminearum*, *F. langsethiae*, *F. moniliforme*, *F. proliferatum*, *F. subglutinans*, *F. solani* and *F. oxysporum* on wheat, barely, rye, oats, maize, cotton, soybean, sugarbeet and other hosts; and *Microdochium nivale*.

A compound of formula (1) may move acropetally, basipetally or locally in plant tissue to be active against one or more fungi. Moreover, a compound of formula (I) may be volatile enough to be active in the vapour phase against one or more fungi on the plant.

The invention therefore provides a method of combating or controlling phytopathogenic fungi which comprises applying a fungicidally effective amount of a compound of formula (I), or a composition containing a compound of formula (I), to a plant, to a seed of a plant, to the locus of the plant or seed or to soil or any other plant growth medium, e.g. nutrient solution.

The term "plant" as used herein includes seedlings, bushes and trees. Furthermore, the fungicidal method of the invention includes protectant, curative, systemic, eradicant and antisporulant treatments.

The compounds of formula (I) are preferably used for agricultural, horticultural and turfgrass purposes in the form of a composition.

In order to apply a compound of formula (I) to a plant, to a seed of a plant, to the locus of the plant or seed or to soil or any other growth medium, a compound of formula (I) is usually formulated into a composition which includes, in addition to the compound of formula (I), a suitable inert diluent or carrier and, optionally, a surface active agent (SFA). SFAs are chemicals that are able to modify the properties of an interface (for example, liquid/solid, liquid/air or liquid/liquid interfaces) by lowering the interfacial tension and thereby leading to changes in other properties (for example dispersion, emulsification and wetting). It is preferred that all compositions (both solid and liquid formulations) comprise, by weight, 0.0001 to 95%, more preferably 1 to 85%, for example 5 to 60%, of a compound of formula (I). The composition is generally used for the control of fungi such that a compound of formula (I) is applied at a rate of from 0.1 g to 10 kg per hectare, preferably from 1 g to 6 kg per hectare, more preferably from 1 g to 1 kg per hectare.

When used in a seed dressing, a compound of formula (I) is used at a rate of 0.0001 g to 10 g (for example 0.001 g or 0.05 g), preferably 0.005 g to 10 g, more preferably 0.005 g to 4 g, per kilogram of seed.

In another aspect the present invention provides a fungicidal composition comprising a fungicidally effective amount of a compound of formula (I) and a suitable carrier or diluent therefor.

In a still further aspect the invention provides a method of combating and controlling fungi at a locus, which comprises treating the fungi, or the locus of the fungi with a fungicidally effective amount of a composition comprising a compound of formula (I).

The compositions can be chosen from a number of formulation types, including dustable powders (DP), soluble powders (SP), water soluble granules (SG), water dispersible granules (WG), wettable powders (WP), granules (GR) (slow or fast release), soluble concentrates (SL), oil miscible liquids (OL), ultra low volume liquids (UL), emulsifiable concentrates (EC), dispersible concentrates (DC), emulsions (both oil in water (EW) and water in oil (EO)), micro-emulsions (ME), suspension concentrates (SC), aerosols, fogging/smoke formulations, capsule suspensions (CS) and seed treatment formulations. The formulation type chosen in any instance will depend upon the particular purpose envisaged and the physical, chemical and biological properties of the compound of formula (I).

Dustable powders (DP) may be prepared by mixing a compound of formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of formula (I) and one or more powdered solid diluents or carriers, or from pre-formed blank granules by absorbing a compound of formula (I) (or a solution thereof, in a suitable agent) in a porous granular material (such as pumice, attapulgite clays, fuller's earth, kieselguhr, diatomaceous earths or ground corn cobs) or by adsorbing a compound of formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters, and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone), alcohols (such as benzyl alcohol, furfuryl alcohol or butanol), N-alkylpyrrolidones (such as N-methylpyrrolidone or N-octyl-pyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment. Preparation of an EW involves obtaining a compound of formula (I) either as a liquid (if it is not a liquid at ambient temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents that have a low solubility in water.

Microemulsions (ME) may be prepared by mixing water with a blend of one or more solvents with one or more SFAs, to produce spontaneously a thermodynamically stable isotropic liquid formulation. A compound of formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of formula (I). SCs may be prepared by ball or bead milling the solid compound of formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of formula (I) may be dry milled and added to water, containing agents hereinbefore described, to produce the desired end product.

Aerosol formulations comprise a compound of formula (I) and a suitable propellant (for example n-butane). A compound of formula (I) may also be dissolved or dispersed in a suitable medium (for example water or a water miscible liquid, such as n-propanol) to provide compositions for use in non-pressurised, hand-actuated spray pumps.

A compound of formula (I) may be mixed in the dry state with a pyrotechnic mixture to form a composition suitable for generating, in an enclosed space, a smoke containing the compound.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of formula (I) and, optionally, a carrier or diluent therefor. The polymeric shell may be produced by either an interfacial polycondensation reaction or by a coacervation procedure. The compositions may provide for controlled release of the compound of formula (I) and they may be used for seed treatment. A compound of formula (I) may also be formulated in a biodegradable polymeric matrix to provide a slow, controlled release of the compound.

A composition may include one or more additives to improve the biological performance of the composition (for example by improving wetting, retention or distribution on surfaces; resistance to rain on treated surfaces; or uptake or mobility of a compound of formula (I)). Such additives include surface active agents, spray additives based on oils, for example certain mineral oils or natural plant oils (such as soy bean and rape seed oil), and blends of these with other bio-enhancing adjuvants (ingredients which may aid or modify the action of a compound of formula (I)).

A compound of formula (I) may also be formulated for use as a seed treatment, for example as a powder composition, including a powder for dry seed treatment (DS), a water soluble powder (SS) or a water dispersible powder for slurry treatment (WS), or as a liquid composition, including a flowable concentrate (FS), a solution (LS) or a capsule suspension (CS). The preparations of DS, SS, WS, FS and LS compositions are very similar to those of, respectively, DP, SP, WP, SC and DC compositions described above. Compositions for treating seed may include an agent for assisting the adhesion of the composition to the seed (for example a mineral oil or a film-forming barrier). Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts. Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefin sulphonates, taurates and lignosulphonates. Suitable SFAs of the amphoteric type include betaines, propionates and glycinates. Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

A compound of formula (I) may be applied by any of the known means of applying fungicidal compounds. For example, it may be applied, formulated or unformulated, to any part of the plant, including the foliage, stems, branches or roots, to the seed before it is planted or to other media in which plants are growing or are to be planted (such as soil surrounding the roots, the soil generally, paddy water or hydroponic culture systems), directly or it may be sprayed on, dusted on, applied by dipping, applied as a cream or paste formulation, applied as a vapour or applied through distribution or incorporation of a composition (such as a granular composition or a composition packed in a water-soluble bag) in soil or an aqueous environment.

A compound of formula (I) may also be injected into plants or sprayed onto vegetation using electrodynamic spraying techniques or other low volume methods, or applied by land or aerial irrigation systems.

Compositions for use as aqueous preparations (aqueous solutions or dispersions) are generally supplied in the form of a concentrate containing a high proportion of the active ingredient, the concentrate being added to water before use. These concentrates, which may include DCs, SCs, ECs, EWs, MEs, SGs, SPs, WPs, WGs and CSs, are often required to withstand storage for prolonged periods and, after such storage, to be capable of addition to water to form aqueous preparations which remain homogeneous for a sufficient time to enable them to be applied by conventional spray equipment. Such aqueous preparations may contain varying amounts of a compound of formula (I) (for example 0.0001 to 10%, by weight) depending upon the purpose for which they are to be used.

A compound of formula (I) may be used in mixtures with fertilisers (for example nitrogen-, potassium- or phosphorus-containing fertilisers). Suitable formulation types include granules of fertiliser. The mixtures suitably contain up to 25% by weight of the compound of formula (I).

The invention therefore also provides a fertiliser composition comprising a fertiliser and a compound of formula (I).

The compositions of this invention may contain other compounds having biological activity, for example micronutrients or compounds having similar or complementary fungicidal activity or which possess plant growth regulating, herbicidal, insecticidal, nematicidal or acaricidal activity.

By including another fungicide, the resulting composition may have a broader spectrum of activity or a greater level of intrinsic activity than the compound of formula (I) alone. Further the other fungicide may have a synergistic effect on the fungicidal activity of the compound of formula (I).

The compound of formula (I) may be the sole active ingredient of the composition or it may be admixed with one or more additional active ingredients such as a pesticide, fungicide, synergist, herbicide or plant growth regulator where appropriate. An additional active ingredient may: provide a composition having a broader spectrum of activity or increased persistence at a locus; synergise the activity or complement the activity (for example by increasing the speed of effect or overcoming repellency) of the compound of formula (I); or help to overcome or prevent the development of resistance to individual components. The particular additional active ingredient will depend upon the intended utility of the composition.

Examples of fungicidal compounds which may be included in the composition of the invention are AC 382042 (N-(1-cyano-1,2-dimethylpropyl)-2-(2,4-dichlorophenoxy) pro-pionamide), acibenzolar-S-methyl, alanycarb, aldimorph, anilazine, azaconazole, azafenidin, azoxystrobin, benalaxyl, benomyl, benthiavalicarb, biloxazol, bitertanol, blasticidin S, boscalid (new name for nicobifen), bromuconazole, bupirimate, captafol, captan, carbendazim, carbendazim chlorhydrate, carboxin, carpropamid, carvone, CGA 41396, CGA 41397, chinomethionate, chlorbenzthiazone, chlorothalonil, chlorozolinate, clozylacon, copper containing compounds such as copper oxychloride, copper oxyquinolate, copper sulphate, copper tallate, and Bordeaux mixture, cyamidazosulfamid, cyazofamid (IKF-916), cyflufenamid, cymoxanil, cyproconazole, cyprodinil, debacarb, di-2-pyridyl disulphide 1,1'-dioxide, dichlofluanid, diclocymet, diclomezine, dicloran, diethofencarb, difenoconazole, difenzoquat, diflumetorim, O,O-di-iso-propyl-5-benzyl thiophosphate, dimeftuazole, dimetconazole, dimethirimol, dimethomorph, dimoxystrobin, diniconazole, dinocap, dithianon, dodecyl dimethyl ammonium chloride, dodemorph, dodine, doguadine, edifenphos, epoxiconazole, ethaboxam, ethirimol, ethyl (Z)—N-benzyl-N([methyl(methyl-thioethylideneaminooxy-carbonyl)amino]thio)-β-alaninate, etridiazole, famoxadone, fenamidone, fenarimol, fenbuconazole, fenfuram, fenhexamid, fenoxanil (AC 382042), fenpiclonil, fenpropidin, fenpropimorph, fentin acetate, fentin hydroxide, ferbam, ferimzone, fluazinam, fludioxonil, flumetover, flumorph, fluoroimide, fluoxastrobin, fluquinconazole, flusilazole, flusulfamide, flutolanil, flutriafol, folpet, fosetyl-aluminium, fuberidazole, furalaxyl, furametpyr, guazatine, hexaconazole, hydroxyisoxazole, hymexazole, imazalil, imibenconazole, iminoctadine, iminoctadine triacetate, ipconazole, iprobenfos, iprodione, iprovalicarb, isopropanyl butyl carbamate, isoprothiolane, kasugamycin, kresoxim-methyl, LY186054, LY211795, LY 248908, mancozeb, maneb, mefenoxam, mepanipyrim, mepronil, metalaxyl, metalaxyl M, metconazole, metiram, metiram-zinc, metominostrobin, metrafenone, MON65500 (N-allyl-4,5-dimethyl-2-trimethylsilylthiophene-3-carboxamide), myclobutanil, NTN0301, neoasozin, nickel dimethyldithiocarbamate, nitrothale-isopropyl, nuarimol, ofurace, organomercury compounds, orysastrobin, oxadixyl, oxasulfuron, oxolinic acid, oxpoconazole, oxycarboxin, pefurazoate, penconazole, pencycuron, phenazin oxide, phosphorus acids, phthalide, picoxystrobin, polyoxin D, polyram, probenazole, prochloraz, procymidone, propamocarb, propamocarb hydrochloride, propiconazole, propineb, propionic acid, proquinazid, prothioconazole, pyraclostrobin, pyrazophos, pyrifenox, pyrimethanil, pyroquilon, pyroxyfur, pyrrolnitrin, quaternary ammonium compounds, quinomethionate, quinoxyfen, quintozene, silthiofam (MON 65500), S-imazalil, simeconazote, sipconazole, sodium pentachlorophenate, spiroxamine, streptomycin, sulphur, tebuconazole, tecloftalam, tecnazene, tetraconazole, thiabendazole, thifluzamide, 2-(thiocyanomethylthio)benzothiazole, thiophanate-methyl, thiram, tiadinil, timibenconazole, tolclofos-methyl, tolylfluanid, triadimefon, triadimenol, triazbutil, triazoxide, tricyclazole, tridemorph, trifloxystrobin, triflumizole, triforine, triticonazole, validamycin A, vapam, vinclozolin, XRD-563, zineb, ziram, zoxamide and the compounds of the formulae:

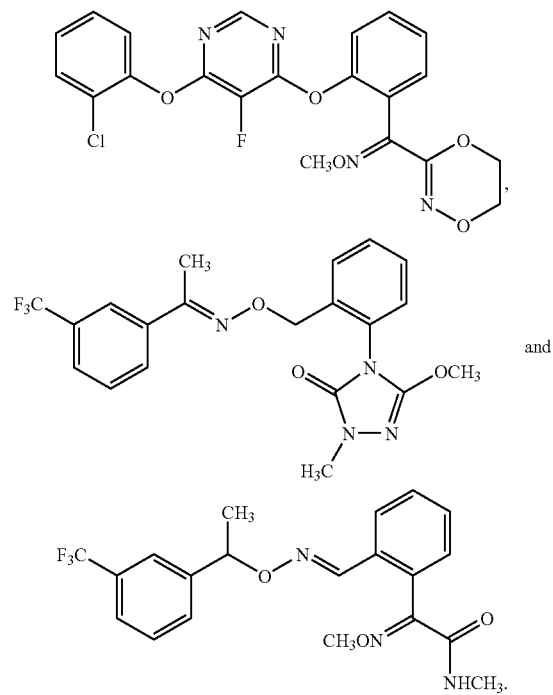

The compounds of formula (I) may be mixed with soil, peat or other rooting media for the protection of plants against seed-borne, soil-borne or foliar fungal diseases. Some mixtures may comprise active ingredients, which have significantly different physical, chemical or biological properties such that they do not easily lend themselves to the same conventional formulation type. In these circumstances other formulation types may be prepared. For example, where one active ingredient is a water insoluble solid and the other a water insoluble liquid, it may nevertheless be possible to disperse each active ingredient in the same continuous aqueous phase by dispersing the solid active ingredient as a suspension (using a preparation analogous to that of an SC) but dispersing the liquid active ingredient as an emulsion (using a preparation analogous to that of an EW). The resultant composition is a suspoemulsion (SE) formulation.

The invention is illustrated by the following Examples in which the following abbreviations are used:
ml=milliliters
m.p.=melting point (uncorrected)
g=grammes
b.p.=boiling point
THF=tetrahydrofuran
DMSO=dimethylsulphoxide
$M^+$=mass ion
DMF=N,N-dimethylformamide
s=singlet
d=doublet
HOBT=1-hydroxybenzotriazole
HOAT=7-aza-1-hydroxybenzotriazole
bs=broad singlet
NMR=nuclear magnetic resonance
t=triplet
HPLC=high performance liquid chromatography
q=quartet
TLC=thin layer chromatography
m=multiplet
glc=gas-liquid chromatography
ppm=parts per million
EDC=1-ethyl-3-N,N-dimethylamino propylcarbodiimide hydrochloride
M=molar

EXAMPLE 1

Sequence 1

Cross-coupling C3 bromo-quinolinyl amides with TMS-acetylene via a Sonogashira reaction and desilylating the resulting acetylene unit as shown below:

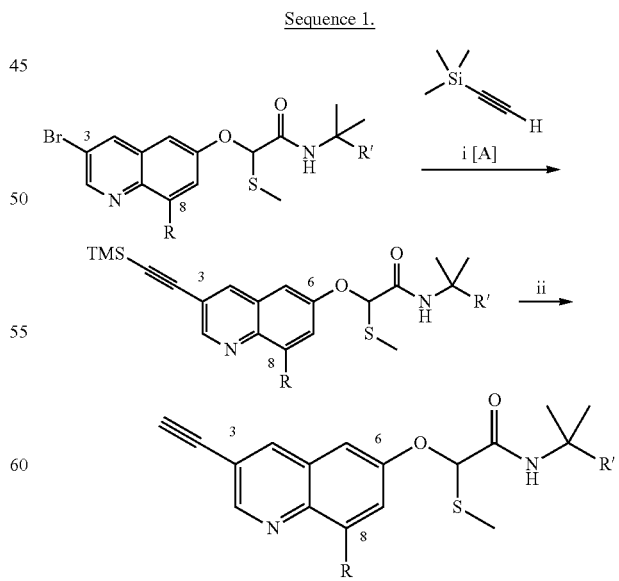

i. TMSC≡CH [A], Pd(II), CuI, iPr2N, dioxane; ii. TBAF, THF, rt or $K_2CO_3$, MeOH, rt.

Step 1: N-tert-Butyl-2-methylsulfanyl-2-(3-trimethylsilanylethynyl-quinolin-6-yloxy)-acetamide 2-(3-Bromo-quinolin-6-yloxy)-N-tert-butyl-2-methylsulfanyl-acetamide (400 mg), Bis(palladium(II)triphenylphosphine)dichloride (36 mg), Copper iodine (8 mg) and diisoproylamine (176 µl) were dissolved in THF (5 ml) and deoxygenated with nitrogen. Trimethylsilylacetylene (179 µl) was added dropwise during 10 min to the reaction mixture. The reaction mixture was stirred at room temperature for 5 hrs. The reaction mixture was diluted with ethyl acetate and was washed with 2×40 ml sat. aq. NaCl. The aqueous layer was extracted with 2×100 ml ethyl acetate. All organic phases were combined, dried over sodium sulfate, filtered and evaporated. The residue was purified by column chromatography (heptane/ethyl acetate 7:3) to give N-tert-Butyl-2-methylsulfanyl-2-(3-trimethylsilanylethynyl-quinolin-6-yloxy)-acetamide as brownish solid (326 mg).

$^1$H NMR (CDCl$_3$) δ ppm: 8.82 (1H, d); 8.17 (1H, d); 8.04 (1H, d); 7.44 (1H, dd); 7.19 (1H, d); 6.42 (1H, s br); 5.57 (1H, s); 2.20 (3H, s); 1.42 (9H, s); 0.3 (9H, s)

Step 2: N-tert-Butyl-2-(3-ethynyl-quinolin-6-yloxy)-2-methylsulfanyl-acetamide A solution of N-tert-Butyl-2-methylsulfanyl-2-(3-trimethylsilanylethynyl-quinolin-6-yloxy)-acetamide (215 mg) in methanol (5 ml) was treated with potassium carbonate (18 mg) at room temperature. The reaction mixture was stirred for 1 h. The reaction mixture was diluted with ethyl acetate and washed with 30 ml sat. aq. sodium hydrogen carbonate. The aqueous layer was extracted with 3×50 ml ethyl acetate. The organic layers were combined, dried over sodium sulfate, filtered and evaporated. The residue was purified by column chromatography (heptane/ethyl acetate 6:4) to give N-tert-Butyl-2-(3-ethynyl-quinolin-6-yloxy)-2-methylsulfanyl-acetamide (125 mg) as brownish solid.

$^1$H NMR (CDCl$_3$) δ ppm: 8.85 (1H, d); 8.20 (1H, d); 8.06 (1H, d); 7.46 (1H, dd); 7.22 (1H, d); 6.43 (1H, s br); 5.59 (1H, s); 3.29 (1H, s); 2.20 (3H, s); 1.42 (9H, s)

Sequence 2

Via Sonogashira cross-coupling reaction of TMS-acetylene with C3-halo quinolinyl-esters followed by a one-pot process for desilylation of the acetylene unit and hydrolysis of ester function. Subsequent amidation of the C3 ethynyl-quinolinyl acid [A] then provided the C3-ethynyl quinolinyl-amides as shown below.

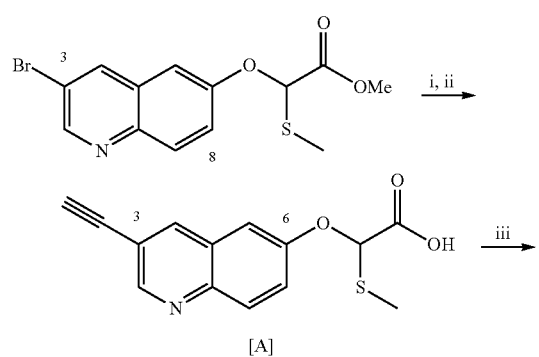

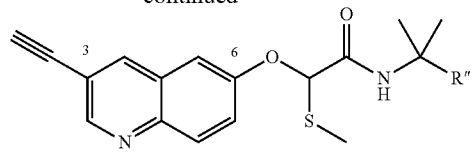

i. R'C≡CH, Pd(II), CuI, iPr$_2$N, dioxane; ii. NaOH, EtOH/H$_2$O, rt; iii. HOAT, EDCl, Et$_3$N, DMF.

Step 1: Methylsulfanyl-(3-trimethylsilanylethynyl-quinolin-6-yloxy)-acetic acid methyl ester (3-Bromo-quinolin-6-yloxy)-methylsulfanyl-acetic acid methyl ester (9.5 g), Bis(palladium(II)triphenylphosphine)dichloride (877 mg), Copper iodine (200 mg) and diisoproylamine (17.5 ml) were dissolved in THF (150 ml) and deoxygenated with nitrogen. Trimethylsilylacetylene (7.1 ml) was added dropwise during 10 min. The reaction mixture was heated up to 45° C. and was stirred at that temperature for 36 hrs. The reaction mixture was diluted with ethyl acetate and was washed with 2×200 ml sat. aq. NaCl. The aqueous layer was extracted with 2×500 ml ethyl acetate. All organic phases were combined, dried over sodium sulfate, filtered and evaporated. The residue was purified by column chromatography (heptane/ethyl acetate 4:1) to give Methylsulfanyl-(3-trimethylsilanylethynyl-quinolin-6-yloxy)-acetic acid methyl ester (7.6 g) as yellowish oil.

$^1$H NMR (CDCl$_3$) δ ppm: 8.81 (1H, d); 8.16 (1H, d); 8.03 (1H, d); 7.48 (1H, dd); 7.17 (1H, d); 5.73 (1H, s); 3.88 (3H, s); 2.24 (3H, s); 0.29 (9H, s)

Step 2: (3-Ethynyl-quinolin-6-yloxy)-methylsulfanyl-acetic acid

To a solution of Methylsulfanyl-(3-trimethylsilanylethynyl-quinolin-6-yloxy)-acetic acid methyl ester (5 g) in ethanol (50 ml), a 2 M solution of sodium hydroxide in water (9.74 ml) was added. The reaction mixture was stirred at room temperature for 1 hour. The reaction mixture was poured into ice-could water (200 ml) and acidified with a 2 M solution of hydrochloric acid in water (9.74 ml). The precipitate was filtered off and washed with water to give (3-Ethynyl-quinolin-6-yloxy)-methylsulfanyl-acetic acid as yellowish solid (3.53 g).

$^1$H NMR (DMSO) δ ppm: 13.45 (1H, s); 8.73 (1H, d); 8.37 (1H, d); 7.93 (1H, d); 7.51 (1H, dd); 7.47 (1H, d); 6.03 (1H, s); 4.45 (1H, s); 2.11 (3H, s)

Step 3: N-tert-Butyl-2-(3-ethynyl-quinolin-6-yloxy)-2-methylsulfanyl-acetamide (3-Ethynyl-quinolin-6-yloxy)-methylsulfanyl-acetic acid (1.1 g), N-tert-Butyl amine (0.467 ml), 1-hydroxy-7-azabenzotriazole (HOAT) (0.602 mg), N-(3-dimethylaminopropyl)-N'-ethylcarbodiimide hydrochloride (EDCl) (849 mg) and triethylamine (0.84 ml) in dry N,N-dimethylformamide (20 ml) were stirred at ambient temperature for 16 hours. The reaction mixture was diluted with ethyl acetate and poured on 60 ml aq. sat. sodium hydrogen carbonate. The water phase was extracted with 3×150 ml ethyl acetate. All organic layers were combined, dried over sodium sulfate, filtered and evaporated. The residue was purified by column chromatography (heptane/ethyl acetate 13:7) to give N-tert-Butyl-2-(3-ethynyl-quinolin-6-yloxy)-2-methylsulfanyl-acetamide (1.11 g) as yellowish solid.

¹H NMR (CDCl₃) δ ppm: 8.85 (1H, d); 8.20 (1H, d); 8.06 (1H, d); 7.46 (1H, dd); 7.22 (1H, d); 6.43 (1H, s br); 5.59 (1H, s); 3.29 (1H, s); 2.20 (3H, s); 1.42 (9H, s)

EXAMPLE 2

N-(1-Cyano-2-fluoro-1-methyl-ethyl)-2-(3-ethynyl-quinolin-6-yloxy)-2-methylsulfanyl-acetamide

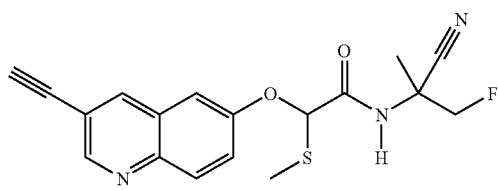 [SMILES: C#Cc1cnc2ccc(OC(SC)C(=O)NC(C)(C#N)CF)cc2c1]

To a solution of 2-amino-3-fluoro-2-methylpropionitrile (168 mg) in dry dimethylformamide (12 mL) were added triethylamine (0.22 mL), 1-hydroxy-7-azabenzotriazole (224 mg), N-(3-dimethylaminopropyl)-N'-ethylcarbodiimide.HCl (316 mg), then (3-ethynyl-quinolin-6-yloxy)-methylsulfanyl-acetic acid (450 mg). The reaction mixture was stirred at room temperature for 2 hours. The mixture was poured over brine and extracted twice with ethyl acetate (thrice). The organic layer was washed with water then with brine, dried over sodium sulphate, filtered and concentrated under reduced pressure. The crude was purified by chromatography eluting with cyclohexane/ethyl acetate (3:2 by volume), to give N-(1-cyano-2-fluoro-1-methyl-ethyl)-2-(3-ethynyl-quinolin-6-yloxy)-2-methylsulfanyl-acetamide (483 mg) as an oil.

¹H NMR (CDCl₃) ppm: 8.88 (1H, d); 8.21 (1H, s); 8.09 (1H, d); 7.48 (1H, dd); 7.25 (1H, m); 6.92, 6.87 (1H, s br, 2 isomeres); 5.73, 5.74 (1H, s, 2 isomeres); 4.53 to 4.98 (2H, m, 2 isomeres); 3.30 (1H, s); 2.21, 2.20 (3H, s, 2 isomeres); 1.96 (3H, m, 2 isomeres).

EXAMPLE 3

N-(1-Cyano-2-fluoro-1-methyl-ethyl)-2-(3-ethynyl-8-methyl-quinolin-6-yloxy)-2-methylsulfanyl-acetamide Step 1: preparation of N-(1-Cyano-2-fluoro-1-methyl-ethyl)-2-(3-iodo-8-methyl-quinolin-6-yloxy)-2-methylsulfanyl-acetamide

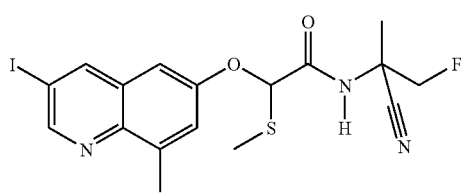 [SMILES: CSC(Oc1cc(C)c2ncc(I)cc2c1)C(=O)NC(C)(C#N)CF]

To a solution of 2-amino-3-fluoro-2-methylpropionitrile (315 mg) in dry dimethylformamide (20 mL) were added triethylamine (0.43 mL), 1-hydroxy-7-azabenzotriazole (420 mg), N-(3-dimethylaminopropyl)-N'-ethylcarbodiimide.HCl (591 mg), then (3-iodo-8-methyl-quinolin-6-yloxy)-methylsulfanyl-acetic acid (1.2 g). The reaction mixture was stirred at room temperature for 18 hours. The mixture was poured over brine and extracted twice with ethyl acetate (thrice). The organic layer was washed with water then with brine, dried over sodium sulphate, filtered and concentrated under reduced pressure. The crude was purified by chromatography eluting with cyclohexane/ethyl acetate (3:2 by volume), to give N-(1-cyano-2-fluoro-1-methyl-ethyl)-2-(3-iodo-8-methyl-quinolin-6-yloxy)-2-methylsulfanyl-acetamide (906 mg) as a solid.

¹H NMR (CDCl₃) ppm: 8.99 (1H, d); 8.48 (1H, d); 7.31 (1H, d); 7.01 (1H, d); 6.90, 6.84 (1H, s br, 2 isomeres); 5.61, 5.60 (1H, s, 2 isomeres); 4.54 to 4.99 (2H, m, 2 isomeres); 2.78 (3H, s); 2.21, 2.19 (3H, s, 2 isomeres); 1.87 (3H, m); mp: 70-79° C.

Step 2: preparation of N-(1-Cyano-2-fluoro-1-methyl-ethyl)-2-methylsulfanyl-2-(8-methyl-3-trimethylsilanylethynyl-quinolin-6-yloxy)-acetamide

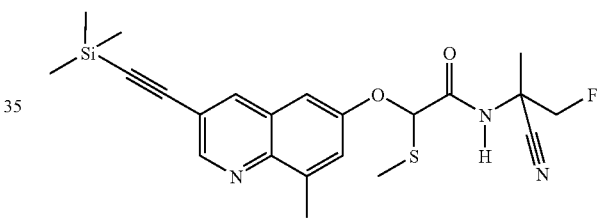

A solution of N-(1-cyano-2-fluoro-1-methyl-ethyl)-2-(3-iodo-8-methyl-quinolin-6-yloxy)-2-methylsulfanyl-acetamide (830 mg), Copper iodide (17 mg), bis(triphenylphosphine) palladium(II)dichloride (62 mg), diisopropylamine (0.29 mL) in dry dioxane (17 mL) was deoxygenated with argon. Then ethynyltrimethylsilane (0.30 mL) was added dropwise. The reaction mixture was stirred at room temperature for 18 hours. The mixture was poured over brine, ethyl acetate was added, the two layers were separated. The organic layer was washed with brine, dried over sodium sulphate, filtered and concentrated under reduced pressure. The crude was purified by chromatography eluting with cyclohexane/ethyl acetate (7:3 by volume), to give N-(1-cyano-2-fluoro-1-methyl-ethyl)-2-methylsulfanyl-2-(8-methyl-3-trimethylsilanylethynyl-quinolin-6-yloxy)-acetamide (727 mg) as an orange oil.

¹H NMR (CDCl₃) δ ppm: 8.83 (1H, d); 8.13 (1H, d); 7.30 (1H, d); 7.05 (1H, d); 6.92, 6.88 (1H, s br, 2 isomeres); 5.62, 5.61 (1H, s, 2 isomeres); 4.56 to 4.98 (2H, m, 2 isomeres); 2.78 (3H, s); 2.22, 2.19 (3H, s, 2 isomeres); 1.85 (3H, m); 0.30 (9H, m).

Step 3: preparation of N-(1-Cyano-2-fluoro-1-methyl-ethyl)-2-(3-ethynyl-8-methyl-quinolin-6-yloxy)-2-methylsulfanyl-acetamide

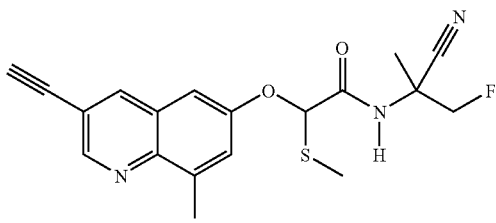 [SMILES: C#Cc1cnc2c(C)cc(OC(SC)C(=O)NC(C)(C#N)CF)cc2c1]

A solution of N-(1-cyano-2-fluoro-1-methyl-ethyl)-2-methylsulfanyl-2-(8-methyl-3-trimethylsilanylethynyl-quinolin-6-yloxy)-acetamide (685 mg) in methanol (20 mL) was added potassium carbonate (107 mg). The reaction mixture was stirred at room temperature for 15 minutes. The mixture was poured on a saturated solution of sodium hydrogencarbonate and extracted with ethyl acetate (thrice), dried over sodium sulphate, filtered and concentrated under reduced pressure. The crude was purified by chromatography eluting with cyclohexane/ethyl acetate (7:3 by volume), to give N-(1-cyano-2-fluoro-1-methyl-ethyl)-2-(3-ethynyl-8-methyl-quinolin-6-yloxy)-2-methylsulfanyl-acetamide (476 mg) as a white solid.

$^1$H NMR (CDCl$_3$) δ ppm: 8.89 (1H, d); 8.20 (1H, s); 7.32 (1H, m); 7.19 (1H, s), 6.92, 6.88 (1H, s br, 2 isomeres); 5.74, 5.72 (1H, s, 2 isomeres); 4.58 to 4.98 (m, 2H, 2 isomeres); 3.3 (1H, s); 2.80 (3H, s); 2.22, 2.20 (3H, s, 2 isomeres); 1.87 (3H, dd); mp: 180-182° C.

EXAMPLE 4

2-(3-Ethynyl-quinolin-6-yloxy)-2-methoxy-N-(2-methoxy-1,1-dimethyl-ethyl)-acetamide Step 1: (3-Iodo-quinolin-6-yloxy)-methoxy-acetic acid methyl ester

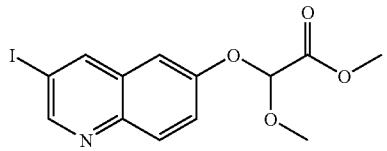 [SMILES: COC(=O)C(OC)Oc1ccc2ncc(I)cc2c1]

To a solution of potassium t-butoxide (1.36 g) in t-butyl alcohol (50 mL) was added a solution of 3-iodo-quinolin-6-ol (3 g) in t-butyl alcohol (5 mL). The reaction mixture was stirred at room temperature for 15 minutes. Bromo-methoxy-acetic acid methyl ester (4.0 g) and a solution of potassium iodide (catalytic quantity) in t-butyl alcohol (5 mL) were then added. The reaction mixture was stirred at room temperature for 18 hours. The mixture was poured on water and chloroform was added. The mixture was stirred. The two layers were separated, the aqueous layer was extracted with chloroform (twice). The organic layers were combined, washed with brine (twice), dried over sodium sulphate, filtered and concentrated under reduced pressure. The crude (4.3 g) was used directly in the next step without purification.

$^1$H NMR (CDCl$_3$) ppm: 8.80 (1H, d), 8.68 (1H, d); 8.05 (1H, d); 7.56 (1H, dd); 7.48 (1H, d); 5.72 (1H, s); 3.82 (3H, s); 3.51 (3H, s).

Step 2: Methoxy-(3-trimethylsilanylethynyl-quinolin-6-yloxy)-acetic acid methyl ester

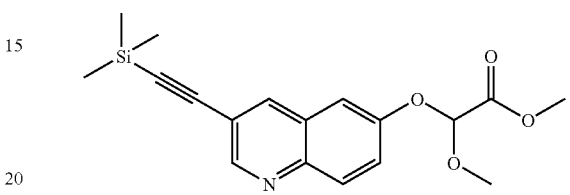

A solution of (3-Iodo-quinolin-6-yloxy)-methoxy-acetic acid methyl ester (3.48 g), Copper iodide (89 mg), bis(triphenylphosphine)palladium(II)dichloride (327 mg), diisopropylamine (1.57 mL) in dry tetrahydrofuran (80 mL) was deoxygenated with argon. Then, ethynyltrimethylsilane (1.6 mL) was added dropwise. The reaction mixture was stirred at room temperature for 2 hours. The mixture was poured over brine, ethyl acetate was added, the two layers were separated. The organic layer was washed with brine, dried over sodium sulphate, filtered and concentrated under reduced pressure. The crude was purified by chromatography eluting with cyclohexane/ethyl acetate (4:1 by volume), to give methoxy-(3-trimethylsilanylethynyl-quinolin-6-yloxy)-acetic acid methyl ester (2.14 g) as an orange oil.

$^1$H NMR (CDCl$_3$) ppm: 8.81 (1H, d); 8.18 (1H, d); 8.02 (1H, d); 7.50 (1H, dd); 7.32 (1H, d); 5.61 (1H, s); 3.88 (3H, s); 3.53 (3H, s); 0.30 (9H, s).

Step 3: (3-Ethynyl-quinolin-6-yloxy)-metoxy-acetic acid

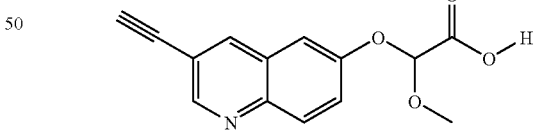

To a solution of methoxy-(3-trimethylsilanylethynyl-quinolin-6-yloxy)-acetic acid methyl ester (1.99 g) in ethanol (14 mL) was added a solution of sodium hydroxide 2N (4 mL) at 0° C. The reaction mixture was stirred at room temperature for 1 hour. Ethyl acetate and water were added. The mixture was stirred. The two layers were separated. The aqueous layer was acidified at pH 1 with HCl 2N. Then it was extracted with ethyl acetate (twice). The organic layer was dried over sodium sulphate, filtered and concentrated under reduced pressure to give (3-ethynyl-quinolin-6-yloxy)-metoxy-acetic acid (1.15 g) as an orange solid.

$^1$H NMR ((CD$_3$)$_2$CO) ppm: 8.81 (1H, d); 8.42 (1H, d); 8.04 (1H, d); 7.02 to 7.52 (2H, m); 5.82 (1H, s); 3.99 (1H, s); 3.57 (3H, s).

Step 4: 2-(3-Ethynyl-quinolin-6-yloxy)-2-methoxy-N-(2-methoxy-1,1-dimethyl-ethyl)-acetamide

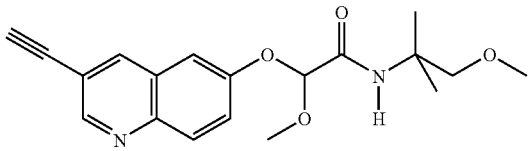 [SMILES: C#Cc1cnc2ccc(OC(OC)C(=O)NC(C)(C)COC)cc2c1]

To a solution of (3-ethynyl-quinolin-6-yloxy)-metoxyacetic acid (150 mg) in dry dimethylformamide (7 mL) were added 2-metoxy-1,1-dimethyl-ethylamine hydrochloride (81 mg) N-ethyldiisopropylamine (0.25 mL), dimethylaminopyridine (catalytic quantity) and (benzotriazol-1-yloxy)tris(dimethylamino)phosphonium hexafluorophosphate (297 mg). The reaction mixture was stirred at room temperature for 18 hours. The mixture was poured over brine and extracted twice with ethyl acetate (thrice). The organic layer was washed with water then with brine, dried over sodium sulphate, filtered and concentrated under reduced pressure. The crude was purified by chromatography eluting with cyclohexane/ethyl acetate (7:3 by volume), to give 2-(3-ethynyl-quinolin-6-yloxy)-2-methoxy-N-(2-methoxy-1,1-dimethyl-ethyl)-acetamide (172 mg) as an oil.

$^1$H NMR (CDCl$_3$) δ ppm: 8.83 (1H, d); 8.20 (1H, d); 8.02 (1H, d); 7.52 (1H, dd); 7.42 (1H, d); 6.77 (1H, s br); 5.41 (1H, s); 4.18 (2H, s); 3.54 (3H, s); 3.34 (3H, s); 3.28 (1H, s); 1.70 (6H, s).

EXAMPLE 5

2-(3-Ethynyl-quinolin-6-yloxy)-N-(2-hydroxy-1-methoxymethyl-1-methyl-ethyl)-2-methyl-sulfanyl-acetamide (3-Ethynyl-quinolin-6-yloxy)-methylsulfanyl-acetic acid (413 mg), 1-hydroxy-7-azabenzotriazole (HOAT) (267 mg), O-(Benzotriazol-1-yl)-N,N,N',N'-tetramethyluronium tetrafluoroborate (TBTU) (630 mg), 2-amino-3-methoxy-2-methyl-propan-1-ol (180 mg) and triethylamine (0.75 ml) in dry CH$_3$CN (20 ml) were stirred at ambient temperature overnight. The reaction mixture was diluted with ethyl acetate and poured on sat. aq. NH$_4$Cl. The water phase was extracted 3 times with ethyl acetate. The combined organic layers were washed with brine, dried over sodium sulfate, filtered and evaporated. The residue was purified by column chromatography (cyclohexane/ethyl acetate 1:1) to give as a yellowish oil 2-(3-Ethynyl-quinolin-6-yloxy)-N-(2-hydroxy-1-methoxymethyl-1-methyl-ethyl)-2-methylsulfanyl-acetamide (200 mg) as a mixture of diastereoisomers.

$^1$H NMR (CDCl$_3$) δ ppm: 8.80 (1H, d); 8.20 (1H, d); 8.05 (1H, d); 7.45 (1H, dd); 7.30 (1H, br s, isomer A); 7.25 (1H, br s, isomer B); 7.22 (1H, d); 5.67 (1H, s); 3.76-3.40 (4H, m); 3.36 (3H, s, isomer A); 3.34 (3H, s, isomer B); 3.30 (1H, s); 2.19 (3H, s, isomer A); 2.18 (3H, s, isomer B); 1.36 (3H, s, isomer A); 1.34 (3H, s, isomer B).

EXAMPLE 6

2-(3-Ethynyl-quinolin-6-yloxy)-N-(1-methoxymethyl-1-methyl-2-oxo-ethyl)-2-methyl-sulfanyl-acetamide A solution of 2-(3-Ethynyl-quinolin-6-yloxy)-N-(2-hydroxy-1-methoxymethyl-1-methyl-ethyl)-2-methylsulfanyl-acetamide (200 mg) in dry CH$_2$Cl$_2$ (15 ml) was treated with Dess-Martin periodinane (295 mg). The mixture was stirred at room temperature during 1 h then poured on sat aq NaHCO$_3$. After separation the water phase was washed twice with CH$_2$Cl$_2$ The combined organic phases were washed with brine, dried over sodium sulfate, filtered and evaporated. The crude residue was purified by column chromatography (cyclohexane/ethyl acetate 1:1) to give (3-Ethynyl-quinolin-6-yloxy)-N-(1-methoxymethyl-1-methyl-2-oxo-ethyl)-2-methylsulfanyl-acetamide (120 mg) as yellowish oil as a mixture of diastereoisomers.

$^1$H NMR (CDCl$_3$) δ ppm: 9.50 (1H, s, isomer A); 9.48 (1H, s, isomer B); 8.85 (1H, d); 8.20 (1H, m); 8.06 (1H, d); 7.55 (1H, br s, isomer A); 7.51 (1H, m); 7.50 (1H, br s, isomer B); 7.25 (1H, m); 5.72 (1H, s); 3.94 (1H, d, isomer A); 3.81 (1H, d, isomer B); 3.70 (1H, m); 3.33 (3H, s, isomer A); 3.32 (3H, s, isomer B); 3.30 (1H, s); 2.20 (3H, s, isomer A); 2.19 (3H, s, isomer B); 1.51 (3H, s, isomer A); 1.50 (3H, s, isomer B).

EXAMPLE 7

2-(3-Ethynyl-quinolin-6-yloxy)-N-(1-methoxymethyl-1-methyl-prop-2-ynyl)-2-methyl-sulfanyl-acetamide A mixture of (1-diazo-2-oxo-propyl)-phosphonic acid dimethyl ester (Bestmann's reagent) (43 mg) and 2-(3-ethynyl-quinolin-6-yloxy)-N-(1-methoxymethyl-1-methyl-2-oxo-ethyl)-2-methylsulfanyl-acetamide (60 mg) in MeOH (6 ml) was cooled to 0° C. Solid K$_2$CO$_3$ (40 mg) was added and the mixture stirred during 16 hour allowing the temperature raising to 25° C. The reaction mixture was diluted with ethyl acetate and poured onto brine. The water phase was extracted twice with ethyl acetate and the combined organic phases dried over sodium sulfate, filtered and evaporated. The crude residue was purified by column chromatography to give 2-(3-ethynyl-quinolin-6-yloxy)-N-(1-methoxymethyl-1-methyl-prop-2-ynyl)-2-methylsulfanyl-acetamide (52 mg) as a light brown oil as a mixture of diastereoisomers.

$^1$H NMR (CDCl$_3$) δ ppm: 8.86 (1H, d); 8.21 (1H, d); 8.06 (1H, d); 7.48 (1H, d); 7.24 (1H, d); 7.05 (1H, br s); 5.68 (1H, s, isomer B); 5.67 (1H, s, isomer A); 3.74 (1H, d, isomer A); 3.68 (2H, s, isomer B); 3.60 (1H, d, isomer A); 3.48 (3H, s, isomer B); 3.46 (3H, s, isomer A); 3.30 (1H, s); 2.47 (1H, s, isomer A); 2.46 (1H, s, isomer B); 2.21 (3H, s, isomer B); 2.20 (3H, s, isomer A); 1.72 (3H, s, isomer A); 1.70 (3H, s, isomer B).

EXAMPLE 8

2-(3-Ethynyl-8-methyl-quinolin-6-yloxy)-N-(2-hydroxy-1-methoxymethyl-1-methyl-ethyl)-2-methyl-sulfanyl-acetamide Step 1: N-(2-Hydroxy-1-methoxymethyl-1-methylethyl)-2-methylsulfanyl-2-(8-methyl-3-trimethylsilanylethynyl-quinolin-6-yloxy)-acetamide 2-(3-Bromo-8-methyl-quinolin-6-yloxy)-N-(2-hydroxy-1-methoxymethyl-1-methylethyl)-2-methylsulfanyl-acetamide (800 mg), palladium tetrakis triphenylphosphine (100 mg) and Copper iodine (14 mg) were added to triethylamine (20 ml) and deoxygenated during 5 min with nitrogen. Trimethylsilylacetylene (0.370 ml) was added to the reaction mixture. The reaction mixture was stirred at 50° C. for 1 day. Trimethylsilylacetylene (0.370 ml) was then added to the reaction mixture together with little amounts of copper iodide and palladium catalyst. After stirring for a day at 48° C. the reaction mixture was evaporated. The crude residue was purified by column chromatography (cyclohexane/ethyl acetate/dichlorometane 1:1:1) to give N-(2-hydroxy-1-methoxymethyl-1-methyl-ethyl)-2-methylsulfanyl-2-(8-methyl-3-trimethylsilanylethynyl-quinolin-6-yloxy)-acetamide (600 mg) as light brown solid as mixture of diastereosisomers.

$^1$H NMR (CDCl$_3$) δ ppm: 8.82 (1H, d); 8.15 (1H, d); 7.31 (1H, d); 7.25 (1H, br s); 7.02 (1H, d); 5.66 (1H, s); 4.0 (1H, m); 3.78-3.43 (4H, m); 3.35 (3H, s, isomer A); 3.34 (3H, s, isomer B); 2.78 (3H, s); 2.20 (3H, s, isomer A); 2.19 (3H, s, isomer B); 1.36 (3H, s, isomer A); 1.32 (3H, s, isomer B); 0.32 (9H, s).

Step 2: 2-(3-Ethynyl-8-methyl-quinolin-6-yloxy)-N-(2-hydroxy-1-methoxymethyl-1-methyl-ethyl)-2-methylsulfanyl-acetamide A solution of N-(2-hydroxy-1-methoxymethyl-1-methyl-ethyl)-2-methylsulfanyl-2-(8-methyl-3-trimethylsilanyl-ethynyl-quinolin-6-yloxy)-acetamide (650 mg) in methanol (16 ml) was treated with potassium carbonate (97 mg) at room temperature. The reaction mixture was stirred for 1 h. The reaction mixture was diluted with ethyl acetate and washed with sat. aq. sodium hydrogen carbonate. The aqueous layer was extracted twice with ethyl acetate. The organic layers were combined, dried over sodium sulfate, filtered and evaporated. The residue was purified by column chromatography (cyclohexane/ethyl acetate/dichloromethane 2:2:1) to give 2-(3-ethynyl-8-methyl-quinolin-6-yloxy)-N-(2-hydroxy-1-methoxymethyl-1-methyl-ethyl)-2-methylsulfanyl-acetamide (480 mg) as a white solid as mixture of diastereoisomers.

$^1$H NMR (CDCl$_3$) δ ppm: 8.85 (1H, d); 8.19 (1H, d); 7.32 (1H, d); 7.27 (1H, br s); 7.06 (1H, d); 5.66 (1H, s); 4.0 (1H, m); 3.81-3.42 (4H, m); 3.39 (3H, s, isomer A); 3.37 (3H, s, isomer B); 3.28 (1H,$); 2.79 (3H, s); 2.20 (3H, s, isomer A); 2.19 (3H, s, isomer B); 1.35 (3H, s, isomer A); 1.33 (3H, s, isomer B).

EXAMPLE 9

2-(3-Ethynyl-8-methyl-quinolin-6-yloxy)-N-(1-methoxymethyl-1-methyl-2-oxo-ethyl)-2-methylsulfanyl-acetamide A solution of 2-(3-ethynyl-8-methyl-quinolin-6-yloxy)-N-(2-hydroxy-1-methoxymethyl-1-methyl-ethyl)-2-methylsulfanyl-acetamide (240 mg) in dry CH$_2$Cl$_2$ (15 ml) was treated with Dess-Martin periodinane (341 mg). The mixture was stirred at room temperature during 1 h then poured on sat aq NaHCO$_3$. After separation the water phase was washed twice with CH$_2$Cl$_2$ The combined organic phases were washed with brine, dried over sodium sulfate, filtered and evaporated. The crude residue was purified by column chromatography (cyclohexane/ethyl acetate 1:1) to give (3-ethynyl-quinolin-6-yloxy)-N-(1-methoxymethyl-1-methyl-2-oxo-ethyl)-2-methylsulfanyl-acetamide (215 mg) as yellowish oil as a mixture of diastereoisomers.

$^1$H NMR (CDCl$_3$) δ ppm: 9.49 (1H, s, isomer A); 9.46 (1H, s, isomer B); 8.86 (1H, d); 8.18 (1H, m); 7.60 (1H, br s, isomer A); 7.50 (1H, br s, isomer B); 7.37 (1H, m); 7.08 (1H, m); 5.72 (1H, s); 3.95 (1H, d, isomer A); 3.82 (1H, d, isomer B); 3.70 (1H, m); 3.35 (3H, s, isomer A); 3.34 (3H, s, isomer B); 3.30 (1H, s); 2.22 (3H, s, isomer A); 2.21 (3H, s, isomer B); 1.51 (3H, s).

EXAMPLE 10

2-(3-ethynyl-8-methyl-quinolin-6-yloxy)-N-(1-methoxymethyl-1-methyl-prop-2-ynyl)-2-methylsulfanyl-acetamide A mixture of (1-diazo-2-oxo-propyl)-phosphonic acid dimethyl ester (Bestmann's reagent) (77 mg) and 2-(3-ethynyl-8-methyl-quinolin-6-yloxy)-N-(1-methoxymethyl-1-methyl-2-oxo-ethyl)-2-methylsulfanyl-acetamide (110 mg) in MeOH (10 ml) was cooled to 0° C. Solid K$_2$CO$_3$ (71 mg) was added and the mixture stirred during 16 hour allowing the temperature raising to 25° C. The reaction mixture was diluted with ethyl acetate and poured onto brine. The water phase was extracted twice with ethyl acetate and the combined organic phases dried over sodium sulfate, filtered and evaporated. The crude residue was purified by column chromatography to give 2-(3-ethynyl-8-methyl-quinolin-6-yloxy)-N-(1-methoxymethyl-1-methyl-prop-2-ynyl)-2-methylsulfanyl-acetamide (60 mg) as a light brown solid as a mixture of diastereoisomers.

$^1$H NMR (CDCl$_3$) δ ppm: 8.85 (1H, d); 8.19 (1H, d); 7.32 (1H, d); 7.06 (1H, d); 7.03 (1H, br s, isomer A); 7.02 (1H, br s, isomer B); 5.66 (1H, s, isomer B); 5.65 (1H, s, isomer A); 3.76 (1H, d, isomer A); 3.69 (2H, s, isomer B); 3.61 (1H, d, isomer A); 3.48 (3H, s, isomer B); 3.47 (3H, s, isomer A); 3.30 (1H, s); 2.79 (3H, s); 2.44 (1H, s, isomer A); 2.43 (1H, s, isomer B); 2.20 (3H, s, isomer B); 2.20 (3H, s, isomer A); 1.72 (3H, s, isomer A); 1.70 (3H, s, isomer B); mp 108-109° C.

EXAMPLE 11

2-(3-Ethynyl-8-methyl-quinolin-6-yloxy)-N-(2-methoxy-1-methoxymethyl-1-methyl-ethyl)-2-methylsulfanyl-acetamide To a solution of 2-(3-ethynyl-8-methyl-quinolin-6-yloxy)-N-(2-hydroxy-1-methoxymethyl-1-methyl-ethyl)-2-methylsulfanyl-acetamide (120 mg) in dry THF (7 ml) NaH (19 mg, 60% in oil) was added at room temperature under a nitrogen atmosphere. After 30 minute iodomethane (30 □l) was added to the reaction mixture. After stirring during 5 h one equivalent of NaH and one equivalent of iodomethane were added. The mixture was stirred overnight at room temperature, then quenched with water and diluted with ethyl acetate. The water phase was extracted twice with ethyl acetate and the combined organic phases dried over sodium sulfate, filtered and evaporated. The crude residue was purified by column chromatography (cyclohexane/ethyl acetate/dichloromethane, 1:1:1) to give 2-(3-ethynyl-8-methyl-quinolin-6-yloxy)-N-(2-methoxy-1-methoxymethyl-1-methyl-ethyl)-2-methylsulfanyl-acetamide (46 mg) as a light brown oil.

$^1$H NMR (CDCl$_3$) δ ppm: 8.85 (1H, d); 8.18 (1H, d); 7.31 (1H, d); 7.05 (1H, d); 6.97 (1H, br s); 5.60 (1H, s); 3.62-3.44 (4H, m); 3.38 (3H, m); 3.28 (1H, s); 2.78 (3H, s); 2.20 (3H, s); 1.45 (3H, s).

EXAMPLE 12

2-(3-Ethynyl-8-methyl-quinolin-6-yloxy)-N-(2-methoxy-1-methyl-1-prop-2-ynyloxymethyl-ethyl)-2-methylsulfanyl-acetamide To a solution of 2-(3-ethynyl-8-methyl-quinolin-6-yloxy)-N-(2-hydroxy-1-methoxymethyl-1-methyl-ethyl)-2-methylsulfanyl-acetamide (120 mg) in dry THF (10 ml) NaH (27 mg, 60% in oil) was added at room temperature under a nitrogen atmosphere. After 30 minute propargyl bromide (115 mg) was added to the reaction mixture. After stirring during 5 h one equivalent of NaH and one equivalent of propargyl bromide were added. The mixture was stirred during 4 h at 55° C., then quenched with water and diluted with ethyl acetate. The water phase was extracted twice with ethyl acetate and the combined organic phases dried over sodium sulfate, filtered and evaporated. The crude residue was purified by column chromatography (cyclohexane/ethyl acetate, 3:2) to give 2-(3-Ethynyl-8-methyl-quinolin-6-yloxy)-N-(2-methoxy-1-methyl-1-prop-2-ynyloxymethyl-ethyl)-2-methylsulfanyl-acetamide (66 mg) as a light brown oil as a mixture of diastereoisomers.

$^1$H NMR (CDCl$_3$) δ ppm: 8.86 (1H, d); 8.19 (1H, d); 7.32 (1H, d); 7.06 (1H, d); 6.98 (1H, br s); 5.61 (1H, s); 4.20 (2H, m); 3.80-3.48 (4H, m); 3.39 (3H, m, isomer A); 3.38 (3H, s, isomer B); 3.29 (1H, s); 2.79 (3H, s); 2.48 (1H, m); 2.21 (3H, s); 1.47 (3H, s).

EXAMPLE 12a

This Example illustrates the preparation of N-(1-Ethynyl-1-methyl-prop-2-ynyl)-2-(3-ethynyl-quinolin-6-yloxy)-2-methylsulfanyl-acetamide

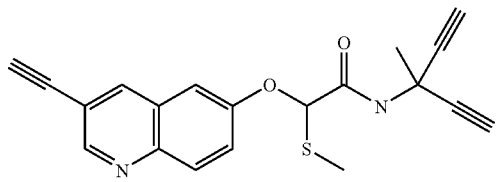 [SMILES: C#Cc1cnc2ccc(OC(SC)C(=O)NC(C)(C#C)C#C)cc2c1]

Stage 1: Preparation of 2-Amino-3-(tert-butyl-diphenyl-silanyloxy)-2-methyl-propan-1-ol

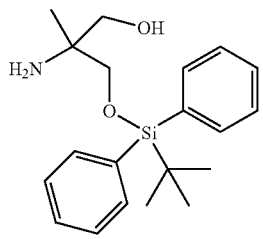 [SMILES: CC(N)(CO)CO[Si](c1ccccc1)(c1ccccc1)C(C)(C)C]

Sodium hydride (55% in dispersion in oil) (1.141 g) was added portion wise to a solution of 2-amino-2-methyl-propane-1,3-diol (2.50 g) in dry THF (35 ml) at 0° C. The reaction mixture was stirred at room temperature for 1 h. tert-Butyldiphenylsilyl chloride (6.54 g) in dry THF (10 ml) was added dropwise 0° C. and the reaction mixture was stirred for 17 hrs at room temperature. The reaction mixture was quenched with water (18 ml) and extracted thrice with ethyl ether. The two layers were separated and the organic layer was washed once with water and then dried over sodium sulphate, filtered and concentrated under reduced pressure to yield 8.94 g of 2-amino-3-(tert-butyl-diphenyl-silanyloxy)-2-methyl-propan-1-ol as a crude product which was used as such in Stage 2 described below. $^1$H NMR (CDCl$_3$) δ ppm: 7.68-7.62 (4H, m); 7.47-7.37 (6H); 3.52 (2H, dd); 3.39 (2H, dd); 1.09 (9H, s); 1.02 (3H, s).

Stage 2: Preparation of N-[1-(tert-Butyl-diphenyl-silanyloxymethyl)-2-hydroxy-1-methyl-ethyl]-2-(3-ethynyl-quinolin-6-yloxy)-2-methylsulfanyl-acetamide

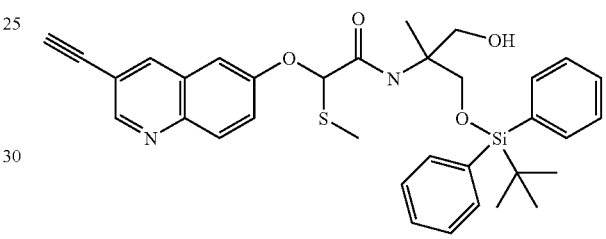

To a solution of (3-ethynyl-quinolin-6-yloxy)-methylsulfanyl-acetic acid (1.525 g) and triethylamine (2.72 ml) in dry acetonitrile (15 ml) at room temperature were added successively 1-hydroxy-7-azabenzotriazole (0.911 g) and O-(1H benzotriazol-1-yl)-N,N,N',N'-tetramethyluronium tetrafluoroborate (2.15 g) in dry acetonitrile (15 ml) and a solution of crude 2-amino-3-(tert-butyl-diphenyl-silanyloxy)-2-methyl-propan-1-ol (2.30 g) from Stage 1 in dry acetonitrile (23 ml). The reaction mixture was stirred at room temperature for 16 hours and poured onto a mixture of saturated NaHCO$_3$, ethyl acetate and brine. The two layers were separated and the aqueous layer was extracted thrice with ethyl acetate. The organic layers were combined, washed with sat. NaHCO$_3$ and with brine and dried over sodium sulphate. After filtration and concentration under reduced pressure, the crude mixture were isolated as a dark orange oil that was dissolved in 40 ml of THF/H$_2$O (1/1) and treated with LiOH monohydrate at room temperature for 2 h. The crude mixture was extracted (pH=11) thrice with ethyl acetate. The organic layers were combined, washed with water and brine and dried over sodium sulphate. After filtration and concentration under reduced pressure, crude N-[1-(tert-butyl-diphenyl-silanyloxymethyl)-2-hydroxy-1-methyl-ethyl]-2-(3-ethynyl-quinolin-6-yloxy)-2-methylsulfanyl-acetamide (1.94 g) was obtained as a yellow oil and used in the next step without any further purification. $^1$H NMR (CDCl$_3$) δ ppm: 8.88 (1H, d); 8.19-8.16 (1H, m), 8.00 (1H, t); 7.66-7.52 (5H, m); 7.48-7.26 (7H, m); 7.21-7.18 (1H, m); [{5.69 (s), 5.66 (s) 1H}, isomer A and isomer B]; 4.32-4.11 (1H, dm); 3.78-3.52 (4H, m); 3.30 (1H, s); [{2.21 (s), 2.19 (s) 3H}, isomer A and isomer B];

[{1.49 (s), 1.34 (s) 3H}, isomer A and isomer B]; [{1.11 (s), 1.08 (s) 9H}, isomer A and isomer B].

Stage 3: Preparation of N-[1-(tert-butyl-diphenyl-silanyloxymethyl)-1-methyl-2-oxo-ethyl]-2-(3-ethynyl-quinolin-6-yloxy)-2-methylsulfanyl-acetamide

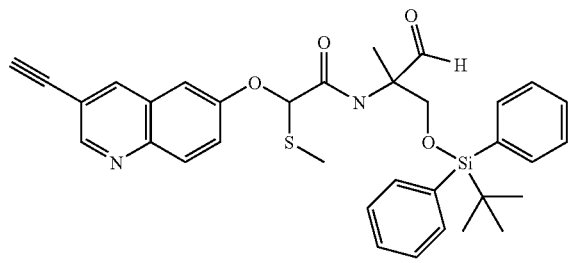 [SMILES: C#Cc1cnc2ccc(OC(SC)C(=O)NC(C)(C=O)CO[Si](c3ccccc3)(c3ccccc3)C(C)(C)C)cc2c1]

N-[1-(tert-Butyl-diphenyl-silanyloxymethyl)-2-hydroxy-1-methyl-ethyl]-2-(3-ethynyl-quinolin-6-yloxy)-2-methyl-sulfanyl-acetamide (1.90 g) from Stage 2 above in dichloromethane (55 ml) was treated with Dess-Martin periodinane (1.615 g). The reaction mixture was stirred at room temperature for 1 h30 and then treated with saturated aqueous NaHCO₃ and saturated aqueous sodium thiosulphate. The organic layer was washed thrice with saturated aqueous NaHCO₃. The organic phase was separated, dried over sodium sulphate, filtered and evaporated to yield 1.694 g of N-[1-(tert-butyl-diphenyl-silanyloxymethyl)-1-methyl-2-oxo-ethyl]-2-(3-ethynyl-quinolin-6-yloxy)-2-methylsulfanyl-acetamide which was used as such in Stage 4 described below.

¹H NMR (CDCl₃) δ ppm: [{9.51 (s), 9.49 (s) 1H}, isomer A and isomer B]; 8.88 (1H, d); 8.19 (1H, d); 8.02 (1H, d); 7.66-7.54 (5H, m); 7.48-7.30 (7H, m); 7.26-7.21 (1H, dd); [{5.70 (s), 5.66 (s) 1H}, isomer A and isomer B]; 4.01-3.88 (2H, m); 3.30 (1H, s); [{2.22 (s), 2.20 (s) 3H}, isomer A and isomer B]; [{1.50 (s), 1.48 (s) 3H}, isomer A and isomer B]; [{1.02 (s), 0.99 (s) 9H}, isomer A and isomer B].

Stage 4: Preparation of N-[1-(tert-butyl-diphenyl-silanyloxymethyl)-1-methyl-prop-2-ynyl]-2-(3-ethynyl-quinolin-6-yloxy)-2-methylsulfanyl-acetamide

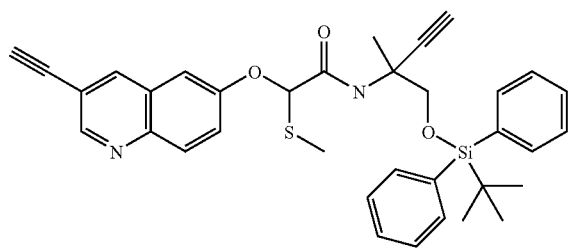 [SMILES: C#Cc1cnc2ccc(OC(SC)C(=O)NC(C)(C#C)CO[Si](c3ccccc3)(c3ccccc3)C(C)(C)C)cc2c1]

A solution of dimethyl-1-diazo-2-oxopropylphosphonate (0.86 g) in dry methanol (20 ml) was added at room temperature to a solution of crude N-[1-(tert-butyl-diphenyl-silanyloxymethyl)-1-methyl-2-oxo-ethyl]-2-(3-ethynyl-quinolin-6-yloxy)-2-methylsulfanyl-acetamide from Stage 3 in dry methanol (40 ml). The reaction medium was cooled down to 0° C. and potassium carbonate (0.773 g) was added portionwise along with additional dry methanol (10 ml). The reaction mixture was allowed to warm up to room temperature, stirred for 16 hours and then poured onto a mixture of ethyl acetate and brine. The two layers were separated and the aqueous layer was extracted thrice with ethyl acetate. The organic layers were combined, washed once with brine and then dried over sodium sulphate. After filtration and concentration under reduced pressure 1.84 g of crude mixture were isolated as a dark orange oil which was purified by flash chromatography on silica gel (hexane/ethyl acetate) to give the desired N-[1-(tert-butyl-diphenyl-silanyloxymethyl)-1-methyl-prop-2-ynyl]-2-(3-ethynyl-quinolin-6-yloxy)-2-methylsulfanyl-acetamide as a yellow oil (1.52 g). ¹H NMR (CDCl₃) δ ppm: 8.88 (1H, d); 8.19 (1H, d); 8.01 (1H, dd); 7.70-7.62 (4H, m); 7.46-7.30 (8H, m); 7.21-7.19, (1H, m); [{5.69 (s), 5.66 (s) 1H}, isomer A and isomer 13]; 3.93-3.72 (2H, dm); 3.30 (1H, s); 2.39 (1H, d); [{2.23 (s), 2.21 (s) 3H}, isomer A and isomer B]; 1.71 (3H, d); [{1.10 (s), 1.08 (s) 9H}, isomer A and isomer B].

Stage 5: Preparation of 2-(3-ethynyl-quinolin-6-yloxy)-N-(1-hydroxymethyl-1-methylprop-2-ynyl)-2-methylsulfanyl-acetamide

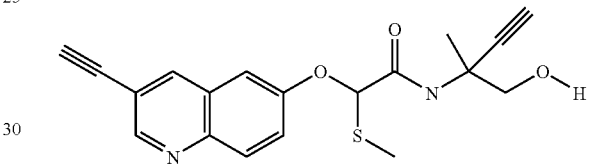

A solution of tetrabutylammonium fluoride (1 M) in THF was added dropwise to a solution of N-[1-(tert-butyl-diphenyl-silanyloxymethyl)-1-methyl-prop-2-ynyl]-2-(3-ethynyl-quinolin-6-yloxy)-2-methylsulfanyl-acetamide (1.49 g) at 0° C. The reaction mixture was allowed to warm up to room temperature, stirred for 1.5 h and then poured onto a mixture of ethyl acetate and brine. The two layers were separated and the aqueous layer was extracted thrice with ethyl acetate. The organic layers were combined, washed once with brine and then dried over sodium sulphate. After filtration and concentration under reduced pressure 2.47 g of crude material was isolated as a yellow oil which was purified by flash chromatography on silica gel (hexane/ethyl acetate) to provide 2-(3-ethynyl-quinolin-6-yloxy)-N-(1-hydroxymethyl-1-methyl-prop-2-ynyl)-2-methylsulfanyl acetamide as a white solid (0.646 g, m.p.=149-150° C.) which was used directly in Stage 6 described below.

Stage 6: Preparation of 2-(3-ethynyl-quinolin-6-yloxy)-N-(1-formyl-1-methyl-prop-2-ynyl)-2-methylsulfanyl acetamide

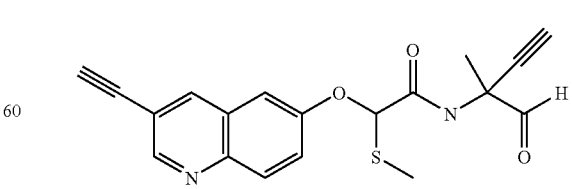

2-(3-Ethynyl-quinolin-6-yloxy)-N-(1-hydroxymethyl-1-methylprop-2-ynyl)-2-methylsulfanyl acetamide (0.513 g) in dichloromethane (25 ml) was treated with Dess-Martin periodinane (0.737 g). The reaction mixture was stirred at 0.646 g for 2 hrs and then treated with sat. aqueous NaHCO₃ and sat. aqueous sodium thiosulphate. The organic layer was washed thrice with sat. aqueous. NaHCO₃. After separation, the organic phase was dried over sodium sulphate, filtered and evaporated to yield crude 2-(3-ethynyl-quinolin-6-yloxy)-N-(1-formyl-1-methyl-prop-2-ynyl)-2-methylsulfanyl acetamide which was used as such in Stage 6. ¹H NMR (CDCl₃) δ ppm: 9.40 (1H, s); 8.86 (1H, d); 8.22 (1H, d); 8.07 (1H, d); 7.52-7.49 (1H, m); [{7.49 (s br), 7.44 (s br) 1H}, isomer A and isomer B]; 7.26 (1H, m); [{5.74 (s), 5.72 (s) 1H}, isomer A and isomer B]; 3.29 (1H, s); 2.54 (1H, s); [{2.23 (s), 2.21 (s) 3H}, isomer A and isomer B]; 1.79 (3H, s).

Stage 6: Preparation of N-(1-ethynyl-1-methyl-prop-2-ynyl)-2-(3-ethynyl-quinolin-6-yloxy)-2-methylsulfanyl-acetamide

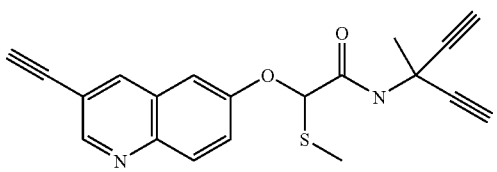 [SMILES: C#Cc1cnc2ccc(OC(SC)C(=O)NC(C)(C#C)C#C)cc2c1]

A solution of dimethyl-1-diazo-2-oxopropylphosphonate (0.109 g) in dry methanol (2 ml) was added at room temperature to a solution of crude 2-(3-ethynyl-quinolin-6-yloxy)-N-(1-formyl-1-methyl-prop-2-ynyl)-2-methylsulfanyl-acetamide (0.125 g) from Stage 5 in methanol (5 ml). The reaction medium was cooled down to 0° C. and potassium carbonate (0.098 g) was added portion wise. The reaction mixture was allowed to warm up to room temperature and stirred for 5.5 hours and then poured onto a mixture of ethyl acetate and brine. The two layers were separated and the aqueous layer was extracted thrice with ethyl acetate. The organic layers were combined, washed once with brine and then dried over sodium sulphate. After filtration and concentration under reduced pressure the resulting crude mixture was purified by flash chromatography on silica gel (hexane/ethyl acetate) of N-(1-ethynyl-1-methyl-prop-2-ynyl)-2-(3-ethynyl-quinolin-6-yloxy)-2-methylsulfanyl-acetamide as a white solid (m.p.: 148-154° C.).

EXAMPLE 12b

This Example illustrates the preparation of 2-(3-ethynyl-quinolin-6-yloxy)-N-(1-methyl-1-prop-2-ynyloxymethyl-prop-2-ynyl)-2-methylsulfanyl-acetamide.

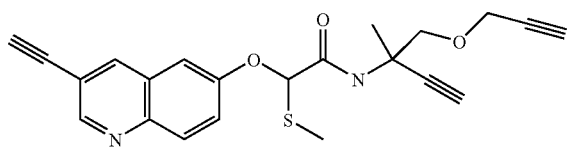 [SMILES: C#CCOCC(C)(C#C)NC(=O)C(Oc1ccc2ncc(C#C)cc2c1)SC]

Stage 1: Preparation of 3-methyl-3-prop-2-ynyloxymethyl-1-oxa-4-aza-spiro[4.5]decane

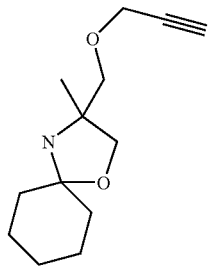 [SMILES: C#CCOCC1(C)COC2(CCCCC2)N1]

Sodium hydride (55% in dispersion in oil) (0.636 g) was added portion wise to a solution of (3-methyl-1-oxa-4-aza-spiro[4.5]dec-3-yl)-methanol (2.0 g) in dry THF (30 ml) at 0° C. The reaction mixture was stirred at room temperature for 1 h. Propargyl bromide (0.972 ml) was added dropwise at 0° C. and the resulting mixture was stirred at room temperature for 2.5 h. The reaction mixture was treated with ethanol (4 ml) and diluted with diethyl ether and the mixture was filtered. The filtrate was concentrated in vacuo to providing a crude residue which was purified by column chromatography (hexane/ethyl acetate 1:1) to give 2.33 g of 3-methyl-3-prop-2-ynyloxymethyl-1-oxa-4-aza-spiro[4.5]decane as an orange liquid. ¹H NMR (CDCl₃) δ ppm: 4.18 (2H, d); 3.82 (1H, d); 3.53 (1H, d); 3.43 (1H, d); 3.38 (1H, d); 2.42 (1H, t); 1.7-1.2 (10H, m); 1.25 (1H, s).

Stage 2: Preparation of 2-amino-2-methyl-3-prop-2-ynyloxy-propan-1-ol hydrochloric salt

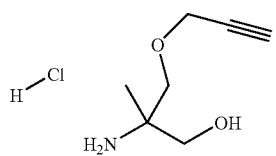

3-Methyl-3-prop-2-ynyloxymethyl-1-oxa-4-aza-spiro[4.5]decane (1.83 g) in an aqueous solution of HCl (6N) (2.73 ml) were refluxed for 1 hr. The reaction mixture was cooled down to room temperature, diluted with water and extracted thrice with ethyl ether. The two layers were separated. The aqueous layer was concentrated under reduced pressure to yield 2-amino-2-methyl-3-prop-2-ynyloxy-propan-1-ol hydrochloric salt (1.205 g) as a white beige solid which was used as such in Stage 3 described below. $^1$H NMR (DMSO) δ ppm: 8.02 (3H, s br); 5.47 (1H, s br); 4.21 (2H, s); 3.54-3.49 (5H, m); 1.15 (3H, s).

Stage 3: Preparation of 2-(3-ethynyl-quinolin-6-yloxy)-N-(2-hydroxy-1-methyl-1-prop-2-ynyloxymethyl-ethyl)-2-methylsulfanyl-acetamide

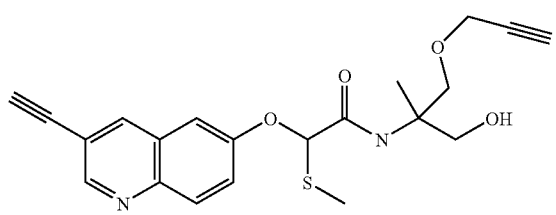 [SMILES: C#CCOCC(C)(CO)NC(=O)C(Oc1ccc2ncc(C#C)cc2c1)SC]

1-Hydroxy-7-azabenzotriazole (0.717 g), O-(1H benzotriazol-1-yl)-N,N,N',N'-tetramethyl-uronium tetrafluoroborate (1.692 g) and 2-mmino-2-methyl-3-prop-2-ynyloxy-propan-1-ol hydrochloric salt (0.947 g) were added at room temperature to a solution of triethylamine (2.14 ml) and (3-ethynyl-quinolin-6-yloxy)-methylsulfanyl-acetic acid (1.20 g) in DMF. The reaction mixture was stirred 16 hrs at room temperature and then poured onto a mixture of ethyl acetate and brine. The two layers were separated and the aqueous layer was extracted thrice with ethyl acetate. The organic layers were combined, washed with sat. sodium hydrogen carbonate, with water and brine and then dried over sodium sulphate. After filtration and concentration under reduced pressure the crude residue was purified was dissolved in 24 ml of THF/H$_2$O (1/1) and treated with of LiOH monohydrate at room temperature for 1 h 45 min. The crude mixture was extracted (pH=11) thrice with ethyl acetate. The organic layers were combined, washed with water and brine and after separation dried over sodium sulphate. Filtration and concentration under reduced pressure provided crude 2-(3-ethynyl-quinolin-6-yloxy)-N-(2-hydroxy-1-methyl-1-prop-2-ynyloxymethyl-ethyl)-2-methylsulfanyl-acetamide as a yellow oil that was used in the next step, Stage 4, without any further purification. $^1$H NMR (CDCl$_3$) δ ppm: 8.88 (1H, d); 8.22 (1H, d); 8.07 (1H, d); 7.49 (1H, dd); 7.39 (1H, s br); 7.22 (1H, m); 5.68 (1H, s); 4.22-4.16 (2H, m); 3.90 (1H, s br); 3.81-3.60 (4H, m); 3.30 (1H, s); 2.45 (1H, dt); [{2.22 (s), 2.20 (s) 3H}, isomer A and isomer B]; [{1.40 (s), 1.34 (s) 3H}, isomer A and isomer B].

Stage 4: Preparation of 2-(3-ethynyl-quinolin-6-yloxy)-N-(1-methyl-2-oxo-1-prop-2-ynyloxymethyl-ethyl)-2-methylsulfanyl-acetamide

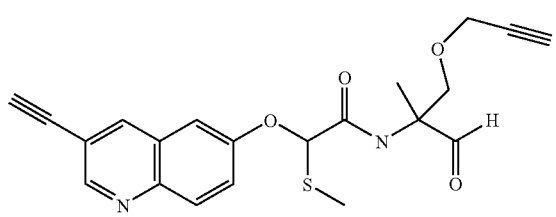 [SMILES: C#CCOCC(C)(C=O)NC(=O)C(Oc1ccc2ncc(C#C)cc2c1)SC]

2-(3-Ethynyl-quinolin-6-yloxy)-N-(2-hydroxy-1-methyl-1-prop-2-ynyloxymethyl-ethyl)-2-methylsulfanyl-acetamide (1.0 g) from Stage 3 above in dichloromethane (40 ml) was treated with Dess-Martin periodinane (1.277 g). The reaction mixture was stirred at room temperature for 2.5 and then treated with sat. aqueous NaHCO$_3$ and sat. aqueous sodium thiosulphate. The organic layer was washed with sat. aqueous NaHCO$_3$. After separation, the organic phase was dried over sodium sulphate, filtered and evaporated to yield 1.10 g of 2-(3-ethynyl-quinolin-6-yloxy)-N-(1-methyl-2-oxo-1-prop-2-ynyloxymethyl-ethyl)-2-methylsulfanyl acetamide as a crude product which was used in the next step (Stage 5, described below) without any further purification. $^1$H NMR (CDCl$_3$) δ ppm: [{9.51 (s), 9.49 (s) 1H}, isomer A and isomer B]; 8.86 (1H, d); 8.22 (1H, d); 8.07 (1H, d); 7.53-7.50 (1H, m); [{7.58 (s br), 7.48 (s br) 1H}, isomer A and isomer B]; 7.26 (1H, m); 5.72 (1H, s); 4.16-3.87 (4H, m); 3.28 (1H, s); 2.48 (1H, m); [{2.22 (s), 2.20 (s) 3H}, isomer A and isomer B]; 1.52 (3H, s).

Stage 5: Preparation of 2-(3-ethynyl-quinolin-6-yloxy)-N-(1-methyl-1-prop-2-ynyloxy-methyl-prop-2-ynyl)-2-methylsulfanyl-acetamide

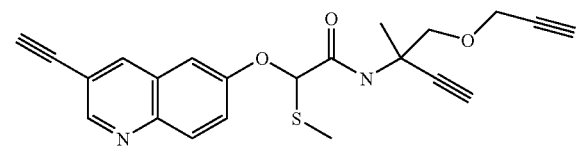 [SMILES: C#CCOCC(C)(C#C)NC(=O)C(Oc1ccc2ncc(C#C)cc2c1)SC]

A solution of dimethyl-1-diazo-2-oxopropylphosphonate (0.291 g) in dry methanol (8 ml) was added at room temperature to a solution of crude 2-(3-ethynyl-quinolin-6-yloxy)-N-(1-methyl-2-oxo-1-prop-2-ynyloxymethyl-ethyl)-2-methylsulfanyl-acetamide (0.400 g) from Stage 4 above in dry methanol (12 ml). The reaction medium was cooled down to 0° C. and potassium carbonate (0.195 g) was added. The reaction mixture was allowed to warm up to room temperature, stirred for 18 hrs and then poured onto a mixture of ethyl acetate and brine. The two layers were separated and the aqueous layer was extracted thrice with ethyl acetate. The organic layers were combined, washed once with brine and then dried over sodium sulphate. After filtration and concentration under reduced pressure the crude residue was isolated as a yellow oil that was purified by flash chromatography on silica gel (hexane/ethyl acetate 4:2, 4:3, 1:1) to give 0.229 g of 2-(3-ethynyl-quinolin-6-yloxy)-N-(1-methyl-1-prop-2-ynyloxymethyl-prop-2-ynyl)-2-methyl-sulfanyl-acetamide. $^1$H NMR (CDCl$_3$) δ ppm: 8.87 (1H, d); 8.22 (1H, d); 8.04 (1H, d); 7.49 (1H, dd); 7.21 (1H, d); 7.02 (1H, s br); [{5.56 (s), 5.54 (s) 1H}, isomer A and isomer B]; 4.38-4.23 (2H, m); 3.92-3.73 (2H, m); 3.29 (1H, s); 2.49-2.47 (1H, m); [{2.44 (s), 2.42 (s) 1H}, isomer A and isomer B]; [{2.21 (s), 2.20 (s) 3H}, isomer A and isomer B]; [{1.73 (s), 1.71 (s) 3H}, isomer A and isomer B].

EXAMPLE 12c

This Example illustrates the preparation of 2-(3-ethynyl-quinolin-6-yloxy)-N-(1-methyl-2-prop-2-ynyloxy-1-prop-2-ynyloxymethyl-ethyl)-2-methylsulfanyl-acetamide.

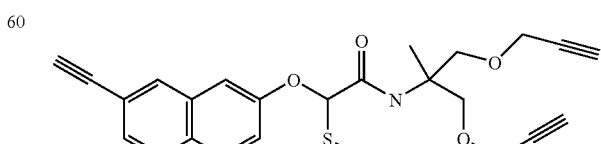

Sodium hydride (55% in dispersion in oil) (0.097 g) was added portionwise to a solution of 2-(3-ethynyl-quinolin-6-yloxy)-N-(2-hydroxy-1-methyl-1-prop-2-ynyloxymethyl-ethyl)-2-methylsulfanyl-acetamide (0.4 g) from Example 12b, Stage 3 described above in dry THF (20 ml) at 0° C. The reaction mixture was stirred at room temperature for 0.5 h. Propargyl bromide (0.166 ml) was added dropwise at 0° C. and the resulting mixture was stirred at room temperature for 23 hrs. The reaction mixture was diluted with ethyl acetate and water was added dropwise. The two phases were separated and the aqueous layer was extracted thrice with ethyl acetate. The organic layers were combined, washed once with brine dried over sodium sulphate, filtered and evaporated to give a dark orange oil which was purified by column chromatography (hexane/ethyl acetate 4:2, 1:1) to yield 2-(3-ethynyl-quinolin-6-yloxy)-N-(1-methyl-2-prop-2-ynyloxy-1-prop-2-ynyloxymethyl-ethyl)-2-methylsulfanyl-acetamide as a white solid (m.p.: 95-100° C.). $^1$H NMR (CDCl$_3$) δ ppm: 8.84 (1H, d); 8.22 (1H, d); 8.04 (1H, d); 7.49 (1H, dd); 7.21 (1H, d); 6.98 (1H, s br); 5.61 (1H, s); 4.19-4.16 (4H, m); 3.82-3.61 (2H, dd); 3.73 (2H, s); 3.29 (1H, s); 2.47-2.43 (2H, m); 2.21 (3H, s); 1.46 (3H, s).

EXAMPLE 12d

This Example illustrates the preparation of N-(1-cyano-2-hydroxy-1-methyl-ethyl)-2-(3-ethynyl-quinolin-6-yloxy)-2-methylsulfanyl-acetamide.

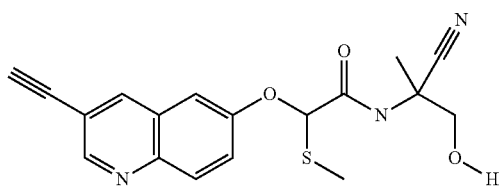 [SMILES: C#Cc1cnc2ccc(OC(SC)C(=O)NC(C)(C#N)CO)cc2c1]

To a solution of (3-ethynyl-quinolin-6-yloxy)-methylsulfanyl-acetic acid (4.0 g) and triethylamine (6 ml) in dry acetonitrile (50 ml) at room temperature were added successively a 1-hydroxy-7-azabenzotriazole (2.39 g) and O-(1H Benzotriazol-1-yl)-N,N,N',N'-tetramethyluronium tetrafluoroborate (5.64 g) and a solution of 2-amino-3-hydroxy-2-methyl-propionitrile (1.76 g) in dry acetonitrile (20 ml). The reaction mixture was stirred at room temperature for 18 hrs and then poured onto a mixture of ethyl acetate and brine. The two layers were separated and the aqueous layer was extracted thrice with ethyl acetate. The organic layers were combined, washed once with brine and then, dried over sodium sulphate. After filtration and concentration under reduced pressure, the crude residue was dissolved in 50 ml of THF/H$_2$O (1/1) and treated with 260 mg of LiOH monohydrate at room temperature for 1 hr. The crude mixture was extracted (pH=11) thrice with ethyl acetate. The organic layers were combined, washed with water, with brine and then dried over sodium sulphate. After filtration and concentration under reduced pressure, the crude residue was purified by flash chromatography on silica gel (hexane/ethyl acetate 1:4, 0:1) to provide 2.02 g of N-(1-cyano-2-hydroxy-1-methyl-ethyl)-2-(3-ethynyl-quinolin-6-yloxy)-2-methylsulfanyl-acetamide as a white solid (m.p. 78-80° C.).

EXAMPLE 12e

This Example illustrates the preparation of N-tert-butyl-2-(3-ethynyl-7-fluoro-8-methyl-quinolin-6-yloxy)-2-methylsulfanyl-acetamide

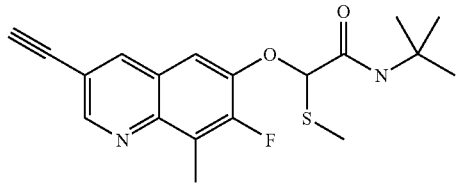 [SMILES: C#Cc1cnc2c(C)c(F)c(OC(SC)C(=O)NC(C)(C)C)cc2c1]

Step 1: Preparation of
2-bromo-3-fluoro-4-methoxy-1-nitro-benzene

NaOMe (9.5 g) was added portion wise to a solution of 2-bromo-3,4-difluoro-1-nitro-benzene (21.0 g) dissolved in DMSO (250 ml) at room temperature under nitrogen atmosphere. The mixture was stirred for 3 hrs and then poured onto water and extracted with ethyl acetate. The organic phase was extracted with water and brine, dried over anhydrous sodium sulphate, filtered and concentrated under reduced pressure. The crude product, 2-bromo-3-fluoro-4-methoxy-1-nitro-benzene was used as such in Step 2 described below. $^1$H NMR (CDCl$_3$) δ ppm: 7.85 (1H, dd); 6.99 (1H, dd); 3.99 (3H, s).

Step 2: Preparation of
2-fluoro-1-methoxy-3-methyl-4-nitro-benzene

Dimethylzinc (67 ml of a 2M toluene) was slowly added to a mixture of 2-bromo-3-fluoro-4-methoxy-1-nitro-benzene (12.0 g) and palladium-(diphenylphosphinoferrocenyl)-dichloride-methylene dichloride complex (1.65 g) in dioxane (300 ml) at 40° C. The mixture was stirred at 55° C. during 2 hours. After cooling to room temperature, MeOH (80 ml) was slowly added followed by aqueous NH$_4$Cl soln. The resulting mixture was extracted with ethyl acetate. The organic phase was washed with brine, dried over anhydrous sodium sulphate, filtered and concentrated under reduced pressure. The crude oil was purified by flash chromatography on silica gel (cyclohexane/ethyl acetate, 9/1) to provide 2-fluoro-1-methoxy-3-methyl-4-nitro-benzene (10.5 g, 90% purity) as a light yellow solid used as such in Step 3. $^1$H NMR (CDCl$_3$) δ ppm: 7.89 (1H, dd); 6.86 (1H, dd); 3.96 (3H, s); 2.53 (3H, d).

Step 3: Preparation of
3-fluoro-4-methoxy-2-methyl-phenylamine

Iron powder (14.25 g) was added portion wise to a solution of 2-fluoro-1-methoxy-3-methyl-4-nitro-benzene (10.5 g, 90% purity) in acetic acid (350 ml) at room temperature. The resulting brown suspension was stirred during 2 hours at room temperature. The reaction mixture was quenched with concentrated aq NaOH solution and extracted with ethyl acetate. The organic phase was washed with water and brine, dried over sodium sulphate anhydrous, filtered and concentrated under reduced pressure to obtain 3-fluoro-4-methoxy-2-methyl-phenylamine as orange oil (8.50 g, 90% purity) which was used in Step 4 without any further purification. $^1$H NMR (CDCl$_3$) δ ppm: 6.66 (1H, dd); 6.38 (1H, dd); 3.80 (3H, s); 3.34 (2H, br s); 2.08 (3H, d).

Step 4: Preparation of 3-bromo-7-fluoro-6-methoxy-8-methyl-quinoline 2,2,3-tribromopropionhaldeyde (570 mg) was slowly added to a solution of 3-fluoro-4-methoxy-2-methyl-phenylamine (200 mg) in acetic acid (3 ml) at 0° C., under a nitrogen atmosphere. The resulting dark mixture was stirred during 1 hr at 0-10° C., quenched with aq NH$_4$OH (pH 7) and extracted with ethyl acetate (3×). The organic phase was washed with aq thiosulphate soln, brine, dried over sodium sulphate anhydrous, filtered and concentrated under reduced pressure. The crude oil was purified by flash chromatography on silica gel (cyclohexane/ethyl acetate, followed by MeOH/CH$_2$Cl$_2$) to give 3-bromo-7-fluoro-6-methoxy-8-methyl-quinoline (355 mg, 85% pure) as a light brown solid. $^1$H NMR (CDCl$_3$) δ ppm: 8.77 (1H, d); 8.15 (1H, d); 6.89 (1H, d); 3.98 (3H, s); 2.66 (3H, d).

Step 5: Preparation of 3-bromo-7-fluoro-8-methyl-quinolin-6-ol

Boron tribromide (80 ml of a 1M solution in CH$_2$Cl$_2$) was slowly added to a solution of 3-bromo-7-fluoro-6-methoxy-8-methyl-quinoline (5.40 g) in CH$_2$Cl$_2$ (300 ml) at 0° C., under an atmosphere of nitrogen. Upon warming to room temperature, the resulting brown mixture was stirred for 24 hrs and then treated with MeOH (100 ml), stirred for 1 hour and then concentrated under reduced pressure. The crude mixture was dissolved in ethyl acetate and washed with water, brine, dried over sodium sulphate anhydrous, filtered and concentrated under reduced pressure to obtain 3-bromo-7-fluoro-8-methyl-quinolin-6-ol as brown solid (5.01 g) which was used for the next step without any further purification. $^1$H NMR (DMSO-d$_6$) δ ppm: 10.75 (1H, s); 8.75 (1H, d); 8.52 (1H, d); 7.18 (1H, d); 3.32 (3H, s); 2.56 (3H, d).

Step 6: Preparation of (3-bromo-7-fluoro-8-methyl-quinolin-6-yloxy)-methylsulfanyl-acetic acid ethyl ester Chloro-methylsulfanyl-acetic acid (6.19 g) was slowly added to a mixture of 3-bromo-7-fluoro-8-methyl-quinolin-6-ol (5.01 g) from Step 5 and dry K$_2$CO$_3$ (8.10 g) in dimethylformamide (80 ml) at room temperature, under nitrogen atmosphere. The resulting brown mixture was stirred during 1 hour, poured into water and then extracted with ethyl acetate. The organic layers were washed with water, brine, dried over sodium sulphate anhydrous, filtered and concentrated under reduced pressure. The crude residue was purified by flash chromatography on silica gel (cyclohexane/ethyl acetate, 15/1) to give (3-bromo-7-fluoro-8-methyl-quinolin-6-yloxy)-methylsulfanyl-acetic acid ethyl ester (6.80 g, 85% pure) as light brown oil. $^1$H NMR (CDCl$_3$) δ ppm: 8.82 (1H, d); 8.16 (1H; d); 7.08 (1H, d); 5.71 (1H, s); 4.37-4.27 (2H, m); 2.67 (3H, d); 2.26 (3H, s); 1.34 (3H, t).

Step 7: Preparation of (7-fluoro-8-methyl-3-trimethylsilanylethynyl-quinolin-6-yloxy)-methylsulfanyl-acetic acid ethyl ester Copper iodide (410 mg) was added to a solution of (3-bromo-7-fluoro-8-methyl-quinolin-6-yloxy)-methylsulfanyl-acetic acid ethyl ester (4.90 g) from Step 6 and di-isopropylamine (4.50 ml) in dioxane (200 ml) at room temperature, under nitrogen atmosphere, followed by addition of bis(triphenylphosphine)palladium dichloride (1.51 g). Argon was bubbled into the mixture during 10 min. Ethynyltrimethylsilane (4.50 ml) was slowly added and the resulting mixture stirred at room temperature during 3 hours. After filtration on celite the mother liquid was concentrated under reduced pressure. The crude residue was purified by flash chromatography on silica gel (cyclohexane/ethyl acetate, 10/1) to provide (7-fluoro-8-methyl-3-trimethylsilanylethynyl-quinolin-6-yloxy)-methylsulfanyl-acetic acid ethyl ester (3.35 g, 90% purity) as a brown oil. $^1$H NMR (CDCl$_3$) δ ppm: 8.82 (1H, d); 8.10 (1H, d); 7.10 (1H, d); 5.70 (1H, s); 4.37-4.27 (2H, m); 2.68 (3H, d); 2.26 (3H, s); 1.34 (3H, t); 0.28 (9H, s).

Step 8: Preparation of (3-ethynyl-7-fluoro-8-methyl-quinolin-6-yloxy)-methylsulfanyl-acetic acid To a solution of (7-fluoro-8-methyl-3-trimethylsilanylethynyl-quinolin-6-yloxy)-methylsulfanyl-acetic acid ethyl ester (3.35 g, 90% purity) from Step 7 in THF (100 ml), a 0.5 M aq NaOH soln (19.5 ml) was slowly added at 0° C. The light yellow mixture was stirred during 2 hrs at 0-10° C., then 2M HCl soln was added (pH 1). The mixture was extracted with ethyl acetate (2×). The combined organic layers were washed with brine, dried over sodium sulphate anhydrous, filtered and concentrated under reduced pressure yielding (3-ethynyl-7-fluoro-8-methyl-quinolin-6-yloxy)-methylsulfanyl-acetic acid which was used as such for the next step. $^1$H NMR (DMSO-d$_6$) δ ppm: 13.60 (1H, br s); 8.85 (1H, d); 8.40 (1H, d); 7.560 (1H, d); 6.11 (1H, s); 4.50 (1H, s); 2.59 (3H, d); 2.17 (3H, s).

Step 9: Preparation of N-tert-butyl-2-(3-ethynyl-7-fluoro-8-methyl-quinolin-6-yloxy)-2-methylsulfanyl-acetamide To a mixture containing (3-ethynyl-7-fluoro-8-methyl-quinolin-6-yloxy)-methylsulfanyl-acetic acid (250 mg) from Step 8, aza-HOBT (116 mg), TBTU (273 mg) and Et$_3$N (0.32 ml) in CH$_3$CN (12 ml), tert-butyl amine was added at room temperature, under a nitrogen atmosphere. The resulting brown suspension was stirred 1 hour at room temperature then poured into aqueous NH$_4$Cl solution and extracted with ethyl acetate. The combined organic layers were washed with brine, dried over sodium sulphate anhydrous, filtered and concentrated under reduced pressure. The crude residue was purified by chromatography on silica gel (cyclohexane/ethyl acetate) to give N-tert-butyl-2-(3-ethynyl-7-fluoro-8-methyl-quinolin-6-yloxy)-2-methylsulfanyl-acetamide (201 mg) as white solid. $^1$H NMR (CDCl$_3$) δ ppm: 8.88 (1H, d); 8.17 1H, d); 7.17 (1H, d); 6.64 (1H, br s); 5.59 (1H, s); 3.27 (1H, s); 2.69 (3H, d); 2.18 (3H, s); 1.44 (9H, s).

EXAMPLE 12f

This Example illustrates the preparation of N-(1-ethynyl-cyclobutyl)-2-(3-ethynyl-quinolin-6-yloxy)-2-methylsulfanyl-acetamide

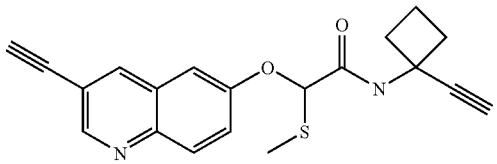 [SMILES: C#Cc1cnc2ccc(OC(SC)C(=O)NC3(C#C)CCC3)cc2c1]

Step 1: Preparation of 2-(3-Ethynyl-quinolin-6-yloxy)-N-(1-hydroxymethyl-cyclobutyl)-2-methylsulfanyl-acetamide

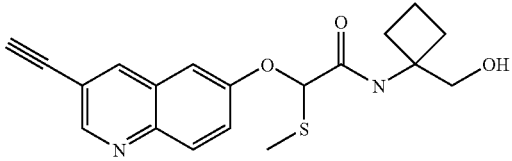 [SMILES: C#Cc1cnc2ccc(OC(SC)C(=O)NC3(CO)CCC3)cc2c1]

To a mixture containing (1-amino-cyclobutyl)-methanol (preparation described in JP 08134044) (860 mg), aza-HOBT (600 mg), TBTU (1.41 g) and Et$_3$N (1 ml) in CH$_3$CN (30 ml), (3-ethynyl-quinolin-6-yloxy)-methyl sulfanyl-acetic acid dissolved in Et$_3$N (1 ml) and CH$_3$CN (30 ml) was added over 1 hr, at room temperature, under nitrogen atmosphere. The resulting brown suspension was stirred overnight at room temperature then poured into aq NH$_4$Cl solution and extracted with ethyl acetate. The combined organic layers were washed with water, brine, dried over sodium sulphate anhydrous, filtered and concentrated under reduced pressure. The crude residue was purified by flash chromatography on silica gel (cyclohexane/ethyl acetate, 1/3) to give 2-(3-ethynyl-quinolin-6-yloxy)-N-(1-hydroxymethyl-cyclobutyl)-2-methylsulfanyl-acetamide (1.09 g) as slightly yellow solid.

$^1$H NMR (CDCl$_3$) δ ppm: 8.85 (1H, d); 8.22 (1H, d); 8.06 (1H, d); 7.47 (1H, dd); 7.23 (1H, d); 6.94 (1H, br s); 5.66 (1H, s); 3.86 (2H, s); 3.30 (1H, s); 2.38-2.16 (4H, m); 2.21 (3H, s); 2.00-1.82 (2H, m).

Step 2: Preparation of 2-(3-ethynyl-quinolin-6-yloxy)-N-(1-formyl-cyclobutyl)-2-methylsulfanyl-acetamide

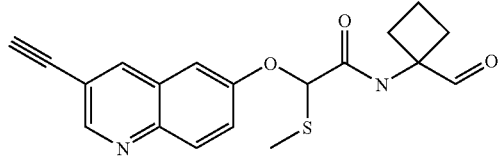 [SMILES: C#Cc1cnc2ccc(OC(SC)C(=O)NC3(C=O)CCC3)cc2c1]

Dess-Martin periodinane (424 mg) was added to a solution of 2-(3-ethynyl-quinolin-6-yloxy)-N-(1-hydroxymethyl-cyclobutyl)-2-methylsulfanyl-acetamide (360 mg) in CH$_2$Cl$_2$, at room temperature, under nitrogen atmosphere. The yellow mixture was stirred during 1 hr, then poured into aq NaHCO$_3$ soln and extracted with CH$_2$Cl$_2$. The combined organic layers were washed with aqueous thiosulphate solution, brine, dried over sodium sulphate anhydrous, filtered and concentrated under reduced pressure. The crude residue was purified by flash chromatography on silica gel (cyclohexane/ethyl acetate, 1/1) to give 2-(3-ethynyl-quinolin-6-yloxy)-N-(1-formyl-cyclobutyl)-2-methylsulfanyl-(260 mg) as slightly green oil which was used as such in the following step.

$^1$H NMR (CDCl3) δ ppm: 9.69 (1H, s); 8.84 (1H, d); 8.20 (1H, d); 8.05 (1H, d); 7.47 (1H, dd); 7.42 (1H, br s); 7.26 (1H, d); 5.72 (1H, s); 3.29 (1H, s); 2.73-2.64 (2H, m); 2.57-2.49 (2H, m); 2.20 (3H, s); 2.16-1.97 (2H, m).

Step 3: Preparation of N-(1-ethynyl-cyclobutyl)-2-(3-ethynyl-quinolin-6-yloxy)-2-methylsulfanyl-acetamide

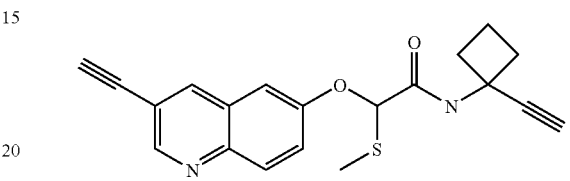

Bestmann's reagent ((1-diazo-2-oxo-propyl)-phosphonic acid dimethyl ester) (123 mg) was added to a solution of 2-(3-ethynyl-quinolin-6-yloxy)-N-(1-formyl-cyclobutyl)-2-methylsulfanyl-acetamide (180 mg) from Step 2 above in MeOH (15 ml) under nitrogen atmosphere. After cooling to 0° C. potassium carbonate (114 mg) was added and the mixture was stirred overnight at temperature from 0° C. to room temperature, then poured into brine and extracted with ethyl acetate (2×). The combined organic layers were washed with water, dried over sodium sulphate anhydrous, filtered and concentrated under reduced pressure. The crude residue was purified by flash chromatography on silica gel (cyclohexane/ethyl acetate/CH$_2$Cl$_2$, 1/1/3) to give N-(1-ethynyl-cyclobutyl)-2-(3-ethynyl-quinolin-6-yloxy)-2-methylsulfanyl-acetamide (106 mg) as white solid.

$^1$H NMR (CDCl3) δ ppm: 8.81 (1H, s); 8.19 (1H, d); 8.04 (1H, d); 7.45 (1H, dd); 7.21 (1H, d); 6.93 (1H, br s); 5.66 (1H, s); 3.28 (1H, s); 2.63-2.48 (4H, m); 2.21 (3H, s); 2.16-1.93 (2H, m).

EXAMPLE 12g

This Example illustrates the preparation of 2-(3-ethynyl-quinolin-6-yloxy)-2-methylsulfanyl-N-(1-prop-2-ynyloxymethyl-cyclobutyl)-acetamide

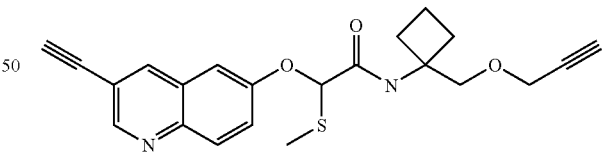

NaH (172 mg, 60% in oil) was added to a solution of 2-(3-ethynyl-quinolin-6-yloxy)-N-(1-hydroxymethyl-cyclobutyl)-2-methylsulfanyl-acetamide (850 mg) in THF (50 ml), at room temperature, under nitrogen atmosphere. The mixture was stirred until gas evolution ceased (30 min). Propargyl bromide (638 mg, 80% toluene solution) was added and the mixture was stirred at 40° C. during 3 hours, and then after cooling to room temperature poured into water and extracted with ethyl acetate. The combined organic layers were washed with water, brine, dried over sodium sulphate anhydrous, filtered and concentrated under reduced pressure. The crude residue was purified by flash chromatography on silica gel (cyclohexane/ethyl acetate/CH$_2$Cl$_2$, 1/1/1) to give 2-(3-ethynyl-quinolin-6-yloxy)-2-methylsulfanyl-N-(1-prop-2-ynyloxymethyl-cyclobutyl)-acet-amide (146 mg) as slightly brown oil. $^1$H NMR (CDCl3) δ ppm: 8.82 (1H, d); 8.18 (1H, d); 8.03 (1H, d); 7.44 (1H, dd); 7.21 (1H, d); 6.88 (1H, br s); 5.62 (1H, s); 4.14 (2H, s); 3.84-3.74 (2H, dd, AB system); 3.28 (1H, s); 2.49-2.13 (4H, m); 2.42 (1H, s); 2.19 (3H, s); 2.01-1.79 (2H, m).

EXAMPLE 12h

This Example illustrates the preparation of N-(1-Dimethoxymethyl-cyclobutyl)-2-(3-ethynyl-quinolin-6-yloxy)-2-methylsulfanyl-acetamide

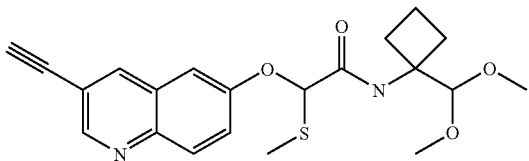 [SMILES: C#Cc1cnc2ccc(OC(SC)C(=O)NC3(C(OC)OC)CCC3)cc2c1]

To a solution of 2-(3-ethynyl-quinolin-6-yloxy)-N-(1-formyl-cyclobutyl)-2-methylsulfanyl-acetamide (180 mg) from Example 12f, Step 2 described above in a 10/1 mixture of toluene/THF (11 ml) p-toluene sulphonic acid (4 mg) was added followed by MeOH (1.10 ml), at room temperature. The mixture was stirred at 50° C. overnight and 60° C. during 6 hrs, then after cooling to room temperature poured into aq NaHCO$_3$ soln and extracted with ethyl acetate. The combined organic layers were washed with brine, dried over sodium sulphate anhydrous, filtered and concentrated under reduced pressure. The crude residue was purified by chromatography on silica gel (cyclohexane/ethyl acetate) to give N-(1-dimethoxymethyl-cyclobutyl)-2-(3-ethynyl-quinolin-6-yloxy)-2methylsulfanyl-acetamide as white solid. $^1$H NMR (CDCl3) δ ppm: 8.84 (1H, d); 8.19 (1H, d); 8.05 (1H, d); 7.46 (1H, dd); 7.23 (1H, d); 6.86 (1H, br s); 5.62 (1H, s); 4.57 (1H, s); 3.51 (3H, s); 3.47 (3H, s); 3.28 (1H, s); 2.47-2.21 (4H, m); 2.21 (3H, 5); 2.01-1.73 (2H, m).

EXAMPLE 13

TABLE 1981

Characterized compounds of the general formula (I)

| Cpd. No. | Formula | Compound | $^1$H-NMR and/or mp |
|---|---|---|---|
| 1 | | N-tert-Butyl-2-methylsulfanyl-2-(8-methyl-3-trimethylsilanylethynyl-quinolin-6-yloxy)-acetamide | 1H NMR (CDCl3) δ ppm: 8.81 (1H, d); 8.13 (1H, d); 7.30 (1H, dd); 7.01 (1H, s); 6.43 (1H, br); 5.56 (1H, s); 2.78 (3H, s); 2.19 (3H, s); 1.42 (9H, s); 0.30 (9H, s). |
| 2 | | N-tert-Butyl-2-(3-ethynyl-8-methyl-quinolin-6-yloxy)-2-methylsulfanyl-acetamide | 1H NMR (CDCl3) δ ppm: 8.85 (1H, d); 8.17 (1H, s); 7.32 (1H, dd); 7.04 (1H, d); 6.42 (1H, br); 5.57 (1H, s); 3.28 (1H, s); 2.78 (3H, s); 2.19 (3H, s); 1.42 (9H, s). |
| 3 | | N-tert-Butyl-2-methylsulfanyl-2-(3-trimethylsilanylethynyl-quinolin-6-yloxy)-acetamide | 1H NMR (CDCl3) δ ppm: 8.82 (1H, d); 8.17 (1H, d); 8.04 (1H, d); 7.43 (1H, dd); 7.19 (1H, d); 6.42 (1H, br); 5.57 (1H, s); 2.20 (3H, s); 1.42 (9H, s); 0.30 (9H, s). |
| 4 | | N-tert-Butyl-2-(3-ethynyl-quinolin-6-yloxy)-2-methylsulfanyl-acetamide | 1H NMR (CDCl3) δ ppm: 8.85 (1H, s); 8.20 (1H, d); 8.06 (1H, d); 7.46 (1H, dd); 7.21 (1H, d); 6.43 (1H, br); 5.59 (1H, s); 3.29 (1H, s); 2.20 (3H, s); 1.45 (9H, s). |

TABLE 1981-continued

Characterized compounds of the general formula (I)

| Cpd. No. | Formula | Compound | $^1$H-NMR and/or mp |
|---|---|---|---|
| 5 | | N-(1-Cyano-2-methoxy-1-methyl-ethyl)-2-(7-fluoro-3-trimethylsilanyl-ethynyl-quinolin-6-yloxy)-2-methylsulfanyl-acetamide | $^1$H NMR (CDCl$_3$) δ ppm: 8.85 (1H, d); 8.20(1H, d); 7.79 (1H, d); 7.35-7.30 (2H, m); 5.73 (1H, s, isomer A); 5.72 (1H, s, isomer B); 3.82-3.62 (2H, m); 3.52 (3H, s, isomer A); 3.50 (3H, s, isomer B); 2.21 (3H, s, isomer A); 2.20 (3H, s, isomer B); 1.81 (3H, s, isomer B); 1.80 (3H, s, isomer A); 0.30 (9H, s) |
| 6 | | N-(1-Cyano-2-methoxy-1-methyl-ethyl)-2-(3-ethynyl-7-fluoro-quinolin-6-yloxy)-2-methylsulfanyl-acetamide | $^1$H NMR (CDCl$_3$) δ ppm: 8.87 (1H, d); 8.21(1H, d); 7.80 (1H, d); 7.38 (1H, dd); 7.35 (1H, br s, isomer A); 7.31 (1H, br s, isomer B); 5.74 (1H, s, isomer A); 5.73 (1H, s, isomer B); 3.82-3.63 (2H, m); 3.53 (3H, s, isomer B); 3.51 (3H, s, isomer A); 3.30 (1H, s); 2.21 (3H, s, isomer A); 2.20 (3H, s, isomer B); 1.81 (3H, s, isomer A); 1.80 (3H, s, isomer B). |
| 7 | | N-(1,1-Dimethyl-prop-2-ynyl)-2-(3-ethynyl-8-methyl-quinolin-6-yloxy)-2-methylsulfanyl-acetamide | 1H NMR (CDCl3) δ ppm: 8.86 (1H, d); 8.17 (1H, d); 7.33 (1H, dd); 7.05 (1H, d); 6.72 (1H, br); 5.62 (1H, s); 3.28 (1H, s); 2.78 (3H, s); 2.39 (1H, s); 2.21 (3H, s); 1.73 (6H, s). |
| 8 | | N-(1,1-Dimethyl-but-2-ynyl)-2-(3-ethynyl-8-methyl-quinolin-6-yloxy)-2-methylsulfanyl-acetamide | 1H NMR (CDCl3) δ ppm: 8.85 (1H, d); 8.17 (1H, d); 7.33 (1H, dd); 7.05 (1H, d); 6.71 (1H, br); 5.60 (1H, s); 3.28 (1H, s); 2.79 (3H, s); 2.21 (3H, s); 1.82 (3H, s); 1.70 (6H, s). |
| 9 | | 2-(3-Ethynyl-8-methyl-quinolin-6-yloxy)-N-(4-methoxy-1,1-dimethyl-but-2-ynyl)-2-methylsulfanyl-acetamide | 1H NMR (CDCl3) δ ppm: 8.86 (1H, d); 8.17 (1H, d); 7.33 (1H, d); 7.05 (1H, d); 6.72 (1H, br); 5.61 (1H, s); 4.12 (2H, s); 3.38 (3H, s); 3.28 (1H, s); 2.79 (3H, s); 2.21 (3H, s): 1.73 (6H, s). |
| 10 | | N-(1,1-Dimethyl-4-prop-2-ynyloxy-but-2-ynyl)-2-(3-ethynyl-8-methyl-quinolin-6-yloxy)-2-methylsulfanyl-acetamide | 1H NMR (CDCl3) δ ppm: 8.86 (1H, d); 8.17 (1H, d); 7.33 (1H, d); 7.05 (1H, d); 6.71 (1H, br); 5.62 (1H, s); 4.28 (2H, s); 4.25 (2H, d); 3.28 (1H, s); 2.79 (3H, s); 2.44 (1H, t); 2.21 (3H, s): 1.72 (6H, s). |

TABLE 1981-continued

Characterized compounds of the general formula (I)

| Cpd. No. | Formula | Compound | ¹H-NMR and/or mp |
|---|---|---|---|
| 11 | | 2-(3-Ethynyl-8-methyl-quinolin-6-yloxy)-N-(4-hydroxy-1,1-dimethyl-but-2-ynyl)-2-methylsulfanyl-acetamide | 1H NMR (CDCl3) δ ppm: 8.86 (1H, d); 8.17 (1H, d); 7.33 (1H, d); 7.05 (1H, d); 6.74 (1H, br); 5.62 (1H, s); 4.29 (2H, s); 3.28 (1H, s); 2.78 (3H, s); 2.20 (3H, s); 1.77 (1H, br); 1.72 (6H, s). |
| 12 | | N-(1-Cyano-2-methoxy-1-methyl-ethyl)-2-(3-ethynyl-8-methyl-quinolin-6-yloxy)-2-methylsulfanyl-acetamide | ¹H NMR (CDCl₃) δ ppm: 8.87 (1H, d); 8.18 (1H, dd); 7.31-7.32 (1H, m); 7.13 (1H, br); 7.06-7.08 (1H, m); (5.71 (s) isomer A, 5.69 (s) isomer B, 1H); 3.81-3.65 (2H, m); (3.52 (s), 3.48 (s), isomers A + B, 3H); 3.28 (1H, s); 2.79 (3H, s); 2.22 (s), 2.21 (s) 3H); (1.81 (s), 1.78 (s), isomers A + B, 3H). |
| 13 | | 2-(3-Ethynyl-8-methyl-quinolin-6-yloxy)-N-(2-methoxy-1,1-dimethyl-ethyl)-2-methylsulfanyl-acetamide | 1H NMR (CDCl3) δ ppm: 8.87 (1H, d); 8.17 (1H, d); 7.32 (1H, dd); 7.05 (1H, d); 6.75 (1H, br); 5.59 (1H, s); 3.41 (2H, dd); 3.38 (3H, s); 3.28 (1H, s); 2.78 (3H, s); 2.20 (3H, s); 1.43 (3H, s); 1.40 (3H, s) |
| 14 | | N-(1,1-Dimethyl-2-prop-2-ynyloxy-ethyl)-2-(3-ethynyl-8-methylquino-lin-6-yloxy)-2-methylsulfanyl-acetamide | 1H NMR (CDCl3) δ ppm: 8.86 (1H, d); 8.18 (1H, d); 7.33 (1H, d); 7.05 (1H, d); 6.75 (1H, br); 5.59 (1H, s); 4.18 (2H, d); 3.58 (2H, dd); 3.28 (1H, s); 2.78 (3H, s); 2.44 (1H, dd) 2.20 (3H, s); 1.44 (3H, s); 1.42 (3H, s) |
| 15 | | 2-(3-Ethynyl-8-methyl-quinolin-6-yloxy)-N-(2-hydroxy-1,1-dimethyl-ethyl)-2-methylsulfanyl-acetamide | 1H NMR (CDCl3) δ ppm: 8.86 (1H, d); 8.18 (1H, d); 7.32 (1H, d); 7.05 (1H, d); 6.69 (1H, br); 5.63 (1H, s); 3.67 (2H, d); 3.29 (1H, s); 2.79 (3H, s); 2.20 (3H, s); 1.39 (3H, s); 1.36 (3H, s) |
| 16 | | N-(1,1-Dimethyl-but-3-ynyl)-2-(3-ethynyl-8-methyl-quinolin-6-yloxy)-2-methylsulfanyl-acetamide | 1H NMR (CDCl3) δ ppm: 8.86 (1H, d); 8.17 (1H, d); 7.32 (1H, dd); 7.05 (1H, d); 6.63 (1H, br); 5.60 (1H, s); 3.28 (1H, s); 2.78 (3H, s); 2.72 (2H, dd); 2.22 (3H, s); 1.96 (1H, dd); 1.49 (6H, s) |
| 17 | | N-tert-Butyl-2-[3-(3-hydroxy-prop-1-ynyl)-8-methyl-quinolin-6-yloxy]-2-methylsulfanyl-acetamide | 1H NMR (CDCl3) δ ppm: 8.83 (1H, d); 8.11 (1H, d); 7.32 (1H, dd); 7.01 (1H, d); 6.42 (1H, br); 5.58 (1H, s); 4.59 (2H, d); 2.78 (3H, s); 2.20 (3H, s); 1.42 (9H, s) |

TABLE 1981-continued

Characterized compounds of the general formula (I)

| Cpd. No. | Formula | Compound | $^1$H-NMR and/or mp |
|---|---|---|---|
| 18 | | N-tert-Butyl-2-(8-chloro-3-ethynyl-quinolin-6-yloxy)-2-methylsulfanyl-acetamide | 1H NMR (CDCl3) δ ppm: 8.84 (1H, d); 8.21 (1H, d); 7.63 (1H, dd); 7.15 (1H, d); 6.38 (1H, br); 5.58 (1H, s); 3.34 (1H, s); 2.20 (3H, s); 1.43 (9H, s) |
| 19 | | 2-(8-Chloro-3-ethynyl-quinolin-6-yloxy)-N-(1,1-dimethyl-2-prop-2-ynyl)-2-methylsulfanyl-acetamide | 1H NMR (CDCl3) δ ppm: 8.84 (1H, d); 8.21 (1H, d); 7.63 (1H, d); 7.17 (1H, d); 6.67 (1H, br); 5.63 (1H, s); 3.34 (1H, s); 2.40 (1H, s); 2.21 (3H, s); 1.74 (6H, s) |
| 20 | | 2-(8-Chloro-3-ethynyl-quinolin-6-yloxy)-N-(1,1-dimethyl-but-2-ynyl)-2-methylsulfanyl-acetamide | 1H NMR (CDCl3) δ ppm: 8.84 (1H, d); 8.21 (1H, d); 7.64 (1H, d); 7.16 (1H, d); 6.66 (1H, br); 5.61 (1H, s); 3.34 (1H, s); 2.40 (1H, s); 2.21 (3H, s); 1.83 (3H, s); 1.70 (3H, s); 1.69 (3H, s) |
| 21 | | N-(1,1-Dimethyl-prop-2-ynyl)-2-(3-ethynyl-quinolin-6-yloxy)-2-methylsulfanyl-acetamide | 1H NMR (CDCl3) δ ppm: 8.85 (1H, d); 8.20 (1H, d); 8.05 (1H, d); 7.47 (1H, dd); 7.23 (1H, d); 6.72 (1H, br); 5.64 (1H, s); 3.30 (1H, s); 2.40 (1H, s); 2.04 (3H, s); 1.73 (6H, s) |
| 22 | | N-(1,1-Dimethyl-but-2-ynyl)-2-(3-ethynyl-quinolin-6-yloxy)-2-methylsulfanyl-acetamide | 1H NMR (CDCl3) δ ppm: 8.85 (1H, d); 8.20 (1H, d); 8.05 (1H, d); 7.47 (1H, dd); 7.22 (1H, d); 6.71 (1H, br); 5.61 (1H, s); 3.29 (1H, s); 2.16 (3H, s); 1.82 (3H, s); 1.70 (3H, s); 1.69 (3H, s) |
| 23 | | 2-(3-Ethynyl-quinolin-6-yloxy)-N-(4-methoxy-1,1-dimethyl-but-2-ynyl)-2-methylsulfanyl-acetamide | 1H NMR (CDCl3) δ ppm: 8.85 (1H, d); 8.21 (1H, s); 8.05 (1H, d); 7.46 (1H, dd); 7.22 (1H, d); 6.72 (1H, br); 5.63 (1H, s); 4.12 (2H, s); 3.37 (3H, s); 3.29 (1H, s); 2.21 (3H, s); 1.73 (6H, s). |
| 24 | | N-(1,1-Dimethyl-4-prop-2-ynyloxy-but-2-ynyl)-2-(3-ethynyl-quinolin-6-yloxy)-2-methylsulfanyl-acetamide | 1H NMR (CDCl3) δ ppm: 8.85 (1H, d); 8.21 (1H, d); 8.07 (1H, d); 7.47 (1H, dd); 7.23 (1H, d); 6.72 (1H, br); 5.63 (1H, s); 4.28 (2H, s); 4.26 (2H, d); 3.30 (1H, s); 2.45 (1H, t); 2.21 (3H, s); 1.73 (6H, s). |

TABLE 1981-continued

Characterized compounds of the general formula (I)

| Cpd. No. | Formula | Compound | ¹H-NMR and/or mp |
|---|---|---|---|
| 25 | | N-(Cyano-methoxymethyl-methyl-methyl)-2-(3-ethynyl-quinolin-6-yloxy)-2-methylsulfanyl-acetamide | ¹H NMR (CDCl₃) δ ppm: 8.86 (1H, d); 8.22 (1H, d); 8.07 (1H, d); 7.45 (1H, dd); 7.24 (1H, d); 7.16 (1H, br s, isomer A); 7.11 (1H, br s, isomer B); 5.73 (1H, s, isomer B); 5.71 (1H, s, isomer A); 3.80-3.65 (2H, m); 3.52 (3H, s, isomer B); 3.48 (3H, s, isomer A); 3.30 (1H, s); 2.22 (3H, s, isomer B); 2.21 (3H, s, isomer A); 1.81 (3H, s, isomer A); 1.79 (3H, s, isomer B); (1H, s); 2.45 (1H, t); 2.21 (3H, s); 1.73 (6H, s) |
| 26 | | 2-(7-Bromo-8-methyl-3-trimethylsilanylethynyl-quinolin-6-yloxy)-N-tert-butyl-2-methylsulfanyl-acetamide | 1H NMR (CDCl3) d ppm: 8.81 (1H, d); 8.15 (1H, d); 7.09 (1H, s); 7.07 (1H, br); 5.52 (1H, s); 2.95 (3H, s); 2.24 (3H, s); 1.47 (9H, s); 0.31 (9H, s) |
| 27 | | N-(Cyano-methoxymethyl-methyl-methyl)-2-[3-(3-hydroxy-prop-1-ynyl)-8-methyl-quinolin-6-yloxy]-2-methylsulfanyl-acetamide | ¹H NMR (CDCl₃) δ ppm: 8.86 (1H, d); 8.11 (1H, d); 7.30 (1H, d); 7.13 (1H, s br, isomer A) 7.09 (1H, s br, isomer B); 7.05 (1H, d); 5.71 (1H, s, isomer B); 5.69 (1H, s, isomer A); 4.58 (2H, s); 3.81-3.63 (2H, m); 3.52 (3H, s, isomer B); 3.48 (3H, s, isomer A); 2.79 (3H, s); 2.21 (3H, s); 1.80 (3H, s, isomer A); 1.78 (3H, s, isomer B) |
| 28 | | 2-[3-(3-Hydroxy-prop-1-ynyl)-8-methyl-quinolin-6-yloxy]-N-(4-methoxy-1,1-dimethyl-but-2-ynyl)-2-methylsulfanyl-acetamide | 1H NMR (CDCl3) δ ppm: 8.82 (1H, d); 8.11 (1H, d): 7.31 (1H, dd); 7.02 (1H, d); 6.72 (1H, br); 5.62 (1H, s); 4.58 (2H, d); 4.11 (2H, s); 3.38 (3H, s); 2.21 (2H, s); 1.73 (6H, s) |
| 29 | | 2-(3-Ethynyl-quinolin-6-yloxy)-N-(2-methoxy-1,1-dimethyl-ethyl)-2-methylsulfanyl-acetamide | 1H NMR (CDCl3) δ ppm: 8.84 (1H, d); 8.20 (1H, d); 8.05 (1H, d); 7.46 (1H, dd); 7.22 (1H, d); 6.76 (1H, br s); 5.60 (1H, s); 3.45-3.35 (2H, m); 3.37 (3H, s); 3.29 (1H, s); 2.20 (3H, s); 1.43 (3H, s); 1.40 (3H, s). |
| 30 | | N-(1,1-Dimethyl-2-prop-2-ynyloxy-ethyl)-2-(3-ethynyl-quinolin-6-yloxy)-2-methylsulfanyl-acetamide | 1H NMR (CDCl3) δ ppm: 8.84 (1H, d); 8.21 (1H, s); 8.04 (1H, d); 7.47 (1H, dd); 7.22 (1H, d); 6.76 (1H, br); 5.60 (1H, s); 4.17 (2H, d); 3.57 (2H, dd); 3.29 (1H, s); 2.44 (1H, t); 2.20 (3H, s); 1.44 (3H, s), 1.42 (3H, s) |

TABLE 1981-continued

Characterized compounds of the general formula (I)

| Cpd. No. | Formula | Compound | $^1$H-NMR and/or mp |
|---|---|---|---|
| 31 | | N-(1,1-Dimethyl-but-3-ynyl)-2-(3-ethynyl-quinolin-6-yloxy)-2-methyl-sulfanyl-acetamide | 1H NMR (CDCl3) δ ppm: 8.85 (1H, d); 8.20 (1H, d); 8.05 (1H, d); 7.47 (1H, dd); 7.23 (1H, d); 6.64 (1H, br); 5.61 (1H, s); 3.29 (1H, s); 2.71 (2H, ddd); 2.22 (3H, s); 1.95 (1H, d) 1.49 (6H, s) |
| 32 | | N-tert-Butyl-2-[3-(3-methoxy-prop-1-ynyl)-8-methyl-quinolin-6-yloxy]-2-methylsulfanyl-acetamide | 1H NMR (CDCl3) δ ppm: 8.81 (1H, d); 8.12 (1H, d); 7.30 (1H, dd); 7.02 (1H, d); 6.42 (1H, br); 5.56 (1H, s); 4.39 (2H, s); 3.50 (3H, s); 2.79 (3H, d); 2.20 (3H, s); 1.42 (9H, s). |
| 33 | | N-(1-Cyano-2-methoxy-1-methyl-ethyl)-2-[3-(3-methoxy-prop-1-ynyl)-8-methyl-quinolin-6-yloxy]-2-methylsulfanyl-acetamide | 1H NMR (CDCl3) δ ppm: 8.82 (1H, d); 8.13 (1H, d); 7.30 (1H, dd); 7.12 (1H, br); 7.05 (1H, dd); 5.70 (1H, s); 4.39 (2H, s); 3.72 (2H, m); 3.50 (6H, t); 2.79 (3H, s); 2.21 (3H, s); 1.80 (3H, d). |
| 34 | | N-(4-Methoxy-1,1-dimethyl-but-2-ynyl)-2-[3-(3-methoxy-prop-1-ynyl)-8-methyl-quinolin-6-yloxy]-2-methylsulfanyl-acetamide | 1H NMR (CDCl3) δ ppm: 8.82 (1H, d); 8.11 (1H, d); 7.32 (1H, dd); 7.04 (1H, d); 6.71 (1H, br); 5.61 (1H, s); 4.39 (2H, s); 4.12 (2H, s); 3.50 (3H, s); 3.38 (3H, s); 2.79 (3H, s); 2.21 (3H, s); 1.72 (6H, s) |
| 35 | | N-(1,1-Dimethyl-but-2-ynyl)-2-[3-(3methoxy-prop-1-ynyl)-8-methyl-quinolin-6-yloxy]-2-methylsulfanyl-acetamide | 1H NMR (CDCl3) δ ppm: 8.82 (1H, d); 8.11 (1H, d); 7.32 (1H. dd): 7.04 (1H, d); 6.71 (1H, br); 5.60 (1H, s); 4.39 (2H, s); 3.50 (3H, s); 2.79 (3H, s); 2.21 (3H, s); 1.81 (3H, s); 1.70 (6H, s). |
| 36 | | N-(1,1-Dimethyl-prop-2-ynyl)-2-[3-(3-methoxy-prop-1-ynyl)-8-methyl-quinolin-6-yloxy]-2-methylsulfanyl-acetamide | 1H NMR (CDCl3) δ ppm: 8.81 (1H, d); 8.11 (1H, d); 7.31 (1H, dd); 7.04 (1H, d); 6.71 (1H, br); 5.61 (1H, s); 4.39 (2H, s); 3.50 (3H, s); 2.79 (3H, s); 2.39 (1H, s); 2.21 (3H, s); 1.72 (6H, s). |
| 37 | | N-tert-Butyl-2-(8-methyl-3-prop-1-ynyl-quinolin-6-yloxy)-2-methylsulfanyl-acetamide | 1H NMR (CDCl3) δ ppm: 8.79 (1H, d); 8.02 (1H, d); 7.28 (1H, dd); 7.00 (1H, d); 6.42 (1H, br); 5.57 (1H, s); 2.78 (3H, s); 2.20 (3H, s); 2.12 (3H, s); 1.40 (1H, s). |

TABLE 1981-continued

Characterized compounds of the general formula (I)

| Cpd. No. | Formula | Compound | $^1$H-NMR and/or mp |
|---|---|---|---|
| 38 | | N-(1-Cyano-2-methoxy-1-methyl-ethyl)-2-(8-methyl-3-prop-1-ynyl-quinolin-6-yloxy)-2-methylsulfanyl-acetamide | 1H NMR (CDCl3) δ ppm: 8.79 (1H, d); 8.03 (1H, d); 7.27 (1H, m); 7.11 (1H, br s, isomer A); 7.05 (1H, br s, isomer B); 7.02 (1H, m); 5.70 (1H, s, isomer B); 5.68 (1H, s, isomer A); 3.80-3.62 (2H, m); 3.51 (3H, s, isomer B); 3.48 (3H, s, isomer A); 2.78 (3H, s); 2.21 (3H, s, isomer B); 2.20 (3H, s, isomer A); 2.12 (3H, s); 1.80 (3H, s, isomer A); 178 (3H, s, isomer B) |
| 39 | | N-(4-Methoxy-1,1-dimethyl-but-2-ynyl)-2-(8-methyl-3-prop-1-ynyl-quinolin-6-yloxy)-2-methylsulfanyl-acetamide | 1H NMR (CDCl3) δ ppm: 8.79 (1H, d); 8.03 (1H, d); 7.28 (1H, dd); 7.01 (1H, d); 6.71 (1H, s); 5.60 (1H, s); 4.11 (2H, s); 3.38 (3H, s), 2.77 (3H, s); 2.21 (3H, s); 2.12 (3H, s); 1.71 (6H, s). |
| 40 | | N-(1,1-Dimethyl-but-2-ynyl)-2-(8-methyl-3-prop-1-ynyl-quinolin-6-yloxy)-2-methylsulfanyl-acetamide | 1H NMR (CDCl3) δ ppm: 8.79 (1H, d); 8.02 (1H, d); 7.29 (1H, dd); 7.02 (1H, d); 6.71 (1H, s); 5.60 (1H, s); 2.78 (3H, s); 2.21 (3H, s); 2.13 (3H, s); 1.82 (3H, s); 1.69 (3H, s); 1.69 (3H, s) |
| 41 | | N-(1,1-Dimethyl-prop-2-ynyl)-2-(8-methyl-3-prop-1-ynyl-quinolin-6-yloxy)-2-methylsulfanyl-acetamide | 1H NMR (CDCl3) δ ppm: 8.79 (1H, d); 8.02 (1H, d); 7.28 (1H, dd); 7.02 (1H, d); 6.71 (1H, s); 5.61 (1H, s); 2.78 (3H, s); 2.39 (1H, s); 2.22 (3H, s); 2.13 (3H, s); 1.72 (6H, s). |
| 42 | | N-tert-Butyl-2-[3-(3-methoxy-prop-1-ynyl)-quinolin-6-yloxy]-2-methylsulfanyl-acetamide | 1H NMR (CDCl3) δ ppm: 8.82 (1H, d); 8.16 (1H, d); 8.06 (1H, d); 7.44 (1H, dd); 7.21 (1H, d); 6.42 (1H, br); 5.59 (1H, s); 4.39 (2H, s); 3.50 (3H, s), 2.21 (3H, s); 1.42 (9H, s) |
| 43 | | N-(1-Cyano-2-methoxy-1-methyl-ethyl)-2-[3-(3-methoxy-prop-1-ynyl)-quinolin-6-yloxy]-2-methylsulfanyl-acetamide | 1H NMR (CDCl3) δ ppm: 8.82 (1H, d); 8.16 (1H, s); 8.07 (1H, d); 7.43 (1H, dd); 7.22 (1H, d); 7.12 (1H, br, d); 5.71 (1H, d); 4.39 (2H, s); 3.71 (2H, m); 3.50 (3H, d); 3.50 (3H, s); 2.21 (3H, s); 1.80 (3H, d). |
| 44 | | N-(4-Methoxy-1,1-dimethyl-but-2-ynyl)-2-[3-(3-methoxy-prop-1-ynyl)-quinolin-6-yloxy]-2-methylsulfanyl-acetamide | 1H NMR (CDCl3) δ ppm: 8.82 (1H, d); 8.15 (1H, d); 8.06 (1H, d); 7.46 (1H, dd); 7.21 (1H, d); 6.72 (1H, br); 5.62 (1H, s); 4.39 (2H, s); 4.11 (2H, s); 3.50 (3H, s); 3.38 (3H, s); 2.21 (3H, s); 1.72 (6H, s) |

TABLE 1981-continued

Characterized compounds of the general formula (I)

| Cpd. No. | Formula | Compound | ¹H-NMR and/or mp |
|---|---|---|---|
| 45 | | N-(1,1-Dimethyl-but-2-ynyl)-2-[3-(3-methoxy-prop-1-ynyl)-quinolin-6-yloxy]-2-methylsulfanyl-acetamide | 1H NMR (CDCl3) δ ppm: 8.82 (1H, d); 8.15 (1H, d); 8.05 (1H, d); 7.46 (1H, dd); 7.21 (1H, d); 6.71 (1H, br); 5.61 (1H, s); 4.39 (2H, s); 3.50 (3H, s); 2.21 (3H, s); 1.82 (3H, s); 1.71 (3H, s); 1.71 (3H, s). |
| 46 | | N-(1,1-Dimethyl-prop-2-ynyl)-2-[3-(3-methoxy-prop-1-ynyl)-quinolin-6-yloxy]-2-methylsulfanyl-acetamide | 1H NMR (CDCl3) δ ppm: 8.82 (1H, d); 8.15 (1H, d); 8.05 (1H, d); 7.46 (1H, dd); 7.21 (1H, d); 6.71 (1H, br); 5.62 (1H, s); 4.39 (2H, s); 3.50 (3H, s); 2.39 (1H, s); 2.21 (3H, s); 1.72 (6H, s). |
| 47 | | 2-(7-Bromo-3-ethynyl-8-methyl-quinolin-6-yloxy)-N-tert-butyl-2-methylsulfanyl-acetamide | 1H NMR (CDCl3) δ ppm: 8.86 (1H, d); 8.19 (1H, d); 7.12 (1H, d); 7.08 (1H, br); 5.64 (1H, s); 3.31 (1H, s); 2.96 (3H, s); 2.16 (3H, s); 1.48 (9H, s). |
| 48 | | N-(1,1-Dimethyl-2-oxo-ethyl)-2-(3-ethynyl-quinolin-6-yloxy)-2-methylsulfanyl acetamide | 1H NMR (CDCl3) δ ppm: 8.87 (1H, d); 8.11 (1H, d); 8.03 (1H, d); 7.43 (1H, dd); 6.44 (1H, br), 5.60 (1H, s); 4.59 (2H, s); 2.20 (3H, s); 1.42 (9H, s) |
| 49 | | 2-[3-(3-Hydroxy-prop-1-ynyl)-quinolin-6-yloxy]-N-(4-methoxy-1,1-dimethyl-but-2-ynyl)-2-methylsulfanyl-acetamide | H NMR (CDCl3) δ ppm: 8.84 (1H, d); 8.13 (1H, d); 8.06 (1H, d); 7.44 (1H, dd); 7.20 (1H, d); 6.72 (1H, br), 5.62 (1H, s); 4.59 (2H, s); 4.11 (2H, s); 3.38 (3H, s); 2.63 (1H, br), 2.21 (3H, s); 1.71 (6H, s). |
| 50 | | N-(1,1-Dimethyl-but-2-ynyl)-2-[3-(3-hydroxy-prop-1-ynyl)-quinolin-6-yloxy]-2-methylsulfanyl-acetamide | 1H NMR (CDCl3) δ ppm: 8.87 (1H, d); 8.12 (1H, d); 8.05 (1H, d); 7.45 (1H, dd); 7.21 (1H, d); 6.72 (1H, br), 5.62 (1H, s); 4.59 (2H, s); 2.92 (1H, s); 2.21 (3H, s); 1.82 (3H, s), 1.70 (3H, s); 1.70 (3H, s) |
| 51 | | N-(1,1-Dimethyl-prop-2-ynyl)-2-[3-(3-hydroxy-prop-1-ynyl)-quinolin-6-yloxy]-2-methylsulfanyl-acetamide | 1H NMR (CDCl3) δ ppm: 8.88 (1H, d); 8.12 (1H, d); 8.06 (1H, d); 7.46 (1H, dd); 7.21 (1H, d); 6.72 (1H, br), 5.64 (1H, s); 4.58 (2H, s); 2.71 (1H, br); 2.40 (1H, s); 2.21 (3H, s); 1.72 (6H, s). |
| 52 | | N-(1-Cyano-2-methoxy-1-methyl-ethyl)-2-[3-(3-hydroxy-prop-1-ynyl)-quinolin-6-yloxy]-2-methylsulfanyl-acetamide | 1H NMR (CDCl3) δ ppm: 8.88 (1H, d); 8.12 (1H, d); 8.05 (1H, d); 7.44 (1H, dd); 7.21 (1H, d); 7.15 (1H, d, br), 5.72 (1H, d); 4.58 (2H, s); 3.71 (2H, m); 3.50 (3H, d); 3.18 (1H, br); 2.21 (3H, s); 1.80 (3H, d) |

TABLE 1981-continued

Characterized compounds of the general formula (I)

| Cpd. No. | Formula | Compound | $^1$H-NMR and/or mp |
|---|---|---|---|
| 53 | | N-(1-Cyano-2-methoxy-1-methyl-ethyl)-2-methylsulfanyl-2-(3-prop-1-ynyl-quinolin-6-yloxy)-acetamide | 1H NMR (CDCl3) δ ppm: 8.78 (1H, d); 8.09 (1H, d); 8.06 (1H, d); 7.41 (1H, dd); 7.21 (1H, d); 7.14 (1H, d, br), 5.71 (1H, d); 3.71 (2H, m); 3.50 (3H, s); 2.21 (3H, s); 2.14 (3H, s); 1.79 (3H, d). |
| 54 | | N-tert-Butyl-2-methylsulfanyl-2-(3-prop-1-ynyl-quinolin-6-yloxy)-acetamide | 1H NMR (CDCl3) δ ppm: 8.78 (1H, d); 8.07 (1H, d); 8.02 (1H, d); 7.41 (1H, dd); 7.17 (1H, d); 6.43 (1H, br), 5.59 (1H, s); 2.21 (3H, s); 2.14 (3H, s); 1.41 (9H, s). |
| 55 | | N-(4-Methoxy-1,1-dimethyl-but-2-ynyl)-2-methylsulfanyl-2-(3-prop-1-ynyl-quinolin-6-yloxy)-acetamide | 1H NMR (CDCl3) δ ppm: 8.78 (1H, d); 8.07 (1H, d); 8.02 (1H, d); 7.41 (1H, dd); 7.18 (1H, d); 6.73 (1H, br), 5.63 (1H, s); 4.11 (2H, s); 3.38 (3H, s); 2.21 (3H, s); 2.13 (3H, s); 1.71 (6H, s). |
| 56 | | N-(1,1-Dimethyl-but-2-ynyl)-2-methylsulfanyl-2-(3-prop-1-ynyl-quinolin-6-yloxy)-acetamide | 1H NMR (CDCl3) δ ppm: 8.78 (1H, d); 8.07 (1H, d); 8.04 (1H, d); 7.42 (1H, dd); 7.19 (1H, d); 6.62 (1H, br), 5.61 (1H, s); 2.21 (3H, s); 2.13 (3H, s); 1.81 (3H, s); 1.70 (3H, s); 1.70 (3H, s). |
| 57 | | N-(1,1-Dimethyl-prop-2-ynyl)-2-methylsulfanyl-2-(3-prop-1-ynyl-quinolin-6-yloxy)-acetamide | 1H NMR (CDCl3) δ ppm: 8.78 (1H, d); 8.07 (1H, d); 8.04 (1H, d); 7.42 (1H, dd); 7.19 (1H, d); 6.72 (1H, br), 5.63 (1H, s); 2.39 (1H, s); 2.22 (3H, s); 2.13 (3H, s); 1.72 (6H, s); 1.70 (3H, s) |
| 58 | | 2-(7-Fluoro-3-trimethylsilanylethynyl-quinolin-6-yloxy)-N-(4-methoxy-1,1-dimethyl-but-2-ynyl)-2-methylsulfanyl-acetamide | 1H NMR (CDCl3) δ ppm: 8.83 (1H, d); 8.18 (1H, d); 7.79 (1H, d); 7.32 (1H, dd); 6.89 (1H, br), 5.65 (1H, s); 4.12 (2H, s); 2.38 (3H, s); 2.22 (3H, s); 1.72 (6H, s); 0.29 (9H, s). |
| 59 | | N-(1-Cyano-1-methyl-2-methylsulfanyl-ethyl)-2-methylsulfanyl-2-(3-trimethylsilanyl-ethynyl-quinolin-6-yloxy)-acetamide | 1H NMR (CDCl3) δ ppm: 8.82 (1H, d); 8.19 (1H, d); 8.06 (1H, d); 7.46-7.41 (1H, m); 7.28 (1H, s br, isomer A), 7.21 (1H, d); 7.18 (1H, s br, isomer B); 5.72 (1H, s, isomer B); 5.71 (1H, s, isomer A); 3.29-3.08 (2H, m); 2.35 (3H, s, isomer A); 2.24 (3H, d, isomer B); 2.22 (3H, s, isomer B); 2.21 (3H, s, isomer A); 1.89 (3H, s, isomer B); 1.87 (3H, s, isomer A); 0.30 (9H, s). |

TABLE 1981-continued

Characterized compounds of the general formula (I)

| Cpd. No. | Formula | Compound | ¹H-NMR and/or mp |
|---|---|---|---|
| 60 | | N-(2-Methoxymethoxy-1,1-dimethyl-ethyl)-2-methylsulfanyl-2-(8-methyl-3-trimethylsilanylethynyl-quinolin-6-yloxy)-acetamide | 1H NMR (CDCl3) δ ppm: 8.81 (1H, d); 8.12 (1H, d); 7.28 (1H, d); 7.02 (1H, d); 6.81 (1H, br s), 5.59 (1H, s); 4.62 (2H, s); 3.62-3.55 (2H, m); 3.38 (3H, s); 2.78 (3H, s); 2.20 (3H, s); 1.45 (3H, s); 1.43 (3H, s); 0.30 (9H, s). |
| 61 | | N-(1,1-Dimethyl-2-oxo-ethyl)-2-(3-ethynyl-quinolin-6-yloxy)-2-methylsulfanyl-acetamide | 1H NMR (CDCl3) δ ppm: 9.42 (1H, s), 8.86 (1H, d); 8.22 (1H, d); 8.08 (1H, d); 7.50 (1H, dd); 7.26-7.25 (2H, br m), 5.69 (1H, s); 4.59 (2H, s); 3.30 (1H, s), 2.21 (3H, s); 1.52 (9H, s). |
| 62 | | 2-(8-Chloro-3-ethynyl-quinolin-6-yloxy)-N-(4-methoxy-1,1-dimethyl-but-2-ynyl)-2-methylsulfanyl-acetamide | 1H NMR (CDCl3) δ ppm: 8.95 (1H, d); 8.22 (1H, d); 7.64 (1H, d); 7.16 (1H, d); 6.66 (1H, br s), 5.70 (1H, s); 4.12 (s, 2H), 3.38 (3H, s); 3.33 (1H, s), 2.21 (3H, s); 1.73 (3H, s). |
| 63 | | 2-(8-Chloro-3-ethynyl-quinolin-6-yloxy)-N-(1,1-dimethyl-4-prop-2-ynyloxy-but-2-ynyl)-2-methylsulfanyl-acetamide | 1H NMR (CDCl3) δ ppm: 8.83 (1H, s), 8.22 (1H, d); 7.63 (1H, d); 7.16 (1H, d); 6.72 (1H, br); 5.61 (1H, s); 4.28 (2H, s); 4.26 (2H, d); 3.32 (1H, s); 2.43 (1H, t); 2.21 (3H, s); 1.72 (6H, s). |
| 64 | | 2-(8-Chloro-3-ethynyl-quinolin-6-yloxy)-N-(1-cyano-2-methoxy-1-methyl-ethyl)-2-methylsulfanyl-acetamide | 1H NMR (CDCl3) δ ppm: 8.84 (1H, s), 8.22 (1H, d); 7.61 (1H, dd); 7.19 (1H, d); 7.05 (1H, d, br); 5.70 (1H, d); 3.71 (2H, m); 3.51 (3H, d); 3.32 (1H, s); 2.43 (1H, t); 2.21 (3H, s); 1.79 (3H, d). |
| 65 | | N-tert-Butyl-2-[3-(3-methoxymethoxy-prop-1-ynyl)-quinolin-6-yloxy]-2-methylsulfanyl-acetamide | 1H NMR (CDCl3) δ ppm: 8.82 (1H, s); 8.21 (1H, d); 7.61 (1H, d); 7.16 (1H, d); 6.63 (1H, br); 5.61 (1H, s); 3.72 (2H, m); 4.26 (2H, d); 3.32 (1H, s); 2.43 (1H, t); 2.21 (3H, s); 1.72 (6H, s) |
| 66 | | 2-(3-Ethynyl-7-fluoro-quinolin-6-yloxy)-N-(4-methoxy-1,1-dimethyl-but-2-ynyl)-2-methylsulfanyl-acetamide | 1H NMR (CDCl3) δ ppm: 8.87 (1H, d); 8.21 (1H, d); 7.80 (1H, d); 7.36 (1H, d); 6.88 (1H, br); 5.66 (1H, s); 4.12 (2H, s); 3.38 (3H, s); 3.29 (1H, s); 2.21 (3H, s); 1.73 (6H, s). |
| 67 | | N-(1-Cyano-1-methyl-2-methylsulfanyl-ethyl)-2-(3-ethynyl-quinolin-6-yloxy)-2-methylsulfanyl-acetamide | 1H NMR (CDCl3) δ ppm: 8.86 (1H, d); 8.22 (1H, d); 8.08 (1H, d); 7.47 (1H, dd); 7.39 (minor isomere, br); 7.38 (1H, d); 7.18 (major isomere, br); 5.72 (1H, d); 3.30 (1H, s); 3.29 to 3.09 (2H, m); 2.30 (3H, d); 2.23 (3H, d); 1.87 (3H, d); 1.73 (6H, s). |

TABLE 1981-continued

Characterized compounds of the general formula (I)

| Cpd. No. | Compound | ¹H-NMR and/or mp |
|---|---|---|
| 68 | 2-(3-Ethynyl-8-methyl-quinolin-6-yloxy)-N-(2-methoxymethoxy-1,1-dimethyl-ethyl)-2-methylsulfanyl-acetamide | 1H NMR (CDCl3) δ ppm: 8.84 (1H, d); 8.17 (1H, d); 7.31(1H, d); 7.05 (1H, d): 6.81 (1H, br); 5.59 (1H, s); 4.62 (2H, s); 3.59 (2H, q); 3.38 (3H, s); 3.28 (1H, s); 2.77 (3H, s); 2.20 (3H, s); 1.44 (3H, s); 1.42 (3H, s) |
| 69 | 2-(3-Bromoethynyl-quinolin-6-yloxy)-N-tert-butyl-2-methylsulfanyl-acetamide | 1H NMR (CDCl3) δ ppm: 8.79 (1H, d); 8.17 (1H, d); 8.04 (1H, d) 7.46 (1H, dd); 7.21 (1H, d); 6.41 (1H, br); 5.58 (1H, s); 2.20 (3H, s); 1.42 (9H, s). |
| 70 | 2-(8-Bromo-3-ethynyl-quinolin-6-yloxy)-N-(4-methoxy-1,1-dimethyl-but-2-ynyl)-2-methylsulfanyl-acetamide | 1H NMR (CDCl3) δ ppm: 8.83 (1H, d); 8.21 (1H, d); 7.83 (1H, d); 7.19 (1H, d); 6.68 (1H, br); 5.61 (1H, s); 4.12 (2H, s); 3.38 (3H, s); 3.33 (1H, s); 2.21 (3H, s); 1.72 (6H, s). |
| 72 | N-(1-Cyano-1-methyl-3-prop-2-ynyloxy-propyl)-2-(3-ethynyl-quinolin-6-yloxy)-2-methylsulfanyl-acetamide | ¹H NMR (CDCl₃) δ ppm: 8.88 (1H, d); 8.3, 8.28 (1H, s br, 2 isomeres); 8.21 (1H, m); 8.09 (1H, d); 7.48 (1H, m); 7.21 (1H, m); 5.70, 5.68 (1H, s, 2 isomeres); 4.24 (1H, t); 4.18 to 3.82 (4H, m); 3.30 (1H, s); 2.19 to 2.20 (2H, m); 2.22, 2.18 (3H, s, 2 isomeres); 1.80, 1.88 (3H, s, 2 isomeres). |
| 73 | N-(1,1-Dimethyl-2-oxo-ethyl)-2-(3-ethynyl-8-methyl-quinolin-6-yloxy)-2-methylsulfanyl-acetamide | 1H NMR (CDCl3) δ ppm: 9.40 (1H, s); 8.86 (1H, d); 8.18 (1H, d); 7.37 (1H, d); 7.24 (1H, br s); 7.08 (1H, d); 5.68 (1H, s); 3.28 (1H, s); 2.79 (3H, s); 2.20 (3H, s); 1.52 (3H, s); 1.51 (3H, s). |
| 74 | 2-(8-Chloro-3-ethynyl-quinolin-6-yloxy)-N-(2-methoxy-1,1-dimethyl-ethyl)-2-methylsulfanyl-acetamide | 1H NMR (CDCl3) δ ppm: 8.93 (1H, d); 8.21 (1H, d); 7.62 (1H, d); 7.15 (1H, d); 6.71 (1H, br); 5.59 (1H, s); 3.44 (2H, d), 3.37 (3H, s); 3.32 (1H, s); 2.20 (3H, s); 1.42 (3H, s); 1.40 (3H, s). |
| 75 | 2-(8-Chloro-3-ethynyl-quinolin-6-yloxy)-N-(1,1-dimethyl-but-3-ynyl)-2-methylsulfanyl-acetamide | 1H NMR (CDCl3) δ ppm: 8.92 (1H, d); 8.21 (1H, d): 7.62 (1H, d); 7.17 (1H, d); 6.58 (1H, br); 5.60 (1H, s); 3.34 (1H, s), 2.78 to 2.65 (2H, qd); 2.22 (3H, s); 1.97 (1H, t); 1.49 (6H, s). |

TABLE 1981-continued

Characterized compounds of the general formula (I)

| Cpd. No. | Formula | Compound | ¹H-NMR and/or mp |
|---|---|---|---|
| 76 | | 2-(8-Chloro-3-ethynyl-quinolin-6-yloxy)-N-(1,1-dimethyl-2-prop-2-ynyloxy-ethyl)-2-methylsulfanyl-acetamide | 1H NMR (CDCl3) δ ppm: 8.93 (1H, d); 8.21 (1H, d); 7.63 (1H, d); 7.16 (1H, d); 6.73 (1H, br); 5.58 (1H, s); 3.58 (2H, q); 3.32 (1H, s); 2.46 (1H, dd); 2.20 (3H, s); 1.45 (3H, s); 1.43 (3H, s). |
| 78 | | N-(3-Methoxy-1,1-dimethyl-propyl)-2-methylsulfanyl-2-(3-trimethylsilanylethynyl-quinolin-6-yloxy)-acetamide | 1H NMR (CDCl3) δ ppm: 8.81 (1H, d); 8.18 (1H, d); 8.03 (1H, d); 7.89 (1H, br); 7.43 (1H, dd); 7.18 (1H, d); 5.55 (1H, s); 3.56 (2H, td); 3.29 (3H, s); 2.19 (3H, s); 1.80 (2H, td); 1.51 (3H, s); 1.48 (3H, s); 0.29 (9H, s) |
| 79 | | N-(1,1-Dimethyl-but-2-ynyl)-2-methoxy-2-(3-trimethylsilanylethynyl-quinolin-6-yloxy)-acetamide | 1H NMR (CDCl3) δ ppm: 8.81 (1H, d); 8.16 (1H, d); 8.01 (1H, d); 7.51 (1H, dd); 7.41 (1H, d); 6.76 (1H, br); 5.40 (1H, s); 3.52 (3H, s); 1.80 (3H, s); 1.64 (3H, s); 1.62 (3H, s); 0.30 (9H, s). |
| 80 | | N-tert-Butyl-2-methoxy-2-(3-trimethylsilanylethynyl-quinolin-6-yloxy)acetamide | 1H NMR (CDCl3) δ ppm: 8.81 (1H, d); 8.16 (1H, d); 8.01 (1H, d); 7.51 (1H, dd); 7.39 (1H, d); 6.49 (1H, br); 5.38 (1H, s); 3.51 (3H, s); 1.41 (9H, s); 0.30 (9H, s). |
| 81 | | N-(2-Methoxy-1-methoxymethyl-1-methyl-ethyl)-2-methylsulfanyl-2-(3-trimethylsilanylethynyl-quinolin-6-yloxy)-acetamide | 1H NMR (CDCl3) δ ppm: 8.81 (1H, d); 8.17 (1H, d); 8.03 (1H, d); 7.52 (1H, dd); 7.19 (1H, d); 6.97 (1H, br); 5.61 (1H, s); 3.63 to 3.42 (2H, dd); 3.57 (2H, s); 2.21 (3H, s); 1.43 (3H, s); 0.30 (9H, s) |
| 82 | | N-(Cyano-dimethyl-methyl)-2-(3-ethynyl-quinolin-6-yloxy)-2-methylsulfanyl-acetamide | 1H NMR (CDCl3) δ ppm: 8.88 (1H, d); 8.22 (1H, d); 8.09 (1H, d); 7.45 (1H, dd); 7.24 (1H, d); 6.71 (1H, br); 5.72 (1H, s); 3.31 (1H, s); 2.21 (3H, s); 1.82 (3H, s); 1.80 (3H, s). |
| 83 | | N-(1-Cyano-cyclobutyl)-2-(3-ethynyl-quinolin-6-yloxy)-2-methylsulfanyl-acetamide | 1H NMR (CDCl3) δ ppm: 8.87 (1H, d); 8.21 (1H, d); 8.08 (1H, d); 7.47 (1H, dd); 7.24 (1H, d); 7.01 (1H, br); 5.72 (1H, s); 3.31 (1H, s); 2.89 (2H, m); 2.49 (2H, m); 2.26 (2H, m); 2.21 (3H, s); 2.12 (2H, m). |

TABLE 1981-continued

Characterized compounds of the general formula (I)

| Cpd. No. | Formula | Compound | $^1$H-NMR and/or mp |
|---|---|---|---|
| 85 | | 2-(3-Ethynyl-quinolin-6-yloxy)-N-(3-methoxy-1,1-dimethyl-propyl)-2-methylsulfanyl-acetamide | 1H NMR (CDCl3) δ ppm: 8.73 (1H, d); 8.21 (1H, d); 8.05 (1H, d); 7.77 (1H, br); 7.45 (1H, dd); 7.18 (1H, d); 5.55 (1H, s); 3.55 (2H, dt), 3.29 (3H, s); 3.29 (1H, s); 2.20 (3H, s); 1.82 (2H, td); 1.51 (3H, s); 1.48 (3H, s). |
| 86 | | N-(1,1-Dimethyl-but-2-ynyl)-2-(3-ethynyl-quinolin-6-yloxy)-2-methoxy-acetamide | 1H NMR (CDCl3) δ ppm: 8.82 (1H, d); 8.18 (1H, d); 8.03 (1H, d); 7.53 (1H, dd); 7.43 (1H, d); 6.76 (1H, br); 5.41 (1H, s); 3.53 (3H, s); 3.29 (1H, s); 1.80 (3H, s); 1.66 (3H, s); 1.64 (3H, s). |
| 87 | | N-tert-Butyl-2-(3-ethynyl-quinolin-6-yloxy)-2-methoxy-acetamide | 1H NMR (CDCl3) δ ppm: 8.83 (1H, d); 8.19 (1H, d); 8.03 (1H, d); 7.53 (1H, dd); 7.42 (1H, d); 6.49 (1H, br); 5.38 (1H, s); 3.52 (3H, s); 3.29 (1H, s); 1.39 (9H, s). |
| 88 | | 2-(3-Ethynyl-quinolin-6-yloxy)-N-(2-methoxy-1-methoxymethyl-1-methyl-ethyl)-2-methylsulfanyl-acetamide | 1H NMR (CDCl3) δ ppm: 8.83 (1H, d); 8.21 (1H, d); 8.06 (1H, d); 7.45 (1H, dd); 7.22 (1H, d); 6.94 (1H, br); 5.61 (1H, s); 3.62 to 3.44 (2H, dd); 3.58 (2H, s); 3.29 (1H, s); 2.21 (3H, s); 1.41 (3H, s). |
| 89 | | N-(2-Ethoxy-1,1-dimethyl-ethyl)-2-methylsulfanyl-2-(8-methyl-3-trimethylsilanylethynyl-quinolin-6-yloxy)-acetamide | 1H NMR (CDCl3) δ ppm: 8.81 (1H, d); 8.12 (1H, d); 7.28 (1H, dd); 7.02 (1H, d); 6.87 (1H, br); 5.57 (1H, s); 3.51 (2H, m); 3.41 (2H, dd), 2.75 (3H, s); 2.20 (3H, s); 1.42 (3H, s); 1.39 (3H, s); 1.18 (3H, t); 0.30 (9H, s). |
| 90 | | N-(2-Fluoro-1,1-dimethyl-ethyl)-2-methylsulfanyl-2-(8-methyl-3-trimethylsilanylethynyl-quinolin-6-yloxy)-acetamide | 1H NMR (CDCl3) δ ppm: 8.81 (1H, d); 8.12 (1H, d); 7.29 (1H, dd); 7.03 (1H, d); 6.56 (1H, br); 5.61 (1H, s); 4.52 (2H, ddd), 2.78 (3H, s); 2.19 (3H, s); 1.42 (6H, t); 0.30 (9H, s). |
| 91 | | N-(1,1-Dimethyl-propyl)-2-methylsulfanyl-2-(3-trimethylsilanylethynyl-quinolin-6-yloxy)-acetamide | 1H NMR (CDCl3) δ ppm: 8.81 (1H, d); 8.16 (1H, d); 8.03 (1H, d); 7.43 (1H, dd); 7.19 (1H, d); 6.33 (1H, br); 6.58 (1H, s); 2.21 (3H, s); 1.79 (2H, q); 1.36 (6H, s); 0.86 (3H, t); 0.30 (9H, s). |

TABLE 1981-continued

Characterized compounds of the general formula (I)

| Cpd. No. | Formula | Compound | $^1$H-NMR and/or mp |
|---|---|---|---|
| 92 | | N-(1-Cyano-2-fluoro-1-methyl-ethyl)-2-(3-ethynyl-quinolin-6-yloxy)-2-methylsulfanyl-acetamide | $^1$H NMR (CDCl$_3$) δ ppm: 8.88 (1H, d); 8.21 (1H, s); 8.09 (1H, d); 7.48 (1H, dd); 7.25 (1H, m); 6.92, 6.87 (1H, s br, 2 isomeres); 5.73, 5.74 (1H, s, 2 isomeres); 4.53 to 4.98 (2H, m, 2 isomeres); 3.30 (1H, s); 2.21, 2.20 (3H, s, 2 isomeres); 1.96 (3H, m, 2 isomeres). |
| 93 | | 2-(3-Ethynyl-8-methyl-quinolin-6-yloxy)-N-(2-fluoro-1,1-dimethyl-ethyl)-2-methylsulfanyl-acetamide | 1H NMR (CDCl3) δ ppm: 8.86 (1H, d); 8.16 (1H, d); 7.32 (1H, dd); 7.06 (1H, d); 6.55 (1H, br); 5.61 (1H, s); 4.53 (2H, ddd); 3.29 (1H, s); 2.78 (3H, s); 2.19 (3H, s); 1.41 (6H, t). |
| 94 | | N-(1,1-Dimethyl-propyl)-2-(3-ethynyl-quinolin-6-yloxy)-2-methylsulfanyl-acetamide | 1H NMR (CDCl3) δ ppm: 8.86 (1H, d); 8.20 (1H, d); 8.07 (1H, d); 7.47 (1H, dd); 7.21 (1H, d); 6.32 (1H, br); 5.59 (1H, s); 3.30 (1H, s); 2.20 (3H, s); 1.79 (2H, q); 1.37 (6H, s); 0.87 (3H, t). |
| 95 | | N-(2-Ethoxy-1,1-dimethyl-ethyl)-2-(3-ethynyl-8-methyl-quinolin-6-yloxy)-2-methylsulfanyl-acetamide | 1H NMR (CDCl3) δ ppm: 8.84 (1H, d); 8.15 (1H, d); 7.31 (1H, dd); 7.05 (1H, d); 6.34 (1H, br); 5.58 (1H, s); 3.51 (3H, m); 3.42 (2H, dd); 3.29 (1H, s); 2.79 (3H, s); 2.20 (3H, s); 1.42 (3H, s); 1.41 (3H, s); 1.18 (3H, t). |
| 96 | | 2-(3-Ethynyl-quinolin-6-yloxy)-N-methyl-2-methylsulfanyl-acetamide | 1H NMR (CDCl3) δ ppm: 8.85 (1H, d); 8.22 (1H, d); 8.07 (1H, d); 7.46 (1H, dd); 7.22 (1H, d); 6.72 (1H, br); 5.72 (1H, s); 3.30 (1H, s), 2.98 (3H, d); 2.20 (3H, s). |
| 97 | | N-Ethyl-2-(3-ethynyl quinolin-6-yloxy)-2-methylsulfanyl-acetamide | 1H NMR (CDCl3) δ ppm: 8.85 (1H, d); 8.21 (1H, d); 8.06 (1H, d); 7.47 (1H, dd); 7.23 (1H, d); 6.65 (1H, t, br); 5.71 (1H, s); 3.45 (2H, dq), 3.30 (1H, s); 2.20 (3H, s). 1.22 (3H, t) |
| 98 | | 2-(3-Ethynyl-quinolin-6-yloxy)-N-isopropyl-2-methylsulfanyl-acetamide | 1H NMR (CDCl3) δ ppm: 8.85 (1H, d); 8.21 (1H, d); 8.07 (1H, d); 7.46 (1H, dd); 7.22 (1H, d); 6.42 (1H, d, br); 5.68 (1H, s); 4.21 (1H, m) 3.30 (1H, s), 2.20 (3H, s), 1.23 (6H, dd). |
| 99 | | 2-(3-Ethynyl-quinolin-6-yloxy)-N-(2-fluoro-1,1-dimethyl-ethyl)-2-methylsulfanyl-acetamide | 1H NMR (CDCl3) δ ppm: 8.85 (1H, d); 8.21 (1H, d); 8.07 (1H, d); 7.47 (1H, dd); 7.23 (1H, d); 6.55 (1H, br); 5.62 (1H, s); 4.53 (2H, ddd); 3.29 (1H, s); 2.21 (3H, s); 1.43 (6H, s). |

TABLE 1981-continued

Characterized compounds of the general formula (I)

| Cpd. No. | Formula | Compound | ¹H-NMR and/or mp |
|---|---|---|---|
| 100 | | N-(5-Methoxy-1,1-dimethyl-pent-2-ynyl)-2-methylsulfanyl-2-(3-trimethylsilanylethynyl-quinolin-6-yloxy)-acetamide | 1H NMR (CDCl3) δ ppm: 8.82 (1H, d); 8.17 (1H, d); 8.05 (1H, d); 7.44 (1H, dd); 7.21 (1H, d); 6.73 (1H, br); 5.70 (1H, s); 3.49 (2H, t); 3.36 (3H, s); 2.48 (2H, t); 2.20 (3H, s); 1.61 (3H, s); 1.60 (3H, s); 0.30 (9H, s). |
| 101 | | N-tert-Butyl-2-(7-fluoro-3-trimethylsilanylethynyl-quinolin-6-yloxy)-2-methylsulfanyl-acetamide | 1H NMR (CDCl3) δ ppm: 8.83 (1H, d); 8.18 (1H, d); 7.78 (1H, d); 7.31 (1H, d); 6.62 (1H, br); 5.51 (1H, s); 2.20 (3H, s); 1.43 (9H, s); 0.30 (9H, s). |
| 102 | | N-(1-Cyano-2-fluoro-1-methyl-ethyl)-2-(3-ethynyl-8-methyl-quinolin-6-yloxy)-2-methylsulfanyl-acetamide | 1H NMR (CDCl3) δ ppm: 8.89 (1H, d); 8.20 (1H, s); 7.32 (1H, m); 7.19 (1H, s), 6.92, 6.88 (1H, s br, 2 isomeres); 5.74, 5.72 (1H, s, 2 isomeres); 4.58 to 4.98 (m, 2H, 2 isomeres); 3.3 (1H, s); 2.80 (3H, s); 2.22, 2.20 (3H, s, 2 isomeres); 1.87 (3H, dd) |
| 103 | | 2-(3-Ethynyl-quinolin-6-yloxy)-N-(5-methoxy-1,1-dimethyl-pent-2-ynyl)-2-methylsulfanyl-acetamide | 1H NMR (CDCl3) δ ppm: 8.85 (1H, d); 8.21 (1H, d); 8.08 (1H, d); 7.48 (1H, dd); 7.22 (1H, d); 6.73 (1H, br); 5.62 (1H, s); 3.49 (2H, t); 3.46 (3H, s); 3.31 (1H, s); 2.48 (2H, t); 2.20 (3H, s); 1.61 (3H, s); 1.61 (3H, s); 0.30 (9H, s). |
| 104 | | N-tert-Butyl-2-(3-ethynyl-7-fluoro-quinolin-6-yloxy)-2-methylsulfanyl-acetamide | 1H NMR (CDCl3) δ ppm: 8.86 (1H, d); 8.21 (1H, d); 7.80 (1H, d); 7.36 (1H, d); 6.62 (1H, br); 5.51 (1H, s); 3.30 (1H, s); 2.20 (3H, s); 1.43 (9H, s). |
| 105 | | 2-[2-(3-Ethynyl-7-fluoro-quinolin-6-yloxy)-2-methylsulfanyl-acetylamino]-2-methyl-propionic acid methyl ester | ¹H NMR (CDCl3) δ ppm: 8.86 (1H, d); 8.21 (1H, d); 7.80 (1H, d); 7.39 (1H, br); 7.36 (1H, d); 5.69 (1H, s); 3.79 (3H, s); 3.30 (1H, s); 2.21 (3H, s); 1.67 (3H, s); 1.67 (3H, s). |
| 106 | | N-(1,1-Dimethyl-prop-2-ynyl)-2-(3-ethynyl-7-fluoro-quinolin-6-yloxy)-2-methylsulfanyl-acetamide | ¹H NMR (CDCl3) δ ppm: 8.87 (1H, d); 8.21 (1H, d); 7.80 (1H, d); 7.36 (1H, d); 6.88 (1H, br); 5.68 (1H, s); 3.30 (1H, s); 2.41 (1H, s); 2.21 (3H, s); 1.73 (6H, s). |
| 107 | | N-(1,1-Dimethyl-but-2-ynyl)-2-(3-ethynyl-7-fluoro-quinolin-6-yloxy)-2-methylsulfanyl-acetamide | ¹H NMR (CDCl3) δ ppm: 8.87 (1H, d); 8.21 (1H, d); 7.80 (1H, d); 7.34 (1H, d); 6.88 (1H, br); 5.66 (1H, s); 3.30 (1H, s); 2.21 (3H, s); 1.82 (3H, s); 1.72 (6H, s). |

TABLE 1981-continued

Characterized compounds of the general formula (I)

| Cpd. No. | Formula | Compound | $^1$H-NMR and/or mp |
|---|---|---|---|
| 108 | | 2-(3-Ethynyl-7-fluoro-quinolin-6-yloxy)-N-(2-methoxy-1,1-dimethyl-ethyl)-2-methylsulfanyl-acetamide | $^1$H NMR (CDCl3) δ ppm: 8.87 (1H, d); 8.21 (1H, d); 7.80 (1H, d); 7.33 (1H, d); 6.98 (1H, br); 5.63 (1H, s); 3.42 (2H, dd); 3.40 (3H, s); 3.30 (1H, s); 2.20 (3H, s); 1.42 (3H, s); 1.41 (3H, s). |
| 109 | | N-(1,1-Dimethyl-2-prop-2-ynyloxy-ethyl)-2-(3-ethynyl-7-fluoro-quinolin-6-yloxy)-2-methylsulfanyl-acetamide | $^1$H NMR (CDCl3) δ ppm: 8.87 (1H, d); 8.21 (1H, d); 7.80 (1H, d); 7.32 (1H, d); 6.90 (1H, br); 5.62 (1H, s); 4.20 (2H, d); 3.61 (2H, dd); 3.30 (1H, s); 2.46 (2H, t); 2.20 (3H, s); 1.47 (3H, s); 1.45 (3H, s). |
| 110 | | 2-(3-Ethynyl-quinolin-6-yloxy)-N-(2-hydroxy-1,1-dimethyl-ethyl)-butyramide | $^1$H NMR (CDCl3) δ ppm: 8.82 (1H, d); 8.18 (1H, d); 8.05 (1H, d); 7.42 (1H, dd); 7.04 (1H, s); 6.36 (1H, br); 4.51 (1H, dt); 3.57 (2H, dd); 3.30 (1H, s); 2.03 (2H, m); 1.27 (3H, s); 1.21 (3H, s); 1.09 (3H, t). |
| 111 | | 2-(3-Ethynyl-8-methyl-quinolin-6-yloxy)-N-(2-hydroxy-1,1-dimethyl-ethyl)-butyramide | $^1$H NMR (CDCl3) δ ppm: 8.82 (1H, d); 8.12 (1H, d); 7.28 (1H, dd); 6.88 (1H, s); 6.37 (1H, br); 4.60 (1H, dd); 4.49 (1H, t); 3.57 (2H, dd); 3.29 (1H, s); 2.78 (3H, s); 2.02 (2H, m); 1.25 (3H, s); 1.20 (3H, s); 1.08 (3H, t). |
| 112 | | 2-(3-Ethynyl-8-methyl-quinolin-6-yloxy)-N-(4-methoxy-1,1-dimethyl-but-2-ynyl)-butyramide | $^1$H NMR (CDCl3) δ ppm: 8.69 (1H, d); 7.99 (1H, d); 7.16 (1H, d); 6.74 (1H, d); 6.24 (1H, br); 4.40 (1H, dd); 3.92 (2H, s); 3.20 (3H, s); 3.12 (1H, s); 2.62 (3H, s); 1.88 (2H, m); 1.48 (6H, s); 0.91 (3H, t). |
| 113 | | N-(1,1-Dimethyl-but-2-ynyl)-2-(3-ethynyl-8-methyl-quinolin-6-yloxy)-butyramide | $^1$H NMR (CDCl3) δ ppm: 8.82 (1H, d); 8.12 (1H, d); 7.30 (1H, dd); 6.89 (1H, d); 6.39 (1H, br); 4.52 (1H, dd); 3.28 (1H, s); 2.77 (3H, s); 2.02 (2H, m); 1.76 (3H, s); 1.58 (6H, s); 1.07 (3H, t). |
| 114 | | N-(1,1-Dimethyl-prop-2-ynyl)-2-(3-ethynyl-8-methyl-quinolin-6-yloxy)-butyramide | $^1$H NMR (CDCl$_3$) δ ppm: 8.82 (1H, d); 8.12 (1H, d); 7.28 (1H, dd); 6.89 (1H, d); 6.39 (1H, br); 4.57 (1H, dd); 3.27 (1H, s); 2.77 (3H, s); 2.31 (1H, s); 2.03 (2H, m); 1.60 (3H, s); 1.58 (3H, s); 1.08 (3H, t). |

TABLE 1981-continued

Characterized compounds of the general formula (I)

| Cpd. No. | Formula | Compound | $^1$H-NMR and/or mp |
|---|---|---|---|
| 115 | | N-tert-Butyl-2-(3-ethynyl-8-methyl-quinolin-6-yloxy)-butyramide | $^1$H NMR (CDCl$_3$) δ ppm: 8.82 (1H, d); 8.12 (1H, d); 7.28 (1H, dd); 6.88 (1H, d); 6.11 (1H, br); 4.50 (1H, dd); 3.26 (1H, s); 2.76 (3H, s); 2.00 (2H, m); 1.30 (9H, s); 1.07 (3H, t). |
| 116 | | N-(1,1-Dimethyl-pent-2-ynyl)-2-methylsulfanyl-2-(3-trimethylsilanylethynyl-quinolin-6-yloxy)-acetamide | 1H NMR (CDCl3) δ ppm: 8.82 (1H, d); 8.17 (1H, d); 8.06 (1H, d); 7.45 (1H, dd); 7.21 (1H, d); 6.72 (1H, br); 6.61 (1H, s); 2.20 (3H, s); 2.20 (2H, q); 1.70 (3H, s); 1.70 (3H, s); 1.11 (3H, s); 0.30 (9H, s). |
| 117 | | N-(1,1-Dimethyl-pent-2-ynyl)-2-(3-ethynyl-quinolin-6-yloxy)-2-methylsulfanyl-acetamide | 1H NMR (CDCl3) δ ppm: 8.85 (1H, d); 8.21 (1H, d); 8.08 (1H, d); 7.48 (1H, dd); 7.22 (1H, d); 6.71 (1H, br); 6.61 (1H, s); 3.30 (1H, s); 2.20 (3H, s); 2.20 (2H, q); 1.70 (3H, s); 1.70 (3H, s); 1.12 (3H, s). |
| 118 | | 2-(8-Chloro-3-trimethylsilanylethynyl-quinolin-6-yloxy)-N-(1-ethyl-1-methyl-but-2-ynyl)-2-methylsulfanyl-acetamide | 1H NMR (CDCl3) δ ppm: 8.89 (1H, d); 8.18 (1H, d); 7.62 (1H, dd); 7.13 (1H, d); 6.58 (1H, br); 5.57, 5.58 (1H, 2s, 2 isomeres); 2.22 to 2.14 (4H, m); 1.85 to 1.80 (4H, m); 1.68, 1.65 (3H, 2s, 2 isomeres); 1.02, 0.97 (3H, 2s); 0.30 (9H, s). |
| 119 | | 2-(8-Chloro-3-trimethylsilanylethynyl-quinolin-6-yloxy)-N-(1,1-dimethyl-pent-2-ynyl)-2-methylsulfanyl-acetamide | 1H NMR (CDCl3) δ ppm: 8.89 (1H, d); 8.18 (1H, d); 7.61 (1H, dd); 7.13 (1H, d); 6.64 (1H, br); 5.59 (1H, d); 2.20 (3H, s); 2.20 (2H, q); 1.69 (3H, s); 1.71 (3H, s); 1.12 (3H, s); 0.30 (9H, s). |
| 120 | | N-(6-Chloro-1,1-dimethyl-hex-2-ynyl)-2-(8-chloro-3-trimethylsilanylethynyl-quinolin-6-yloxy)-2-methylsulfanyl-acetamide | 1H NMR (CDCl3) δ ppm: 8.89 (1H, d); 8.17 (1H, d); 7.61 (1H, dd); 7.12 (1H, d); 6.62 (1H, br); 5.59 (1H, s); 3.66 (2H, q); 2.38 (2H, t); 2.20 (3H, s); 1.95 (2H, m); 1.69 (6H, s); 0.30 (9H, s). |
| 121 | | 2-(8-Chloro-3-ethynyl-quinolin-6-yloxy)-N-(1-ethyl-1-methyl-but-2-ynyl)-2-methylsulfanyl-acetamide | 1H NMR (CDCl3) δ ppm: 8.93 (1H, d); 8.22 (1H, d); 7.64 (1H, dd); 7.16 (1H, d); 6.57 (1H, br); 5.57, 5.58 (1H, 2s, 2 isomeres); 3.30 (1H, s); 2.22 to 2.14 (4H, m); 1.90 to 1.76 (4H, m); 1.68, 1.66 (3H, 2s, 2 isomeres); 1.00, 0.96 (3H, 2s, 2 isomeres). |

TABLE 1981-continued

Characterized compounds of the general formula (I)

| Cpd. No. | Compound | ¹H-NMR and/or mp |
|---|---|---|
| 122 | 2-(8-Chloro-3-ethynyl-quinolin-6-yloxy)-N-(1,1-dimethyl-pent-2-ynyl)-2-methylsulfanyl-acetamide | 1H NMR (CDCl3) δ ppm: 8.92 (1H, d); 8.20 (1H, d); 7.62 (1H; d); 7.15 (1H, d); 6.63 (1H, br); 5.59 (1H, s); 3.32 (1H, s); 2.20 (3H, s); 2.20 (2H, q); 1.70 (3H, s); 1.69 (3H, s); 1.11 (3H, t). |
| 123 | N-(6-Chloro-1,1-dimethyl-hex-2-ynyl)-2-(8-chloro-3-ethynyl-quinolin-6-yloxy)-2-methylsulfanyl-acetamide | 1H NMR (CDCl3) δ ppm: 8.93 (1H, d); 8.21 (1H, d); 7.62 (1H; d); 7.14 (1H, d); 6.60 (1H, br s); 5.60 (1H, s); 3.66 (2H, t); 3.31 (1H, s); 2.39 (2H, t); 2.20 (3H, s); 1.95 (2H, q); 1.70 (6H, s). |
| 124 | N-(1,1-Dimethyl-prop-2-ynyl)-2-(3-ethynyl-quinolin-6-yloxy)-2-methoxy-acetamide | 1H NMR (CDCl3) δ pm: 8.82 (1H, d); 8.20 (1H, d); 8.02 (1H, d); 7.52 (1H, dd); 7.42 (1H, d); 6.79 (1H, s br); 5.41 (1H, s); 3.53 (3H, s); 3.28 (1H, s); 2.38 (1H, s); 1.69 (6H, s). |
| 125 | 2-(3-Ethynyl-quinolin-6-yloxy)-2-methoxy-N-(4-methoxy-1,1-dimethyl-but-2-ynyl)-acetamide. | 1H NMR (CDCl3) δ ppm: 8.83 (1H, d); 8.20 (1H, d); 8.02 (1H, d); 7.52 (1H, dd); 7.42 (1H, d); 6.79 (1H, s br); 5.41 (1H, s); 4.10 (2H, s); 3.52 (3H, s); 3.33 (3H, s); 3.28 (1H, s); 1.69 (6H, s). |
| 126 | Step 4: 2-(3-Ethynyl-quinolin-6-yloxy)-2-methoxy-N-(2-methoxy-1,1-dimethyl-ethyl)-acetamide | 1H NMR (CDCl3) δ ppm: 8.83 (1H, d); 8.20 (1H, d); 8.02 (1H, d); 7.52 (1H, dd); 7.42 (1H, d); 6.77 (1H, s br); 5.41 (1H, s); 4.18 (2H, s); 3.54 (3H, s); 3.34 (3H, s); 3.28 (1H, s); 1.70 (6H, s). |
| 127 | N-(1,1-Dimethyl-2-prop-2-ynyloxy-ethyl)-2-(3-ethynyl-quinolin-6-yloxy)-2-methoxy-acetamide | 1H NMR (CDCl3) δ ppm: 8.83 (1H, d); 8.21 (1H, d); 8.04 (1H, d); 7.52 (1H, dd); 7.42 (1H, d); 6.80 (1H, s br); 5.41 (1H, s); 4.18 (2H, d); 3.56 (2H, m); 3.52 (3H, s); 3.28 (1H, s); 2.44 (1H, t); 1.40 (6H, d). |
| 128 | N-(1-Cyano-2-methoxy-1-methyl-ethyl)-2-(3-ethynyl-quinolin-6-yloxy)-2-methoxy-acetamide | H NMR (CDCl$_3$) δ ppm: 8.83 (1H, d); 8.21 (1H, d); 8.04 (1H, d); 7.52 (1H, dd); 7.49 (1H, dd); 7.13, 7.04 (1H, s br, 2 isomeres); 5.51, 5.49 (1H, s, 2 isomeres); 3.60 to 3.78 (2H, m, 2 isomeres); 3.55 (3H, s); 3.52, 3.48 (3H, s, 2 isomeres), 3.29 (1H, s); 1.78, 1.72 (3H. s. 2 isomeres) |

TABLE 1981-continued

Characterized compounds of the general formula (I)

| Cpd. No. | Formula | Compound | ¹H-NMR and/or mp |
|---|---|---|---|
| 129 | | 2-(3-Ethynyl-quinolin-6-yloxy)-N-(1-methoxymethyl-1-methyl-prop-2-ynyl)-2-methylsulfanyl-acetamide | ¹H NMR (CDCl$_3$) δ ppm: 8.86 (1H, d); 8.21 (1H, d); 8.06 (1H, d); 7.48 (1H, d); 7.24 (1H, d); 7.05 (1H, br s); 5.68 (1H, s, isomer B); 5.67 (1H, s, isomer A); 3.74 (1H, d, isomer A); 3.68 (2H, s, isomer B); 3.60 (1H, d, isomer A); 3.48 (3H, s, isomer B); 3.46 (3H, s, isomer A); 3.30 (1H, s); 2.47 (1H, s, isomer A); 2.46 (1H, s, isomer B); 2.21 (3H, s, isomer B); 2.20 (3H, s, isomer A); 1.72 (3H, s, isomer A); 1.70 (3H, s, isomer B). |
| 130 | | 2-(8-Bromo-3-ethynyl-quinolin-6-yloxy)-N-(1,1-dimethyl-prop-2-ynyl)-2-methylsulfanyl acetamide | 1H NMR (CDCl3) δ ppm: 8.96 (1H, d); 8.20 (1H, d); 7.85 (1H, d); 7.22 (1H, d); 6.65 (1H, br s); 5.62 (1H, s); 3.32 (1H, s); 2.40 (1H, s); 2.20 (3H, s); 1.72 (6H, s). |
| 131 | | 2-(8-Bromo-3-ethynyl-quinolin-6-yloxy)-N-(1,1-dimethyl-but-2-ynyl)-2-methylsulfanyl-acetamide | 1H NMR (CDCl3) δ ppm: 8.96 (1H, d); 8.21 (1H, d); 7.85 (1H, d); 7.21 (1H, d); 6.64 (1H, br s); 5.58 (1H, s); 3.33 (1H, s); 2.20 (3H, s); 1.83 (3H, s); 1.69 (3H, s); 1.68 (3H, s). |
| 132 | | 2-(8-Bromo-3-ethynyl-quinolin-6-yloxy)-N-tert-butyl-2-methylsulfanyl-acetamide | 1H NMR (CDCl3) δ ppm: 8.95 (1H, d); 8.19 (1H, d); 7.84 (1H, d); 7.20 (1H, d); 6.38 (1H, br s); 5.59 (1H, s); 3.31 (1H, s); 2.20 (3H, s); 1.40 (9H, s). |
| 133 | | 2-(3-Ethynyl-8-methyl-quinolin-6-yloxy)-N-(2-methoxy-1-methoxymethyl-1-methyl-ethyl)-2-methylsulfanyl-acetamide | 1H NMR (CDCl3) δ ppm: 8.85 (1H, d); 8.18 (1H, d); 7.31 (1H, d); 7.05 (1H, d); 6.97 (1H, br s); 5.60 (1H, s); 3.62-3.44 (4H, m); 3.38 (3H, m); 3.28 (1H, s); 2.78 (3H, s); 2.20 (3H, s); 1.45 (3H, s). |

TABLE 1981-continued

Characterized compounds of the general formula (I)

| Cpd. No. | Formula | Compound | $^1$H-NMR and/or mp |
|---|---|---|---|
| 134 | | 2-(3-Ethynyl-8-methyl-quinolin-6-yloxy)-N-(1-methoxymethyl-1-methyl-2-oxo-ethyl)-2-methylsulfanyl-acetamide | $^1$H NMR (CDCl$_3$) δ ppm: 9.49 (1H, s, isomer A); 9.46 (1H. s. isomer B); 8.86 (1H, d); 8.18 (1H, m); 7.60 (1H, br s, isomer A), 7.50 (1H, br s, isomer B); 7.37 (1H, m); 7.08 (1H, m); 5.72 (1H, s); 3.95 (1H, d, isomer A); 3.82 (1H, d, isomer B); 3.70 (1H, m); 3.35 (3H, s, isomer A); 3.34 (3H, s, isomer B); 3.30 (1H, s); 2.22 (3H, s, isomer A); 2.21 (3H, s, isomer B); 1.51 (3H, s). |
| 135 | | 2-(3-ethynyl-8-methyl-quinolin-6-yloxy)-N-(1-methoxymethyl-1-methyl-prop-2-ynyl)-2-methylsulfanyl-acetamide | $^1$H NMR (CDCl$_3$) δ ppm: 8.85 (1H, d); 8.19 (1H, d); 7.32 (1H, d); 7.06 (1H, d); 7.03 (1H, br s, isomer A); 7.02 (1H, br s, isomer B); 5.66 (1H, s, isomer B); 5.65 (1H, s, isomer A); 3.76 (1H, d, isomer A); 3.69 (2H, s, isomer B); 3.61 (1H, d, isomer A); 3.48 (3H, s, isomer B); 3.47 (3H, s, isomer A); 3.30 (1H, s); 2.79 (3H, s); 2.44 (1H, s, isomer A); 2.43 (1H, s, isomer B); 2.20 (3H, s, isomer B); 2.20 (3H, s, isomer A); 1.72 (3H, s, isomer A); 1.70 (3H, s, isomer B) |
| 136 | | 2-(3-Ethynyl-8-methyl-quinolin-6-yloxy)-N-(2-methoxy-1-methyl-1-prop-2-ynyloxymethyl-ethyl)-2-methylsulfanyl-acetamide | $^1$H NMR (CDCl$_3$) δ ppm: 8.86 (1H, d); 8.19 (1H, d); 7.32 (1H, d); 7.06 (1H, d); 6.98 (1H, br s); 5.61 (1H, s); 4.20 (2H, m); 3.80-3.48 (4H, m); 3.39 (3H, m, isomer A); 3.38 (3H, s, isomer B); 3.29 (1H, s); 2.79 (3H, s); 2.48 (1H, m); 2.21 (3H, s); 1.47 (3H, s). |
| 137 | | N-(1-Cyano-2-fluoro-1-methyl-ethyl)-2-methylsulfanyl-2-(8-methyl-3-trimethylsilanylethynyl-quinolin-6-yloxy)-acetamide | 1H NMR (CDCl3) δ ppm: 8.83 (1H, d); 8.13 (1H, d); 7.30 (1H, d); 7.05 (1H, d); 6.92, 6.88 (1H, s br, 2 isomeres); 5.62, 5.61 (1H, s, 2 isomeres); 4.56 to 4.98 (2H, m, 2 isomeres); 2.78 (3H, s); 2.22, 2.19 (3H, s, 2 isomeres); 1.85 (3H, m); 0.30 (9H, m). |

TABLE 1981-continued

Characterized compounds of the general formula (I)

| Cpd. No. | Formula | Compound | $^1$H-NMR and/or mp |
|---|---|---|---|
| 138 | | 2-(3-Ethynyl-quinolin-6-yloxy)-N-(2-hydroxy-1-methoxymethyl-1-methyl-ethyl)-2-methylsulfanyl-acetamide | H NMR (CDCl$_3$) δ ppm: 8.80 (1H, d); 8.20 (1H, d); 8.05 (1H, d); 7.45 (1H, dd); 7.30 (1H, br s, isomer A); 7.25 (1H, br s, isomer B), 7.22 (1H, d); 5.67 (1H, s); 3.76-3.40 (4H, m); 3.36 (3H, s, isomer A); 3.34 (3H, s, isomer B); 3.30 (1H, s); 2.19 (3H, s, isomer A); 2.18 (3H, s, isomer B); 1.36 (3H, s, isomer A); 1.34 (3H, s, isomer B). |
| 139 | | 2-(3-Ethynyl-quinolin-6-yloxy)-N-(1-methoxymethyl-1-methyl-2-oxo-ethyl)-2-methylsulfanyl-acetamide | $^1$H NMR (CDCl$_3$) δ ppm: 9.50 (1H, s, isomer A); 9.48 (1H, s, isomer B); 8.85 (1H, d); 8.20 (1H, m); 8.06 (1H, d); 7.55 (1H, br s, isomer A); 7.51 (1H, m); 7.50 (1H, br s, isomer B); 7.25 (1H, m); 5.72 (1H, s); 3.94 (1H, d, isomer A); 3.81 (1H, d, isomer B); 3.70 (1H, m); 3.33 (3H, s, isomer A); 3.32 (3H, s, isomer B); 3.30 (1H, s); 2.20 (3H, s, isomer A); 2.19 (3H, s, isomer B); 1.51 (3H, s, isomer A); 1.50 (3H, s, isomer B). |
| 140 | | 2-(3-Ethynyl-8-methyl-quinolin-6-yloxy)-N-(2-hydroxy-1-methoxymethyl-1-methyl-ethyl)-2-methylsulfanyl-acetamide | 1H NMR (CDCl3) δ ppm: 8.85 (1H, d); 8.19 (1H, d); 7.32 (1H, d); 7.27 (1H, br s); 7.06 (1H, d); 5.66 (1H, s); 4.0 (1H, m); 3.81-3.42 (4H, m); 3.39 (3H, s, isomer A); 3.37 (3H, s, isomer B); 3.28 (1H, s); 2.79 (3H, s); 2.20 (3H, s, isomer A); 2.19 (3H, s, isomer B); 1.35 (3H, s, isomer A); 1.33 (3H, s, isomer B) |
| 141 | | N-tert-Butyl-2-[3-(3-hydroxy-3-methyl-but-1-ynyl)-quinolin-6-yloxy]-2-methylsulfanyl-acetamide | m/z = 401 |
| 142 | | N-tert-Butyl-2-[3-(3-hydroxy-3-methyl-but-1-ynyl)-8-methyl-quinolin-6-yloxy]-2-methylsulfanyl-acetamide | m/z = 397 |

TABLE 1981-continued

Characterized compounds of the general formula (I)

| Cpd. No. | Compound | ¹H-NMR and/or mp |
|---|---|---|
| 143 | N-tert-butyl-2-[3-(3-chloro-prop-1-ynyl)-quinolin-6-yloxy]-2-methylsulfanyl-acetamide | ¹H NMR (CDCl₃) δ ppm: 8.81 (1H, d); 8.18 (1H, d); 8.08 (1H, d); 7.48 (1H, dd); 7.2 (1H, d); 6.43 (1H, bs); 5.6 (1H, s); 4.45 (2H, s); 2.2 (3H, s); 1.42 (9H, s) |
| 144 | N-tert-butyl-2-[3-(3-fluoro-prop-1-ynyl)-quinolin-6-yloxy]-2-methylsulfanyl-acetamide | ¹H NMR (CDCl₃) δ ppm: 8.83 (1H, d); 8.2 (1H, d); 8.08 (1H, d); 7.49 (1H, dd); 7.2 (1H, d); 6.43 (1H, bs); 5.6 (1H, s); (2H, m); 2.2 (3H, s); 1.41 (9H, s) |
| 145 | 2-(3-Ethynyl-quinolin-6-yloxy)-N-(2-methoxy-1-methoxy-methyl-1-methyl-ethyl)-butyramide | 1H NMR (CDCl3) δ ppm: 8.80 (1H, d); 8.14 (1H, d); 8.01 (1H, d); 7.40 (1H, dd); 7.05 (1H, d); 6.62 (1H, br s); 4.52 (1H, dd); 3.49-3.24 (4H, m); 3.27 (3H, s); 3.22 (3H, s); 2.06-1.95 (2H, m); 1.30 (3H, s); 1.06 (3H, s). |
| 146 | 2-(3-Ethynyl-quinolin-6-yloxy)-N-(1-methoxymethyl-1-methyl-prop-2-ynyl)-butyramide | ¹H NMR (CDCl₃) δ ppm: 8.80 (1H, d); 8.13 (1H, d); 8.01 (1H, d); 7.41 (1H, dd); 7.05 (1H, m); 6.69 (1H, br s); 4.60-4.56 (1H, m); 3.59 (1H, d, AB system, isomer A); 3.52 (2H, s, isomer B); 3.43 (1H, d, AB system, isomer A); 3.32 (3H, s, isomer B); 3.27 (3H, s, isomer A); 3.26 (1H, s); 2.36 (1H, s, isomer A); 2.32 (1H, s, isomer B); 2.07-1.97 (2H, m); 1.60 (3H, s, isomer A); 1.55 (3H, s, isomer B); 1.08-1.04 (3H, m). |
| 147 | N-tert-Butyl-2-(3-ethynyl-quinolin-6-yloxy)-N-hydroxy-2-methylsulfanyl-acetamide | 1H NMR (DMSO-d6) δ ppm: 9.87 (1H, s); 8.75 (1H, d); 8.41 (1H, d); 7.96 (1H, d); 7.50 (1H, dd); 7.34 (1H, d); 6.27 (1H, s); 4.51 (1H, s); 3.28 (1H, s); 2.17 (3H, s); 1.36 (9H, s). Mp: 164° C. |
| 148 | 2-(3-Ethynyl-quinolin-6-yloxy)-N-(1-hydroxymethyl-cyclobutyl)-2-methyl sulfanyl-acetamide | 1H NMR (CDCl3) δ ppm: 8.85 (1H, d); 8.22 (1H, d); 8.06 (1H, d); 7.47 (1H, dd); 7.23 (1H, d); 6.94 (1H, br s); 5.66 (1H, s); 3.86 (2H, s), 3.30 (1H, s); 2.38-2.16 (4H, m); 2.21 (3H, s); 2.00-1.82 (2H, m). |
| 149 | Acetic acid 4-[2-(3-ethynyl-quinolin-6-yloxy)-2-methylsulfanyl-acetylamino]-4-methyl-pent-2-ynyl ester | 1H NMR (CDCl3) δ ppm: 8.85 (1H, d); 8.20 (1H, d); 8.06 (1H, d); 7.47 (1H, dd); 7.21 (1H, d); 6.71 (1H, br s); 5.62 (1H, s); 4.68 (2H, s); 3.28 (1H, s); 2.19 (3H, s); 2.08 (3H, s); 1.71 (6H, s). |

TABLE 1981-continued

Characterized compounds of the general formula (I)

| Cpd. No. | Formula | Compound | ¹H-NMR and/or mp |
|---|---|---|---|
| 150 | | 2-(3-Ethynyl-quinolin-6-yloxy)-N-(1-formyl-cyclobutyl)-2-methylsulfanyl-acetamide | 1H NMR (CDCl3) δ ppm: 9.69 (1H, s); 8.84 (1H, d); 8.20 (1H, d); 8.05 (1H, d); 7.47 (1H, dd); 7.42 (1H, br s); 7.26 (1H, d); 5.72 (1H, s); 3.29 (1H, s); 2.73-2.64 (2H, m); 2.57-2.49 (2H, m); 2.20 (3H, s); 2.16-1.97 (2H, m). |
| 151 | | N-(1-Ethynyl-cyclobutyl)-2-(3-ethynyl-quinolin-6-yloxy)-2-methylsulfanyl-acetamide | 1H NMR (CDCl3) δ ppm: 8.81 (1H, s); 8.19 (1H, d); 8.04 (1H, d); 7.45 (1H, dd); 7.21 (1H, d); 6.93 (1H, br s); 5.66 (1H, s); 3.28 (1H, s); 2.63-2.48 (4H, m); 2.21 (3H, s); 2.16-1.93 (2H, m). |
| 152 | | 2-(3-Ethynyl-quinolin-6-yloxy)-2-methylsulfanyl-N-(1-prop-2-ynyloxymethyl-cyclobutyl)-acetamide | ¹H NMR (CDCl₃) δ ppm: 8.82 (1H, d); 8.18 (1H, d); 8.03 (1H, d); 7.44 (1H, dd); 7.21 (1H, d); 6.88 (1H, br s); 5.62 (1H, s); 4.14 (2H, s); 3.84-3.74 (2H, dd, AB system); 3.28 (1H, s); 2.49-2.13 (4H, m); 2.42 (1H, s); 2.19 (3H, s); 2.01-1.79 (2H, m). |
| 153 | | N-(1-Dimethoxymethyl-cyclobutyl)-2-(3-ethynyl-quinolin-6-yloxy)-2-methylsulfanyl-acetamide | ¹H NMR (CDCl₃) δ ppm: 8.84 (1H, d); 8.19 (1H, d); 8.05 (1H, d); 7.46 (1H, dd); 7.23 (1H, d); 6.86 (1H, br s); 5.62 (1H, s); 4.57 (1H, s); 3.51 (3H, s); 3.47 (3H, s); 3.28 (1H, s); 2.47-2.21 (4H, m); 2.21 (3H, s); 2.01-1.73 (2H, m). |
| 154 | | 2-(3-Ethynyl-quinolin-6-yloxy)-N-(1-hydroxymethyl-cyclobutyl)-N-methyl-2-methylsulfanyl-acetamide | ¹H NMR (CDCl₃) δ ppm: 8.82 (1H, d); 8.18 (1H, d); 8.03 (1H, d); 7.49 (1H, dd); 7.16 (1H, d); 5.79 (1H, s); 4.14 (2H, s); 3.87 (2H, s); 3.27 (1H, s); 3.06 (3H, s); 2.27 (3H, s); 2.32-2.12 (4H, m); 1.79-1.71 (2H, m). |
| 155 | | 2-(3-Ethynyl-quinolin-6-yloxy)-2-methoxy-N-(1-methoxymethyl-1-methyl-prop-2-ynyl)-acetamide | ¹H NMR (CDCl₃) δ ppm: 8.81 (1H, d); 8.17 (1H, d); 8.01 (1H, d); 7.51 (1H, m); 7.41 (1H, m); 7.05 (1H, br s, isomer B); 7.02 (1H, br s, isomer A); 5.43 (1H, s); 3.68-3.54 (2H, m); 3.51 (3H, s); 3.43 (3H, s, isomer B); 3.42 (3H, s, isomer A); 3.26 (1H, s); 2.39 (1H, s, isomer B); 2.36 (1H, s, isomer A); 1.67 (3H, s, isomer B); 1.64 (3H, s, isomer A). |

TABLE 1981-continued

Characterized compounds of the general formula (I)

| Cpd. No. | Formula | Compound | ¹H-NMR and/or mp |
|---|---|---|---|
| 156 | | N-tert-Butyl-2-(3-ethynyl-7-fluoro-8-methyl-quinolin-6-yloxy)-2-methyl sulfanyl-acetamide | ¹H NMR (CDCl$_3$) δ ppm: 8.88 (1H, d); 8.17 1H, d); 7.17 (1H, d); 6.64 (1H, br s); 5.59 (1H, s); 3.27 (1H, s); 2.69 (3H, d); 2.18 (3H, s); 1.44 (9H, s). |
| 157 | | N-(1,1-Dimethyl-prop-2-ynyl)-2-(3-ethynyl-7-fluoro-8-methyl-quinolin-6-yloxy)-2-methylsulfanyl-acetamide | 1H NMR (CDCl3) δ ppm: 8.88 (1H, d); 8.17 1H, d); 7.18 (1H, d); 6.91 (1H, br s); 5.65 (1H, s); 3.27 (1H, s); 2.70 (3H, d); 2.39 (1H, s); 2.20 (3H, s); 1.74 (6H, s). |
| 158 | | 2-(3-Ethynyl-7-fluoro-8-methyl-quinolin-6-yloxy)-N-isopropyl-2-methylsulfanyl-acetamide | 1H NMR (CDCl3) δ ppm: 8.86 (1H, d); 8.16 1H, d); 7.17 (1H, d); 6.61 (1H, br d); 5.68 (1H, s); 4.39-4.17 (1H, m); 3.27 (1H, s); 2.69 (3H, d); 2.17 (1H, s); 1.26 (3H, d); 1.22 (3H, d). |
| 159 | | N-(1-Ethynyl-1-methyl-prop-2-ynyl)-2-(3-ethynyl-quinolin-6-yloxy)-2-methylsulfanyl-acetamide | mp = 148-154° C. |
| 160 | | 2-(3-ethynyl-quinolin-6-yloxy)-N-(1-hydroxymethyl-1-methylprop-2-ynyl)-2-methylsulfanyl-acetamide | mp = 149-150° C. |
| 161 | | 2-(3-ethynyl-quinolin-6-yloxy)-N-(1-formyl-1-methyl-prop-2-ynyl)-2-methylsulfanyl acetamide | ¹H NMR (CDCl$_3$) δ ppm: 9.40 (1H, s); 8.86 (1H, d); 8.22 (1H. d); 8.07 (1H, d); 7.52-7.49 (1H, m); [{7.49 (s br), 7.44 (s br) 1H}, isomer A and isomer B]; 7.26 (1H, m); [{5.74 (s), 5.72 (s) 1H}, isomer A and isomer B]; 3.29 (1H, s); 2.54 (1H, s); [{2.23 (s), 2.21 (s) 3H}, isomer A and isomer B]; 1.79 (3H, s). |

TABLE 1981-continued

Characterized compounds of the general formula (I)

| Cpd. No. | Formula | Compound | ¹H-NMR and/or mp |
|---|---|---|---|
| 162 | | 2-(3-ethynyl-quinolin-6-yloxy)-N-(1-methyl-1-prop-2-ynyloxymethyl-prop-2-ynyl)-2-methylsulfanyl-acetamide. | ¹H NMR (CDCl₃) d ppm: 8.87 (1H, d); 8.22 (1H, d); 8.04 (1H, d); 7.49 (1H, dd); 7.21 (1H, d); 7.02 (1H, s br); [{5.56 (s), 5.54 (s) 1H}, isomer A and isomer B]; 4.38-4.23 (2H, m); 3.92-3.73 (2H, m); 3.29 (1H, s); 2.49-2.47 (1H, m); [{2.44 (s), 2.42 (s) 1H}, isomer A and isomer B]; [{2.21 (s), 2.20 (s) 3H}, isomer A and isomer B]; [{1.73 (s), 1.71 (s) 3H}, isomer A and isomer B]. |
| 163 | | 2-(3-ethynyl-quinolin-6-yloxy)-N-(1-methyl-2-oxo-1-prop-2-ynyloxymethyl-ethyl)-2-methylsulfanyl-acetamide | ¹H NMR (CDCl₃) δ ppm: [{9.51(s), 9.49 (s) 1H}, isomer A and isomer B]; 8.86 (1H, d); 8.22 (1H, d); 8.07 (1H, d); 7.53-7.50 (1H, m); [{7.58 (s br), 7.48 (s br) 1H}, isomer A and isomer B]; 7.26 (1H, m); 5.72 (1H, s); 4.16-3.87 (4H, m); 3.28 (1H, s); 2.48 (1H, m); [{2.22 (s), 2.20 (s) 3H}, isomer A and isomer B]; 1.52 (3H, s). |
| 164 | | 2-(3-ethynyl-quinolin-6-yloxy)-N-(2-hydroxy-1-methyl-1-prop-2-ynyloxymethyl-ethyl)-2-methylsulfanyl-acetamide | ¹H NMR (CDCl₃) δ ppm: 8.88 (1H, d); 8.22 (1H, d); 8.07 (1H, d); 7.49 (1H, dd); 7.39 (1H, s br); 7.22 (1H, m); 5.68 (1H, s); 4.22-4.16 (2H, m); 3.90 (1H, s br); 3.81-3.60 (4H, m); 3.30 (1H, s); 2.45 (1H, dt); [{2.22 (s), 2.20 (s) 3H}, isomer A and isomer B]; [{1.40 (s), 1.34 (s) 3H}, isomer A and isomer B]. |
| 165 | | 2-(3-ethynyl-quinolin-6-yloxy)-N-(1-methyl-2-prop-2-ynyloxy-1-prop-2-ynyloxymethyl-ethyl)-2-methylsulfanyl-acetamide. | ¹H NMR (CDCl₃) δ ppm: 8.84 (1H, d); 8.22 (1H, d); 8.04 (1H, d); 7.49 (1H, dd); 7.21 (1H, d); 6.98 (1H, s br); 5.61 (1H, s); 4.19-4.16 (4H, m); 3.82-3.61 (2H, dd); 3.73 (2H, s); 3.29 (1H, s); 2.47-2.43 (2H, m); 2.21 (3H, s); 1.46 (3H, s). |
| 166 | | N-(2-ethoxy-1-methyl-1-prop-2-ynyloxymethyl-ethyl)-2-(3-ethynyl-quinolin-6-yloxy)-2-methylsulfanyl-acetamide | ¹H NMR (CDCl₃) δ ppm: 8.84 (1H, d); 8.22 (1H, d); 8.04 (1H, d); 7.48-7.45 (1H, m); 7.21 (1H, d); 7.02 (1H, s br); 5.61 (1H, s); 4.18-4.15 (2H, m); 3.80-3.41 (4H, m); 3.53-3.49 (2H, m); 3.39 (1H, s); 2.43 (1H, m); 2.21 (3H, s); [{1.47 (s), 1.46 (s) 3H}, isomer A and isomer B]; 1.21-1.16 (3H, m). |

TABLE 1981-continued

Characterized compounds of the general formula (I)

| Cpd. No. | Formula | Compound | ¹H-NMR and/or mp |
|---|---|---|---|
| 167 | | N-(1-cyano-2-hydroxy-1-methyl-ethyl)-2-(3-ethynyl-quinolin-6-yloxy)-2-methylsulfanyl-acetamide. | mp = 78-80° C. |
| 168 | | 2-(3-ethynyl-quinolin-6-yloxy)-N-(2-hydroxy-1,1-dimethyl-ethyl)-2-methylsulfanyl-acetamide | mp = 149-151° C. |
| 169 | | 2-(3-Ethynyl-quinolin-6-yloxy)-N-(1-methyl-1-prop-2-ynyloxymethyl-prop-2-ynyl)-2-methylsulfanyl-acetamide | ¹H NMR (CDCl$_3$) δ ppm: 8.87 (1H, d); 8.22 (1H, d); 8.04 (1H, d); 7.49 (1H, dd); 7.21 (1H, d); 7.02 (1H, s br); [{5.56 (s), 5.54 (s) 1H}, isomer A and isomer B]; 4.38-4.23 (2H, m); 3.92-3.73 (2H, m); 3.29 (1H, s); 2.49-2.47 (1H, m); [{2.44 (s), 2.42 (s) 1H}, isomer A and isomer B]; [{2.21 (s), 2.20 (s) 3H}, isomer A and isomer B]; [{1.73 (s), 1.71 (s) 3H}, isomer A and isomer B]. |
| 170 | | N-[2-(tert-butyl-diphenyl-silanyloxy)-1-hydroxymethyl-1-methyl-ethyl]-2-(3-ethynyl-quinolin-6-yloxy)-2-methylsulfanyl-acetamide | ¹H NMR (CDCl$_3$) δ ppm: 8.88 (1H, d); 8.19-8.16 (1H, m), 8.00 (1H, t); 7.66-7.52 (5H, m); 7.48-7.26 (7H, m); 7.21-7.18 (1H, m); [{5.69 (s), 5.66 (s) 1H}, isomer A and isomer B]; 4.32-4.11 (1H, dm); 3.78-3.52 (4H, m); 3.30 (1H, s); [{2.21 (s), 2.19 (s) 3H}, isomer A and isomer B]; [{1.49 (s), 1.34 (s) 3H}, isomer A and isomer B]; [{1.11 (s), 1.08 (s) 9H}, isomer A and isomer B]. |
| 171 | | N-[2-(tert-Butyl-diphenyl-silanyloxy)-1-formyl-1-methyl-ethyl]-2-(3-ethynyl-quinolin-6-yloxy)-2-methylsulfanyl-acetamide | ¹H NMR (CDCl$_3$) δ ppm: [{9.51 (s), 9.49 (s) 1H}, isomer A and isomer B]; 8.88 (1H, d); 8.19 (1H, d); 8.02 (1H, d); 7.66-7.54 (5H, m); 7.48-7.30 (7H, m); 7.26-7.21 (1H, dd); [{5.70 (s), 5.66 (s) 1H}, isomer A and isomer B]; 4.01-3.88 (2H, m); 3.30 (1H, s); [{2.22 (s), 2.20 (s) 3H}, isomer A and isomer B]; [{1.50 (s), 1.48 (s) 3H}, isomer A and isomer B]; [{(1.02 (s), 0.99 (s) 9H}, isomer A and isomer B]. |

TABLE 1981-continued

Characterized compounds of the general formula (I)

| Cpd. No. | Formula | Compound | $^1$H-NMR and/or mp |
|---|---|---|---|
| 172 | | N-[1-tert-Butyl-diphenyl-silanyloxymethyl]-1-methyl-prop-2-ynyl]-2-(3-ethynyl-quinolin-6-yloxy)-2-methylsulfanyl-acetamide | $^1$H NMR (CDCl$_3$) δ ppm: 8.88 (1H, d); 8.19 (1H, d); 8.01 (1H, dd); 7.70-7.62 (4H, m); 7.46-7.30 (8H, m); 7.21-7.19, (1H, m); [{5.69 (s), 5.66 (s) 1H}, isomer A and isomer B]; 3.93-3.72 (2H, dm); 3.30 (1H, s); 2.39 (1H, d); [{2.23 (s), 2.21 (s) 3H}, isomer A and isomer B]; 1.71 (3H, d); [{1.10 (s), 1.08 (s) 9H}, isomer A and isomer B]. |
| 173 | | 2-(3-Ethynyl-quinolin-6-yloxy)-N-(1-hydroxymethyl-1-methyl-prop-2-ynyl)-2-methylsulfanyl-acetamide | mp: 150-155° C. |
| 174 | | N-(1-Cyano-2-hydroxy-1-methyl-ethyl)-2-(3-ethynyl-7-fluoro-quinolin-6-yloxy)-2-methylsulfanyl-acetamide | mp: 80-83° C. |
| 175 | | 2-(3-Ethynyl-7-fluoro-quinolin-6-yloxy)-N-(3-fluoro-1,1-dimethyl-propyl)-2-methylsulfanyl-acetamide | $^1$H NMR (CDCl$_3$) δ ppm: 8.9 (1H, s); 8.2 (1H, s); 7.8 (1H, d); 7.35 (1H. d): 6.9 (1H, bs); 5.62 (1H, s); 4.7-4.5 (2H, dt); 3.3 (1H, s); 2.2-2.1 (4H, m); 1.5 (6H, s) |
| 176 | | N-tert-butyl-2-(3-ethynyl-7-fluoro-quinolin-6-yloxy)-butyramide | $^1$H NMR (CDCl$_3$) δ ppm: 8.84 (1H, d); 8.15 (1H, d); 7.8 (1H, d); 7.15 (1H, d); 6.27 (1H, bs); 4.58 (1H, t); 3.29 (1H, s); 2.1 (2H, m); 1.33 (9H, s); 1.1 (3H, t) |
| 177 | | N-(1,1-Dimethyl-prop-2-ynyl)-2-(3-ethynyl-7-fluoro-quinolin-6-yloxy)-butyramide | $^1$H NMR (CDCl$_3$) δ ppm: 8.83 (1H, d); 8.15 (1H, d); 7.8 (1H, d); 7.15 (1H, d); 6.55 (1H, bs); 4.66 (1H, t); 3.3 (1H, s); 2.32 (1H, s); 2.13-2.05 (2H, m); 1.63 (6H, d); 1.1 (3H, t) |
| 178 | | 2-(3-Ethynyl-quinolin-6-yloxy)-2-methylsulfanyl-N-oxetan-3-yl-acetamide | mp: 98-100° C. |
| 179 | | N-(1,1-Dimethyl-but-2-ynyl)-2-(3-ethynyl-7-fluoro-quinolin-6-yloxy)-butyramide | $^1$H NMR (CDCl$_3$) δ ppm: 8.84 (1H, d); 8.16 (1H, d); 7.8 (1H, d); 7.15 (1H, d); 6.5 (1H, bs); 4.6 (1H, t); 3.28 (1H, s); 2.1 (2H, m); 1.78 (3H, s); 1.6 (6H, d); 1.1 (3H, t) |

TABLE 1981-continued

Characterized compounds of the general formula (I)

| Cpd. No. | Formula | Compound | ¹H-NMR and/or mp |
|---|---|---|---|
| 180 | | 2-(3-Ethynyl-7-fluoro-quinolin-6-yloxy)-N-(4-methoxy-1,1-dimethyl-but-2-ynyl)-butyramide | ¹H NMR (CDCl₃) δ ppm: 8.84 (1H, d); 8.16 (1H, d); 7.8 (1H, d); 7.14 (1H, d); 6.54 (1H, bs); 4.6 (1H, t); 4.08 (2H, s); 3.33 (3H, s); 3.29 (1H, s); 2.1 (2H, m); 1.62 (6H, d); 1.1 (3H, t) |
| 181 | | 2-(3-Ethynyl-7-fluoro-quinolin-6-yloxy)-N-isopropyl-2-methylsulfanyl-acetamide | ¹H NMR (CDCl₃) δ ppm: 8.89 (1H, s); 8.24 (1H, s); 7.88 (1H, d); 7.38 (1H, d); 6.55 (1H, bd); 5.7 (1H, s); 4.2 (1H, m); 3.3 (1H, s); 2.2 (3H, s); 1.29 (3H, d); 1.23 (3H, d) |
| 182 | | N-(1,1-Dimethyl-propyl)-2-(3-ethynyl-7-fluoro-quinolin-6-yloxy)-2-methylsulfanyl-acetamide | ¹H NMR (CDCl₃) δ ppm: 8.88 (1H, s); 8.2 (1H, s); 7.82 (1H, d); 7.37 (1H, d); 7.53 (1H, bs); 5.6 (1H, s); 3.3 (1H, s); 2.2 (3H, s); 1.8 (2H, m); 1.8 (6H, m); 0.9 (3H, t) |
| 183 | | 2-(3-Ethynyl-7-fluoro-quinolin-6-yloxy)-N-(2-hydroxy-1,1-dimethyl-ethyl)-2-methylsulfanyl-acetamide | ¹H NMR (CDCl₃) δ ppm: 8.88 (1H, s); 8.2 (1H, s); 7.82 (1H. d); 7.38 (1H, d); 6.85 (1H, bs); 5.68 (1H, s); 4.0 (1H, b); 3.7 (2H, m); 3.3 (1H, s); 2.2 (3H, s); 1.4 (6H, d) |
| 184 | | 2-(3-Ethynyl-7-fluoro-quinolin-6-yloxy)-N-methyl-2-methylsulfanyl-acetamide | ¹H NMR (CDCl₃) δ ppm: 8.87 (1H, d); 8.21 (1H, d); 7.8 (1H, d); 7.33 (1H, d); 6.8 (1H, bs); 5.75 (1H, s); 3.3 (1H, s); 3.0 (3H, d); 2.19 (3H, s) |
| 185 | | N-Ethyl-2-(3-ethynyl-7-fluoro-quinolin-6-yloxy)-2-methylsulfanyl-acetamide | ¹H NMR (CDCl₃) δ ppm: 8.87 (1H, d); 8.21 (1H, d); 7.82 (1H, d); 7.4 (1H, d); 6.75 (1H, bs); 5.73 (1H, s); 3.4-3.52 (2H, m); 3.3 (1H, s); 2.19 (3H, s); 1.25 (3H, t) |
| 186 | | 2-(3-Ethynyl-quinolin-6-yloxy)-N-(3-methyl-oxetan-3-yl)-2-methylsulfanyl-acetamide | mp: 61-65° C. |
| 187 | | N-(1,1-Dimethyl-but-3-ynyl)-2-(3-ethynyl-7-fluoro-quinolin-6-yloxy)-2-methylsulfanyl-acetamide | ¹H NMR (CDCl₃) δ ppm: 8.87 (1H, d); 8.2 (1H, d); 7.8 (1H, d); 7.35 (1H, d); 6.8 (1H, bs); 5.63 (1H, s); 3.3 (1H, s); 2.62-2.82 (2H, m); 2.2 (3H, s); 2.0 (1H, t); 1.5 (6H, s) |
| 188 | | N-(1-Ethyl-1-methyl-prop-2-ynyl)-2-(3-ethynyl-7-fluoro-quinolin-6-yloxy)-2-methylsulfanyl-acetamide | ¹H NMR (CDCl₃) δ ppm: 8.87 (1H, bs); 8.2 (1H, bs); 7.8 (1H, d); 7.38 (1H, bd); 6.83 (1H, bd); 5.68 (1H, bs); 3.3 (1H, s); 2.4 (1H, d); 2.2 (3H, s); 2.1-2.2 (1H, m); 1.85-1.98 (1H, m); 1.72 (3H, d); 1.05 (3H, t) |

TABLE 1981-continued

Characterized compounds of the general formula (I)

| Cpd. No. | Formula | Compound | $^1$H-NMR and/or mp |
|---|---|---|---|
| 189 | | 2-(3-Ethynyl-7-fluoro-quinolin-6-yloxy)-N-(5-methoxy-1,1-dimethyl-pent-2-ynyl)-2-methylsulfanyl-acetamide | $^1$H NMR (CDCl$_3$) δ ppm: 8.88 (1H, s); 8.21 (1H, s); 7.82 (1H, d); 7.35 (1H, d); 6.86 (1H, bs); 5.65 (1H, s); 3.5 (2H, t); 3.38 (3H, s); 3.3 (1H, s); 2.49 (2H, t); 2.2 (3H, s); 1.7 (6H, d) |
| 190 | | N-(1,1-Dimethyl-pent-2-ynyl)-2-(3-ethynyl-7-fluoro-quinolin-6-yloxy)-2-methylsulfanyl-acetamide | $^1$H NMR (CDCl$_3$) δ ppm: 8.88 (1H, s); 8.21 (1H, s); 7.81 (1H, d); 7.35 (1H, d); 6.88 (1H, bs); 5.65 (1H, s); 3.3 (1H, s); 2.2 (5H, m); 1.7 (6H, d); 1.12 (3H, t) |
| 191 | | N-(4-Ethoxy-1,1-dimethyl-but-2-ynyl)-2-(3-ethynyl-7-fluoro-quinolin-6-yloxy)-2-methylsulfanyl-acetamide | $^1$H NMR (CDCl$_3$) δ ppm: 8.88 (1H, s); 8.21 (1H, s); 7.81 (1H, d); 7.35 (1H, d); 6.89 (1H, bs); 5.65 (1H, s); 4.18 (2H, s); 3.56 (2H, q); 3.3 (1H, s); 2.2 (3H, s); 1.7 (6H, s); 1.2 (3H, t) |
| 192 | | 2-(3-Ethynyl-7-fluoro-quinolin-6-yloxy)-N-(2-hydroxy-1,1-dimethyl-ethyl)-butyramide | $^1$H NMR (CDCl$_3$) δ ppm: 8.88 (1H, s); 8.2 (1H, s); 7.82 (1H, d); 7.38 (1H, d); 6.85 (1H, bs); 5.68 (1H, s); 4.0 (1H, b); 3.7 (2H, m); 3.3 (1H, s); 2.2 (3H, s); 1.4 (6H, d) |
| 193 | | N-(1,1-Dimethyl-2-oxo-ethyl)-2-(3-ethynyl-7-fluoro-quinolin-6-yloxy)-butyramide | $^1$H NMR (DMSO) δ ppm: 9.28 (1H, s); 8.8 (2H, d); 8.49 (1H, d); 7.85 (1H, dd); 7.4 (1H, dd); 4.8 (1H, m); 4.5 (1H, d); 1.98 (2H, m); 1.2 (6H, dd); 1.0 (3H, m) |
| 194 | | 2-(3-Ethynyl-quinolin-6-yloxy)-N-(2-hydroxy-ethyl)-2-methylsulfanyl-acetamide | $^1$H NMR (DMSO) δ ppm: 8.8 (1H, d); 8.42 (1H, d); 8.3 (1H, t); 8.0 (1H, d); 7.62 (1H, dd); 7.5 (1H, d); 6.0 (1H, s); 4.75 (1H, bs); 4.5 (1H, s); 3.5 (2H, t); 3.32 (2H, m); 2.1 (3H, s) |
| 195 | | 2-(3-Ethynyl-quinolin-6-yloxy)-N-(2-hydroxy-1-methyl-ethyl)-2-methylsulfanyl-acetamide | $^1$H NMR (DMSO) δ ppm: 8.6 (1H, d); 8.24 (1H, d); 7.83 (2H, m); 7.43 (1H, m); 7.3 (1H, dd); 5.8 (1H, d); 4.6 (1H, bs); 4.35 (1H, s); 3.7 (1H, m); 3.2 (2H, m); 1.98 (3H, d); 0.9 (3H, dd) |
| 196 | | N-Cyanomethyl-2-(3-ethynyl-quinolin-6-yloxy)-2-methylsulfanyl-acetamide | $^1$H NMR (CDCl$_3$) δ ppm: 8.72 (1H, d); 8.1 (1H, d); 7.94 (1H, d); 7.3 (1H, dd); 7.2 (1H, bt); 7.1 (1H, d); 5.68 (1H, s); 4.13-4.3 (2H, m); 3.2 (1H, s); 2.08 (3H, s) |

TABLE 1981-continued

Characterized compounds of the general formula (I)

| Cpd. No. | Formula | Compound | $^1$H-NMR and/or mp |
|---|---|---|---|
| 197 | | N-(2-Cyano-1,1-dimethyl-ethyl)-2-(3-ethynyl-quinolin-6-yloxy)-2-methylsulfanyl-acetamide | $^1$H NMR (CDCl$_3$) δ ppm: 8.86 (1H, s); 8.26 (1H, s); 8.14 (1H, d); 7.5 (1H, dd); 7.26 (1H, s); 6.64 (1H, bs); 5.65 (1H, s); 3.3 (1H, s); 3.23-3.03 (2H, dd); 2.2 (3H, s); 1.56 (3H, s); 1.54 (3H, s) |
| 198 | | N-(1,1-Dimethyl-4-prop-2-ynyloxy-but-2-ynyl)-2-(3-ethynyl-7-fluoro-quinolin-6-yloxy)-2-methylsulfanyl-acetamide | $^1$H NMR (CDCl$_3$) δ ppm: 8.88 (1H, s); 8.22 (1H, s); 7.82 (1H. d); 7.35 (1H, d); 6.88 (1H, bs); 5.67 (1H, s); 4.3 (2H, s); 4.27 (2H, d); 3.3 (1H, s); 2.44 (1H, t); 2.2 (3H, s); 1.72 (6H, s) |
| 199 | | N-(4-Allyloxy-1,1-dimethyl-but-2-ynyl)-2-(3-ethynyl-7-fluoro-quinolin-6-yloxy)-2-methylsulfanyl-acetamide | $^1$H NMR (CDCl$_3$) δ ppm: 8.88 (1H, s); 8.22 (1H, s); 7.8 (1H, d); 7.35 (1H, d); 6.89 (1H, bs); 5.9 (1H, m); 5.67 (1H, s); 5.18-5.35 (2H, m); 4.2 (2H, s); 4.07 (2H, dd); 3.3 (1H, s); 2.2 (3H, s); 1.73 (6H, s) |
| 200 | | N-(2-Ethoxy-1,1-dimethyl-ethyl)-2-(3-ethynyl-7-fluoro-quinolin-6-yloxy)-2-methylsulfanyl-acetamide | $^1$H NMR (CDCl$_3$) δ ppm: 8.88 (1H, s); 8.22 (1H, s); 7.8 (1H, d); 7.32 (1H, d); 7.05 (1H, bs); 5.62 (1H, bs); 3.55 (2H, m); 3.34-3.5 (2H, dd); 3.29 (1H, s); 2.2 (3H, s); 1.45 (6H, d); 1.2 (3H, t) |
| 201 | | N-tert-Butyl-2-(3-ethynyl-8-fluoro-quinolin-6-yloxy)-2-methylsulfanyl-acetamide | $^1$H NMR (CDCl$_3$) δ ppm: 8.89 (1H, bs); 8.2 (1H, bs); 7.2 (1H, bd); 7.02 (1H, bs); 6.35 (1H, bs); 5.58 (1H, bs); 3.32 (1H, s); 2.2 (3H, s); 1.42 (9H, s) |
| 202 | | 2-(3-Ethynyl-quinolin-6-yloxy)-N-(1-methyl-cyclobutyl)-2-methyl-sulfanyl-acetamide | mp: 115-116° C. |
| 203 | | 2-(8-Chloro-3-ethynyl-quinolin-6-yloxy)-N-(1-methyl-cyclobutyl)-2-methylsulfanyl-acetamide | mp: 121-123° C. |
| 204 | | N-(1-Ethyl-1-methyl-but-2-ynyl)-2-(3-ethynyl-quinolin-6-yloxy)-2-methylsulfanyl-acetamide | $^1$H NMR (CDCl$_3$) δ ppm: 8.83 (1H, d); 8.22 (1H, d); 8.1 (1H, bd); 7.5 (1H, dd); 7.22 (1H, d); 6.62 (1H, b); 5.6 (1H, d); 3.3 (1H, s). |

TABLE 1981-continued

Characterized compounds of the general formula (I)

| Cpd. No. | Formula | Compound | $^1$H-NMR and/or mp |
|---|---|---|---|
| 205 | | N-(1-Ethyl-1-methyl-prop-2-ynyl)-2-(3-ethynyl-quinolin-6-yloxy)-2-methylsulfanyl-acetamide | $^1$H NMR (CDCl$_3$) δ ppm: 8.85 (1H, d); 8.2 (1H, d); 8.1 (1H, d); 7.48 (1H, dd); 7.22 (1H, d); 6.67 (1H, bs); 5.63 (1H, d); 3.3 (1H, s); 2.4 (1H, d); 2.21 (3H, s); 2.15 (1H, m); 1.9 (1H, m); 1.7 (3H, d); 1.03 (3H, m) |
| 206 | | N-(1-Ethynyl-cyclohexyl)-2-(3-ethynyl-quinolin-6-yloxy)-2-methylsulfanyl-acetamide | $^1$H NMR (CDCl$_3$) δ ppm: 8.87 (1H, d); 8.22 (1H, d); 8.1 (1H, d); 7.5 (1H, dd); 7.22 (1H, d); 6.5 (1H, bs); 5.63 (1H, s); 3.3 (1H, s); 2.44 (1H, s); 2.1-2.23 (5H, m); 1.9 (2H, m); 1.55-1.77 (5H, m); 1.2-1.36 (1H, m) |
| 207 | | N-(1,1-Diethyl-prop-2-ynyl)-2-(3-ethynyl-quinolin-6-yloxy)-2-methylsulfanyl-acetamide | $^1$H NMR (CDCl$_3$) δ ppm: 8.87 (1H, d); 8.22 (1H, d); 8.1 (1H, d); 7.5 (1H, dd); 7.22 (1H, d); 6.54 (1H, bs); 5.6 (1H, s); 3.3 (1H, s); 2.4 (1H, s); 2.17-2.3 (5H, m); 1.8-1.93 (2H, m); 1.03 (3H, t); 0.95 (3H, t) |
| 208 | | 2-(3-Ethynyl-quinolin-6-yloxy)-2-methylsulfanyl-N-prop-2-ynyl-acetamide | $^1$H NMR (CDCl$_3$) δ ppm: 8.87 (1H, d); 8.24 (1H, d); 8.1 (1H, d); 7.5 (1H, dd); 7.22 (1H, d); 6.9 (1H, bs); 5.72 (1H, s); 4.1-4.3 (2H, m); 3.3 (1H, s); 2.3 (1H, d); 2.2 (3H, s) |
| 209 | | N-(1-Cyano-cyclobutyl)-2-(3-ethynyl-7-fluoro-quinolin-6-yloxy)-2-methylsulfanyl-acetamide | $^1$H NMR (CDCl$_3$) δ ppm: 8.9 (1H, d); 8.22 (1H, d); 8.1 (1H, d); 7.5 (1H, dd); 7.23 (1H, d); 6.9 (1H, bs); 5.74 (1H, s); 4.1-4.3 (2H, m); 3.3 (1H, s); 2.2-2.33 (1H, m); 2.2 (3H, s); 2.15 (1H, m) |
| 210 | | 2-(3-Ethynyl-7-fluoro-quinolin-6-yloxy)-N-(1-formyl-2-methoxy-1-methyl-ethyl)-2-methylsulfanyl-acetamide | $^1$H NMR (CDCl$_3$) δ ppm: 9.5 (1H, d); 8.89 (1H, d); 8.2 (1H, d); 7.82 (1H, d); 7.55-7.7 (1H, bd), 7.4 (1H, dd); 5.74 (1H, s); 3.67-3.9 (2H, m); 3.37 (3H, s); 3.3 (1H, s); 2.2 (3H, d); 1.55 (3H, s) |
| 211 | | 2-(3-Ethynyl-7-fluoro-quinolin-6-yloxy)-N-(1-methoxymethyl-1-methyl-prop-2-ynyl)-2-methylsulfanyl-acetamide | $^1$H NMR (CDCl$_3$) δ ppm: 8.88 (1H, d); 8.2 (1H, d); 7.8 (1H, d); 7.35 (1H, dd), 7.2 (1H, bs); 5.7 (1H, d); 3.55-3.78 (2H, m); 3.48 (3H, d); 3.3 (1H, s); 2.43 (1H, d); 2.2 (3H, d); 1.72 (3H, d) |
| 212 | | N-Cyclopropyl-2-(3-ethynyl-quinolin-6-yloxy)-2-methylsulfanyl-acetamide | $^1$H NMR (CDCl$_3$) δ ppm: 8.87 (1H, d); 8.23 (1H, s); 8.1 (1H, d); 7.45 (1H, dd); 7.2 (1H, d); 6.7 (1H, bs); 5.7 (1H, s); 3.3 (1H, s); 2.84 (1H, m); 2.18 (3H, s); 0.88 (2H, m); 0.6 (2H, d) |

TABLE 1981-continued

Characterized compounds of the general formula (I)

| Cpd. No. | Formula | Compound | $^1$H-NMR and/or mp |
|---|---|---|---|
| 213 | | N-Cyclobutyl-2-(3-ethynyl-quinolin-6-yloxy)-2-methylsulfanyl-acetamide | $^1$H NMR (CDCl$_3$) δ ppm: 8.85 (1H, d); 8.2 (1H, d); 8.1 (1H, d); 7.5 (1H, dd); 7.21 (1H, d); 6.72 (1H, bd); 5.68 (1H, s); 4.5 (1H, m); 3.3 (1H, s); 2.35-2.5 (2H, m); 2.2 (3H, s); 1.88-2.0 (2H, m); 1.7-1.8 (2H, m) |
| 214 | | N-Cyclopentyl-2-(3-ethynyl-quinolin-6-yloxy)-2-methylsulfanyl-acetamide | $^1$H NMR (CDCl$_3$) δ ppm: 8.85 (1H, d); 8.2 (1H, d); 8.1 (1H, d); 7.5 (1H, dd); 7.2 (1H, d); 6.52 (1H, bd); 5.69 (1H, s); 4.32 (1H, m); 3.3 (1H, s); 2.2 (3H, s); 1.99-2.1 (2H, m); 1.6-1.72 (4H, m); 1.38-1.52 (2H, m) |
| 215 | | 2-(3-Ethynyl-7,8-difluoro-quinolin-6-yloxy)-N-(4-methoxy-1,1-dimethyl-but-2-ynyl)-2-methylsulfanyl-acetamide | $^1$H NMR (CDCl$_3$) δ ppm: 8.9 (1H, d); 8.3 (1H, d); 7.12 (1H, dd); 6.8 (1H, bs); 5.67 (1H, s); 4.1 (2H, s); 3.39 (3H, s); 2.2 (3H, s); 1.72 (6H, s) |
| 216 | | N-(1-Cyano-2-methoxy-1-methyl-ethyl)-2-(3-ethynyl-7,8-difluoro-quinolin-6-yloxy)-2-methylsulfanyl-acetamide | $^1$H NMR (CDCl$_3$) δ ppm: 8.9 (1H, d); 8.3 (1H, s); 7.31 (1H, bd); 7.15 (1H, d); 5.78 (1H, d); 3.8 (1H,); 3.65 (1H, m); 3.54 (5H, d); 2.2 (3H, d); 1.8 (3H, d) |
| 217 | | N-tert-Butyl-2-(7,8-difluoro-3-trimethylsilanylethynyl-quinolin-6-yloxy)-2-methylsulfanyl-acetamide | $^1$H NMR (CDCl$_3$) δ ppm: 8.9 (1H, d); 8.2 (1H, s); 7.13 (1H, dd); 6.55 (1H, bs); 5.6 (1H, s); 2.2 (3H, s); 1.45 (9H, s); 0.3 (9H, s) |
| 218 | | 2-(3-Ethynyl-8-fluoro-quinolin-6-yloxy)-N-(4-methoxy-1,1-dimethyl-but-2-ynyl)-2-methylsulfanyl-acetamide | $^1$H NMR (CDCl$_3$) δ ppm: 8.9 (1H, d); 8.25 (1H, d); 7.23 (1H, d); 7.05 (1H, d); 6.64 (1H, bs); 5.6 (1H, s); 4.1 (2H, s); 3.39 (3H, s); 3.36 (1H, s); 2.2 (3H, s); 1.72 (6H, s) |
| 219 | | N-tert-Butyl-2-(3-ethynyl-7,8-difluoro-quinolin-6-yloxy)-2-methylsulfanyl-acetamide | $^1$H NMR (CDCl$_3$) δ ppm: 8.92 (1H, d); 8.22 (1H, d); 7.18 (1H, dd); 6.55 (1H, bs); 5.64 (1H, s); 3.33 (1H, s); 2.2 (3H, s); 1.45 (9H, s) |

TABLE 1981-continued

Characterized compounds of the general formula (I)

| Cpd. No. | Formula | Compound | $^1$H-NMR and/or mp |
|---|---|---|---|
| 220 | | 2-(3-Ethynyl-quinolin-6-yloxy)-N-(2-hydroxy-1,1-dimethyl-ethyl)-2-methoxy-acetamide | $^1$H NMR (CDCl$_3$) δ ppm: 8.85 (1H, d); 8.2 (1H, d); 8.05 (1H, d); 7.51 (1H, dd); 7.4 (1H, d); 6.75 (1H, bs); 5.43 (1H, s); 4.06 (1H, bs); 3.64 (2H, bs); 3.55 (3H, s); 3.3 (1H, s); 1.35 (6H, d) |
| 221 | | N-(1,1-Dimethyl-2-oxo-ethyl)-2-(3-ethynyl-quinolin-6-yloxy)-2-methoxy-acetamide | $^1$H NMR (CDCl$_3$) δ ppm: 9.39 (1H, s); 8.85 (1H, d); 8.2 (1H, d); 8.06 (1H, d); 7.56 (1H, dd); 7.43 (1H, d); 7.25 (1H, bs); 5.5 (1H, s); 3.57 (3H, s); 3.3 (1H, s); 1.48 (6H, d) |
| 222 | | 2-(3-Ethynyl-8-fluoro-quinolin-6-yloxy)-N-isopropyl-2-methylsulfanyl-acetamide | mp 135-136° C. |
| 223 | | 2-(3-Ethynyl-quinolin-6-yloxy)-2-methylsulfanyl-N-thietan-3-yl-acetamide | mp: 150-152° C. |
| 224 | | 2-(3-Ethynyl-quinolin-6-yloxy)-2-methylsulfanyl-N-(3-methyl-thietan-3-yl)-acetamide | mp: 132-134° C. |
| 225 | | N-(6-Chloro-1,1-dimethyl-hex-2-ynyl)-2-(3-ethynyl-quinolin-6-yloxy)-2-methylsulfanyl-acetamide | $^1$H NMR (CDCl$_3$) δ ppm: 8.85 (1H, d); 8.22 (1H, d); 8.1 (1H, d); 7.5 (1H, dd); 7.23 (1H, d); 6.7 (1H, bs); 5.62 (1H, s); 3.67 (2H, t); 3.3 (1H, s); 2.4 (2H, t); 2.2 (3H, s); 1.94 (2H, m); 1.7 (6H, s) |
| 226 | | N-(4-Allyloxy-1,1-dimethyl-but-2-ynyl)-2-(3-ethynyl-quinolin-6-yloxy)-2-methylsulfanyl-acetamide | $^1$H NMR (CDCl$_3$) δ ppm: 8.86 (1H, d); 8.21 (1H, d); 7.08 (1H, d); 7.48 (1H, dd); 7.22 (1H, d); 6.72 (1H, bs); 5.9 (1H, m); 5.63 (1H, s); 5.2-5.34 (2H, m); 4.18 (2H, s); 4.07 (2H, dd); 3.3 (1H, s); 2.2 (3H, s); 1.73 (6H, s) |
| 227 | | 2-[8-Chloro-3-(3-fluoro-prop-1-ynyl)-quinolin-6-yloxy]-N-(4-methoxy-1,1-dimethyl-but-2-ynyl)-2-methylsulfanyl-acetamide | m/z = 449 |

Screening Methods Soil Drench Application:

*Blumeria* (Erysiphe) *graminis*/Wheat/Soil Drench (Powdery Mildew on Wheat):

Each pot (soil volume: 40 ml) with 1 week old wheat plants cv. Anna were poured with 4 ml compound solution. 4 days after application wheat plants were inoculated by spreading mildew spores over the test plants in an inoculation chamber. After an incubation period of 6 days at 20o° C./18° C. (day/night) and 60% r. h. in a greenhouse the percentage leaf area covered by disease was assessed.

*Phytophthora infestans*/tomato/soil drench (late blight on tomato): Each pot (soil volume: 40 ml) with 3 weeks old tomato plants cv. Roter Gnom were poured with 4 ml compound solution. 4 days after application the plants were inoculated by spraying a sporangia suspension on the test plants. After an incubation period of 4 days at 18° C. and 100% r. h. in a growth chamber the percentage leaf area covered by disease was assessed.

*Phytophthora infestans*/potato/soil drench (late blight on potato): Each pot (soil volume: 40 ml) with 2 weeks old potato plants cv. Bintje were poured with 4 ml compound solution. 4 days after application the plants were inoculated by spraying a sporangia suspension on the test plants. After an incubation period of 4 days at 18° C. and 100% r. h. in a growth chamber the percentage leaf area covered by disease was assessed.

*Plasmopara viticola*/grape/soil drench (Grape downy mildew): Each pot (soil volume: 40 ml) with 5 weeks old grape seedlings cv. Gutedel were poured with 4 ml compound solution. 3 days after application grape plants were inoculated by spraying a sporangia suspension on the lower leaf side of the test plants. After an incubation period of 6 days at 22° C. and 100% r. h. in a greenhouse the percentage leaf area covered by disease was assessed.

*Puccinia recondita*/wheat/soil drench (Brown rust on wheat): Each pot (soil volume: 40 ml) with 1 week old wheat plants cv. Anna were poured with 4 ml compound solution. 3 days after application wheat plants were inoculated by spraying a spore suspension ($1\times10^5$ uredospores/ml) on the test plants. After an incubation period of 1 day at 20° C. and 95% r. h. plants were kept for 10 days 20° C./18° C. (day/night) and 60% r.h. in a greenhouse. The percentage leaf area covered by disease was assessed 11 days after inoculation.

*Magnaporthe grisea* (*Pyricularia oryzae*)/rice/soil drench (Rice Blast): Each pot (soil volume: 40 ml) with 3 weeks old rice plants cv. Koshihikari were poured with 4 ml compound solution. 4 days after application rice plants were inoculated by spraying a spore suspension ($1\times10^5$ conidia/ml) on the test plants. After an incubation period of 6 days at 25° C. and 95% r. h. the percentage leaf area covered by disease was assessed.

Screening Methods Seed Treatment Application:

*Pythium ultimum*/cotton (damping-off on cotton): A defined amount of mycelium of *P. ultimum* is mixed with a previously sterilized soil. After application of the formulated seed treatment onto cotton seeds (cv. Sure Grow 747) the seeds are sown 2 cm deep into the infected soil. The trial is incubated at 18° C. until seedlings do emerge. From this time on the trial is kept at 22° C. and 14 h light period. The evaluation is made by assessing the emergence and the number of plants that wilt and die.

*Plasmopara halstedii*/sunflower (downy mildew of sunflower): After application of the formulated seed treatments sunflower seeds are sown 1.5 cm deep into sterile soil. The trial is kept at 22° C. with a 14 h light period. After 2 days a spore suspension ($1\times10^5$ zoospores/ml) of *Plasmopara halstedii* is pipetted onto the soil surface close to the germinating seeds. After 16 days the trial is incubated under high humidity and the number of infected plants is assessed 2 days later.

EXAMPLE 14

This Example illustrates the fungicidal properties of compounds of formula (I).

The compounds were tested in a leaf disk assay, with methods described below. The test compounds were dissolved in DMSO and diluted into water to 200 ppm. In the case of the test on *Pythium ultimum*, they were dissolved in DMSO and diluted into water to 20 ppm.

*Etysiphe graminis* f.sp. *tritici* (wheat powdery mildew): Wheat leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Puccinia recondita* f.sp. *tritici* (wheat brown rust): Wheat leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed nine days after inoculation as preventive fungicidal activity.

*Septoria nodorum* (wheat glume blotch): Wheat leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Pyrenophora teres* (barley net blotch): Barley leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Pyricularia oryzae* (rice blast): Rice leaf segments were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Botrytis cinerea* (grey mould): Bean leaf disks were placed on agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Phytophthora infestans* (late blight of potato on tomato): Tomato leaf disks were placed on water agar in a 24-well plate and sprayed with a solution of the test compound. After allowing to dry completely, for between 12 and 24 hours, the leaf disks were inoculated with a spore suspension of the fungus. After appropriate incubation the activity of a compound was assessed four days after inoculation as preventive fungicidal activity.

*Plasmopara viticola* (downy mildew of grapevine): Grapevine leaf disks were placed on agar in a 24-well plate and sprayed a solution of the test compound. After allowing to dry completely, for between 12 and 24 hours, the leaf disks were inoculated with a spore suspension of the fungus. After appropriate incubation the activity of a compound was assessed seven days after inoculation as preventive fungicidal activity.

*Septoria tritici* (leaf blotch): Conidia of the fungus from cryogenic storage were directly mixed into nutrient broth (PDB potato dextrose broth). After placing a (DMSO) solution of the test compounds into a microtiter plate (96-well format) the nutrient broth containing the fungal spores was added. The test plates were incubated at 24 C and the inhibition of growth was determined photometrically after 72 hrs.

*Fusarium culmorum* (root rot): Conidia of the fungus from cryogenic storage were directly mixed into nutrient broth (PDB potato dextrose broth). After placing a (DMSO) solution of the test compounds into a microtiter plate (96-well format) the nutrient broth containing the fungal spores was added. The test plates were incubated at 24 C and the inhibition of growth was determined photometrically after 48 hrs.

*Pythium ultimum* (Damping off): Mycelial fragments of the fungus, prepared from a fresh liquid culture, were mixed into potato dextrose broth. A solution of the test compound in dimethyl sulphoxide was diluted with water to 20 ppm then placed into a 96-well microtiter plate and the nutrient broth containing the fungal spores was added. The test plate was incubated at 24° C. and the inhibition of growth was determined photometrically after 48 hours.

The following compounds from table 1981 gave at least 60% control of the following fungal infections at 200 ppm:

*Phytophthora infestans*, compounds 2, 3, 4, 5, 6, 7, 8, 9, 10, 11, 12, 13, 14, 15, 16, 17, 18, 19, 20, 21, 22, 23, 24, 25, 28, 29, 30, 31, 33, 34, 39, 42, 43, 44, 45, 46, 48, 49, 50, 51, 52, 53, 54, 55, 56, 57, 59, 61, 62, 63, 64, 65, 66, 67, 68, 69, 70, 72, 73, 74, 75, 76, 78, 79, 80, 81, 82, 83, 85, 86, 87, 88, 92, 93, 94, 95, 96, 97, 98, 99, 100, 102, 103, 104, 105, 106, 107, 108, 109, 110, 111, 112, 113, 114, 115, 116, 117, 121, 122, 123, 124, 125, 126, 127, 128, 129, 130, 131, 132, 133, 134, 135, 136, 144, 148, 150, 152, 153, 159, 161, 165, 173, 181, 187, 188, 189, 190, 191, 192, 193, 194, 196, 197, 198, 199, 200, 201, 202, 222, 203, 204, 205, 206, 207, 208, 212, 213, 214, 215, 218, 219, 220, 221, 227,

*Plasmopara viticola*, compounds 2, 3, 4, 5, 6, 7, 8, 9, 10, 11, 12, 13, 14, 15, 16, 17, 18, 19, 20, 21, 22, 23, 24, 25, 27, 29, 30, 31, 34, 35, 39, 42, 44, 45, 48, 49, 50, 51, 54, 55, 56, 57, 61, 62, 63, 64, 66, 67, 68, 69, 70, 72, 73, 74, 75, 76, 78, 79, 80, 82, 83, 85, 86, 87, 88, 91, 92, 93, 94, 95, 96, 97, 98, 99, 100, 102, 103, 104, 105, 106, 107, 108, 109, 111, 112, 113, 114, 115, 116, 117, 119, 121, 122, 123, 124, 125, 126, 127, 128, 129, 130, 131, 132, 133, 134, 135, 136, 144, 148, 150, 152, 153, 159, 161, 165, 173, 181, 187, 188, 189, 190, 191, 192, 193, 194, 196, 197, 198, 199, 200, 201, 202, 203, 204, 205, 206, 207, 208, 210, 212, 213, 214, 215, 216, 218, 219, 220, 221, 222, 227,

*Botrytis cinerea*, compounds 3, 8, 13, 14, 17, 20, 28, 30, 31, 44, 45, 56, 63, 66, 70, 72, 73, 75, 79.

*Erysiphe graminis* f.sp. *tritici*, compounds 2, 3, 4, 5, 6, 9, 10, 12, 13, 14, 16, 18, 19, 20, 21, 22, 23, 24, 25, 27, 29, 30, 31, 38, 42, 43, 44, 45, 46, 54, 55, 56, 58, 61, 62, 63, 64, 66, 67, 68, 70, 72, 73, 74, 75, 76, 78, 79, 80, 82, 83, 85, 86, 87, 88, 91, 92, 93, 94, 95, 96, 97, 98, 99, 100, 102, 103, 104, 105, 106, 107, 108, 109, 110, 111, 112, 113, 114, 115, 116, 117, 121, 122, 123, 124, 125, 126, 127, 128, 129, 130, 131, 132, 133, 134, 135, 136, 144, 148, 150, 152, 153, 155, 159, 165, 173, 181, 187, 188, 189, 191, 196, 198, 199, 200, 201, 202, 203, 204, 205, 206, 207, 208, 210, 212, 213, 214, 215, 216, 218, 219, 220, 221, 222, 227,

*Pyricularia oryzae*, compounds 2, 4, 6, 7, 8, 9, 10, 11, 12, 13, 14, 15, 16.

*Puccinia recondita* f.sp. *tritici*, compounds 2, 4, 6, 9, 11, 12, 13, 14, 16, 18, 19, 20, 21, 22, 23, 24, 25, 29, 30, 31, 42, 49, 55, 61, 62, 63, 64, 66, 67, 68, 70, 72, 74, 75, 76, 82, 83, 85, 86, 87, 88, 92, 93, 94, 95, 97, 98, 99, 102, 103, 104, 105, 106, 107, 108, 109, 112, 113, 114, 115, 117, 122, 123, 126, 127, 129, 130, 131, 132, 133, 134, 135, 136, 143, 148, 155, 159, 165, 181, 187, 188, 189, 191, 198, 199, 200, 202, 203, 204, 206, 207, 208, 210, 212, 213, 214, 215, 218, 219, 222,

*Pyrenophora teres*, compounds, 2, 4, 7, 8, 13, 14, 16, 18, 19, 20, 21, 22, 23, 24, 29, 30, 31, 62, 63, 66, 68, 70, 72, 73, 74, 75, 76, 82, 93, 94, 95, 99, 102, 104, 106, 108, 109, 113, 114, 115, 117, 122, 129, 130, 131, 132, 133, 135, 144, 202, 203, 219,

*Septoria nodorum*, compounds, 2, 3, 4, 6, 7, 8, 9, 10, 11, 12, 13, 14, 15, 16, 18, 19, 20, 21, 22, 23, 24, 25, 29, 30, 31, 53, 54, 55, 56, 57, 62, 63, 64, 66, 68, 70, 72, 73, 74, 75, 76, 78, 81, 82, 83, 85, 86, 87, 88, 92, 93, 94, 95, 96, 97, 98, 99, 102, 103, 104, 105, 106, 107, 108, 109, 110, 111, 112, 113, 114, 115, 117, 121, 122, 123, 124, 126, 127, 128, 129, 130, 131, 132, 133, 134, 135, 136, 143, 144, 150, 152, 153, 155, 159, 165, 173, 181, 187, 188, 189, 191, 194, 196, 198, 199, 200, 201, 202, 203, 204, 206, 208, 210, 212, 213, 214, 218, 219, 222, The following compounds gave at least 60% control of the following fungal infection at 60 ppm: *Septoria tritici*, compounds 2, 3, 4, 5, 6, 7, 8, 9, 10, 11, 12, 13, 14, 15, 16, 17, 18, 20, 21, 22, 23, 24, 25, 29, 30, 31, 32, 33, 34, 35, 36, 37, 38, 39, 40, 41, 42, 44, 45, 46, 53, 54, 55, 56, 57, 58, 59, 60, 61, 62, 63, 64, 65, 66, 67, 68, 69, 70, 72, 73, 74, 75, 76, 78, 79, 80, 81, 82, 83, 85, 86, 87, 88, 89, 91, 93, 94, 95, 96, 97, 98, 99, 100, 101, 104, 105, 106, 107, 108, 109, 110, 111, 112, 113, 114, 115, 116, 117, 119, 120, 121, 122, 123, 124, 125, 126, 127, 128, 129, 130, 131, 132, 133, 134, 135, 136, 143, 144, 148, 152, 153, 159, 165, 181, 187, 188, 189, 191, 196, 198, 199, 200, 201, 202, 203, 204, 206, 208, 210, 212, 213, 214, 215, 216, 217, 218, 219, 220, 221, 222, 224,

*Fusarium culmorum*, compounds, 4, 7, 8, 9, 10, 13, 14, 16, 18, 20, 21, 22, 23, 24, 29, 30, 31, 42, 54, 57, 61, 66, 69, 75, 87, 93, 94, 97, 98, 99, 104, 106, 107, 108, 109, 110, 111, 114, 115, 117, 124, 125, 127, 130, 131, 132, 143, 144, 159, 181, 187, 188, 189, 190, 191, 192, 193, 196, 197, 198, 199, 200, 201, 204, 206, 205, 207, 208, 210, 212, 213, 214, 218, 219, 222, The following compounds gave at least 60% control of the following fungal infection at 20 ppm: *Pythium ultimum*, compounds 4, 6, 7, 8, 9, 10, 11, 12, 13, 14, 15, 16, 17, 18, 20, 21, 22, 23, 24, 25, 27, 28, 29, 30, 31, 33, 34, 36, 38, 42, 43, 44, 45, 46, 48, 49, 50, 51, 52, 53, 54, 55, 56, 61, 63, 64, 66, 67, 69, 70, 72, 73, 74, 75, 76, 82, 85, 88, 92, 93, 94, 95, 96, 97, 98, 100, 104, 106, 110, 111, 117, 121, 122, 124, 125, 127, 128, 129, 130, 131, 132, 135, 136, 143, 144, 153, 154, 159, 161, 165, 173, 181, 187, 188, 189, 190, 191, 192, 193, 194, 196; 197, 198, 199, 200, 201, 202, 203, 204, 205, 206, 207, 208, 210, 212, 213, 214, 215, 218, 219, 220, 221, 222, 224.

The invention claimed is:

1. A compound of the general formula I

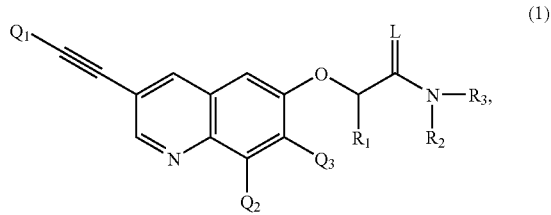

wherein $Q^1$ is hydrogen, $C_{1-4}$ alkyl, tri-$C_{1-4}$ alkylsilanyl, hydroxy-$C_{1-6}$ alkyl, alkoxy-$C_{1-6}$ alkyl, halo-$C_{1-6}$ alkyl or halogen, $Q^2$ and $Q^3$, independently of each other, are hydrogen, $C_{1-3}$ alkyl, halo-$C_{1-3}$ alkyl or halogen, $R^1$ is $C_{1-4}$ alkyl, halo($C_{1-4}$)alkyl, $C_{3-4}$cycloalkyl, $C_{1-4}$alkoxy, halo($C_{1-4}$)alkoxy, $C_{3-4}$-cycloalkoxy, $C_{1-4}$alkylsulphinyl, $C_{1-4}$alkylsulphonyl, halo($C_{1-4}$)alkylthio, halo($C_{1-4}$) alkylsulphinyl, halo($C_{1-4}$) alkylsulphonyl, $C_{3-4}$cycloalkylthio, $C_{3-4}$cyclo-alkylsulphinyl or $C_{3-4}$cycloalkylsulphonyl, $R^2$ is hydrogen, $C_{1-6}$ alkyl, $C_{3-4}$ cycloalkyl, $C_{2-8}$ alkenyl, cyano, hydroxy, $C_{1-4}$ alkoxy, halo($C_{1-4}$)alkyl, cyano($C_{1-4}$)alkyl, $C_{1-4}$ alkoxy($C_{1-4}$)alkyl, $C_{1-4}$ alkoxy($C_{1-4}$)alkoxy($C_{1-4}$)alkyl or benzyloxy($C_{1-4}$)alkyl, wherein the phenyl ring is optionally substituted with $C_{1-4}$ alkoxy, $R^3$ is —$(CR^aR^b)_p(CR^cR^d)_q(X)_r(CR^eR^f)_sR^4$, wherein $R^a$, $R^b$, $R^c$, $R^d$, $R^e$ and $R^f$, independently of each other, are hydrogen, $C_{1-6}$ alkyl, halogen, halo($C_{1-6}$)alkyl, hydroxy($C_{1-6}$)alkyl, $C_{1-4}$alkoxy($C_{1-4}$)alkyl, $C_{3-5}$ alkenyloxy($C_{1-4}$)alkyl, $C_{3-5}$ alkynyloxy-$C_{1-4}$-alkyl, $C_{2-5}$ alkenyl or $C_{2-5}$ alkynyl, cyano, hydroxy, $C_{1-4}$ alkoxy, $C_{3-5}$ alkenyloxy, $C_{3-5}$ alkynyloxy or $C_{1-4}$ alkoxycarbonyl, or $R^aR^b$, $R^cR^d$ or $R^eR^f$ may join to form a 3 to 8 membered carbocyclic or heterocyclic ring containing a heteroatom selected from sulfur, oxygen and $NR^o$, wherein $R^o$ is hydrogen or optionally substituted $C_{1-6}$alkyl, where the carbocyclic or heterocyclic ring is optionally substituted with halo or $C_{1-4}$ alkyl, X is (CO), (CO)O, O(CO), O or $S(O)_t$, wherein t is 0, 1 or 2, or X is NH or N($C_{1-6}$)alkyl, p, r and s, independently of each other, are 0 or 1, q is 0, 1 or 2, $R^4$ is hydrogen, optionally substituted $C_{1-6}$ alkyl, formyl, cyano, optionally substituted $C_{2-6}$ alkenyl, or —C≡C—$R^5$, wherein $R^5$ is hydrogen, $C_{1-8}$ alkyl optionally substituted with halogen, hydroxy, $C_{1-6}$ alkoxy, $C_{1-3}$ alkoxy($C_{1-3}$)alkoxy, cyano, $C_{1-4}$ alkylcarbonyloxy, aminocarbonyloxy, mono- or di($C_{1-4}$)-alkylaminocarbonyloxy, tri($C_{1-4}$)alkylsilyloxy or —$S(O)_g(C_{1-6})$alkyl, wherein g is 0, 1 or 2, or $R^5$ is $C_{3-6}$ cycloalkyl optionally substituted with halogen, hydroxy, $C_{1-6}$ alkoxy, $C_{1-3}$ alkoxy-($C_{1-3}$)alkoxy, cyano, $C_{1-4}$ alkylcarbonyloxy, aminocarbonyloxy, mono- or di($C_{1-4}$)alkyl-aminocarbonyloxy, tri($C_{1-4}$)alkylsilyloxy or —$S(O)_g(C_{1-6})$alkyl, wherein g is 0, 1 or 2, or $R^5$ is $C_{3-6}$ cycloalkyl($C_{1-4}$)alkyl, wherein the alkyl and/or cycloalkyl moiety is optionally substituted with halogen, hydroxy, $C_{1-6}$ alkoxy, $C_{1-3}$ alkoxy($C_{1-3}$)alkoxy, cyano, $C_{1-4}$ alkyl-carbonyloxy, aminocarbonyloxy, mono- or di($C_{1-4}$)alkylaminocarbonyloxy, tri($C_{1-4}$)alkyl-silyloxy or —$S(O)_g(C_{1-6})$alkyl, wherein g is 0, 1 or 2, or $R^5$ is optionally substituted aryl, optionally substituted aryl($C_{1-4}$)alkyl, optionally substituted aryloxy($C_{1-4}$)alkyl, optionally substituted heteroaryl or optionally substituted heteroaryl($C_{1-4}$)alkyl or optionally substituted heteroaryloxy($C_{1-4}$)alkyl, where these heteroaryls contain a heteroatom selected from sulphur, oxygen or $NR^{ooo}$, wherein $R^{ooo}$ is hydrogen or optionally substituted $C_{1-6}$alkyl, or $R^4$ is optionally substituted $C_{3-6}$ cycloalkyl, optionally substituted $C_{5-6}$ cycloalkenyl, optionally substituted aryl, optionally substituted heteroaryl or an optionally substituted 5- to 8-membered ring optionally containing a heteroatom selected from sulfur, oxygen or $NR^o$, wherein $R^o$ is hydrogen or optionally substituted $C_{1-6}$alkyl, or $R^2$ and $R^3$ may join to form a 5- or 6-membered ring optionally substituted with halogen, $C_{1-4}$ alkyl, mono- or di-($C_{1-4}$)alkylaminocarbonyl, and optionally containing a heteroatom selected from sulphur, oxygen and $NR^{oo}$, wherein $R^{oo}$ is $C_{1-4}$ alkyl optionally substituted with halogen, $C_{1-6}$ alkoxy or cyano, or $R^{oo}$ is phenyl optionally substituted with nitro, $C_{1-4}$ alkyl, halo($C_{1-4}$)alkyl, $C_{1-4}$ alkylcarbonyl or heteroaryl, or $R^2$ and $R^3$ may join to form an optionally substituted 6,6-membered bicycle, L is sulfur or oxygen, and salts and N-oxides of the compounds of the formula I.

2. A compound according to claim 1, wherein $Q^1$ is hydrogen, $C_{1-4}$ alkyl, halo($C_{1-4}$)alkyl, hydroxy($C_{1-4}$) alkyl or tri-$C_{1-3}$ alkylsilanyl, $Q^2$ and $Q^3$, independently of each other, are hydrogen, $C_{1-3}$ alkyl or halogen, $R^1$ is $C_{1-4}$ alkyl, ($C_{1-4}$)alkoxy or ($C_{1-4}$)alkylthio, $R^2$ is hydrogen, $R^3$ is —$(CR^aR^b)_p(CR^cR^d)_q(X)_r(CR^eR^f)_sR^4$, wherein $R^a$, $R^b$, $R^c$, $R^d$, $R^e$ and $R^f$, independently of each other, are hydrogen, $C_{1-6}$ alkyl, halo($C_{1-6}$)alkyl, hydroxy($C_{1-6}$)alkyl, $C_{2-3}$ alkenyl or $C_{2-3}$ alkynyl, halogen, cyano, hydroxyl or ($C_{1-4}$)alkoxy, $C_{3-5}$ alkenyloxy or $C_{3-5}$ alkynyloxy, or $R^a$ und $R^b$ may join to form a 3 to 8 membered carbocyclic ring, X is (CO) or O, p, r and s, independently of each other, are 0 or 1, q is 0, 1 or 2, $R^4$ is hydrogen, $C_{1-6}$ alkyl, $C_{1-6}$ alkyl substituted with halo, hydroxy, $C_{1-4}$ alkoxy, $C_{1-4}$ alkoxy($C_{1-4}$)alkoxy, $C_{3-5}$ alkenyl, $C_{3-5}$ alkynyl or cyano, or $R^4$ is formyl, cyano or —C≡C—$R^5$, wherein $R^5$ is hydrogen or $C_{1-4}$ alkyl or $C_{1-4}$ alkyl substituted with halo, hydroxy, $C_{1-4}$ alkoxy, $C_{1-4}$ alkoxy($C_{1-4}$)alkoxy, $C_{3-5}$ alkenyl, $C_{3-5}$ alkynyl or cyano, and L is oxygen.

3. A compound according to claim 2, wherein $Q^1$ is hydrogen, methyl, ethyl, fluoromethyl, hydroxymethyl, or trimethylsilanyl, $Q^2$ and $Q^3$, independently of each other, are hydrogen, methyl, fluoro, chloro or bromo, $R^1$ is ethyl, methoxy or methylthio, $R^2$ is hydrogen, $R^3$ is $(CR^aR^b)_p(CR^cR^d)_q(X)_r(CR^eR^f)_sR^4$, wherein $R^a$, $R^b$, $R^c$, $R^d$, $R^e$ and $R^f$, independently of each other, are hydrogen, $C_{1-4}$ alkyl, halo($C_{1-4}$)alkyl, hydroxy($C_{1-4}$)alkyl, $C_{2-3}$ alkynyl, $C_{3-5}$ alkenyloxy or $C_{3-5}$ alkynyloxy, cyano or ($C_{1-3}$)alkoxy, or $R^a$ und $R^b$ may join to form a 3 or 4 membered carbocyclic ring, X is (CO) or O, p, r and s, independently of each other, are 0 or 1, q is 0, 1 or 2, $R^4$ is hydrogen, $C_{1-6}$ alkyl, halo($C_{1-4}$)alkyl, hydroxy($C_{1-4}$)alkyl, $C_{1-4}$ alkoxy-$C_{1-6}$alkyl, formyl, cyano or —C≡$CR^5$, wherein $R^5$ is hydrogen, methyl, ethyl, methoxymethyl, allyloxymethyl or propargyloxymethyl and L is oxygen.

4. A compound according to claim 1, wherein $Q^1$ is hydrogen, methyl, hydroxymethyl, fluoromethyl or trimethylsilyl.

5. A compound according to claim 1, wherein $Q^1$ is hydrogen and $R^3$ is $(CR^aR^b)_p(CR^cR^d)_q(X)_r(CR^eR^f)_sR^4$, wherein p, q and r are 0, s is 1, $R^e$ and $R^f$ are methyl and $R^4$ is ethynyl, propynyl, methoxymethylethynyl or propargyloxymethylethynyl.

6. A compound according to claim 1, wherein $Q^1$ is hydrogen and $R^3$ is $(CR^aR^b)_p(CR^cR^d)_q(X)_r(CR^eR^f)_sR^4$, wherein $R^a$, $R^b$, $R^c$, $R^d$, $R^e$ and $R^f$, independently of each other, are hydrogen, methyl or cyano, X is O, p, r and s are 0 or 1, q is 0, 1 or 2 and $R^4$ is hydrogen, methyl, methoxymethyl, formyl, cyano, ethenyl or ethynyl, or $R^a$ und $R^b$ may join to form a cyclobutylene ring.

7. A compound according to claim 6, wherein $Q^1$ is hydrogen and $R^3$ is $(CR^aR^b)_p(CR^cR^d)_q(X)_r(CR^eR^f)_sR^4$, wherein $R^a$ and $R^b$ are methyl, p is 1, q is 0, r is 0, s is 1, $R^e$ and $R^f$ are hydrogen and $R^4$ is hydrogen.

8. A compound according to claim 6, wherein $Q^1$ is hydrogen and $R^3$ is —$(CR^aR^b)_p(CR^cR^d)_q(X)_r(CR^eR^f)_sR^4$, wherein $R^a$ is methyl, $R^b$ is cyano, p is 1, $R^c$ anti $R^d$ are hydrogen, q is 1, X is O, r is 1, $R^e$ and $R^f$ are hydrogen, s is 1, and $R^4$ is hydrogen, methyl, ethenyl or ethynyl.

9. A compound according to claim 1, wherein $R^1$ is methylthio.

10. A compound according to claim 1, wherein $R^2$ is hydrogen.

11. A compound according to claim 1, wherein L is oxygen.

12. A process for preparing a compound of the formula I according to claim 1, which comprises reacting a compound of the formula (2)

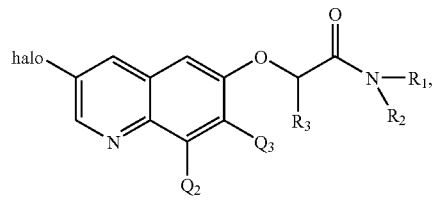
(2)

wherein $R_1$, $R_2$, $R_3$, $Q_2$ and $Q_3$ are as defined in claim 1 and halo is chloro, bromo or iodo with a compound of the formula (3)

(3)

wherein $Q_1$ is as defined in claim 1, in the presence of a catalyst, a base and a solvent.

13. A fungicidal composition comprising a fungicidally effective amount of a compound according to claim 1 and a suitable carrier or diluent therefor.

14. A method of combating or controlling phytopathogenic fungi which comprises applying a fungicidally effective amount of a compound according to claim 1 to a plant, to a seed of a plant, to the locus of the plant or seed or to soil or any other plant growth medium.

* * * * *